(12) United States Patent  (10) Patent No.: US 12,344,594 B2
Lavis et al.  (45) Date of Patent: Jul. 1, 2025

(54) RED-SHIFTED FLUOROPHORES

(71) Applicant: HOWARD HUGHES MEDICAL INSTITUTE, Chevy Chase, MD (US)

(72) Inventors: Luke D. Lavis, Leesburg, VA (US); Jonathan B. Grimm, Ashburn, VA (US)

(73) Assignee: HOWARD HUGHES MEDICAL INSTITUTE, Chevy Chase, MD (US)

( * ) Notice: Subject to any disclaimer, the term of this patent is extended or adjusted under 35 U.S.C. 154(b) by 877 days.

(21) Appl. No.: 17/116,987

(22) Filed: Dec. 9, 2020

(65) Prior Publication Data

US 2021/0171490 A1   Jun. 10, 2021

Related U.S. Application Data

(60) Provisional application No. 62/945,295, filed on Dec. 9, 2019.

(51) Int. Cl.

| C07D 311/82 | (2006.01) |
|---|---|
| C07C 63/72 | (2006.01) |
| C07D 335/12 | (2006.01) |
| C07D 405/14 | (2006.01) |
| C07D 409/14 | (2006.01) |
| C07D 413/10 | (2006.01) |
| C07D 491/147 | (2006.01) |
| C07F 7/08 | (2006.01) |
| C07F 9/6568 | (2006.01) |
| G01N 21/64 | (2006.01) |

(52) U.S. Cl.
CPC ............ C07D 311/82 (2013.01); C07C 63/72 (2013.01); C07D 335/12 (2013.01); C07D 405/14 (2013.01); C07D 409/14 (2013.01); C07D 413/10 (2013.01); C07D 491/147 (2013.01); C07F 7/0816 (2013.01); C07F 9/65685 (2013.01); G01N 21/6428 (2013.01); G01N 21/6458 (2013.01); G01N 2201/06193 (2013.01)

(58) Field of Classification Search
CPC .................. C07D 311/82; C07D 491/147
See application file for complete search history.

(56) References Cited

U.S. PATENT DOCUMENTS

2003/0232818 A1   12/2003  Anderson et al.

FOREIGN PATENT DOCUMENTS

| JP | 03284649 A  * | 12/1991 | |
|---|---|---|---|
| WO | WO-9739064 A1 * | 10/1997 | .......... C07C 201/08 |
| WO | WO-9915517 A1 * | 4/1999 | .......... C07D 311/82 |
| WO | WO-02079216 A1 * | 10/2002 | .......... C07H 21/00 |
| WO | 2014/040965 A1 | 3/2014 | |
| WO | 2018/007827 A1 | 1/2018 | |
| WO | 2018/075937 A1 | 4/2018 | |
| WO | 2019/153080 A1 | 8/2019 | |
| WO | 2023/064790 A1 | 4/2023 | |

OTHER PUBLICATIONS

Grimm et al. Nature Methods 2020, 17, 815-821 (Year: 2020).*
Polyakova et al. Eur. J. Org. Chem. 2009, 5162-5177 (Year: 2009).*
Wanat et al. Org. Lett. 2015, 17, 3062-3065 (Year: 2015).*
Makwana et al. Biomacromolecules 2017, 18, 1532-1543 and its supporting information (Year: 2017).*
Schafer et al. Angew. Chem. Int. Ed. 2012, 51, 9173-9175 (Year: 2012).*
Lavis, L.D., "Chemistry is Dead. Long Live Chemistry!" Biochemistry 56, 5165-5170 (2017).
Grimm, J.B., et al., "A general method to improve fluorophores for live-cell and single-molecule microscopy," Nat. Methods 12(3), 244-250 (2015).

(Continued)

*Primary Examiner* — Matthew P Coughlin
(74) *Attorney, Agent, or Firm* — Stites & Harbison, PLLC; Mandy Wilson Decker

(57) ABSTRACT

A compound of the following structure is provided:

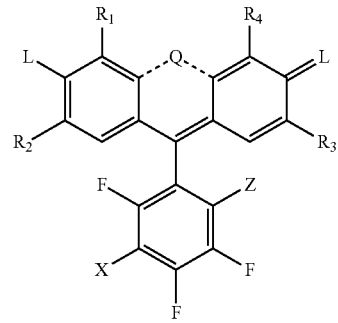

or

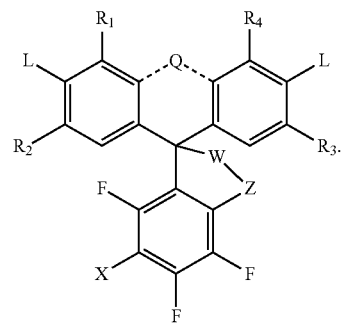

35 Claims, 11 Drawing Sheets

(56) References Cited

OTHER PUBLICATIONS

Grimm, J.B., et al., "A general method to fine-tune fluorophores for live-cell and in vivo imaging," Nat. Methods vol. 14, No. 10 987-994 (2017).

Grimm, J.B., et al., "General Synthetic Method for Si-Fluoresceins and Si-Rhodamines," ACS Cent. Sci. 3, 975-985 (2017).

Panchuk-Voloshina, N., et al., "Alexa Dyes, a Series of New Fluorescent Dyes that Yield Exceptionally Bright, Photostable Conjugates," J. Histochem. Cytochem. vol. 47(9), 1179-1188 (1999).

Lukinavičius, G., et al., "A near-infrared fluorophore for live-cell super-resolution microscopy of cellular proteins," Nature Chem. vol. 5, 132-139 (2013).

Liu, J., et al., "Sulfone-Rhodamines: A New Class of Near-Infrared Fluorescent Dyes for Bioimaging," ACS Appl. Mater. Interfaces 8, 22953-22962 (2016).

Zhou, X., et al., "Nebraska Red: a phosphinate-based near-infrared fluorophore scaffold for chemical biology applications," Chem. Commun. (Camb) 52, 12290-12293 (2016).

Grzybowski, M., et al., "A Highly Photostable Near-Infrared Labeling Agent Based on a Phospha-rhodamine for Long-Term and Deep Imaging," Angew. Chem. Int. Ed. 57, 10137-10141 (2018).

Los, G.V., et al., "HaloTag: A Novel Protein Labeling Technology for Cell Imaging and Protein Analysis," ACS Chem. Biol. vol. 3, No. 6, 373-382 (2008).

Gee, K.R., et al., "Novel Derivatization of Protein Thiols With Fluorinated Fluoresceins," Tetrahedron Lett. vol. 37, No. 44, pp. 7905-7908 (1996).

Nemoto, H., et al., "Development of a New Acyl Anion Equivalent for the Preparation of Masked Activated Esters and Their Use to Prepare a Dipeptide," J. Org. Chem. 55, 4515-4516 (1990).

Wysocki, L.M., et al., "Facile and General Synthesis of Photoactivatable Xanthene Dyes," Angew. Chem., Int. Ed. 50, 11206-11209 (2011).

Hinckley, D.A., et al., "A spectoscopic/thermodynamic study of the rhodamine B lactone-zwitterion equilibrium," Spectrochimica. Acta, vol. 44A, No. 10, pp. 1053-1059 (1988).

Suzuki, K., et al., "Reevaluation of absolute luminescence quantum yields of standard solutions using a spectrometer with an integrating sphere and a back-thinned CCD detector," Phys. Chem. Chem. Phys. 11, 9850-9860 (2009).

Mitronova, G.Y., et al., "Functionalization of the meso-Phenyl Ring of Rhodamine Dyes Through SnAr with Sulfur Nucleophiles: Synthesis, Biophysical Characterizations, and Comprehensive NMR Analysis," Eur. J. Org. Chem. 337-349 (2015).

Bassolino, et al. "Practical and Scalable Synthesis of 7-Azetidine-1-yl-4-(hydroxymethyl)coumarin: An Improved Photoremovable Group." Synthesis 2018, 50, 846-852.

Magennis, E.P., et al. "Polymers for binding of the gram-positive oral pathogen *Streptococcus* mutans." PLOS ONE https://doi.org/10.1371/journal.pone.0180087. Jul. 3, 2017.

\* cited by examiner

RED-SHIFTED FLUOROPHORES

RELATED APPLICATIONS

This application claims priority from U.S. Provisional Application Ser. No. 62/945,295 filed Dec. 9, 2019, the entire disclosure of which is incorporated herein by this reference.

TECHNICAL FIELD

The presently-disclosed subject matter relates to fluorescent compounds. In particular, the presently-disclosed subject matter relates to polycyclic chemical fluorophores as well as method for making and using the same.

INTRODUCTION

Fluorescence imaging using far-red or near-infrared (NIR) light is desirable due to less scattering and lower autofluorescence. Although rhodamine dyes remain an important small-molecule fluorophore type due to their brightness, their far-red variants suffer from poor performance due to their propensity to adopt a nonfluorescent form. The presently-disclosed subject matter includes a general chemical modification for rhodamines that optimizes long-wavelength variants and enables facile functionalization with different chemical groups.

The development of hybrid small-molecule:protein labeling strategies enable the use of chemical fluorophores in living cells and in vivo.[1] Optimizing small-molecule dyes for these complex biological environments is vital for pushing the frontier of biological imaging, as synthetic fluorophores are often brighter and more photostable than fluorescent proteins[2].

Recently, general methods were developed to improve[3] and fine-tune[4] rhodamine fluorophores by incorporating four-membered azetidines into the structure, yielding the 'Janelia Fluor' dyes. Although those tuning strategies allow optimization of short-wavelength rhodamines, the present inventors discovered they cannot be applied to analogs excited with far-red and NIR light where autofluorescence and scattering are minimized. Herein, a unique complementary tuning strategy is disclosed, which allows rational optimization of a broader palette of dyes. This general method also serves as a basis for facile functionalization, enabling the synthesis of cell- and tissue-permeable rhodamine labels for biological imaging experiments.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes polycyclic chemical fluorophores as well as method for making and using the same.

In some embodiments the compound has the following formula:

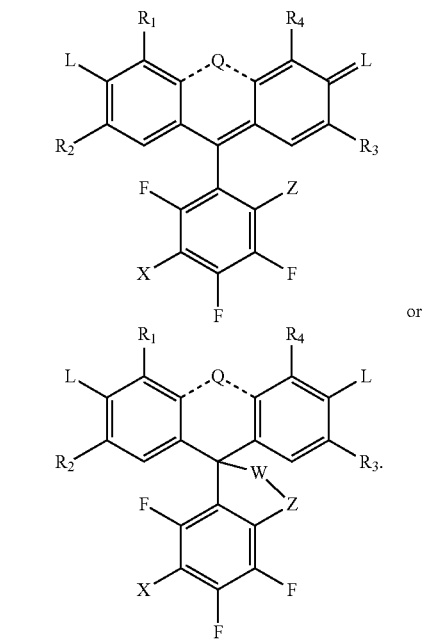

In the compound, Q is selected from the group consisting of C(alkyl), C(alkyl)$_2$, NH, N(alkyl), O, S, SO$_2$, Si(alkyl)$_2$, P(O)(aryl), P(O)(alkyl), PO$_2$H, PO$_2$(alkyl), and Se or replaced with two H atoms. L is independently selected from the group consisting of O, OH, NH$_2$, NH(alkyl), NH(deuterated alkyl), N(alkyl)$_2$, N(deuterated alkyl)$_2$, NH(aryl), N(aryl)$_2$, N(alkyl)(aryl), N(deuterated alkyl)(aryl), substituted or unsubstituted cyclic amines with a ring size of 3, 4, 5, 6, 7, 8, or 9 atoms, and substituted or unsubstituted deuterated cyclic amines with a ring size of 3, 4, 5, 6, 7, 8, or 9 atoms.

$R_1$, $R_2$, $R_3$, and $R_4$ are independently selected from the group consisting of H, D, halogen, CN, OH, O(alkyl), O(aryl), SH, S(alkyl), S(aryl), N$_3$, NH$_2$, NH(alkyl), N(alkyl)$_2$, NH(aryl), NH(aryl)$_2$, NO$_2$, CHO, C(O)(alkyl), C(O)(aryl), COOH, COO(alkyl), COO(aryl), C(O)NH(alkyl), C(O)NH(aryl), PO$_3$H$_2$, SO$_3$H, alkyl and substituted alkyl, aryl and substituted aryl, alkenyl and substituted alkenyl, alkynyl or substituted alkynyl, or where the R substituents and L substituents, taken together with the carbon atoms to which they are bonded, form a substituted or unsubstituted ring containing 3, 4, 5, 6, 7, 8, or 9 atoms.

X is selected from the group consisting of alkyl, substituted alkyl, aryl, substituted aryl, alkenyl, substituted alkenyl, alkynyl, substituted alkynyl, CN, COOH, COO(alkyl), COO(aryl), C(O)NH(alkyl), C(O)N(alkyl)$_2$, C(O)NH(aryl), C(O)N(aryl)$_2$, H, N$_3$, NH$_2$, NH(alkyl), N(alkyl)$_2$, NH(aryl), NH(aryl)$_2$, NHNH$_2$, NHOH, PO$_3$H$_2$, and SO$_3$H, so long as when X is N$_3$ then neither Q nor L are O or OH;

When W is not present in the compound, Z is selected from the group consisting of H, halogen, OH, O(alkyl), O(aryl), COOH, COO(alkyl), COO(aryl), C(O)NH(alkyl), C(O)N(alkyl)$_2$, C(O)NH(aryl), C(O)N(aryl)$_2$, C(O)N(alkyl)(aryl), PO$_3$H$_2$, SO$_3$H, alkyl, substituted alkyl, alkenyl, and substituted alkenyl. When W is present in the structure, Z is selected from the group consisting of C(O), SO$_2$, PO$_2$H, or CR$_2$ where each R is independently selected from the group consisting of H, alkyl, and substituted alkyl; and W is selected from the group consisting of O, S, C(O), C(N$_2$), NH, N(alkyl), N(aryl), N(SO$_2$R) where R can be alkyl, substituted alkyl, and CN.

The presently-disclosed subject matter further includes a method for detecting a target substance using a compound as disclosed herein. In some embodiments, the method involves contacting a sample with the compound, and detecting an emission light from the compound, the emission light indicating the presence of the target substance.

In some embodiments of the method, the target substance is selected from a protein, a carbohydrate, a polysaccharide, a glycoprotein, a hormone, a receptor, an antigen, an antibody, a virus, a substrate, a metabolite, an inhibitor, a drug, a nutrient, a growth factor, a liprotein, and a combination thereof.

The presently-disclosed subject matter further includes methods of making a compound as described further herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1:
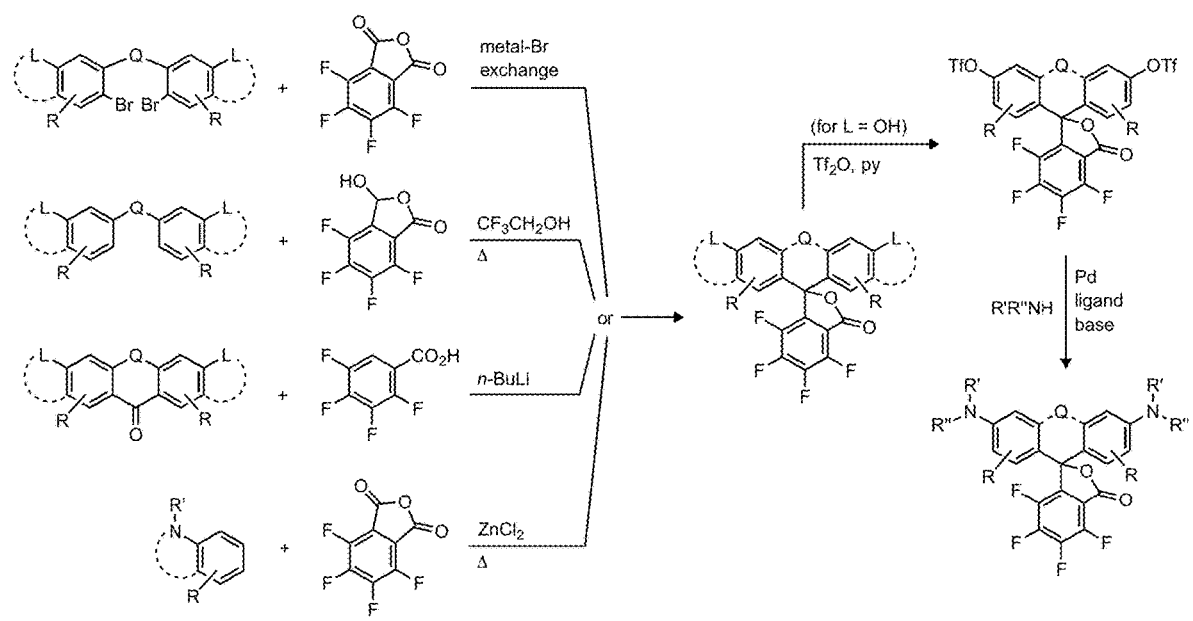
FIG. 1 illustrates the general synthesis of xanthene dyes bearing a fluorinated pendant phenyl ring.
Figure 2:
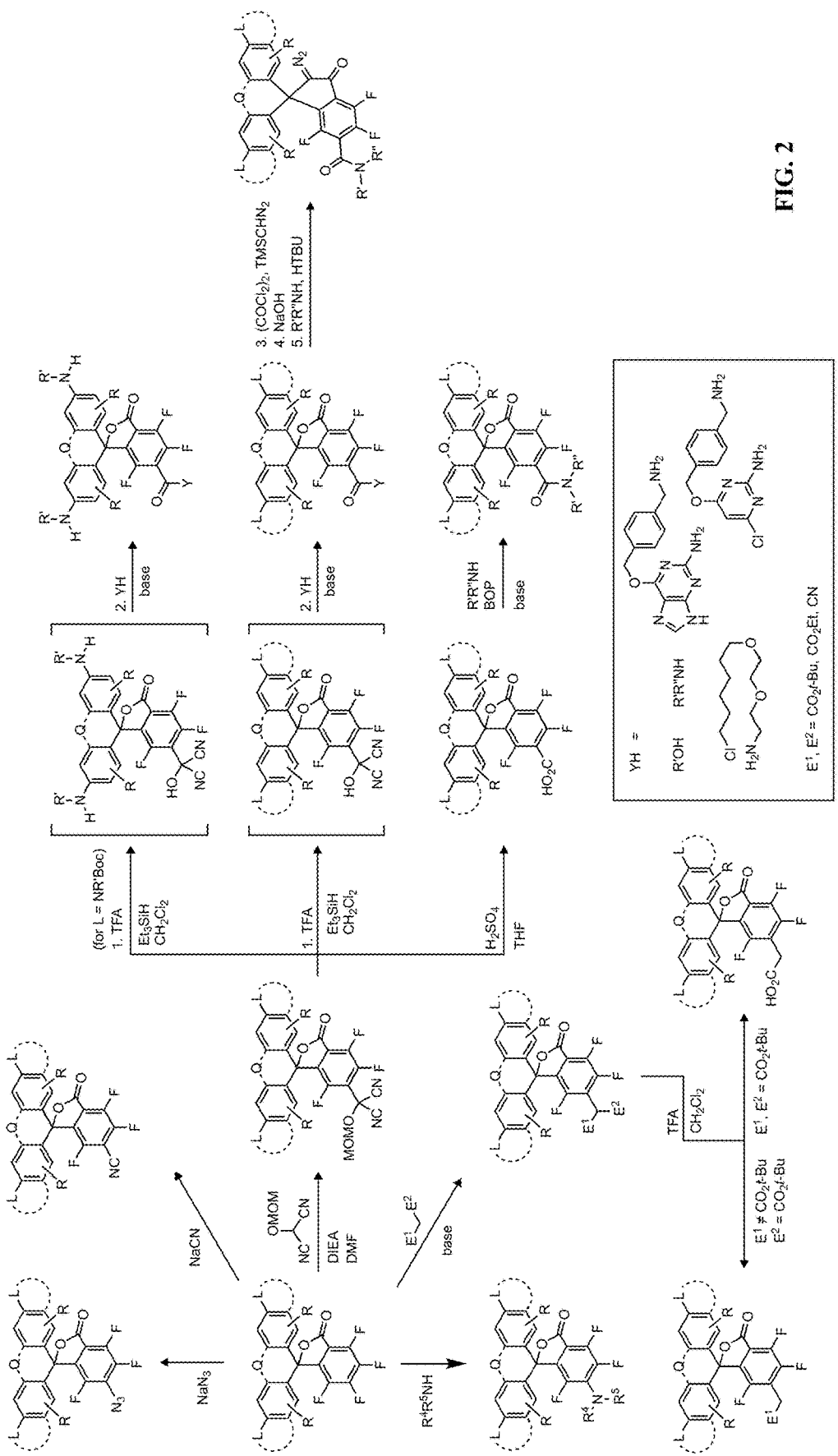
FIG. 2 illustrates the general synthesis of exemplary compounds as disclosed herein.
Figure 3:
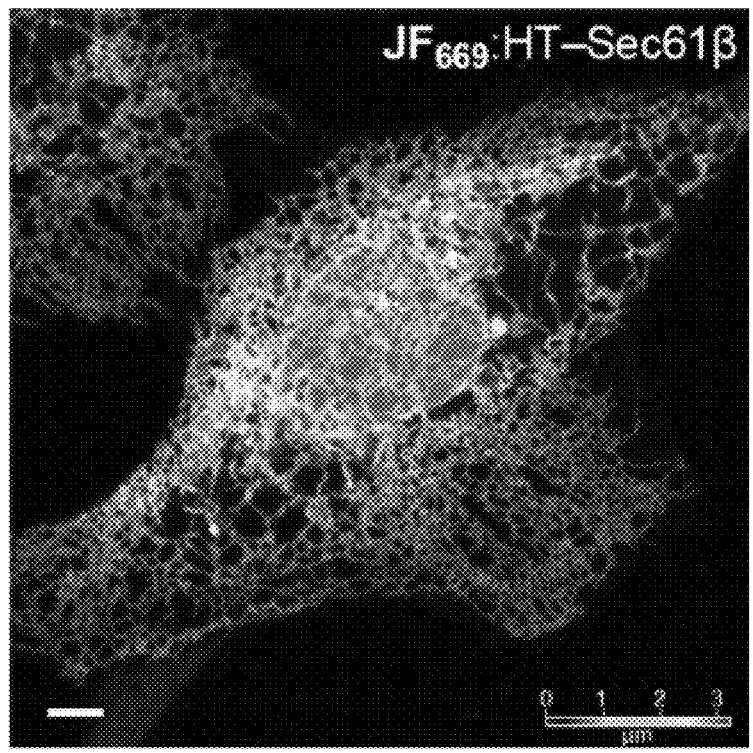
FIG. 3 includes an airyscan image of U2OS cell expressing endoplasmic reticulum-localized Sec61β-HaloTag labeled with exemplary compound (JF$_{669}$-HaloTag ligand); color scale indicates z-depth; scale bar=5 μm. For the Airyscan imaging experiments U2OS cells were used, which were transiently transfected with Sec61β-HaloTag expressing plasmid or TOMM20-HaloTag expressing plasmid using FuGENE HD (Promega). Sec61β is an endoplasmic reticulum membrane protein translocator protein and TOMM20 is an outer mitochondrial membrane protein as part of a protein translocase complex.
Figure 4:
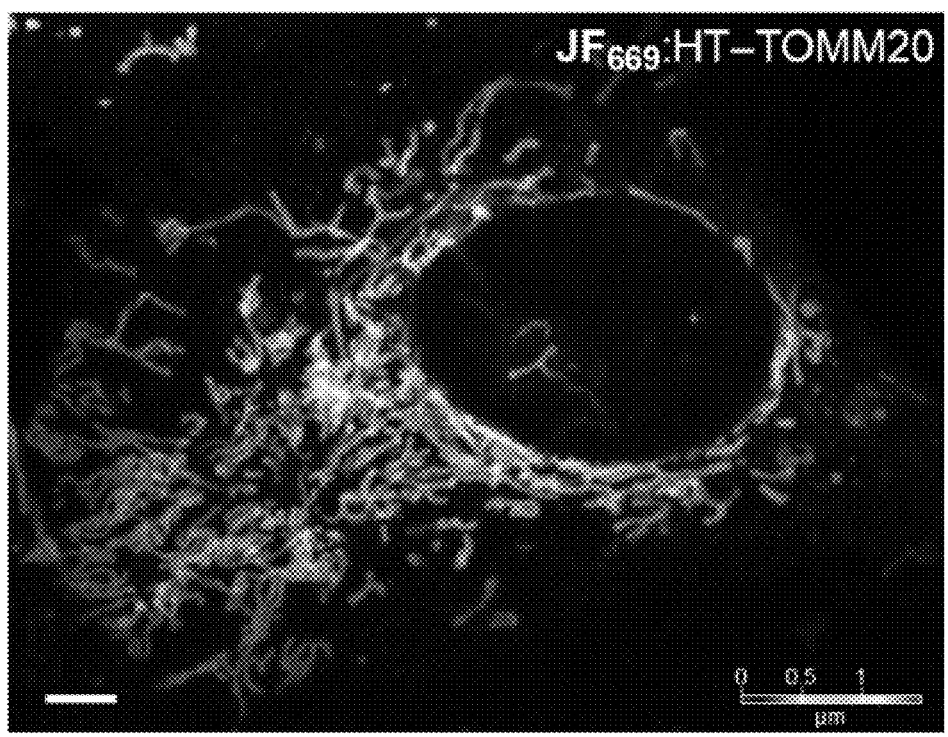
FIG. 4 includes an airyscan image of U2OS cell expressing mitochondria-localized TOMM20-HaloTag labeled with exemplary compound (JF$_{669}$-HaloTag ligand); color scale indicates z-depth; scale bar=5 μm.
Figure 5:
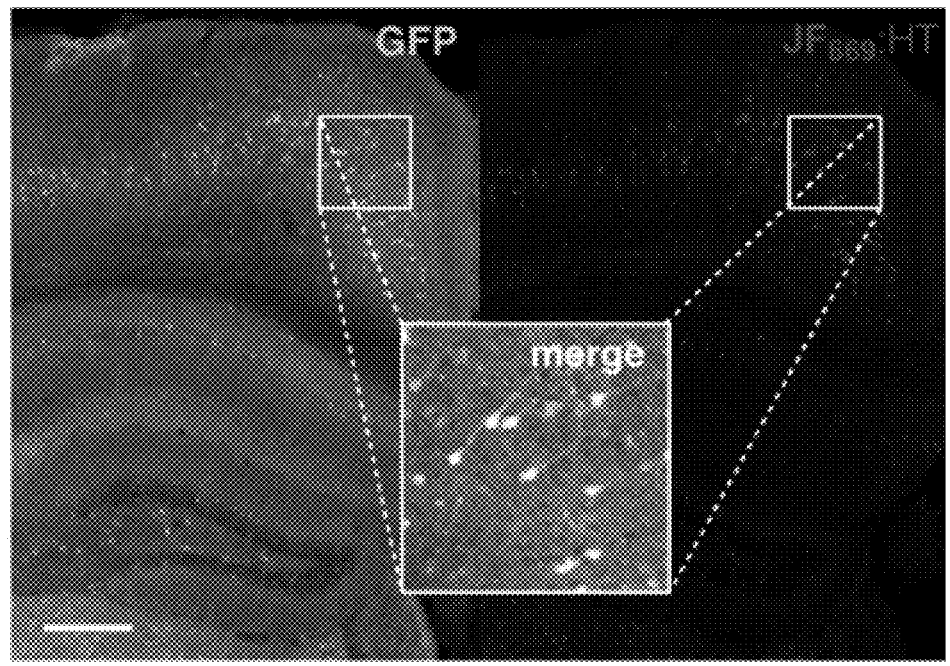
FIG. 5 includes an image of fixed coronal mouse brain slice from animal expressing GFP-HaloTag fusion protein in neurons after intravenous injection of exemplary compound (JF$_{669}$-HaloTag ligand); scale bar=500 μm.
Figure 6:
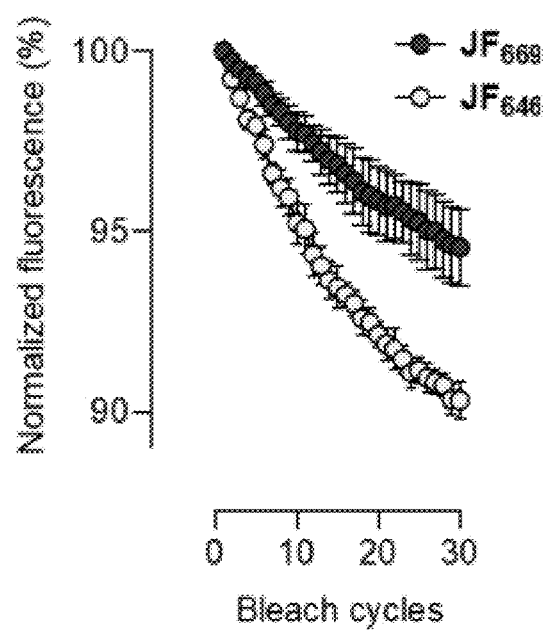
FIG. 6 includes a photobleaching plot of fluorescence from fixed cells expressing HaloTag-histone H2B fusion proteins labeled with fluorinated JF$_{669}$-HaloTag ligand or nonfluorinated JF$_{646}$-HaloTag ligand (200 nM, 30 min, 3× wash) over 30 bleach cycles; error bars indicate SE; n=3 independent cellular samples.
Figure 7:
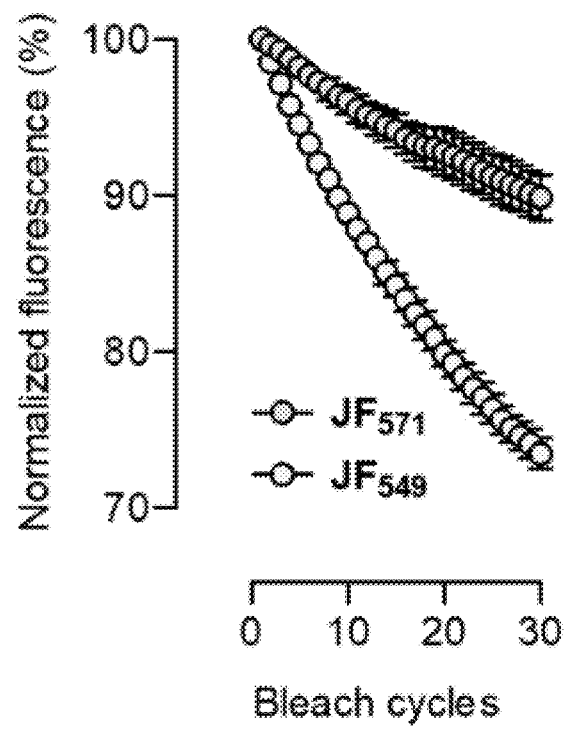
FIG. 7 includes a photobleaching plot of fluorescence from fixed cells expressing HaloTag-histone H2B fusion proteins labeled with fluorinated JF$_{571}$-HaloTag ligand or nonfluorinated JF$_{549}$-HaloTag ligand (200 nM, 30 min, 3× wash) over 30 bleach cycles; error bars indicate SE; n=3 independent cellular samples.
Figure 8:
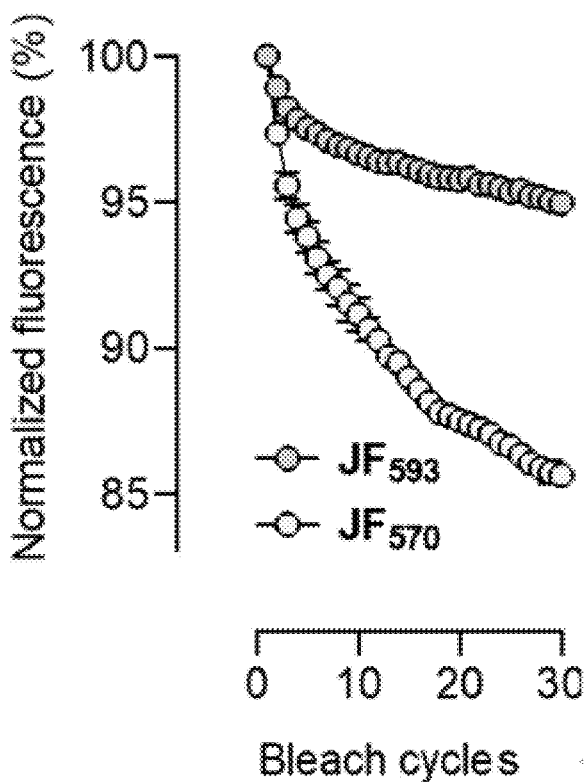
FIG. 8 includes a photobleaching plot of fluorescence from fixed cells expressing HaloTag-histone H2B fusion proteins labeled with fluorinated JF$_{593}$-HaloTag ligand or nonfluorinated JF$_{570}$-HaloTag ligand (200 nM, 30 min, 3× wash) over 30 bleach cycles; error bars indicate SE; n=3 independent cellular samples.
Figure 9:
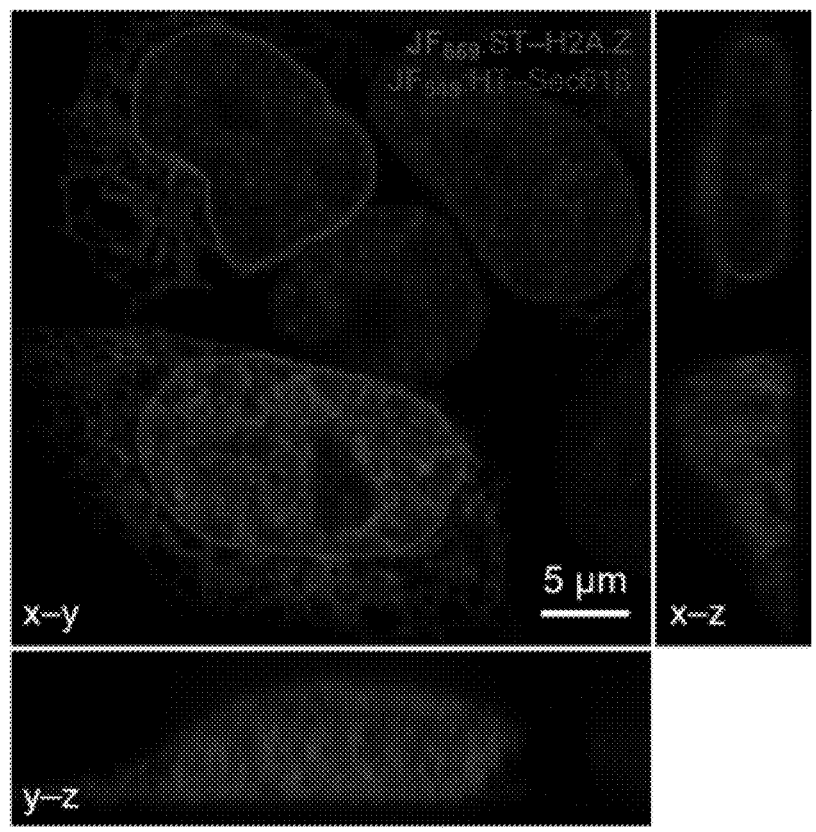
FIG. 9 includes an airyscan confocal fluorescence microscopy image of live U2OS cells expressing Sec61β-HaloTag labeled with JF$_{549}$-HaloTag ligand (30 nM, 30 min, 3× wash) and nucleus-localized SNAP-tag-histone variant H2A.Z labeled with exemplary compound JF$_{669}$-SNAP-tag ligand (30 nM, 30 min, 3× wash); co-stained with Hoechst 33342 (1 μM, 30 min, 3× wash); scale bar: 5 μm.
Figure 10:
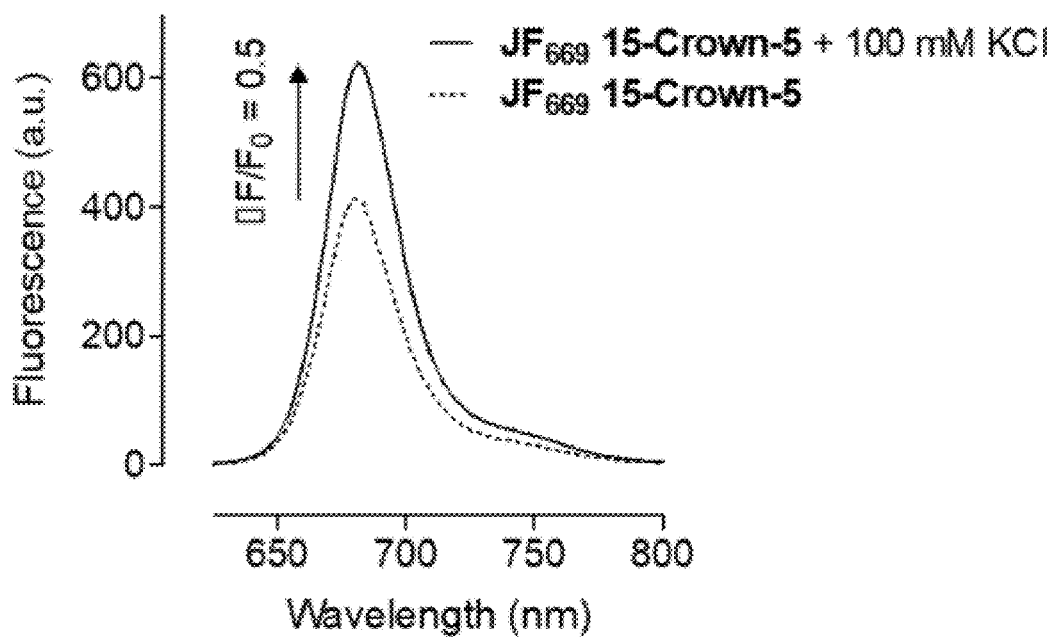
FIG. 10 includes fluorescence emission spectra of exemplary compound JF$_{669}$-15-Crown-5 in the absence or presence of 100 mM K$^+$.
Figure 11:
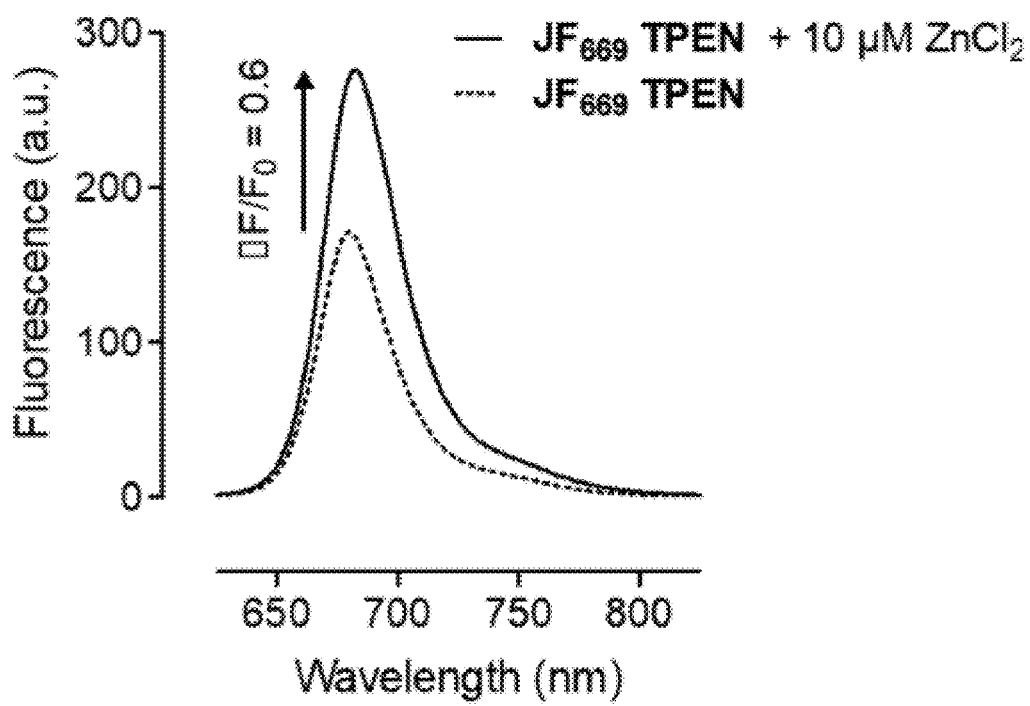
FIG. 11 includes fluorescence emission spectra of exemplary compound JF$_{669}$-TPEN in the absence or presence of 10 μM Zn$^{2+}$.
Figure 12:
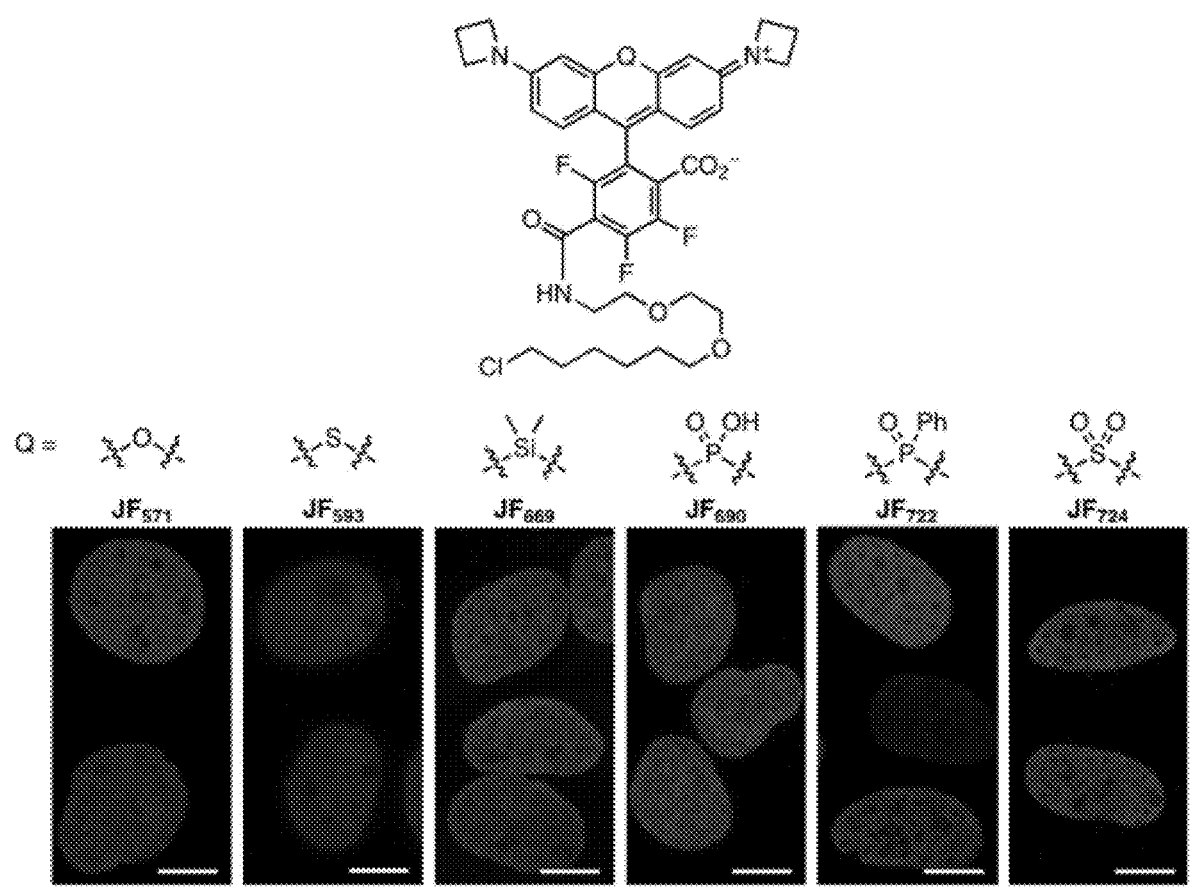
FIG. 12 includes structures of exemplary compounds JF$_{571}$-HaloTag ligand, JF$_{593}$-HaloTag ligand, JF$_{669}$-HaloTag ligand, JF$_{690}$-HaloTag ligand, JF$_{722}$-HaloTag ligand, and JF$_{724}$-HaloTag ligand and high-magnification images of U2OS cell nuclei expressing histone H2B HaloTag fusion protein and labeled with JF$_{571}$-HaloTag ligand, JF$_{593}$-HaloTag ligand, JF$_{669}$-HaloTag ligand, JF$_{690}$-HaloTag ligand, JF$_{722}$-HaloTag ligand, and JF$_{724}$-HaloTag ligand; scale bar=10 μm.
Figure 13:
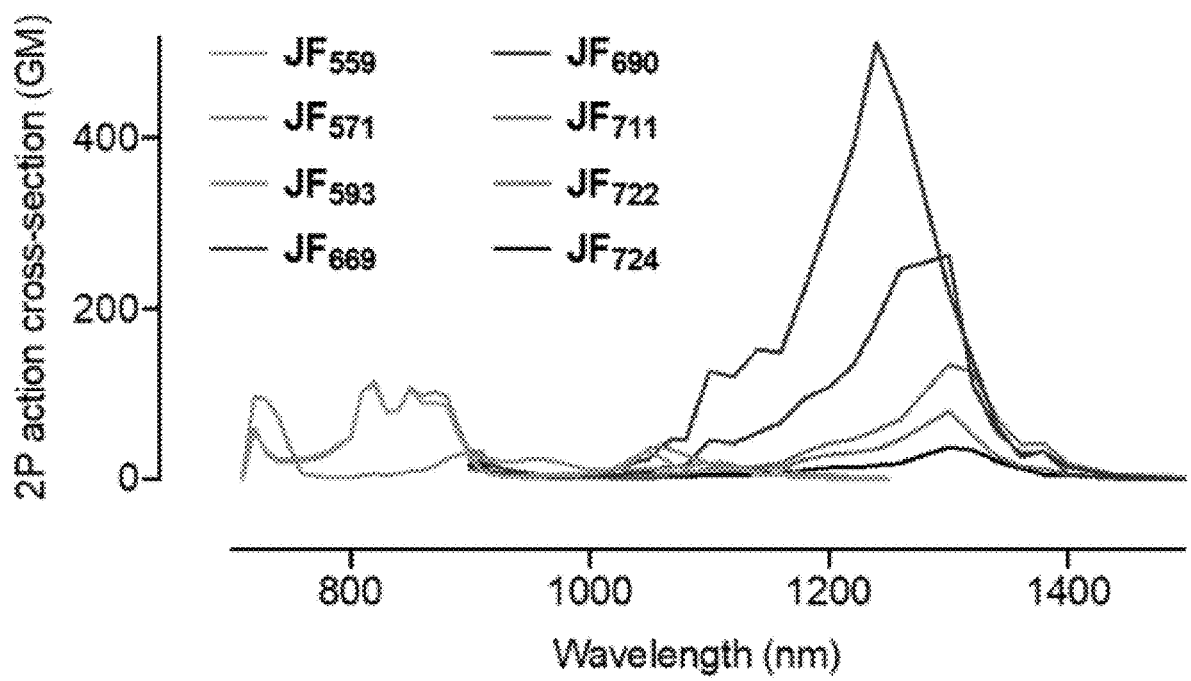
FIG. 13 includes a two-photon absorption spectra of the HaloTag conjugates of exemplary compounds JF$_{559}$-HaloTag ligand, JF$_{571}$-HaloTag ligand, JF$_{593}$-HaloTag ligand, JF$_{669}$-HaloTag ligand, JF$_{690}$-HaloTag ligand, JF$_{722}$-HaloTag ligand, JF$_{711}$-HaloTag ligand, and JF$_{724}$-HaloTag ligand.
Figure 14:
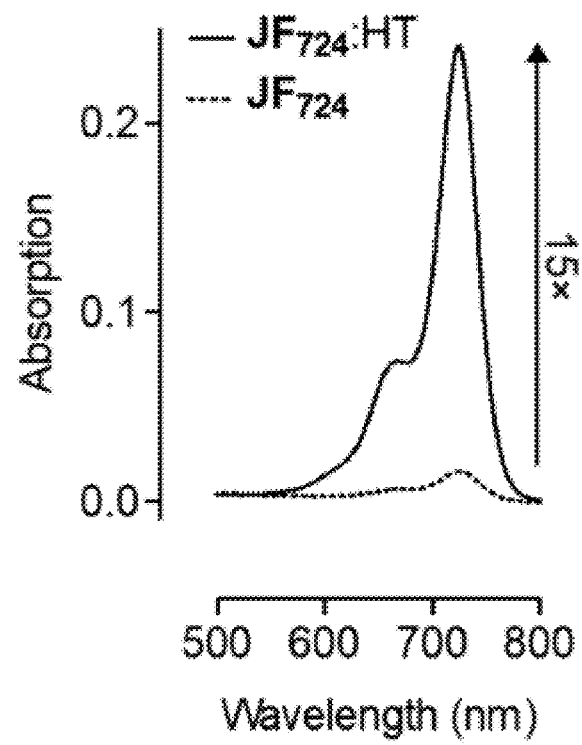
FIG. 14 includes an absorption spectra of exemplary compound JF$_{724}$-HaloTag ligand in the absence (−HT) or presence (+HT) of excess HaloTag protein.
Figure 15:
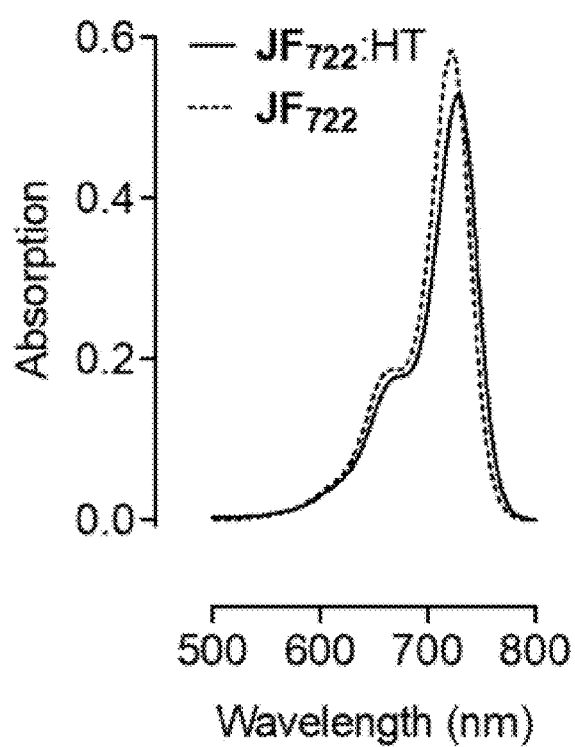
FIG. 15 includes an absorption spectra of exemplary compound JF$_{722}$-HaloTag ligand in the absence (−HT) or presence (+HT) of excess HaloTag protein.
Figure 16:
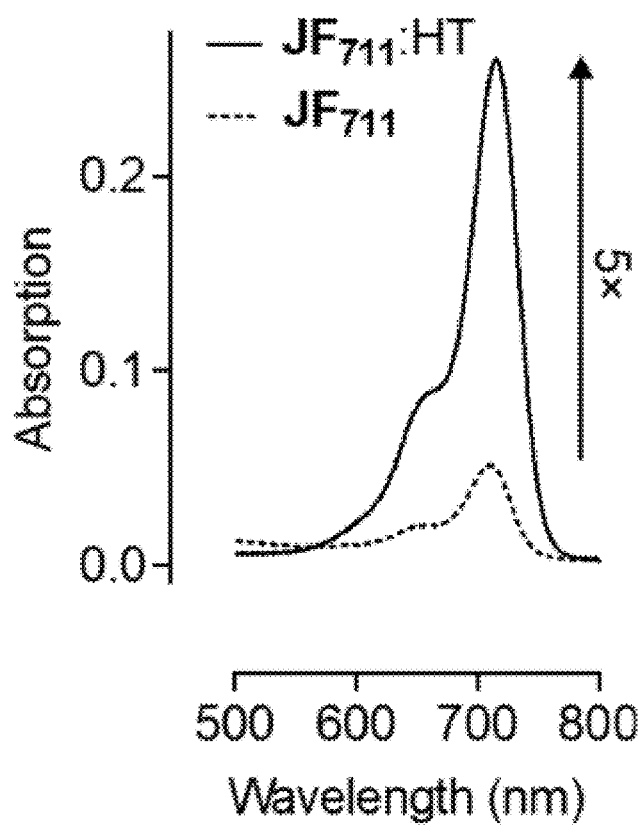
FIG. 16 includes an absorption spectra of exemplary compound JF$_{711}$-HaloTag ligand in the absence (−HT) or presence (+HT) of excess HaloTag protein.
Figure 17:
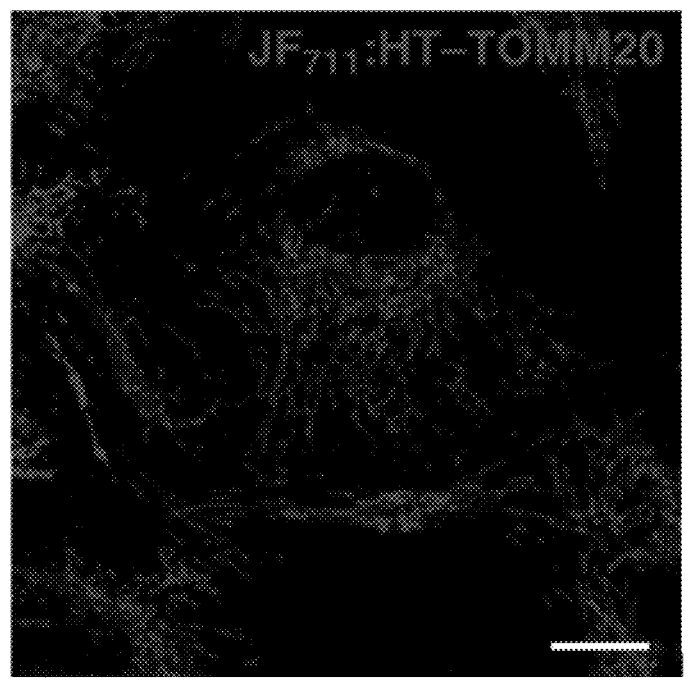
FIG. 17 includes a confocal imaging experiment of U2OS cells expressing TOMM20-HaloTag fusion protein labeled with exemplary compound exemplary compound JF$_{711}$-HaloTag ligand; scale bar=20 μm. For confocal imaging of mitochondria U2OS cells were used, which included an integrated a TOMM20-HaloTag expressing plasmid via the piggyback transposase.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes polycyclic chemical fluorophores as well as method for making and using the same.

In some embodiments the compound has the following formula:

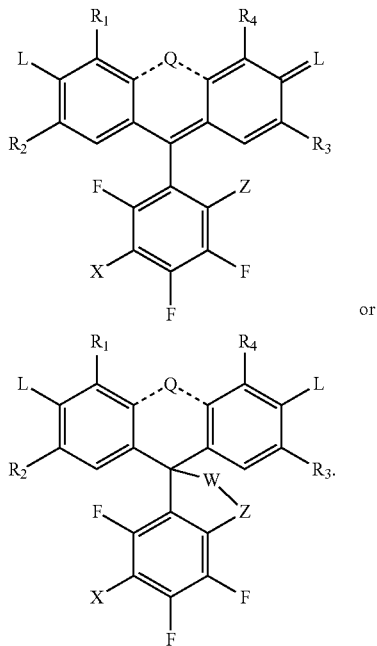

or

In the compound, Q is selected from the group consisting of C(alkyl), C(alkyl)₂, NH, N(alkyl), O, S, SO₂, Si(alkyl)₂, P(O)(aryl), P(O)(alkyl), PO₂H, PO₂(alkyl), and Se or replaced with two H atoms. L is independently selected from the group consisting of O, OH, NH₂, NH(alkyl), NH(deuterated alkyl), N(alkyl)₂, N(deuterated alkyl)₂, NH(aryl), N(aryl)₂, N(alkyl)(aryl), N(deuterated alkyl)(aryl), substituted or unsubstituted cyclic amines with a ring size of 3, 4, 5, 6, 7, 8, or 9 atoms, and substituted or unsubstituted deuterated cyclic amines with a ring size of 3, 4, 5, 6, 7, 8, or 9 atoms.

$R_1$, $R_2$, $R_3$, and $R_4$ are independently selected from the group consisting of H, D, halogen, CN, OH, O(alkyl), O(aryl), SH, S(alkyl), S(aryl), N₃, NH₂, NH(alkyl), N(alkyl)₂, NH(aryl), NH(aryl)₂, NO₂, CHO, C(O)(alkyl), C(O)(aryl), COOH, COO(alkyl), COO(aryl), C(O)NH(alkyl), C(O)NH(aryl), PO₃H₂, SO₃H, alkyl and substituted alkyl, aryl and substituted aryl, alkenyl and substituted alkenyl, alkynyl or substituted alkynyl, or where the R substituents and L substituents, taken together with the carbon atoms to which they are bonded, form a substituted or unsubstituted ring containing 3, 4, 5, 6, 7, 8, or 9 atoms.

X is selected from the group consisting of alkyl, substituted alkyl, aryl, substituted aryl, alkenyl, substituted alkenyl, alkynyl, substituted alkynyl, CN, COOH, COO(alkyl), COO(aryl), C(O)NH(alkyl), C(O)N(alkyl)₂, C(O)NH(aryl), C(O)N(aryl)₂, H, N₃, NH₂, NH(alkyl), N(alkyl)₂, NH(aryl), NH(aryl)₂, NHNH₂, NHOH, PO₃H₂, and SO₃H, so long as when X is N₃ then neither Q nor L are O or OH.

When W is not present in the compound, Z is selected from the group consisting of H, halogen, OH, O(alkyl), O(aryl), COOH, COO(alkyl), COO(aryl), C(O)NH(alkyl), C(O)N(alkyl)₂, C(O)NH(aryl), C(O)N(aryl)₂, C(O)N(alkyl)(aryl), PO₃H₂, SO₃H, alkyl, substituted alkyl, alkenyl, and substituted alkenyl. When W is present in the structure, Z is selected from the group consisting of C(O), SO₂, PO₂H, or CR₂ where each R is independently selected from the group consisting of H, alkyl, and substituted alkyl; and W is selected from the group consisting of O, S, C(O), C(N₂), NH, N(alkyl), N(aryl), N(SO₂R) where R can be alkyl, substituted alkyl, and CN.

In some embodiments of the compound X is selected from the group consisting of alkyl, substituted alkyl, aryl, substituted aryl, alkenyl, substituted alkenyl, alkynyl, substituted alkynyl, CN, COOH, COO(alkyl), COO(aryl), C(O)NH(alkyl), C(O)N(alkyl)₂, C(O)NH(aryl), C(O)N(aryl)₂. In some embodiments of the compound X is selected from the group consisting of

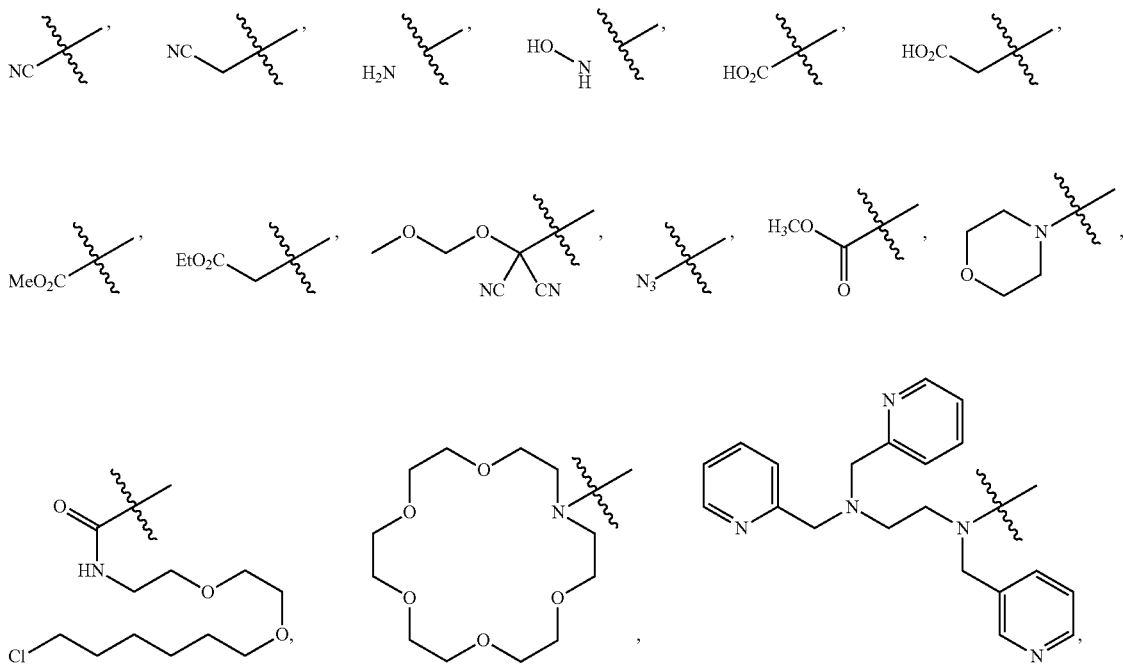

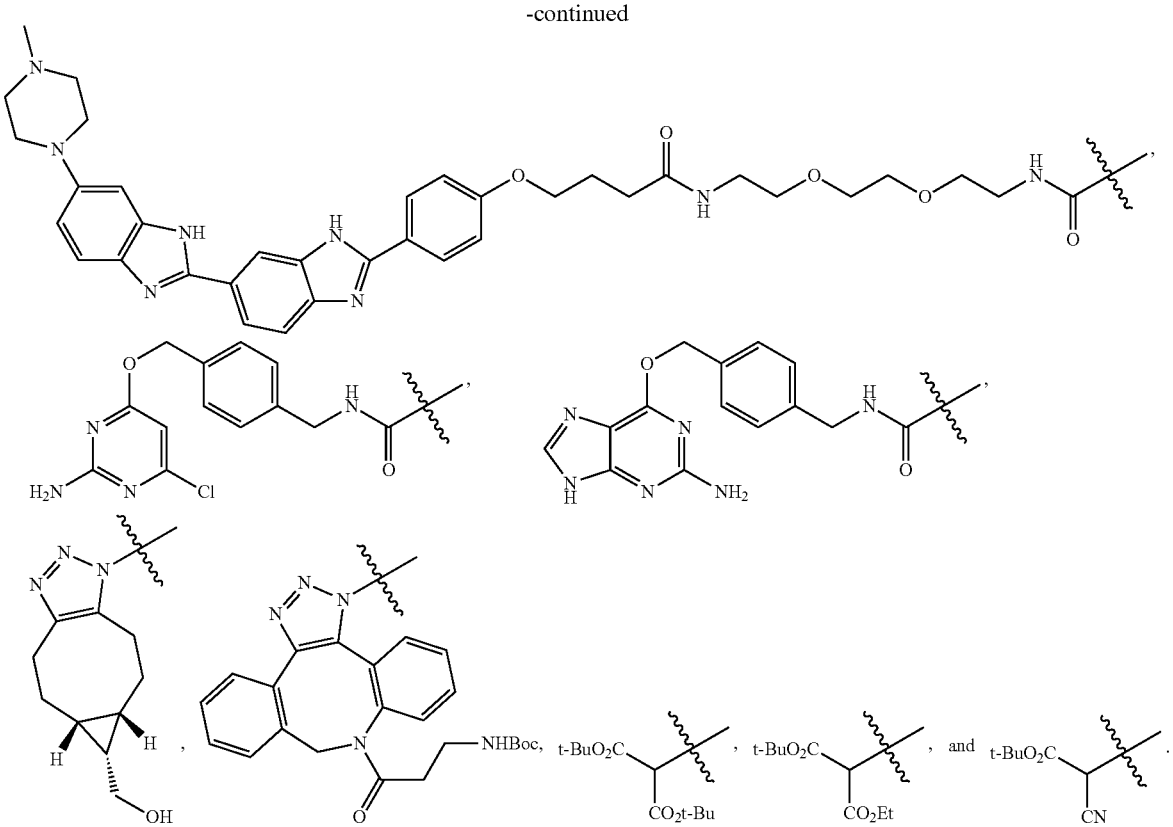

In some embodiments of the compound Q is selected from the group consisting of C(alkyl)$_2$, O, S, SO$_2$, Si(alkyl)$_2$, P(O)(aryl), P(O)(alkyl), PO$_2$H, and replaced with two H atoms. In some embodiments of the compound Q is selected from selected from the group consisting of

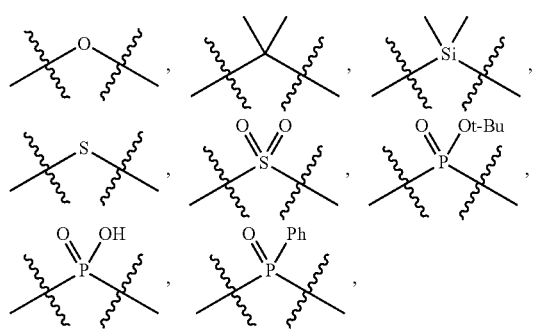

and replaced with two H atoms.

In some embodiments of the compound one or both L substituents are independently selected from the group consisting of O and OH. In some embodiments of the compound one or both L substituents are independently selected from the group consisting of NH$_2$, NCH$_2$(phenyl), NH(tert-butoxycarbonyl), and N(CH$_3$)$_2$. In some embodiments of the compound one or both L substituents are independently selected from the group consisting of substituted or unsubstituted cyclic amines with a ring size of 4, 5, 6, 7, or 8 atoms. In some embodiments where there is a substituted or unsubstituted cyclic amine with a ring size of 4, 5, or 6 atoms, one or both L substituents can be independently is selected from the group consisting of

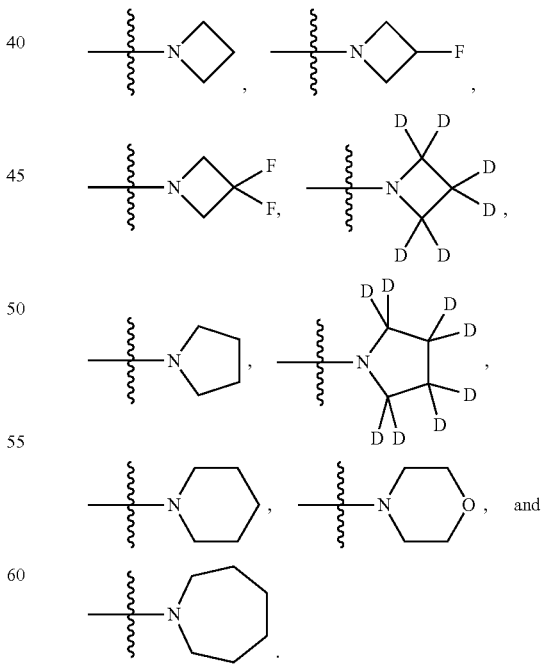

In some embodiments of the compound the R$_2$ substituents, or the R$_3$ substituents, and L substituents are taken together with the carbon atoms to which they are bonded to form a substituted or unsubstituted ring containing 5, 6, 7, 8, or 9 atoms.

In some embodiments, the compound has a structure chosen from the following, where X is selected from the group consisting of alkyl, substituted alkyl, aryl, substituted aryl, alkenyl, substituted alkenyl, alkynyl, substituted alkynyl, CN, COOH, COO(alkyl), COO(aryl), C(O)NH(alkyl), C(O)N(alkyl)$_2$, C(O)NH(aryl), C(O)N(aryl)$_2$, H, N$_3$, NH$_2$, NH(alkyl), N(alkyl)$_2$, NH(aryl), NH(aryl)$_2$, NHNH$_2$, NHOH, PO$_3$H$_2$, and SO$_3$H, so long as when X is N$_3$ then neither Q nor L are O or OH:

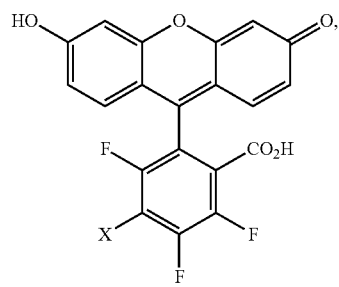

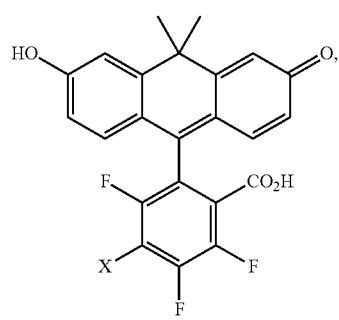

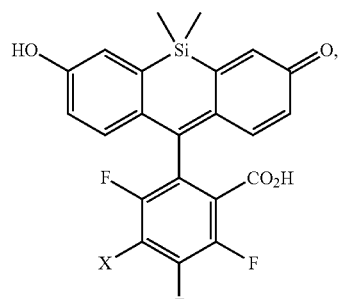

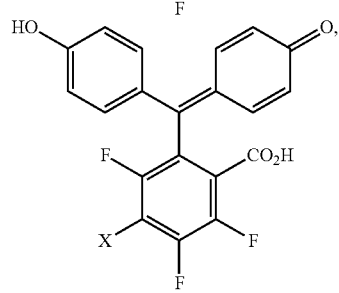

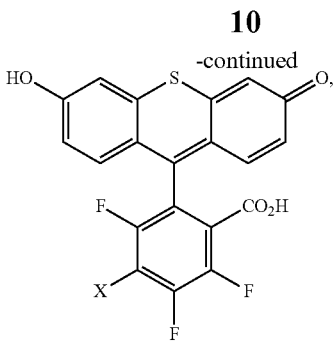

-continued

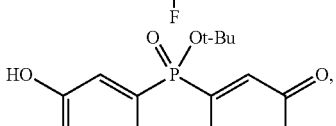

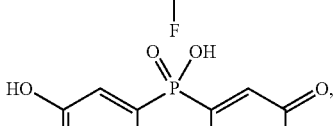

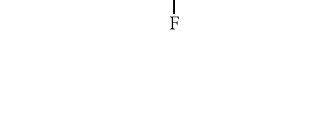

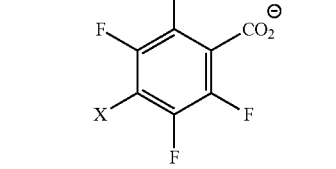

11
-continued
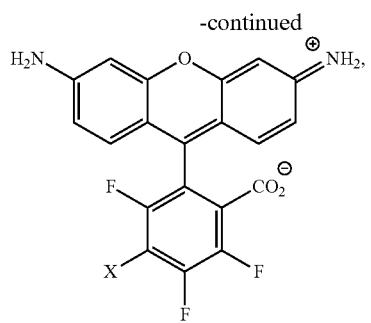
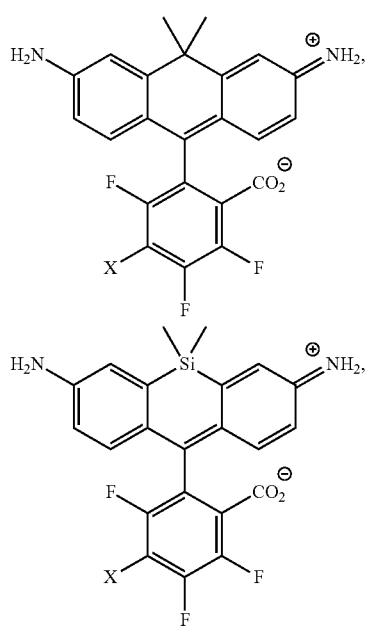
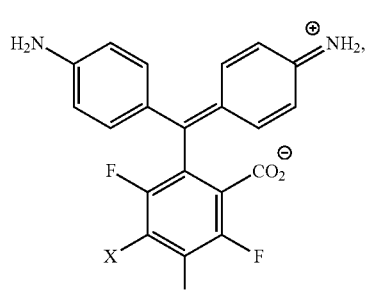
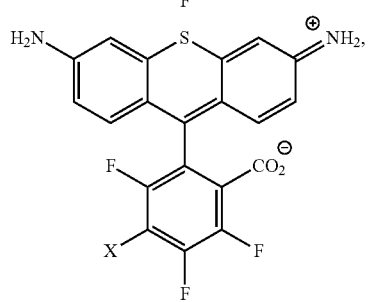
12
-continued
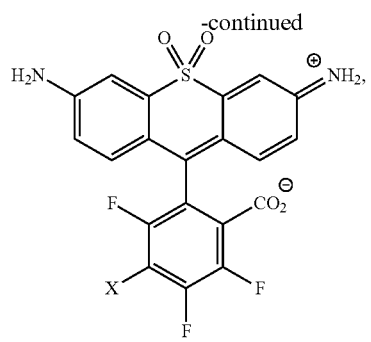
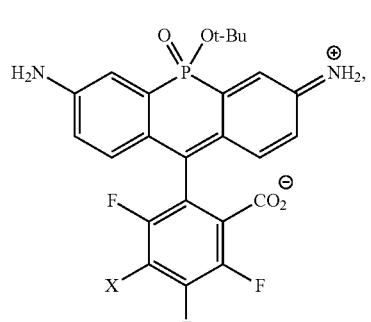
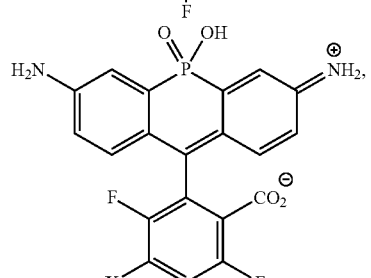
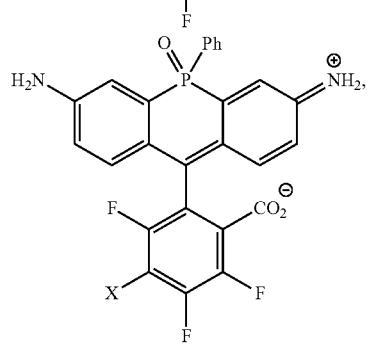
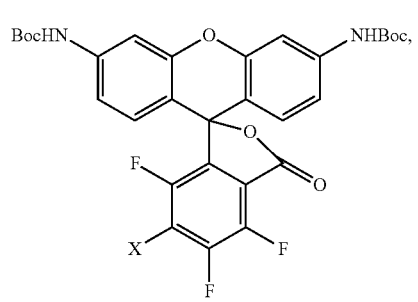

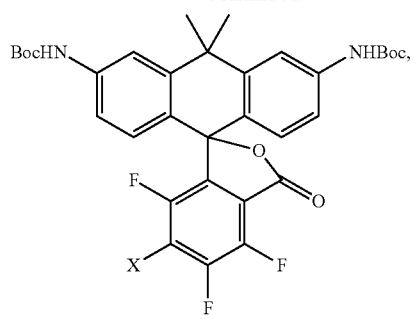
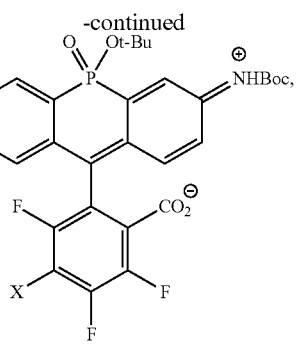
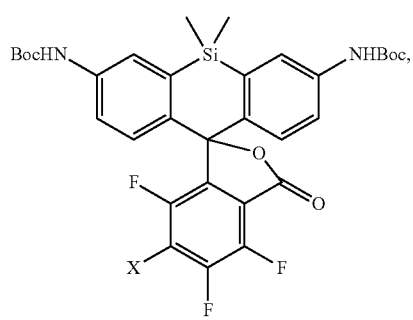
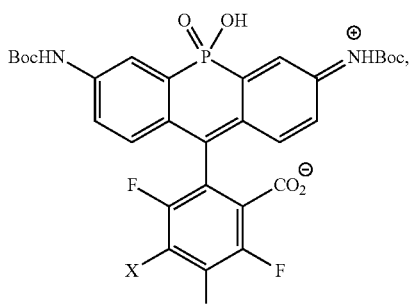
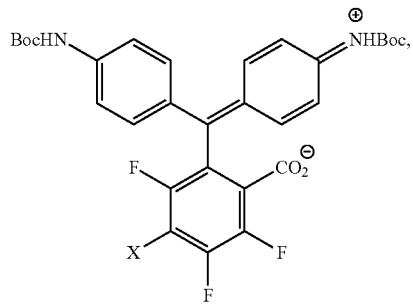
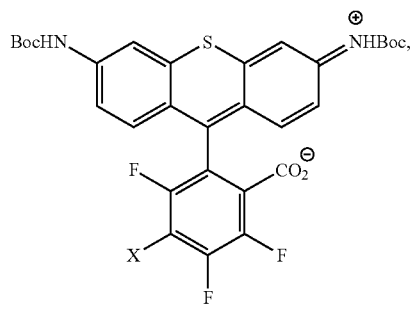
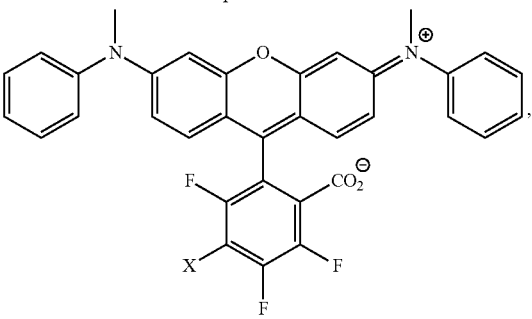
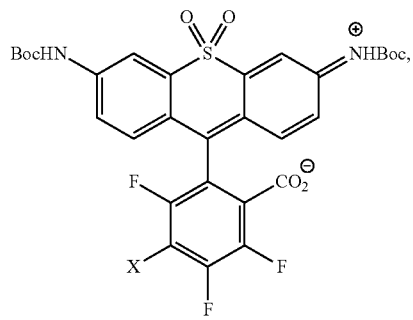
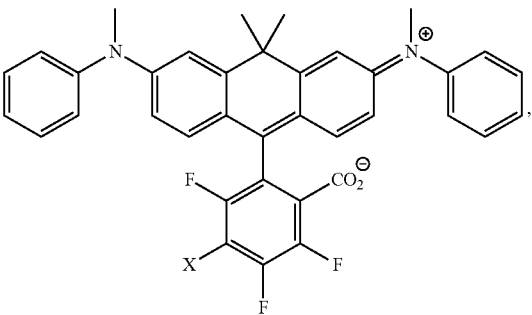

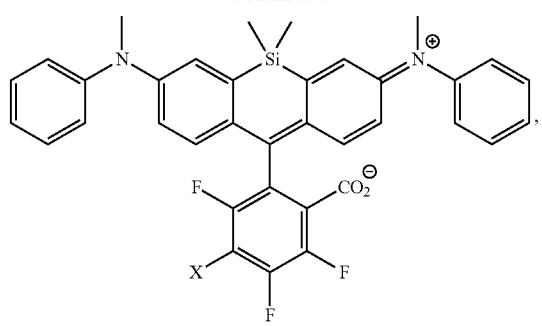
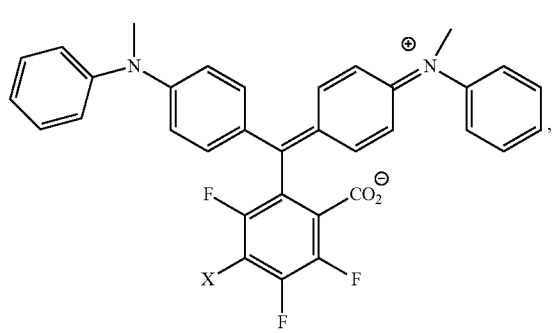
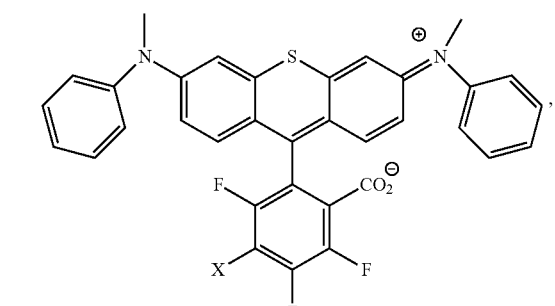
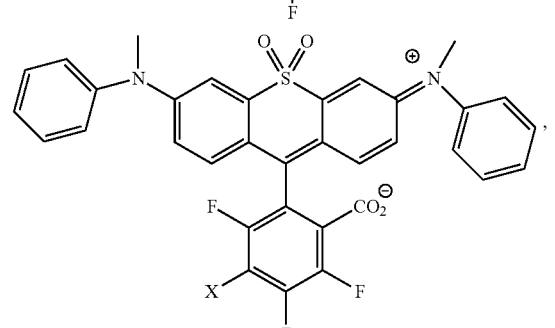
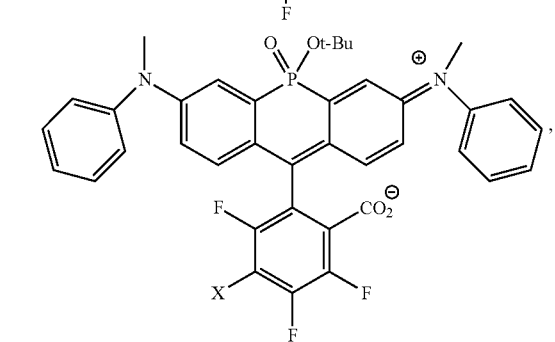
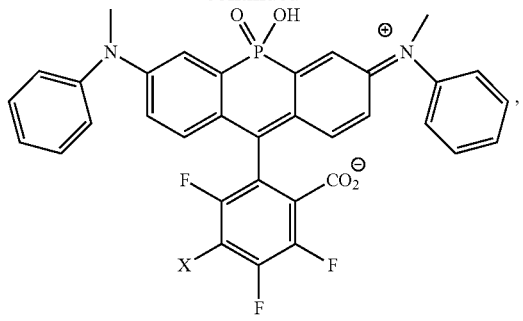
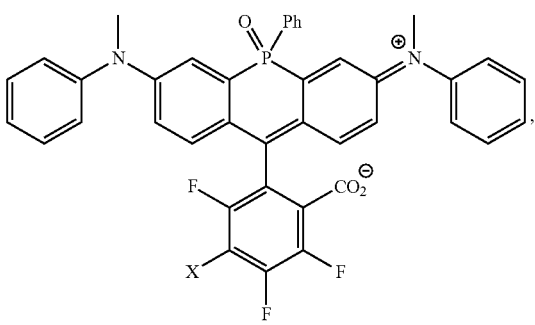
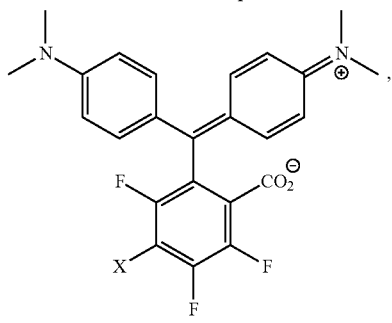
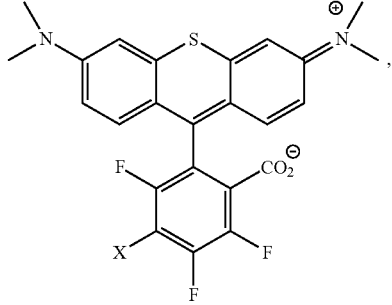
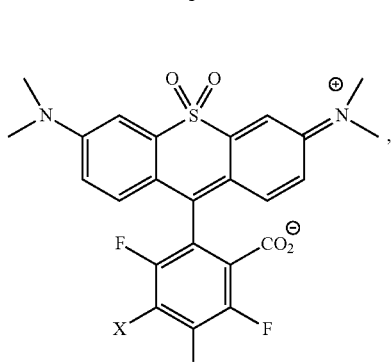

17
-continued
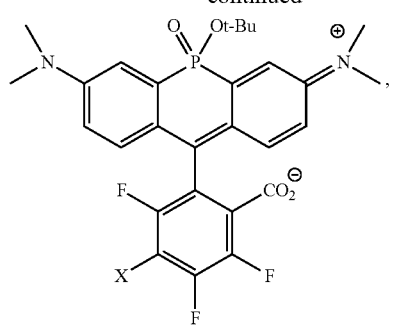
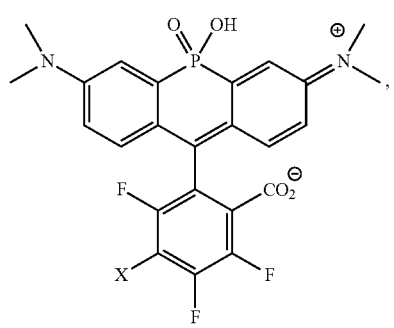
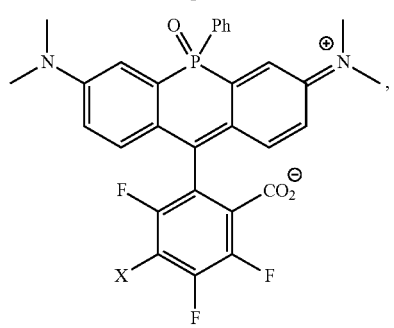
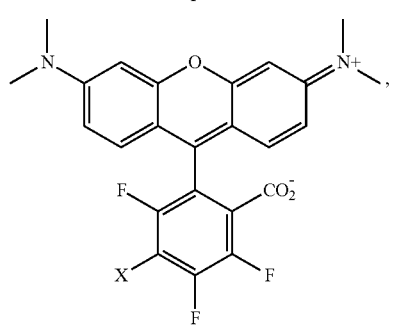
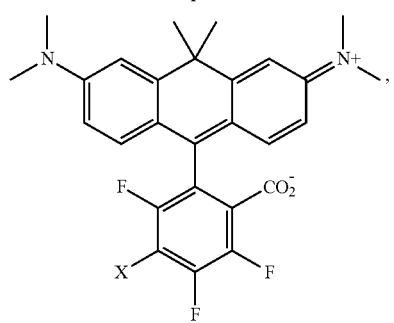
18
-continued
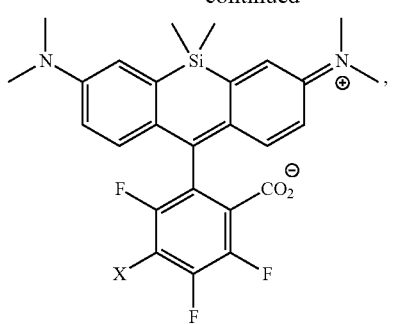
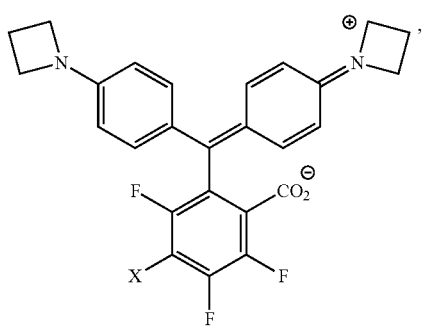
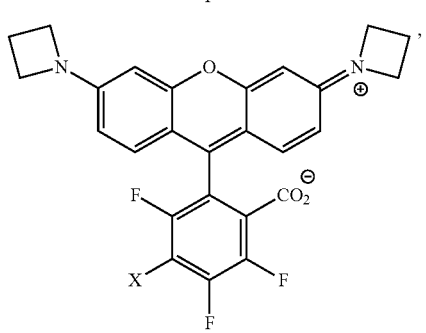
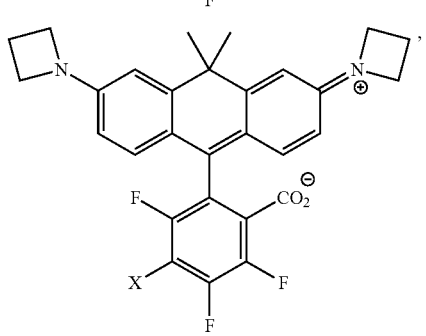
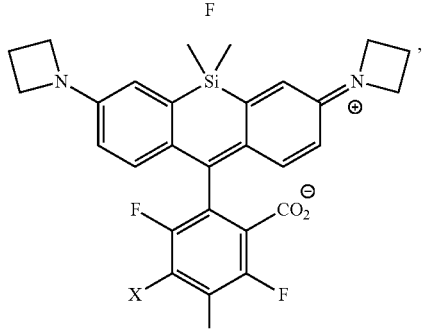

19
-continued
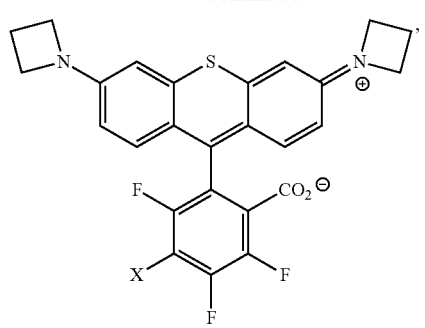
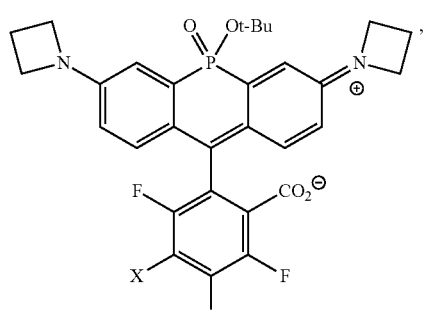
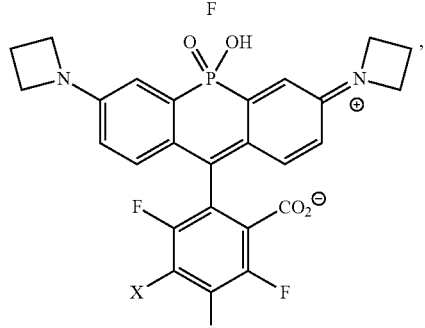
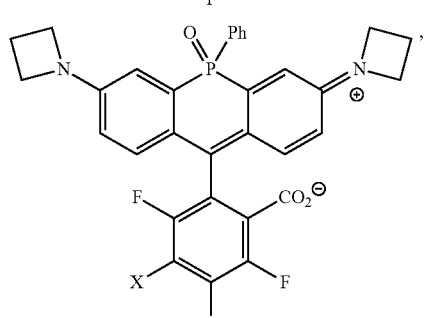
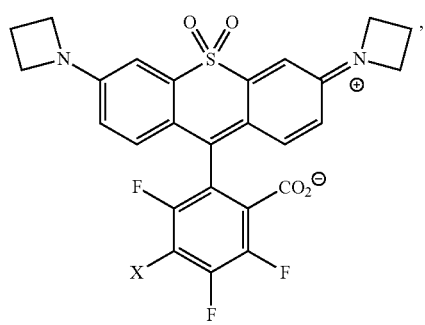
20
-continued
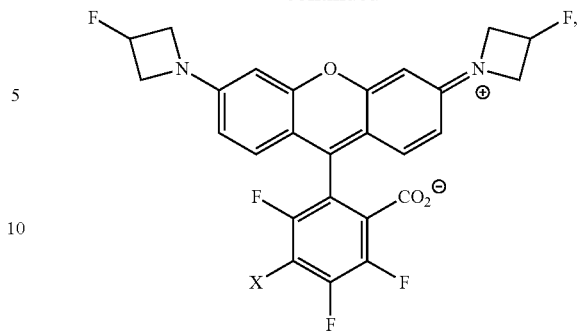
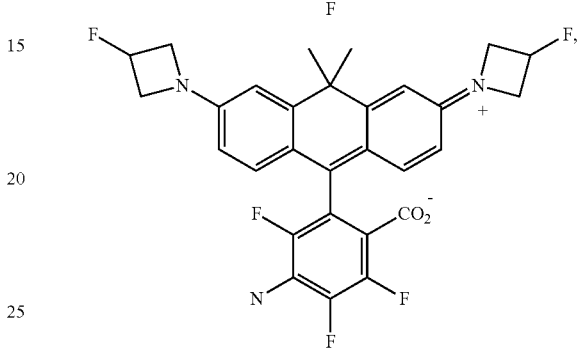
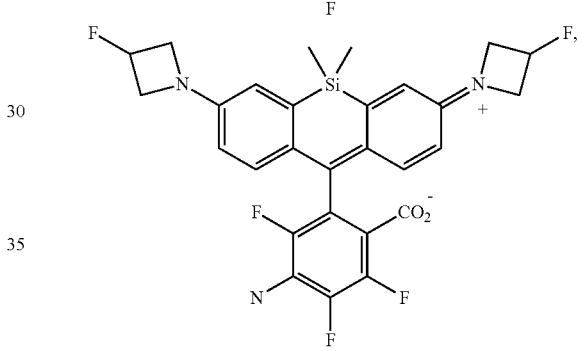
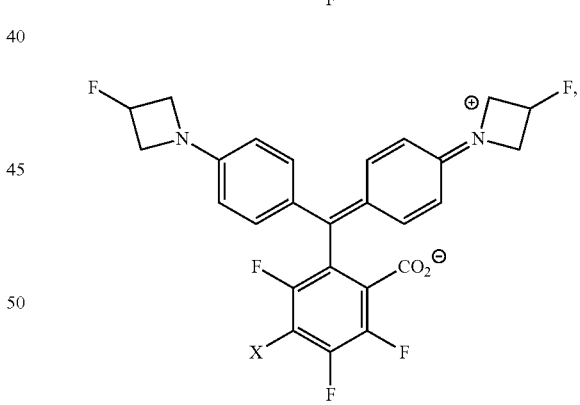
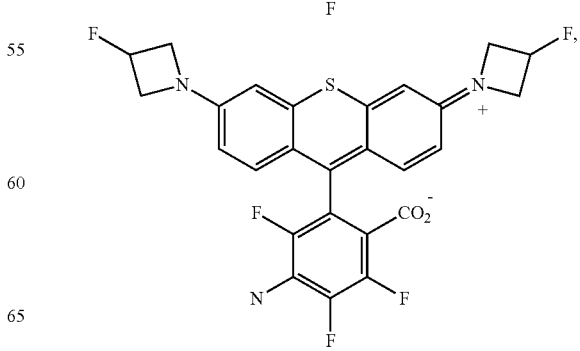

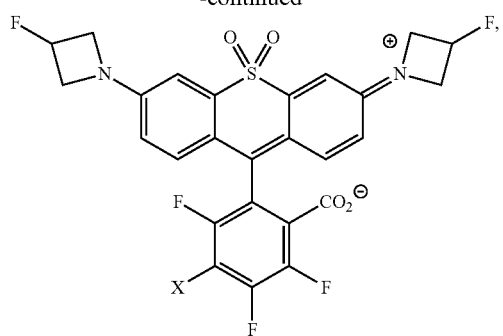
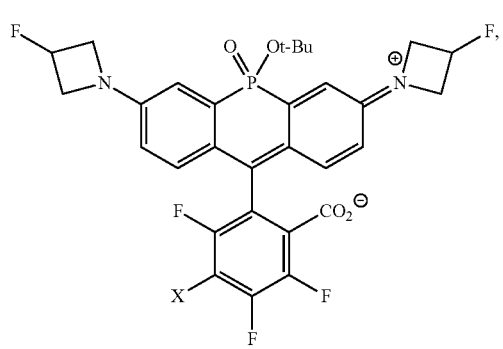
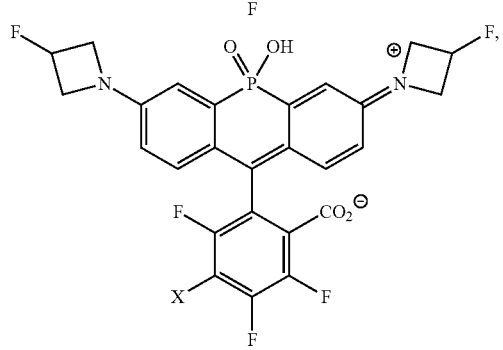
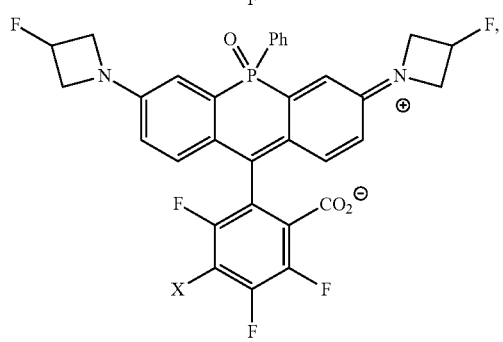
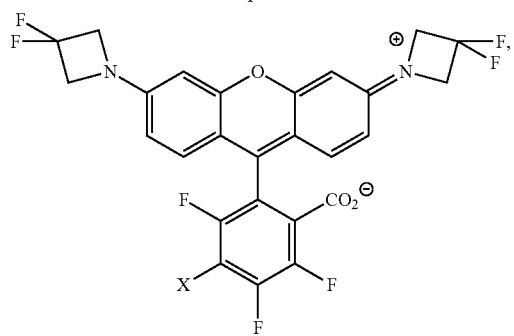
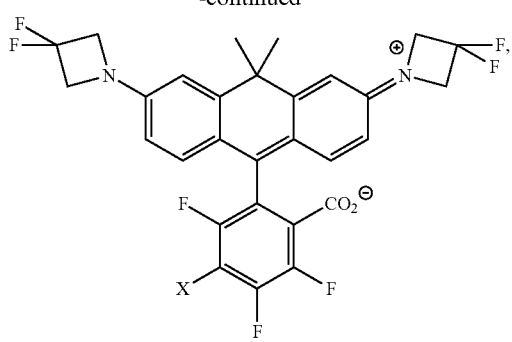
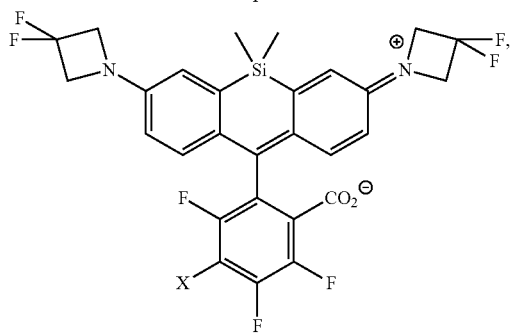
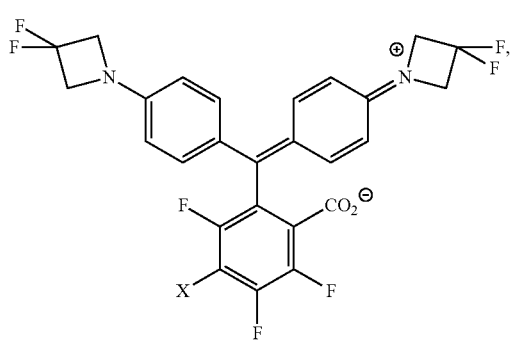
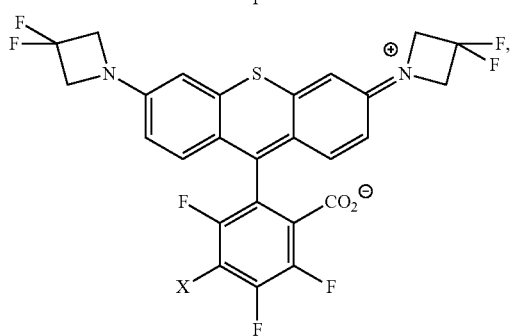
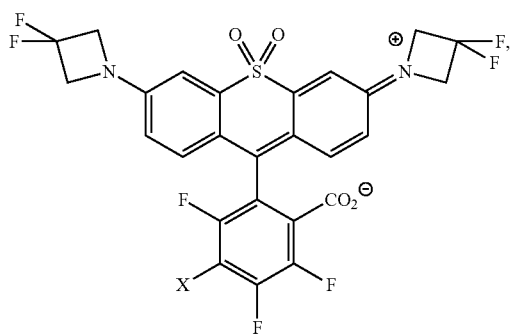

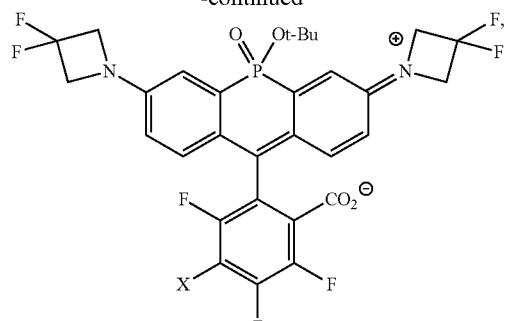
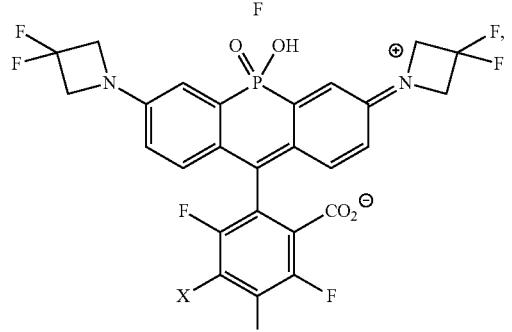
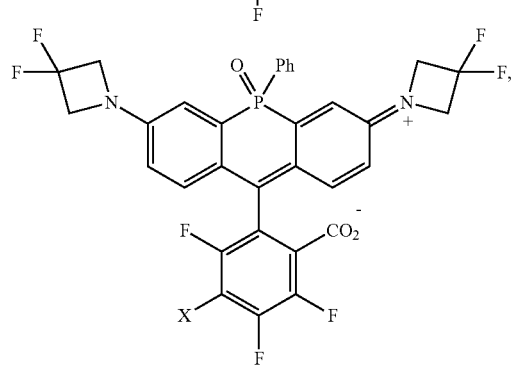
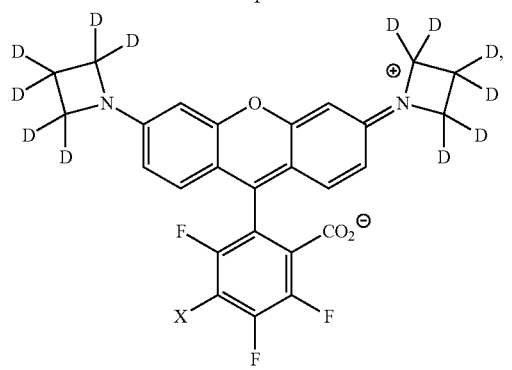
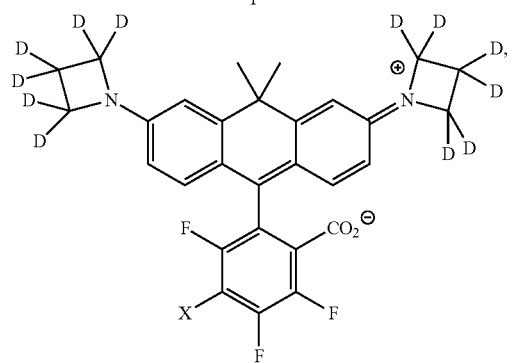
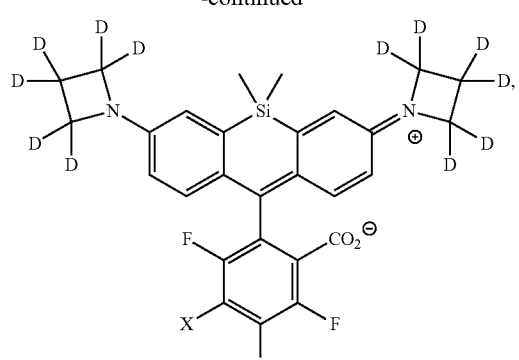
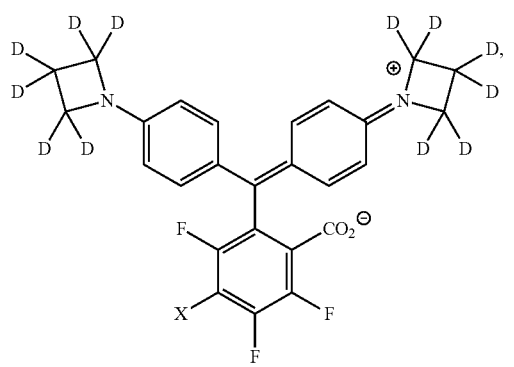
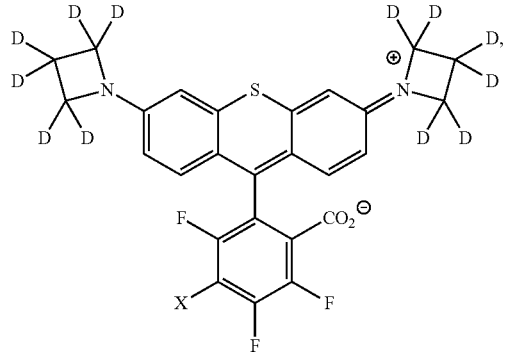
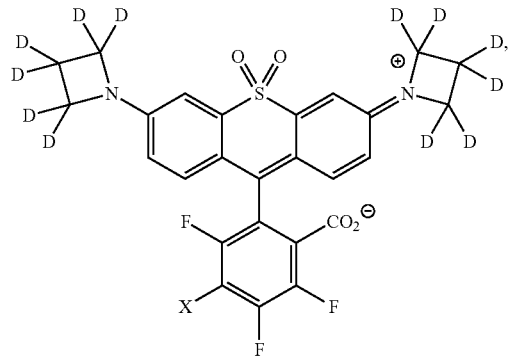

25
-continued
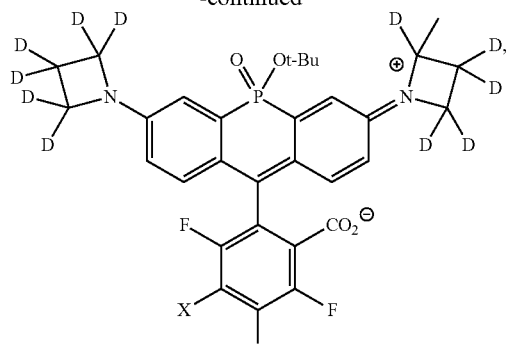
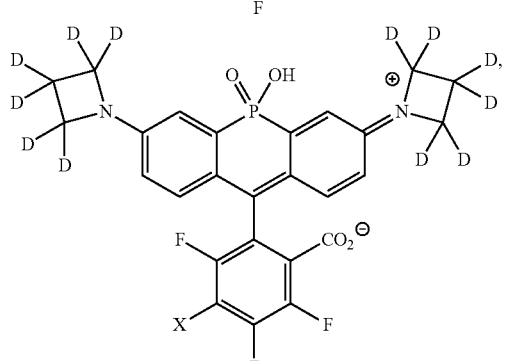
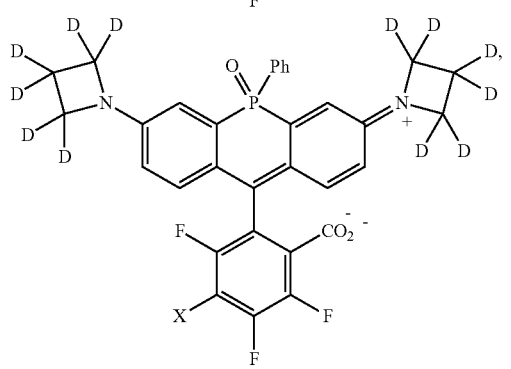
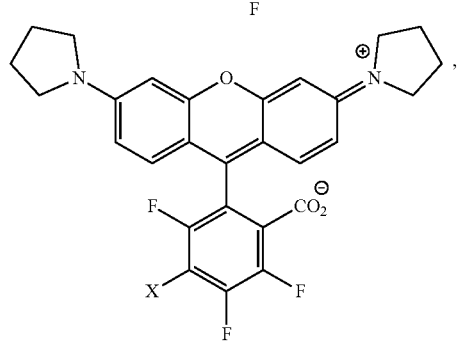
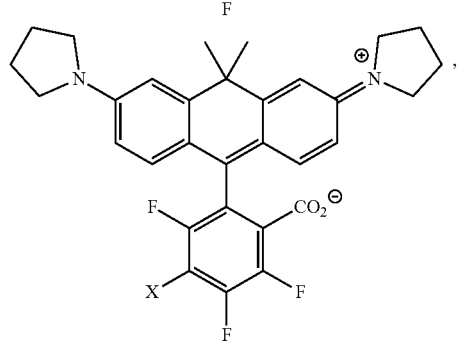
26
-continued
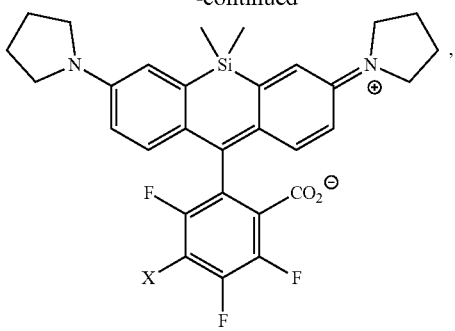
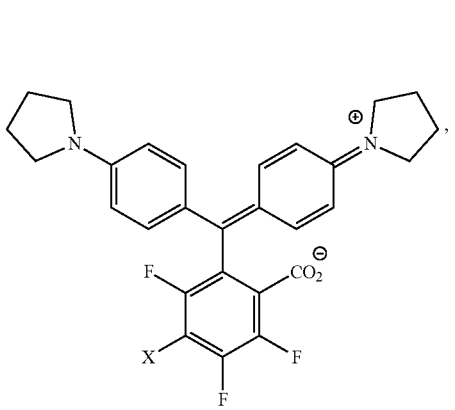
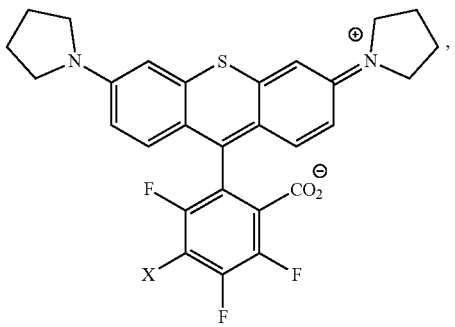
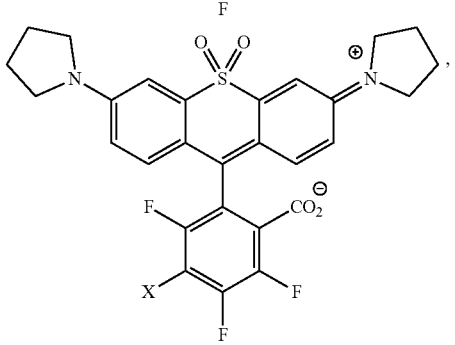
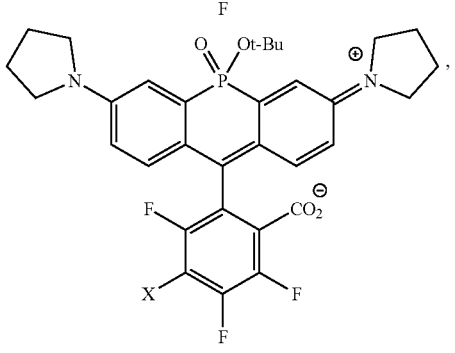

-continued
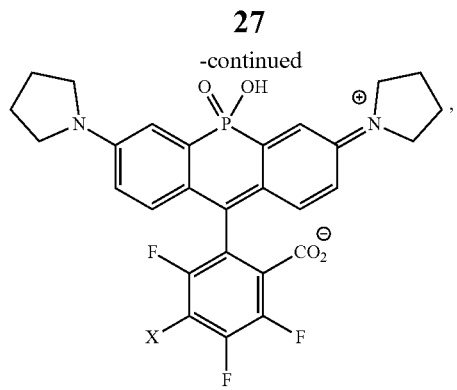
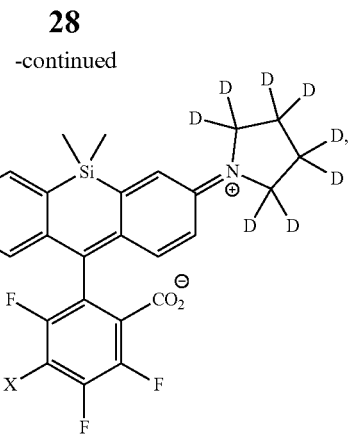
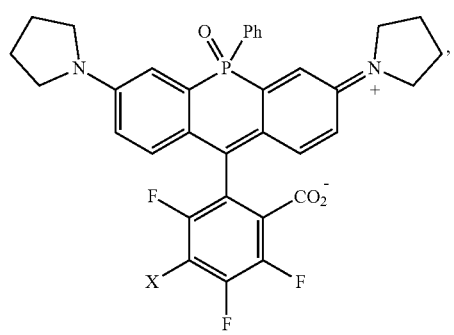
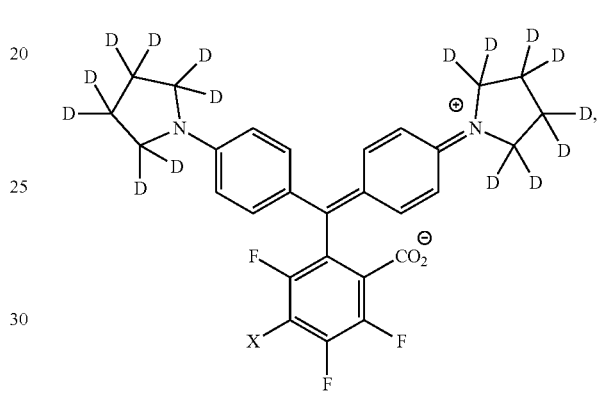
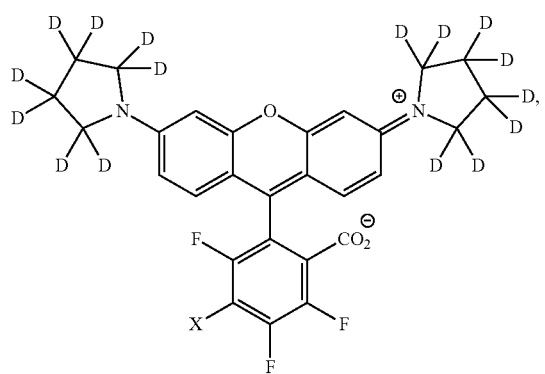
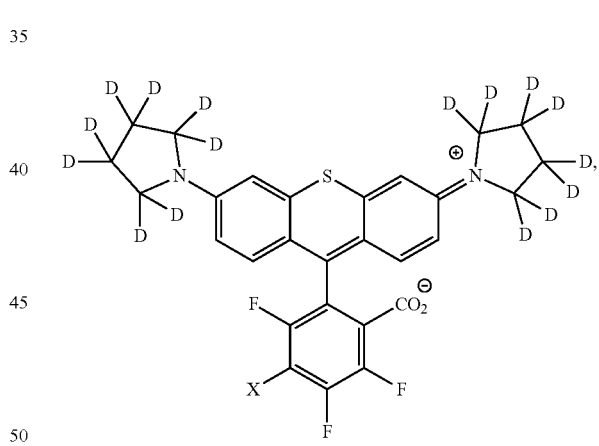
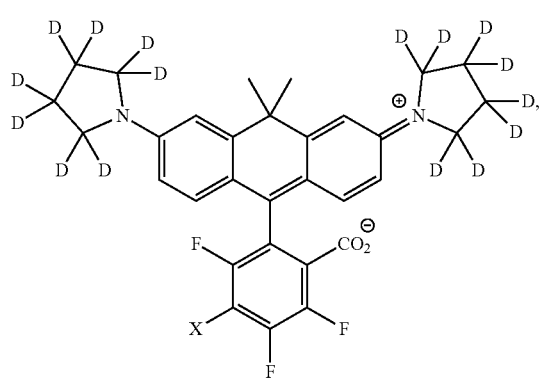
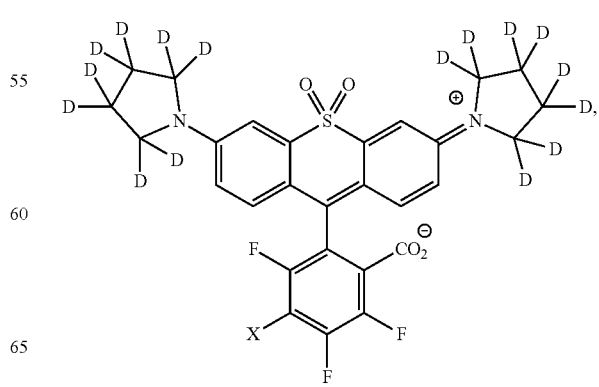

29
-continued
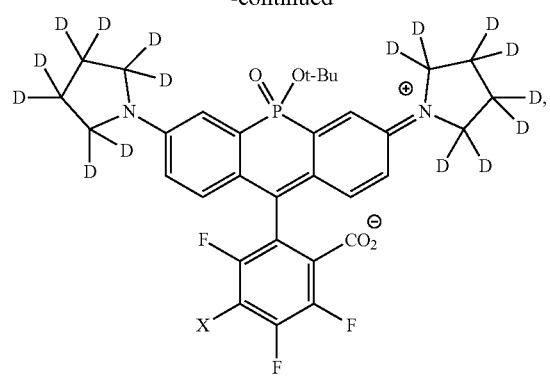
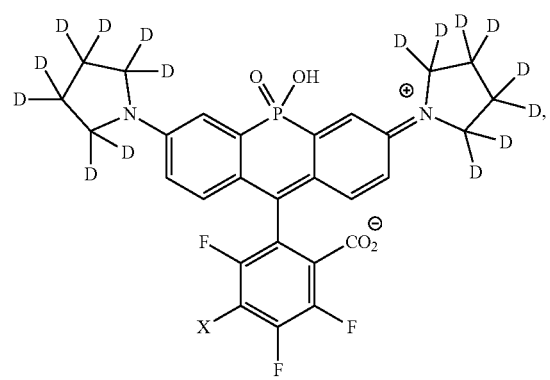
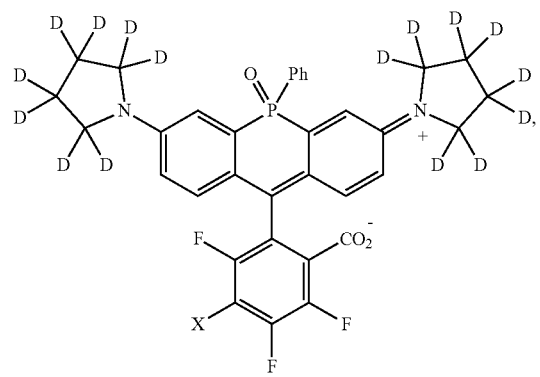
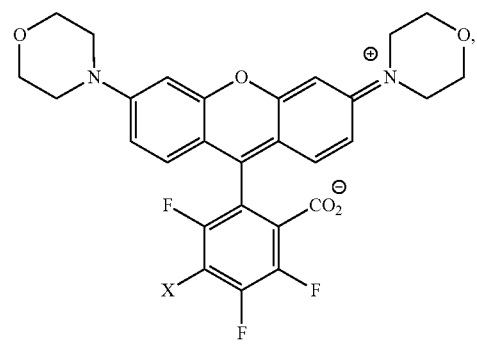
30
-continued
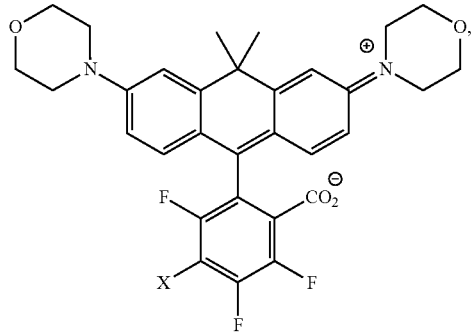
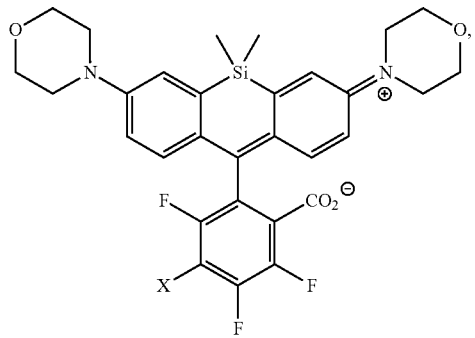
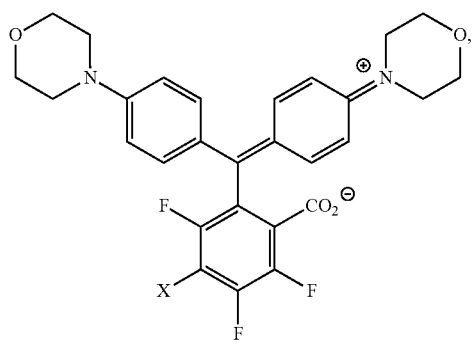
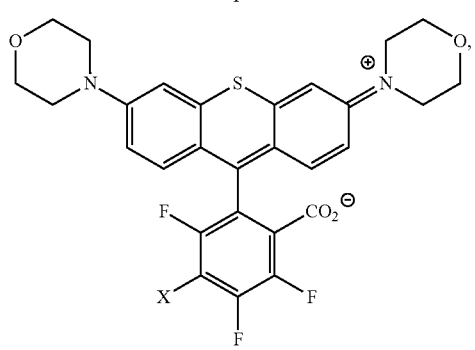
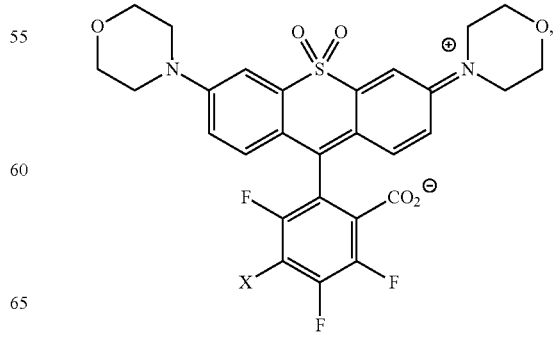

31
-continued
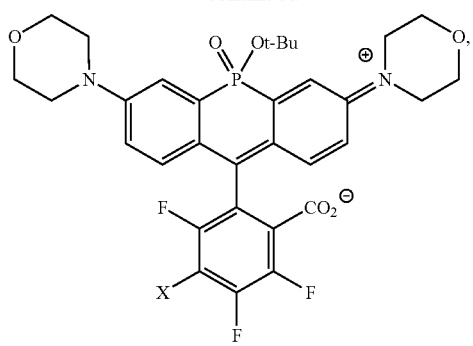
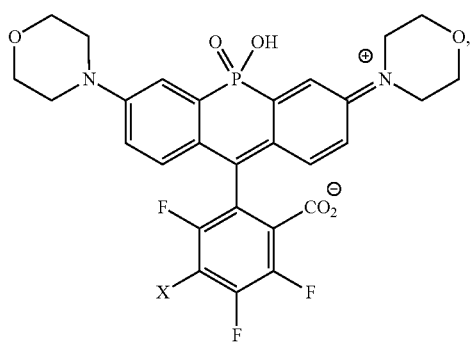
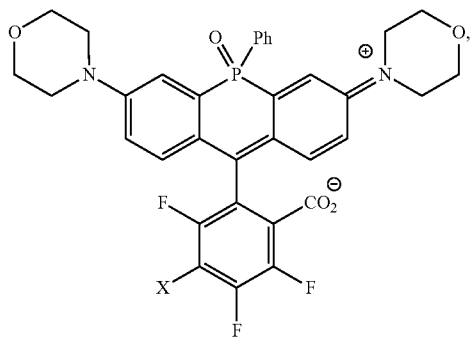
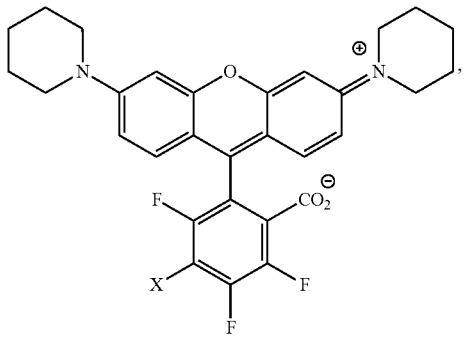
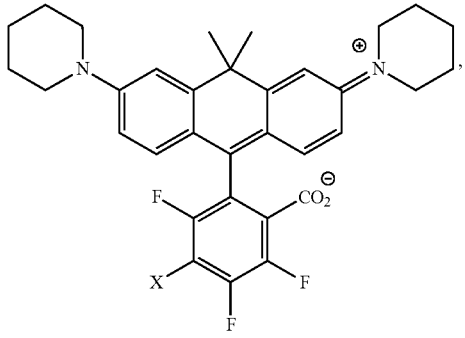
32
-continued
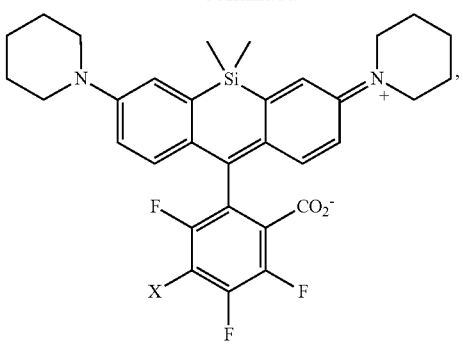
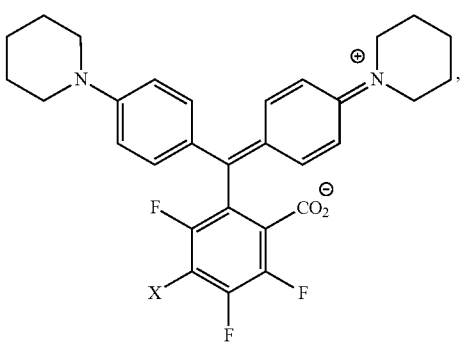
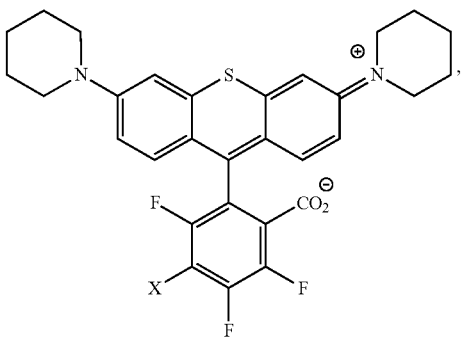
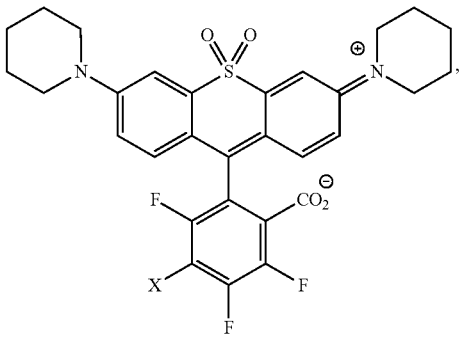
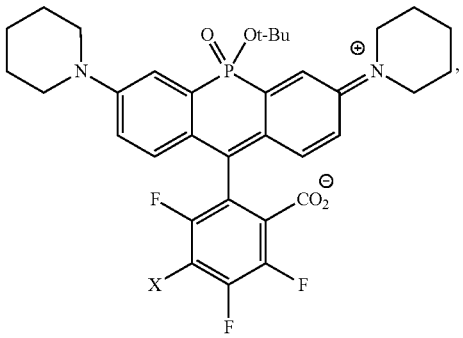

33
-continued
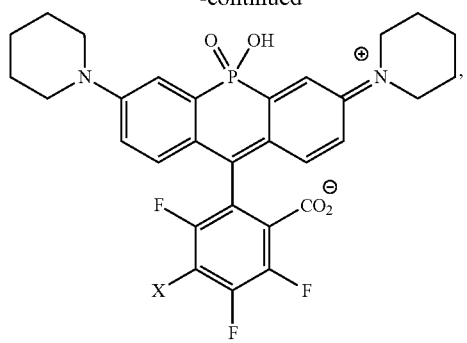
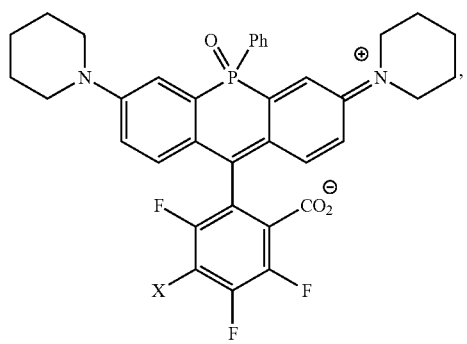
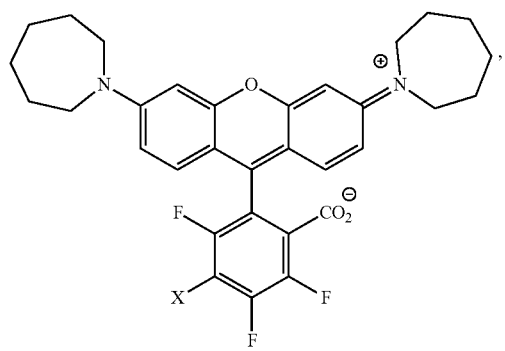
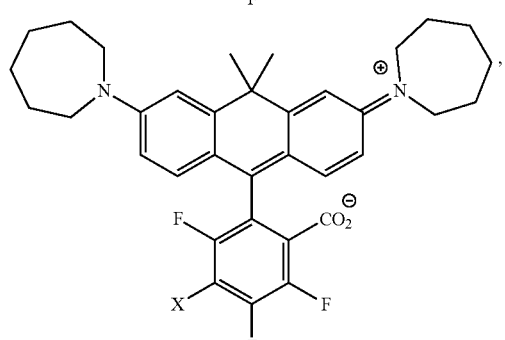
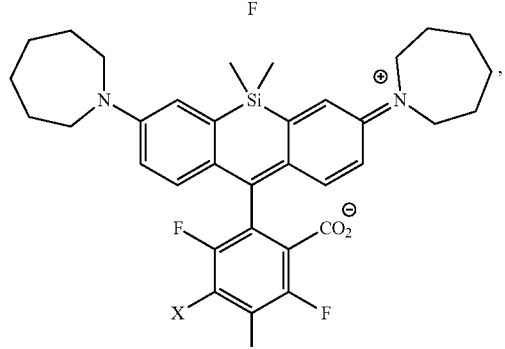
34
-continued
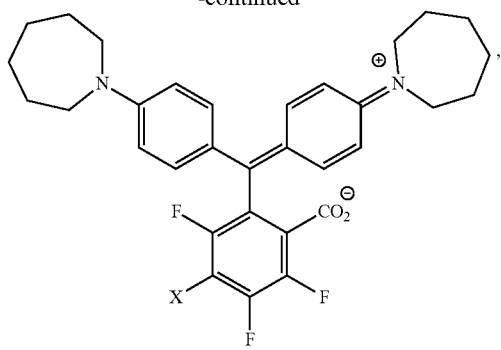
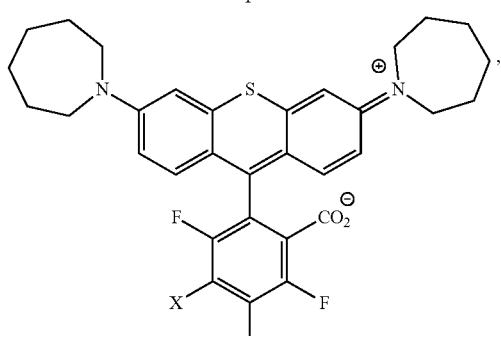
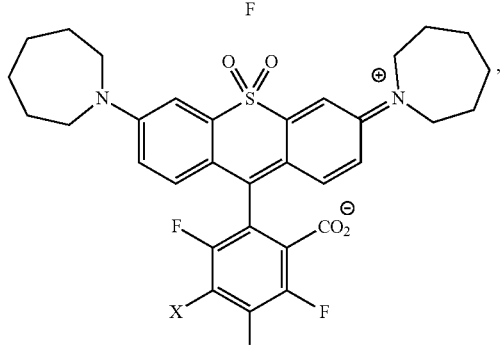
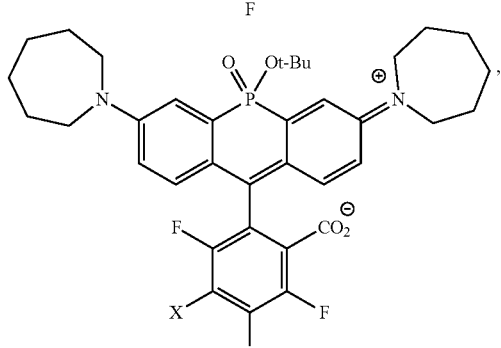
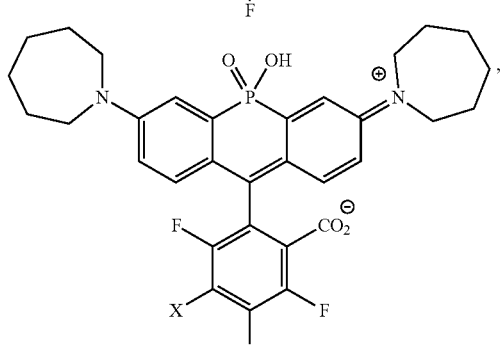

35
-continued
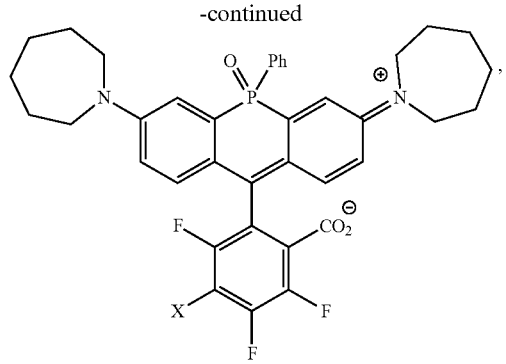
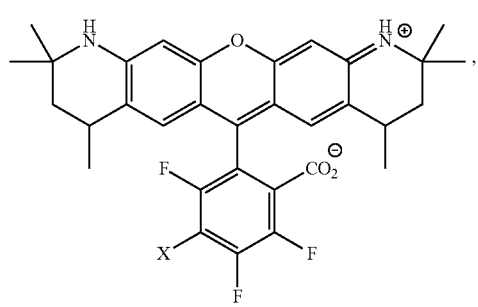
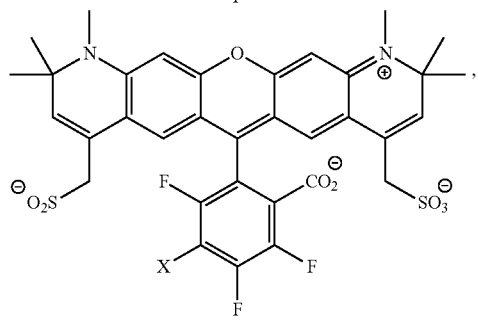
36
-continued
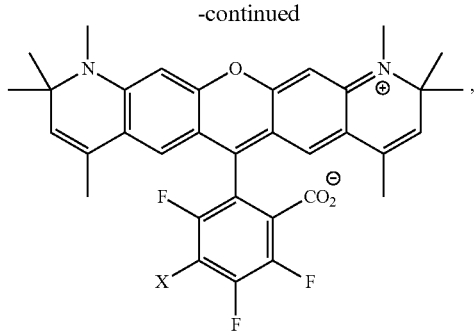
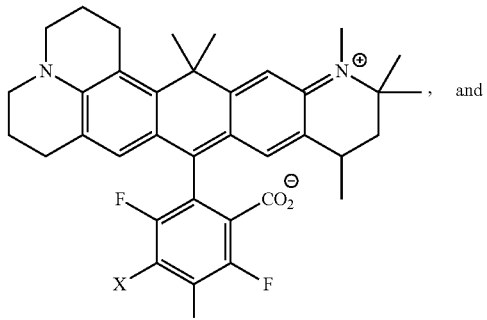, and
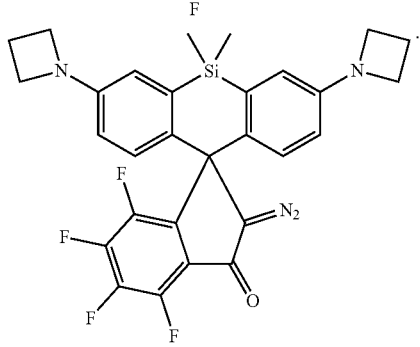
In some embodiments, the compound has a structure chosen from the following:
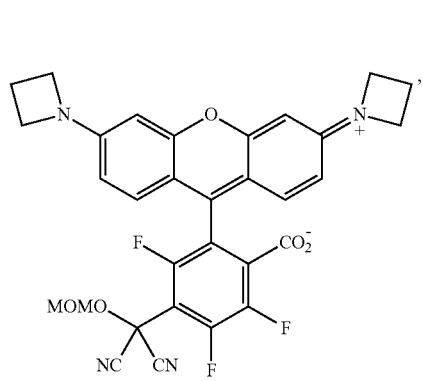,
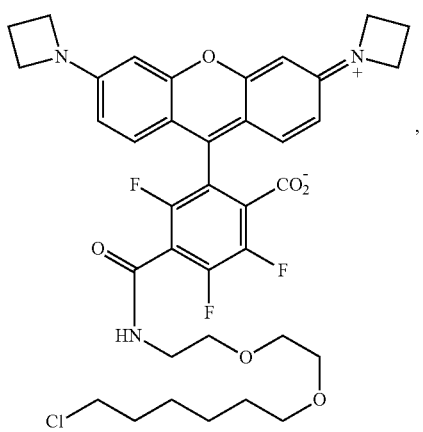, -continued
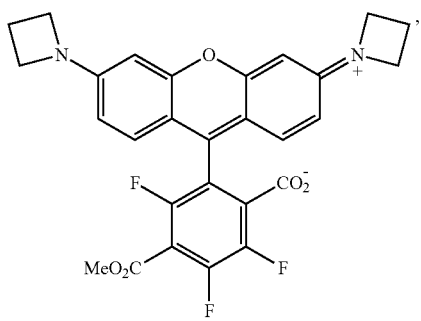
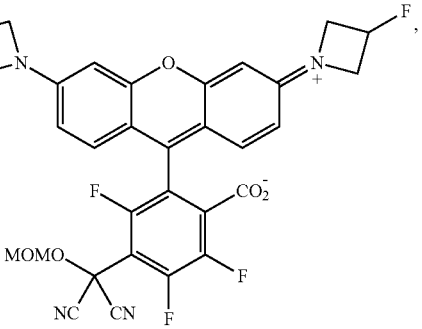
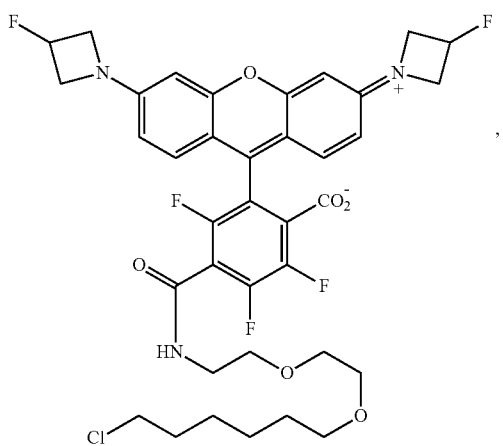
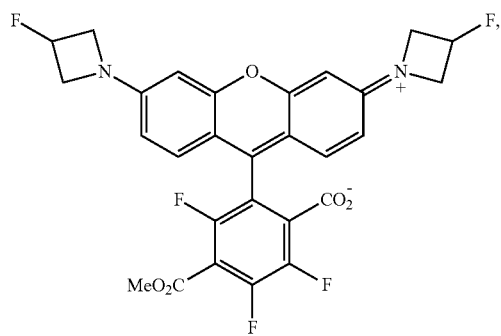
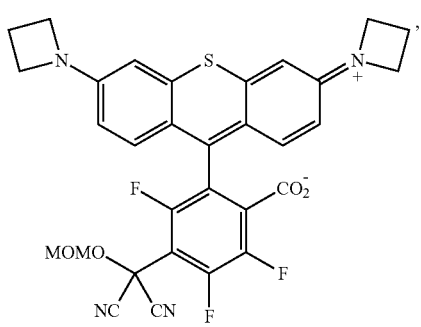
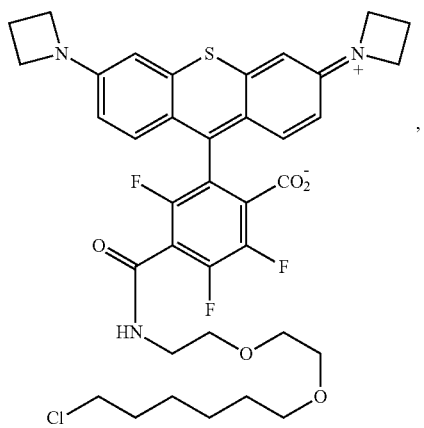
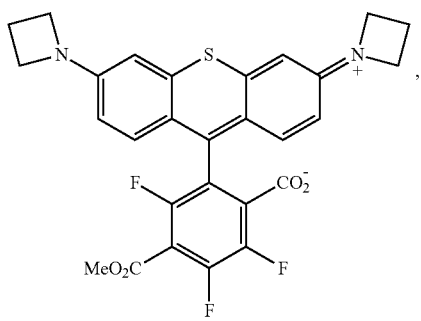
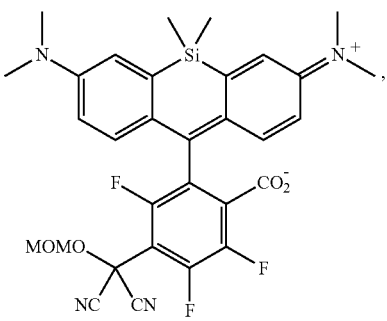

-continued
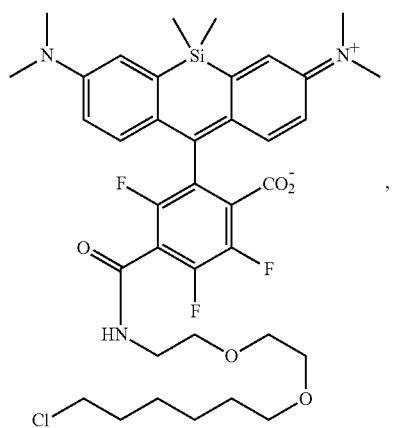
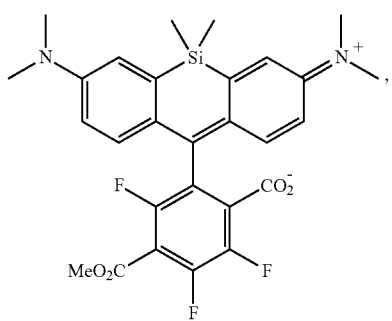
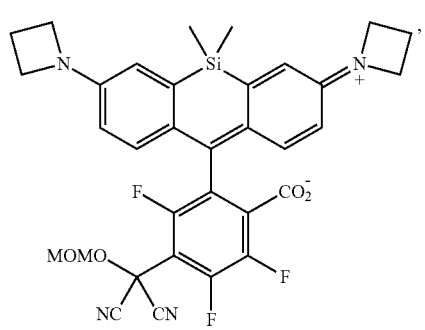
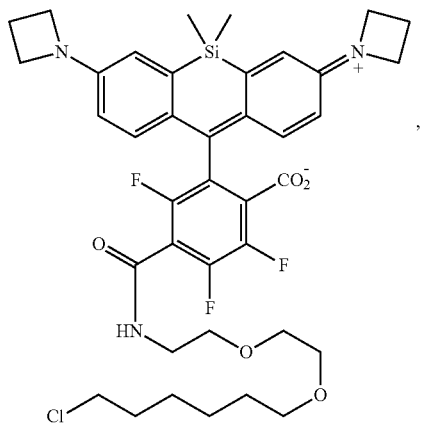
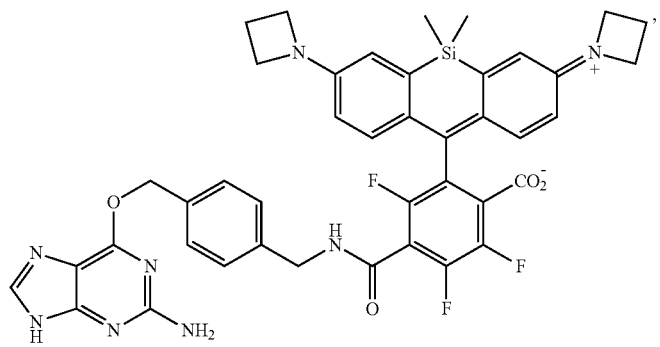
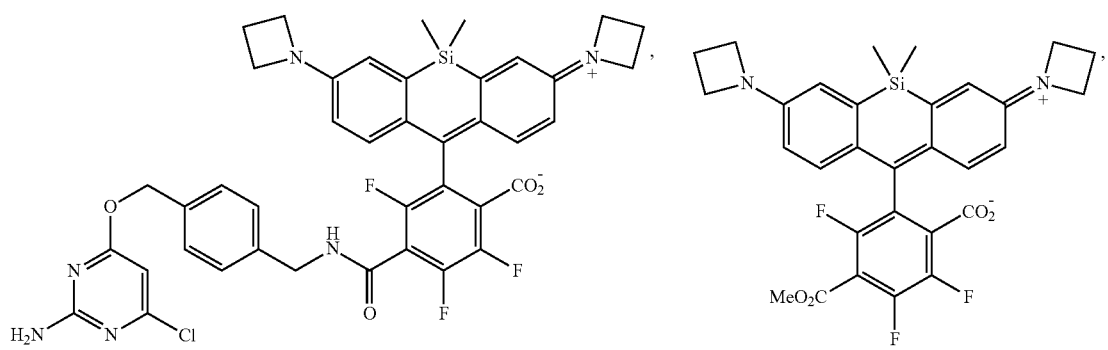

41
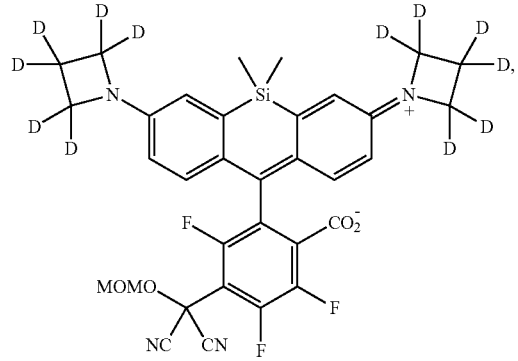
42
-continued
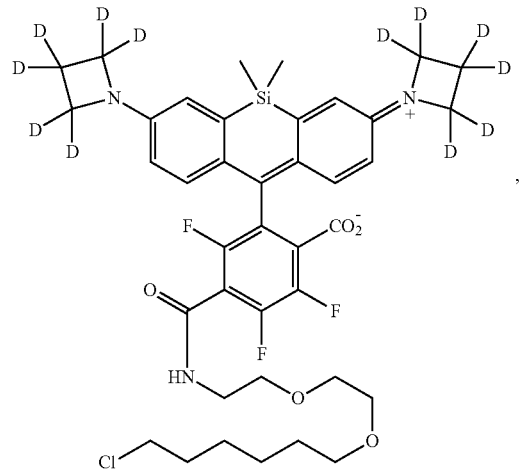
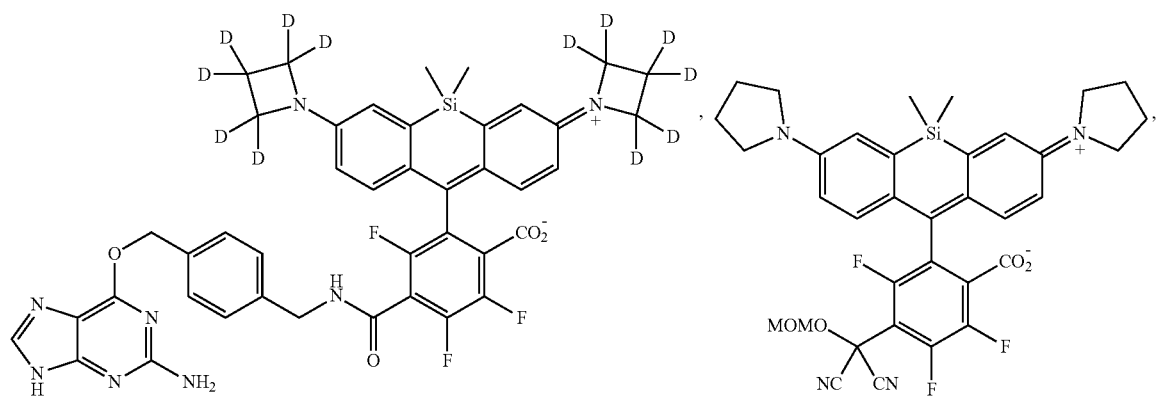
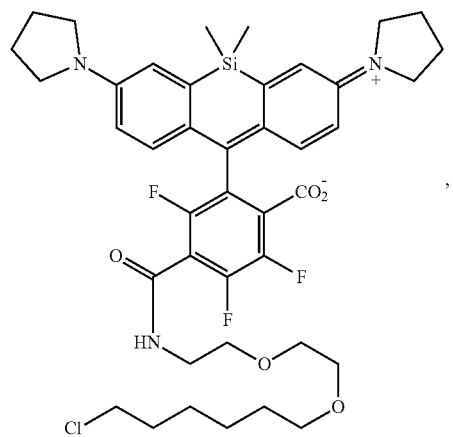
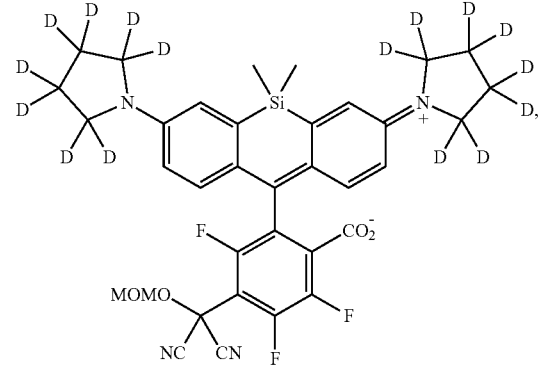

-continued
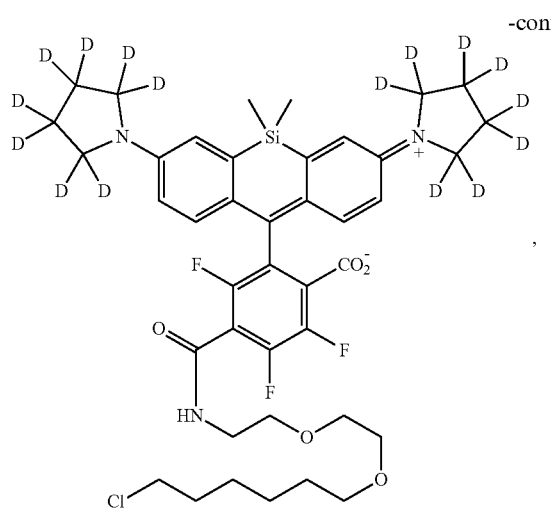
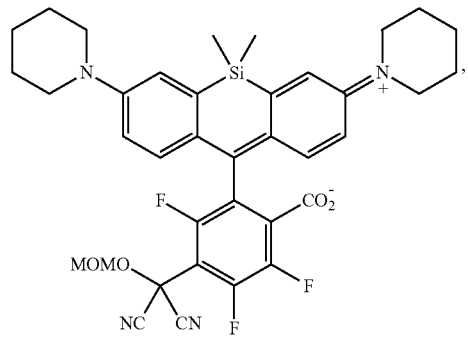
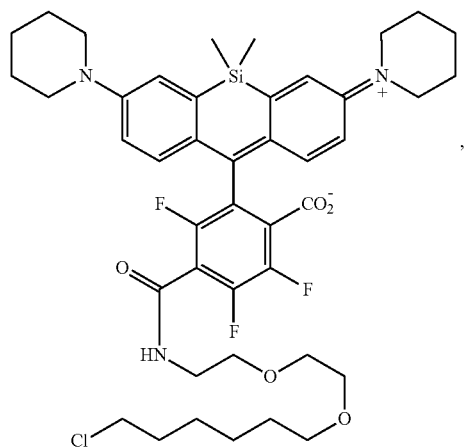
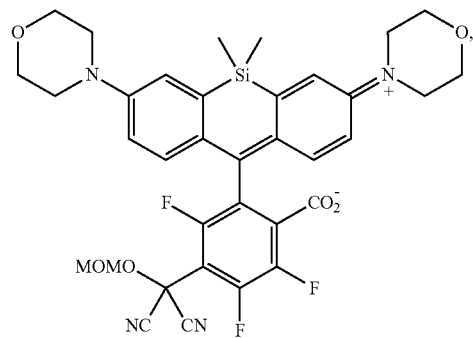
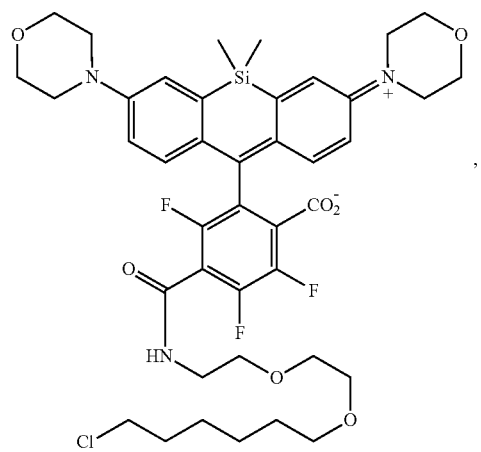
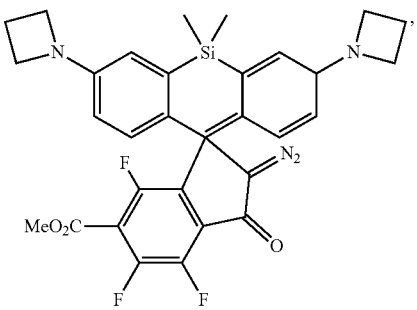

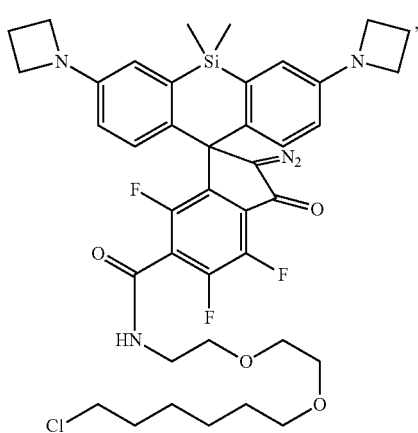
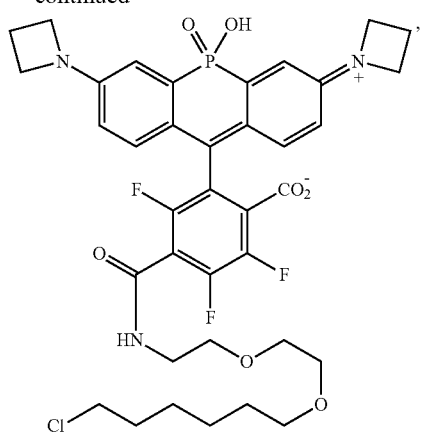
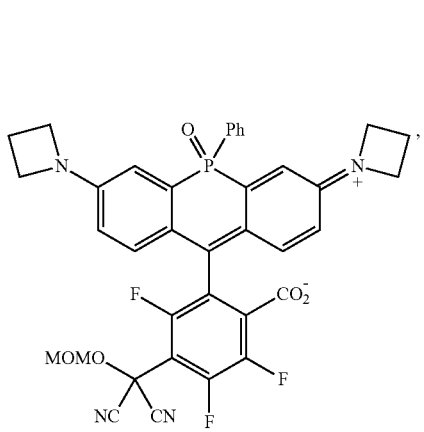
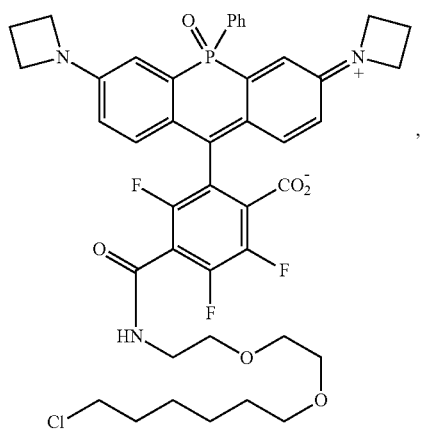
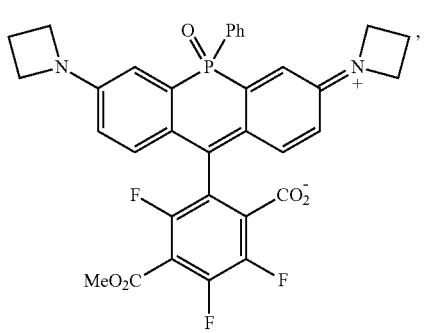
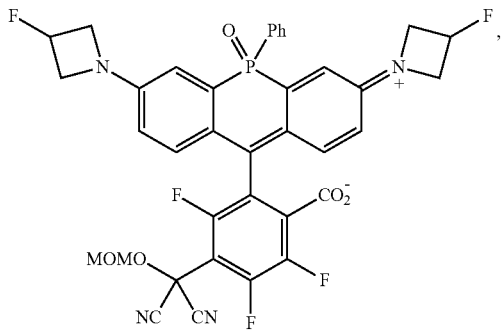
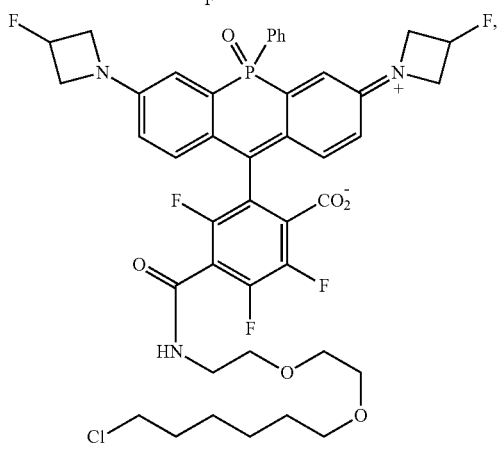

-continued
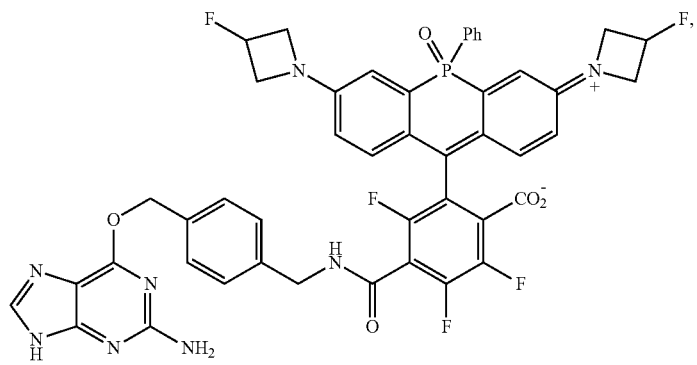
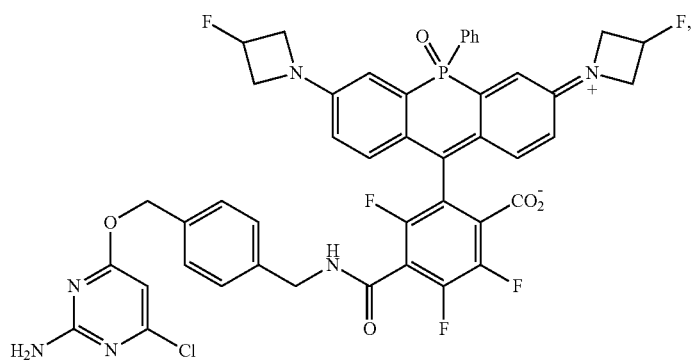
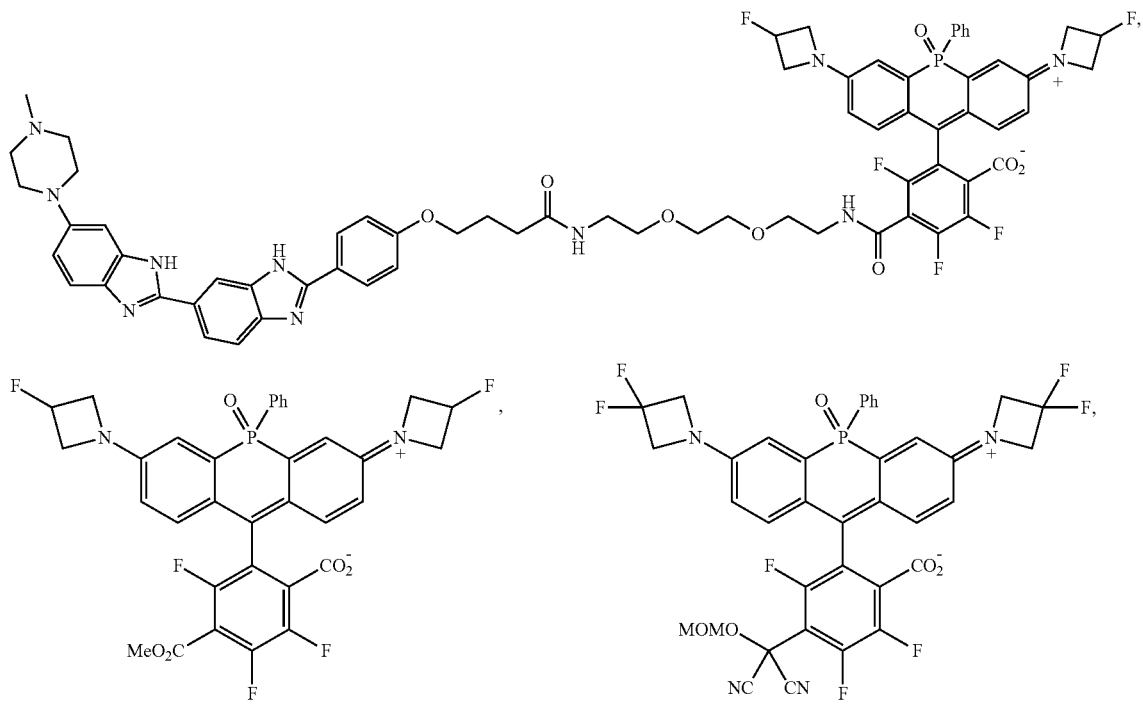

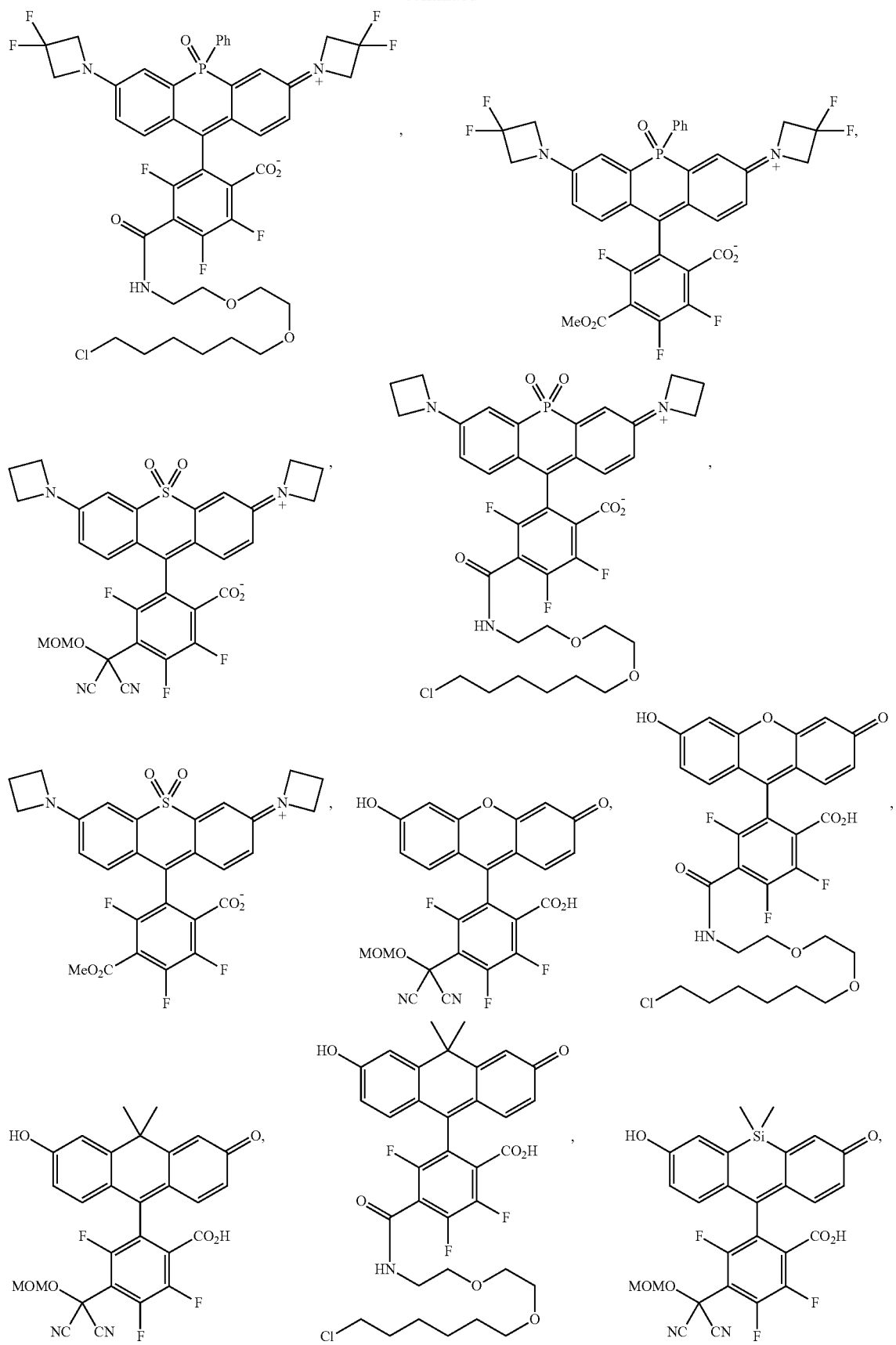

-continued
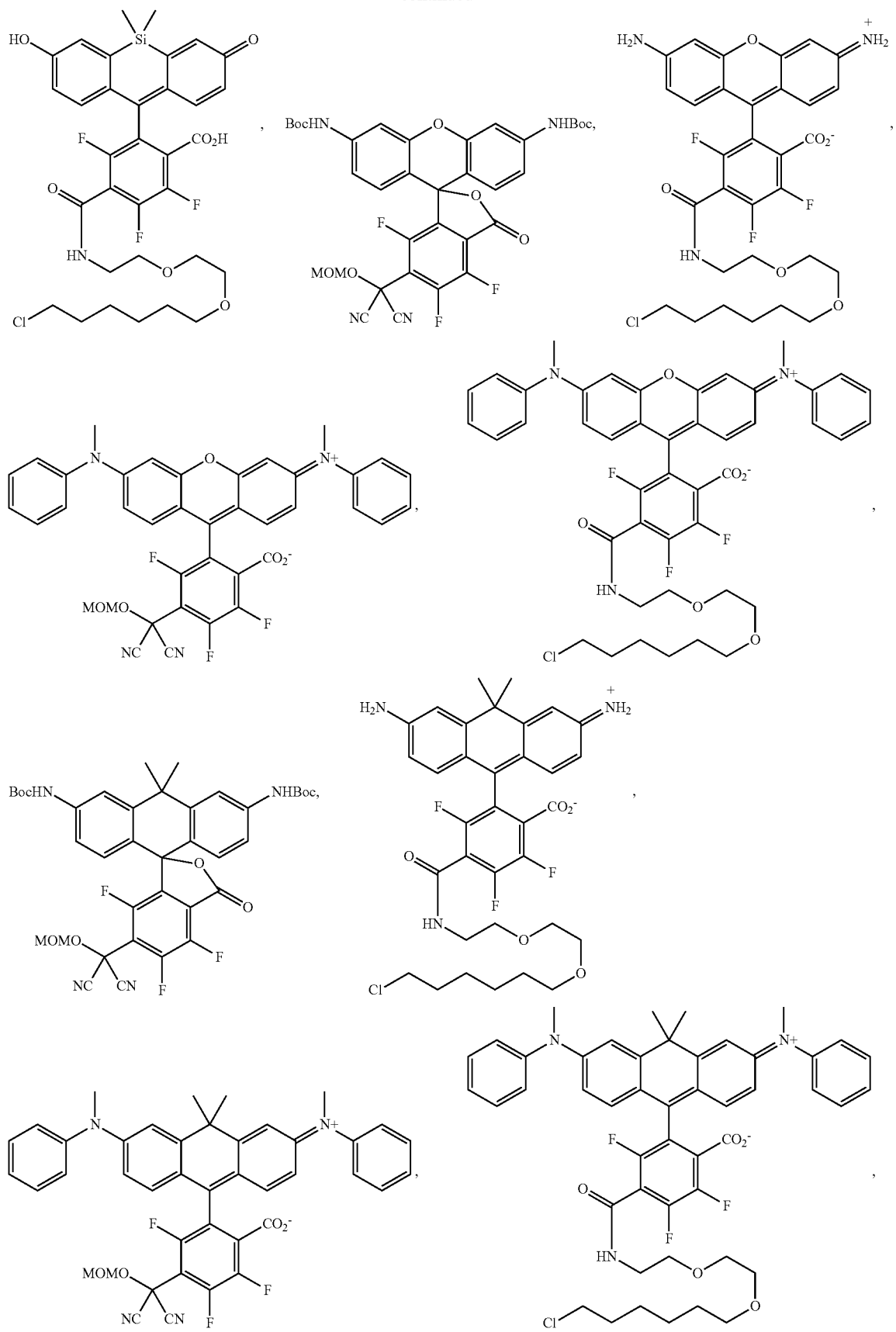

-continued
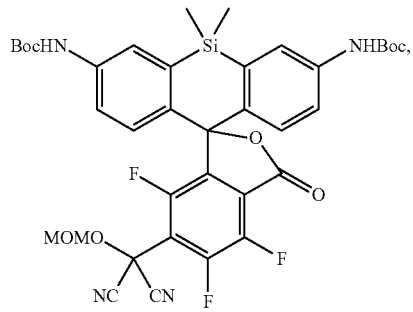
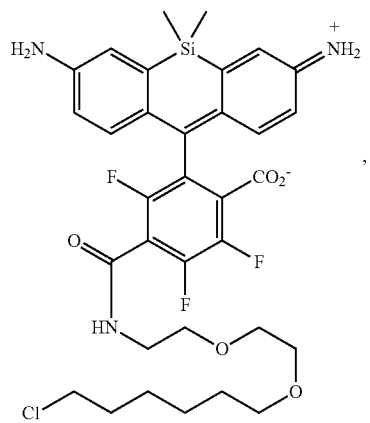
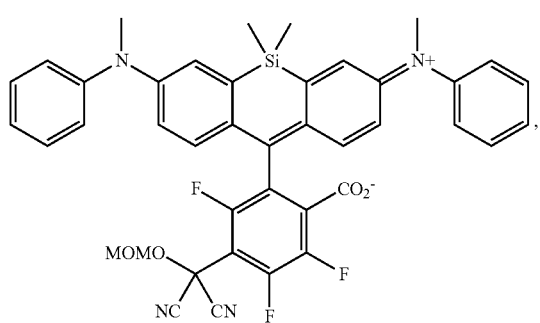
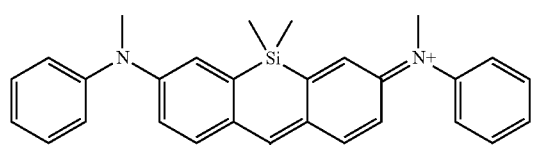
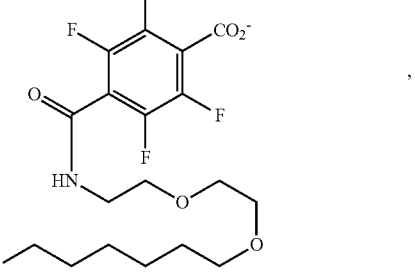
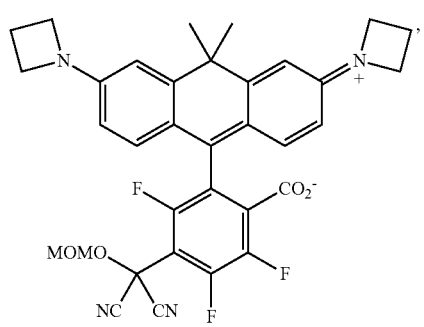
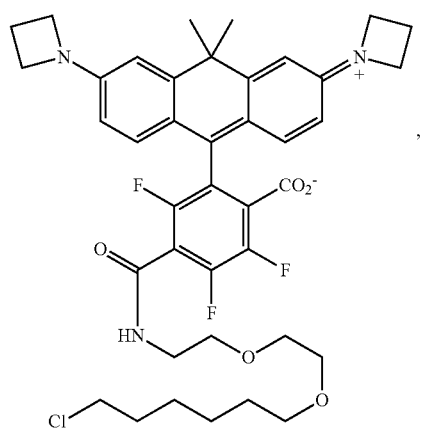
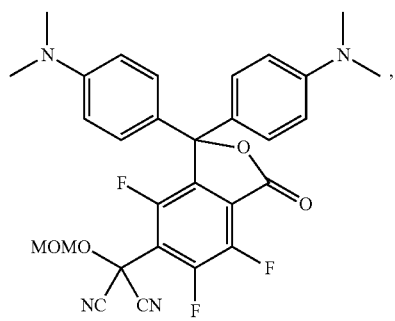
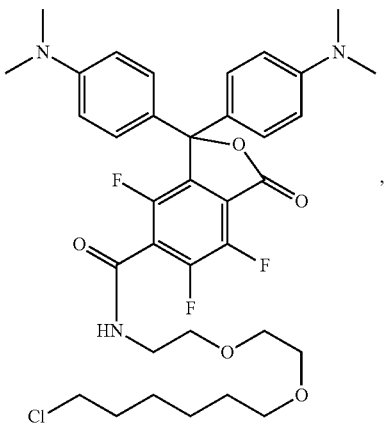

55
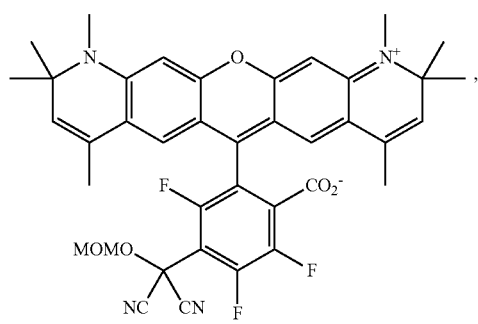
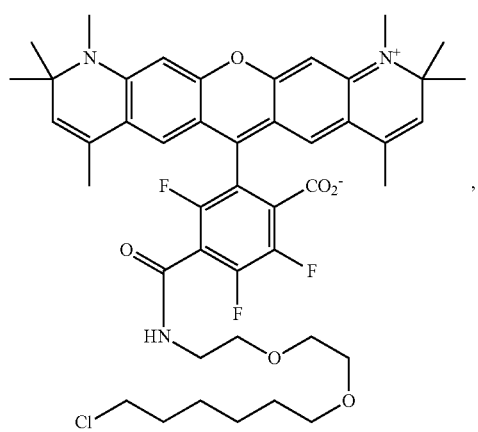
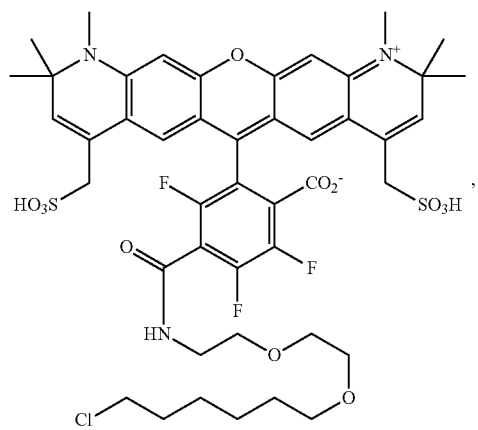
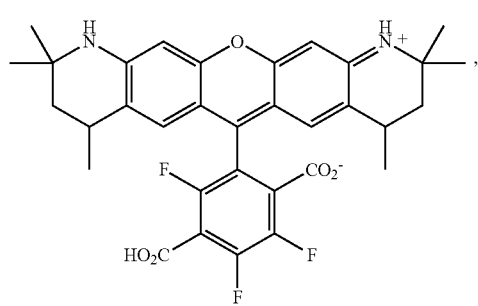
56
-continued
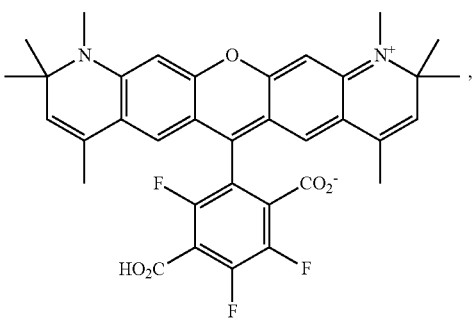
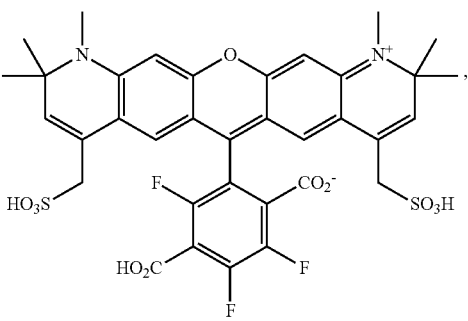
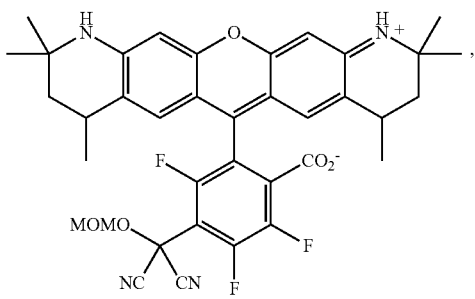
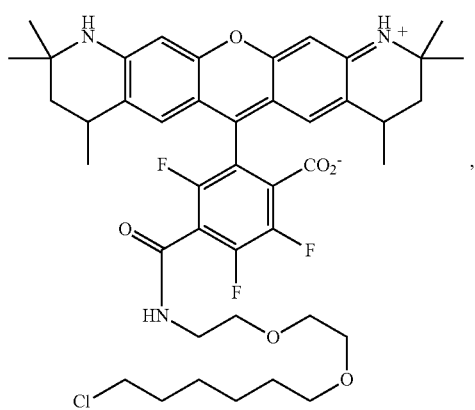

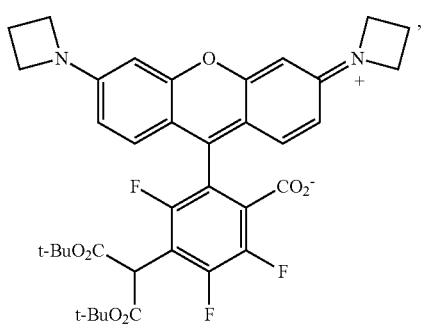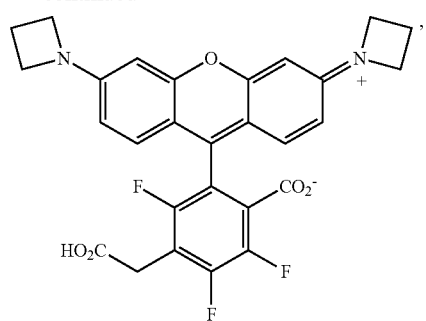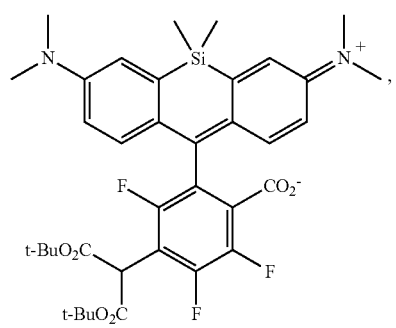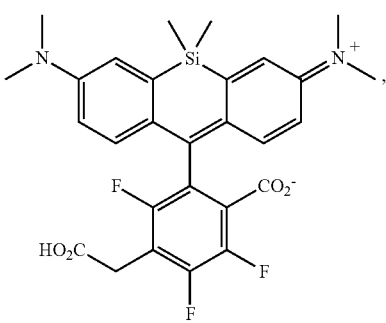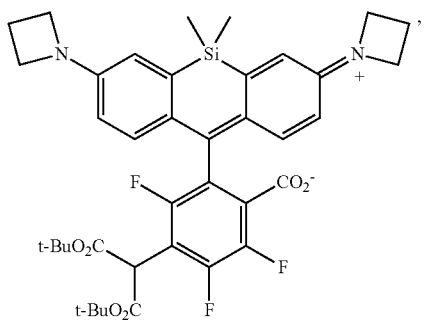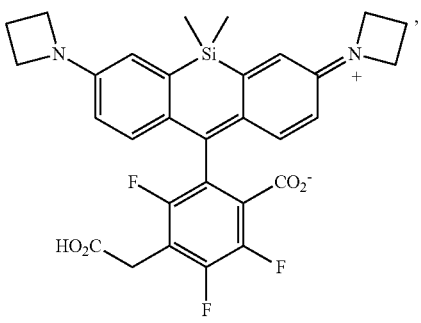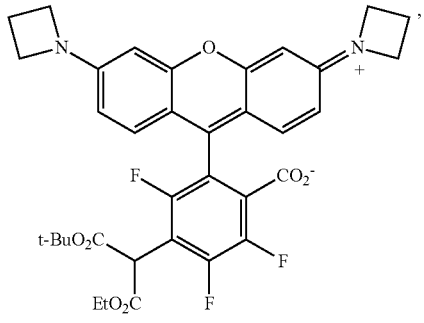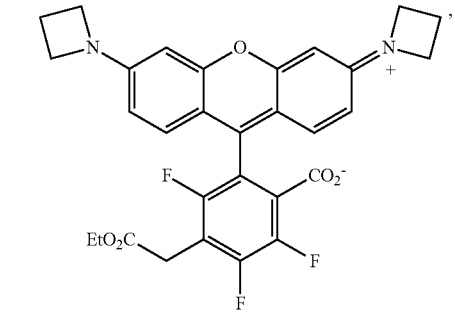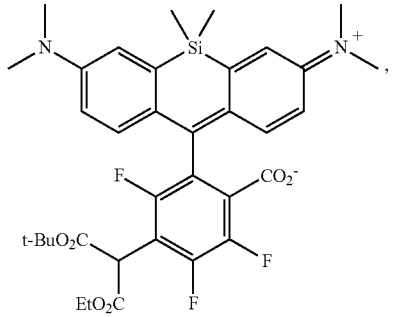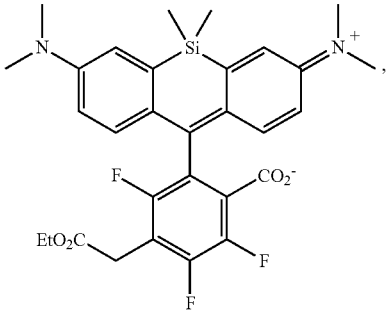

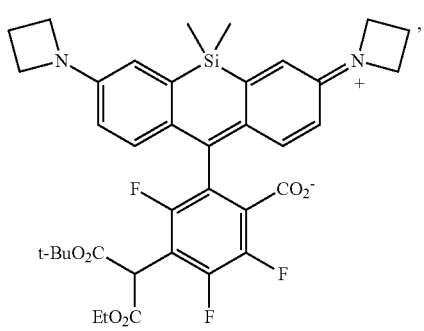
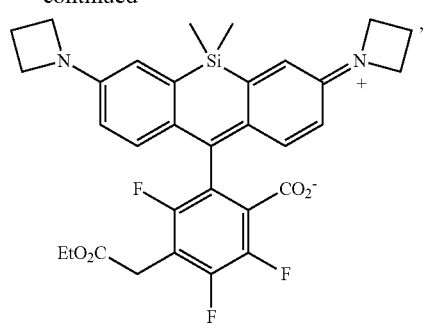
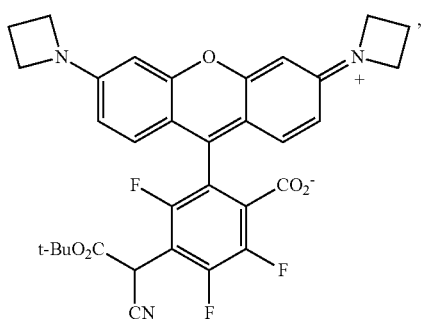
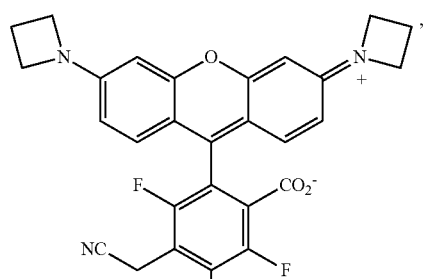
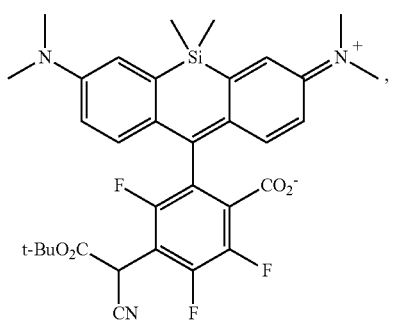
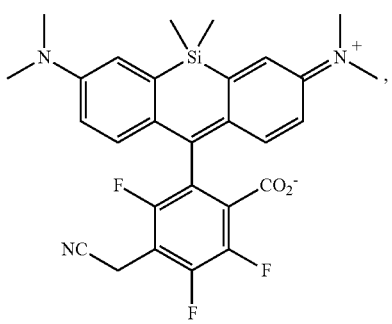
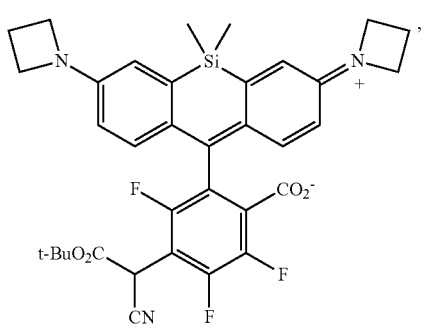
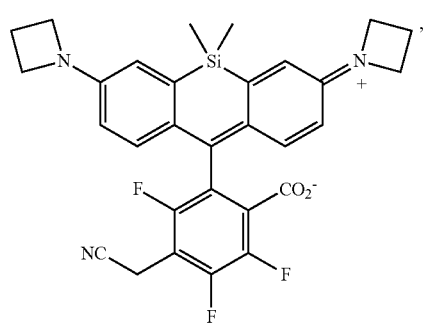
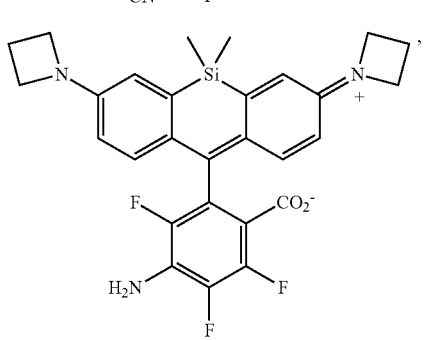
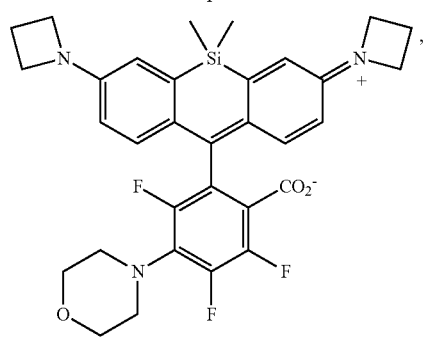

-continued
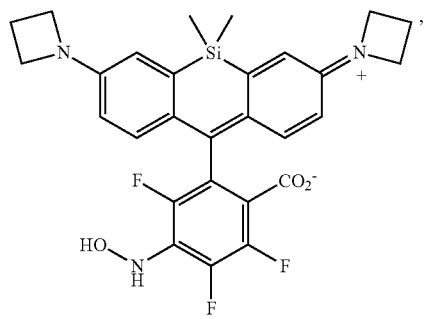
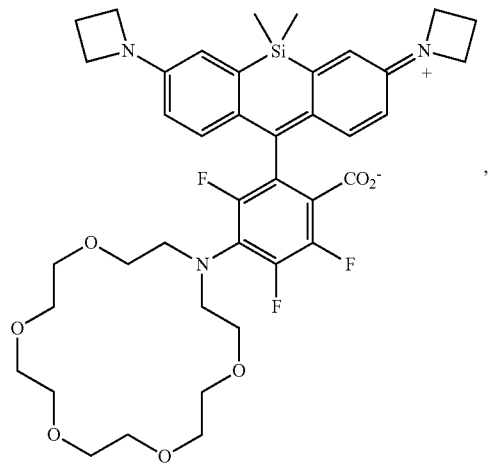
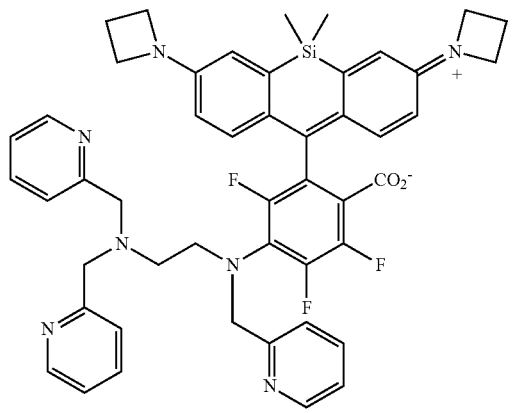
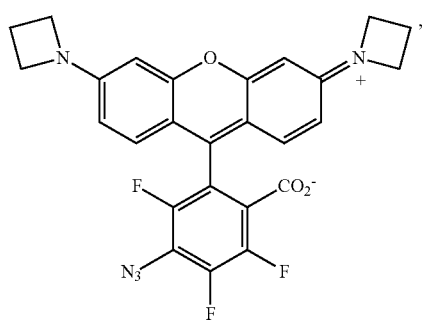
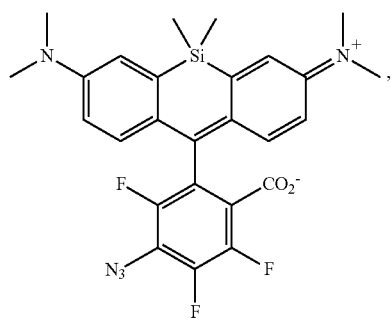
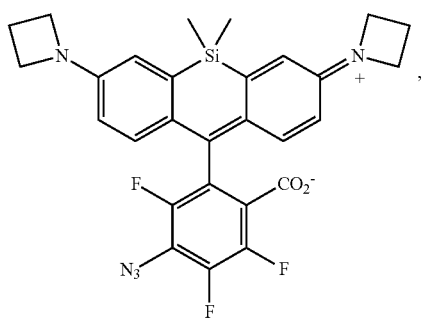
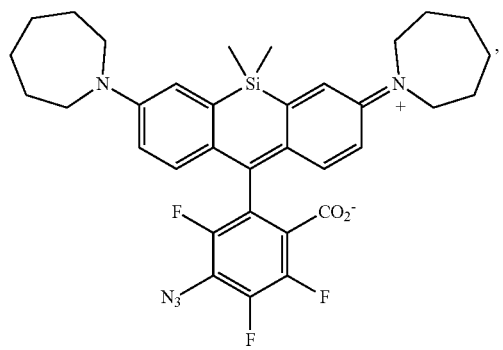
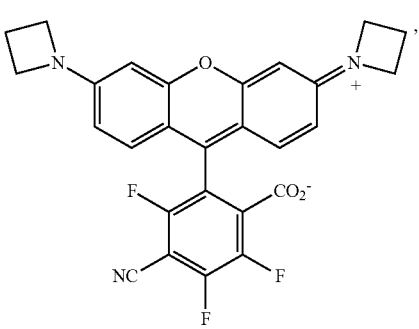

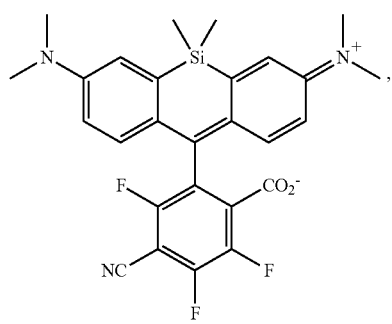 and 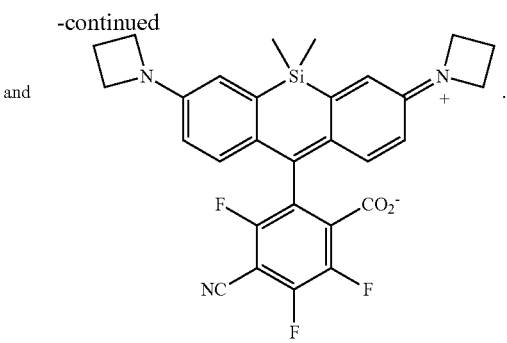

The presently disclosed subject matter also includes a method for detecting a target substance. In some embodiments, the method involves contacting a sample with a compound as disclosed herein, and detecting an emission light from the compound, the emission light indicating the presence of the target substance. The detection can be performed, for example, using a microscope. The target substance can be, for example, a protein, a carbohydrate, a polysaccharide, a glycoprotein, a hormone, a receptor, an antigen, an antibody, a virus, a substrate, a metabolite, an inhibitor, a drug, a nutrient, a growth factor, a liprotein, and a combination thereof.

In some embodiments of the method the contact step and the detecting step are performed in a live cell.

In some embodiments of the method, the compound includes a first compound and a second compound; the first compound being selective for a first target substance and capable of emitting a first emission light; the second compound being selective for a second target substance and capable of emitting a second emission light, and the detecting step includes detecting the first emission light that indicates the presence of the first target substance and the second emission light that indicates the presence of the second target substance.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, in some embodiments ±0.01%, and in some embodiments ±0.001% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The term "absorption wavelength" as used herein refers to the wavelength of light capable of being absorbed by a compound in order to excite the compound to emit a light. The light emitted from a compound that has been excited with an absorption light will have an "emission wavelength."

As used herein, the term "derivative" refers to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds.

As used herein, the term "protein" means any polymer comprising any of the 20 protein amino acids, regardless of its size. Although "polypeptide" is often used in reference to relatively large proteins, and "peptide" is often used in reference to small proteins, usage of these terms in the art overlaps and varies. The term "protein" as used herein refers to peptides, polypeptides and proteins, unless otherwise noted.

The term "selectively bind" is used herein to refer to the property of an atom, moiety, and/or molecule preferentially being drawn to or binding a particular compound. In some instances the atom, moiety, and/or molecule selectively binds to a particular site on a compound, such as an active site on a protein molecule.

The term "detect" is used herein to refer to the act of viewing, imagining, indicating the presence of, measuring, and the like a target substance based on the light emitted from the present compounds. More specifically, in some instances the present compounds can be bound to a target substance, and, upon being exposed to an absorption light, will emit an emission light. The presence of an emission light can indicate the presence of a target substance, whereas the quantification of the light intensity can be used to measure the concentration of a target sub stance.

The term "target substance" refers to a substance that is selectively bound directly by the presently-disclosed compounds and/or indirectly by a molecule that is bound to the present compound. A target substances can include, but is not limited to, a protein, carbohydrates, polysaccharide, glycoprotein, hormone, receptor, antigen, antibody, virus, substrate, metabolite, inhibitor, drug, nutrient, growth factor, and the like. In some embodiments the target substance refers to an entire molecule, and in other embodiments the target substances refers to a site on a molecule, such as a binding site on a particular protein.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds.

Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Unless stated otherwise, all chemical groups described herein include both unsubstituted and substituted varieties.

Where substituent groups are specified by their conventional chemical formula written from left to right, they equally encompass the chemically identical substituents that would result from writing the structure from right to left. For instance, —CH$_2$O— also encompasses recite —OCH$_2$—.

It should be understood that the bond types and locations in the chemical structures provided herein may adapt depending on the substituents in the compound, even if not specifically recited. For instance, —X— where X can be either C or N can refer to, respectively, —CH2- or —NH—, where the lone pair of electrons on N is not illustrated. Thus, even if not specifically illustrated, the chemical compounds described herein include any hydrogen atoms, lone pair of electrons, and the like necessary for completing a chemical structure.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also refer to both substituted or unsubstituted alkyls. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term. The term "alkyl" is inclusive of "cycloalkyl."

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

In this regard, the term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1\text{-}OA^2$ or $-OA^1\text{-}(OA^2)_a\text{-}OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. The term is include of linear and ring-forming (i.e., cycloakenyl) groups. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "ring" as used herein refers to a substituted or unsubstituted cycloalkyl, substituted or unsubstituted heterocycloalkyl, substituted or unsubstituted aryl, or substituted or unsubstituted heteroaryl. A ring includes fused ring moieties, referred to as a fused ring system wherein a ring may be fused to one or more rings selected from a substituted or unsubstituted cycloalkyl, substituted or unsubstituted heterocycloalkyl, substituted or unsubstituted aryl, and substituted or unsubstituted heteroaryl in any combination. The number of atoms in a ring is typically defined by the number of members in the ring. For example, a "5- to 8-membered ring" means there are 5 to 8 atoms in the encircling arrangement. A ring can optionally include a heteroatom. The term "ring" further includes a ring system comprising more than one "ring", wherein each "ring" is independently defined as above.

Some of the unsaturated structures described herein, such as ring structures including cycloalkyl and aryl, are illustrated with dashed bonds to signify the potential existence of a resonance structure. Structures having dashed bonds are intended to reflect every possible configuration of the structure, but does not necessarily imply that all possible structures are in existence. It should be understood that the types of bonds (e.g., single bond, double bond) in such structures will vary depending on the atoms in the structure as well as whether the structures are substituted with one or more additional atoms or moieties.

The term "aldehyde" as used herein is represented by a formula —C(O)H. Throughout this specification "C(O)" is a short hand notation for a carbonyl group, i.e., C=O.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein. In specific embodiments amine refers to any of $NH_2$, NH(alkyl), NH(aryl), $N(alkyl)_2$, and $N(aryl)_2$.

The term "carboxylic acid" as used herein is represented by a formula —C(O)OH.

The term "halide" or "halogen" refers to at least one of the halogens selected from fluorine, chlorine, bromine, and iodine.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is further illustrated by the following specific but non-limiting examples. The following examples may include compilations of data that are representative of data gathered at various times during the course of development and experimentation related to the present invention.

EXAMPLES

Commercial reagents were obtained from reputable suppliers and used as received. All solvents were purchased in septum-sealed bottles stored under an inert atmosphere. All reactions were sealed with septa through which a nitrogen atmosphere was introduced unless otherwise noted. Reactions were conducted in round-bottomed flasks or septum-capped crimp-top vials containing Teflon-coated magnetic stir bars. Heating of reactions was accomplished with a silicon oil bath or an aluminum reaction block on top of a stirring hotplate equipped with an electronic contact thermometer to maintain the indicated temperatures.

Reactions were monitored by thin layer chromatography (TLC) on precoated TLC glass plates (silica gel 60 $F_{254}$, 250 μm thickness) or by LC/MS (Phenomenex Kinetex 2.1 mm×30 mm 2.6 μm C18 column; 5 μL injection; 5-98% MeCN/$H_2O$, linear gradient, with constant 0.1% v/v $HCO_2H$ additive; 6 min run; 0.5 mL/min flow; ESI; positive ion mode). TLC chromatograms were visualized by UV illumination or developed with p-anisaldehyde, ceric ammonium molybdate, or $KMnO_4$ stain. Reaction products were purified by flash chromatography on an automated purification system using pre-packed silica gel columns or by preparative HPLC (Phenomenex Gemini-NX 30×150 mm 5 μm C18 column). Analytical HPLC analysis was performed with an Agilent Eclipse XDB 4.6×150 mm 5 μm C18 column under the indicated conditions. High-resolution mass spectrometry was performed by the High Resolution Mass Spectrometry Facility at the University of Iowa.

NMR spectra were recorded on a 400 MHz spectrometer. $^1$H and $^{13}$C chemical shifts were referenced to TMS or residual solvent peaks, and $^{19}$F chemical shifts were referenced to $CFCl_3$. Data for $^1$H NMR spectra are reported as follows: chemical shift (δ ppm), multiplicity (s=singlet, d=doublet, t=triplet, q=quartet, dd=doublet of doublets, m=multiplet), coupling constant (Hz), integration. Data for $^{13}$C NMR spectra are reported by chemical shift (δ ppm) with hydrogen multiplicity (C, CH, $CH_2$, $CH_3$) information obtained from DEPT spectra. The $^{13}$C NMR spectra are not reported for compounds containing trifluoro- or tetrafluoro-substituted aryl rings, as the numerous distinct fluorine couplings confounded interpretation of the spectra.

Example 1: 2-(3,6-Di(azetidin-1-yl)xanthylium-9-yl)-4-(dicyano(methoxymethoxy)methyl)-3,5,6-trifluorobenzoate

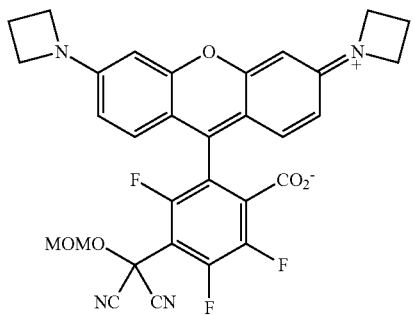

2-(3,6-Di(azetidin-1-yl)xanthylium-9-yl)-3,4,5,6-tetrafluorobenzoate (Grimm, J. B. et al. *ACS Cent. Sci.* 2017, 3, 975-985; 155 mg, 0.321 mmol) and 2-(methoxymethoxy)malononitrile (40.5 mg, 0.321 mmol, 1 eq) were combined in DMF (5 mL), and DIEA (112 μL, 0.643 mmol, 2 eq) was added. After stirring the reaction at room temperature for 2 h, it was evaporated to dryness. Flash chromatography on silica gel (0-15% MeOH/$CH_2Cl_2$, linear gradient, with constant 1% v/v AcOH additive) afforded the title compound as a dark red-purple solid (108 mg, 52%, acetate salt). $^1$H NMR ($CDCl_3$, 400 MHz) δ 7.30 (d, J=9.1 Hz, 2H), 6.46 (dd, J=9.1, 2.2 Hz, 2H), 6.27 (d, J=2.2 Hz, 2H), 5.15 (s, 2H), 4.22 (t, J=7.6 Hz, 8H), 3.55 (s, 3H), 2.56 (p, J=7.6 Hz, 4H); $^{19}$F NMR ($CDCl_3$, 376 MHz) δ −114.38 (d, J=16.5 Hz, 1F), −127.29 (d, J=22.6 Hz, 1F), −138.86 (dd, J=22.5, 16.6 Hz, 1F); Analytical HPLC: $t_R$=10.4 min, 99.0% purity (10-95% MeCN/$H_2O$, linear gradient, with constant 0.1% v/v TFA additive; 20 min run; 1 mL/min flow; ESI; positive ion mode; detection at 575 nm); HRMS (ESI) calcd for $C_{31}H_{24}F_3N_4O_5$ $[M+H]^+$ 589.1693, found 589.1698.

Example 2: 4-((2-(2-(((6-Chlorohexyl)oxy)ethoxy)ethyl)carbamoyl)-2-(3,6-di(azetidin-1-yl)xanthylium-9-yl)-3,5,6-trifluorobenzoate

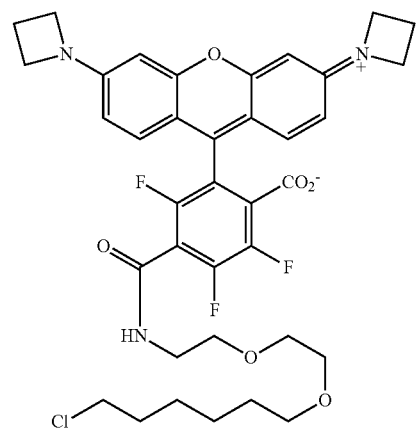

2-(3,6-Di(azetidin-1-yl)xanthylium-9-yl)-4-(dicyano(methoxymethoxy)methyl)-3,5,6-trifluorobenzoate (Example 1; 50 mg, 77.1 μmol) was taken up in $CH_2Cl_2$ (5 mL); triethylsilane (500 μL) was added, followed by trifluoroacetic acid (1 mL). The reaction was stirred at room temperature for 6 h. Toluene (5 mL) was added, and the reaction mixture was concentrated to dryness. The residue was combined with a premixed solution of 2-(2-(((6-chlorohexyl)oxy)ethoxy)ethan-1-amine (TFA salt; 52.1 mg, 0.154 mmol, 2 eq) and DIEA (134 μL, 0.771 mmol, 10 eq) in $CH_2Cl_2$ (4 mL), and the reaction was stirred at room temperature for 18 h. The solvent was removed by rotary evaporation, and the crude material was purified by reverse phase HPLC (30-60% MeCN/$H_2O$, linear gradient, with constant 0.1% v/v TFA additive) to yield 33.7 mg (53%, TFA salt) of the title compound as a dark red-purple solid. $^1$H NMR ($CD_3OD$, 400 MHz) δ 9.08 (t, J=5.3 Hz, 1H), 7.28 (d, J=9.2 Hz, 2H), 6.67 (dd, J=9.2, 2.2 Hz, 2H), 6.53 (d, J=2.2 Hz, 2H), 4.34 (t, J=7.6 Hz, 8H), 3.67-3.55 (m, 8H), 3.52 (t, J=6.7 Hz, 2H), 3.43 (t, J=6.5 Hz, 2H), 2.57 (p, J=7.6 Hz, 4H), 1.76-1.67 (m, 2H), 1.54-1.46 (m, 2H), 1.44-1.29 (m, 4H); $^{19}$F NMR ($CD_3OD$, 376 MHz) δ −116.71 (d, J=15.3 Hz, 1F), −132.53 (d, J=22.4 Hz, 1F), −140.20 (dd, J=22.6, 15.3 Hz, 1F); Analytical HPLC: $t_R$=12.8 min, >99% purity (10-95% MeCN/$H_2O$, linear gradient, with constant 0.1% v/v TFA additive; 20 min run; 1 mL/min flow; ESI; positive ion mode; detection at 575 nm); HRMS (ESI) calcd for $C_{37}H_{40}ClF_3N_3O_6$ $[M+H]^+$ 714.2552, found 714.2561.

Example 3: 2-(3,6-Di(azetidin-1-yl)xanthylium-9-yl)-3,5,6-trifluoro-4-(methoxycarbonyl)benzoate

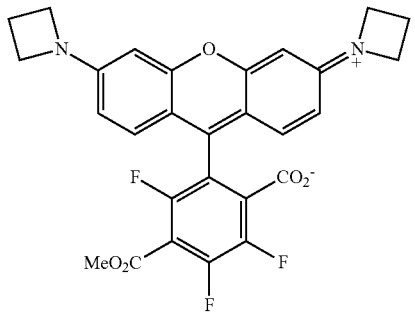

2-(3,6-Di(azetidin-1-yl)xanthylium-9-yl)-4-(dicyano(methoxymethoxy)methyl)-3,5,6-trifluorobenzoate (Example 1; 40 mg, 61.7 μmol) was taken up in $CH_2Cl_2$ (4 mL); triethylsilane (400 μL) was added, followed by trifluoroacetic acid (800 μL). The reaction was stirred at room temperature for 6 h. Toluene (5 mL) was added, and the reaction mixture was concentrated to dryness. The residue was combined with a premixed solution of MeOH (62.4 μL, 1.54 mmol, 25 eq) and $Et_3N$ (86.0 μL, 0.617 mmol, 10 eq) in $CH_2Cl_2$ (3 mL), and the reaction was stirred at room temperature for 18 h. The solvent was removed by rotary evaporation, and the crude material was purified by reverse phase HPLC (20-50% $MeCN/H_2O$, linear gradient, with constant 0.1% v/v TFA additive) to afford the title compound as a dark purple solid (26.8 mg, 68%, TFA salt). $^1H$ NMR ($CD_3OD$, 400 MHz) δ 7.27 (d, J=9.2 Hz, 2H), 6.67 (dd, J=9.2, 2.2 Hz, 2H), 6.52 (d, J=2.2 Hz, 2H), 4.34 (t, J=7.7 Hz, 8H), 3.98 (s, 3H), 2.57 (p, J=7.7 Hz, 4H); $^{19}F$ NMR ($CD_3OD$, 376 MHz) δ 114.14 (d, J=15.4 Hz, 1F), 129.35 (d, J=21.2 Hz, 1F), 139.46 (dd, J=21.5, 15.4 Hz, 1F); Analytical HPLC: $t_R$=11.2 min, >99% purity (10-95% $MeCN/H_2O$, linear gradient, with constant 0.1% v/v TFA additive; 20 min run; 1 mL/min flow; ESI; positive ion mode; detection at 575 nm); HRMS (ESI) calcd for $C_{24}H_{22}F_3N_2O_5$ [M+H]$^+$ 523.1475, found 523.1480.

Example 4: 2-(3,6-Bis(3-fluoroazetidin-1-yl)xanthylium-9-yl)-4-(dicyano(methoxymethoxy)methyl)-3,5,6-trifluorobenzoate

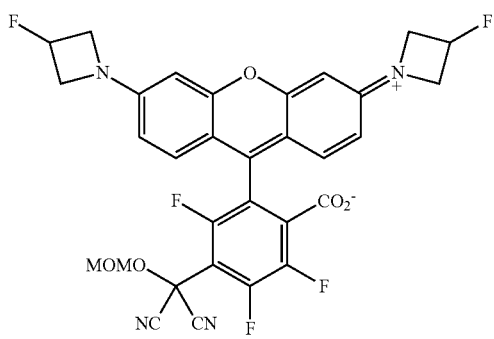

Step 1: An oven-dried round-bottom flask was charged with 3-fluoroazetidine hydrochloride (2.04 g, 18.3 mmol, 2.4 eq), $Pd_2dba_3$ (698 mg, 0.762 mmol, 0.1 eq), XPhos (1.09 g, 2.29 mmol, 0.3 eq), and $Cs_2CO_3$ (11.92 g, 36.6 mmol, 4.8 eq). The flask was sealed and evacuated/backfilled with nitrogen (3×). A solution of 3,3'-oxybis(bromobenzene) (Grimm, J. B. et al. ACS Cent. Sci. 2017, 3, 975-985; 2.50 g, 7.62 mmol) in dioxane (40 mL) was added, and after flushing the reaction again with nitrogen (3×), it was stirred at 100° C. for 18 h. It was then cooled to room temperature, filtered through Celite with $CH_2Cl_2$, and concentrated to dryness. Purification by flash chromatography (0-50% $Et_2O$/hexanes, linear gradient) yielded 1.43 g (59%) of 1,1'-(oxybis(3,1-phenylene))bis(3-fluoroazetidine) as a yellow gum. $^1H$ NMR ($CDCl_3$, 400 MHz) δ 7.15 (t, J=8.1 Hz, 2H), 6.41 (ddd, J=8.1, 2.2, 0.7 Hz, 2H), 6.21 (ddd, J=8.0, 2.2, 0.7 Hz, 2H), 6.15 (t, J=2.3 Hz, 2H), 5.39 (dtt, $^2J_{HF}$=57.0 Hz, J=5.9, 3.8 Hz, 2H), 4.21-4.09 (m, 4H), 3.99-3.87 (m, 4H); $^{19}F$ NMR ($CDCl_3$, 376 MHz) δ −180.65 (dtt, $J_{FH}$=57.2, 23.9, 18.0 Hz); $^{13}C$ NMR ($CDCl_3$, 101 MHz) δ 158.2 (C), 152.6 (d, $^4J_{CF}$=1.1 Hz, C), 130.2 (CH), 108.7 (CH), 107.0 (CH), 102.8 (CH), 82.8 (d, $^1J_{CF}$=204.5 Hz, CFH), 59.7 (d, $^2J_{CF}$=23.7 Hz, $CH_2$); HRMS (ESI) calcd for $C_{18}H_{19}F_2N_2O$ [M+H]$^+$ 317.1460, found 317.1456.

Step 2: The product from Step 1 (1.50 g, 4.74 mmol) was taken up in DMF (30 mL). N-Bromosuccinimide (1.69 g, 9.48 mmol, 2 eq) was added portion-wise over 5 min, and the reaction was then stirred at room temperature for 2 h. The reaction mixture was concentrated in vacuo; the resulting residue was diluted with water and extracted with EtOAc (2×). The combined organic extracts were washed with brine, dried over anhydrous $MgSO_4$, filtered, and evaporated to dryness. Silica gel chromatography (0-10% EtOAc/toluene, linear gradient; mixed fractions repurified with 0-50% EtOAc/hexanes, linear gradient) provided 1.92 g (85%) of 1,1'-(oxybis(4-bromo-3,1-phenylene))bis(3-fluoroazetidine) as a white solid. $^1H$ NMR ($CDCl_3$, 400 MHz) δ 7.41 (d, J=8.6 Hz, 2H), 6.13 (dd, J=8.6, 2.6 Hz, 2H), 5.93 (d, J=2.7 Hz, 2H), 5.36 (dtt, $^2J_{HF}$=56.9 Hz, J=5.9, 3.6 Hz, 2H), 4.15-4.04 (m, 4H), 3.96-3.82 (m, 4H); $^{19}F$ NMR ($CDCl_3$, 376 MHz) δ −180.71 (dtt, $J_{FH}$=57.1, 23.8, 18.3 Hz); $^{13}C$ NMR ($CDCl_3$, 101 MHz) δ 153.8 (C), 151.6 (d, $^4J_{CF}$=1.3 Hz, C), 133.9 (CH), 108.9 (CH), 103.2 (CH), 101.9 (C), 82.5 (d, $^1J_{CF}$=205.0 Hz, CFH), 59.7 (d, $^2J_{CF}$=23.9 Hz, $CH_2$); HRMS (ESI) calcd for $C_{18}H_{17}Br_2F_2N_2O$ [M+H]$^+$ 472.9670, found 472.9677.

Step 3: A solution of the product from Step 2 (500 mg, 1.05 mmol) in THF (20 mL) was cooled to −78° C. under nitrogen. tert-Butyllithium (1.7 M in pentane, 2.73 mL, 4.64 mmol, 4.4 eq) was added, and the reaction was stirred at −78° C. for 30 min. It was then warmed to −10° C. before adding a solution of $MgBr_2·OEt_2$ (599 mg, 2.32 mmol, 2.2 eq) in THF (10 mL). After an additional 30 min at −10° C., a solution of tetrafluorophthalic anhydride (S49; 511 mg, 2.32 mmol, 2.2 eq) in THF (10 mL) was added dropwise over 30 min via addition funnel. The reaction was then allowed to warm to room temperature overnight (18 h). Following the addition of AcOH (100 μL), the mixture was diluted with MeOH, deposited onto Celite, and concentrated to dryness. Silica gel chromatography (0-10% MeOH (2 M $NH_3$)/$CH_2Cl_2$, linear gradient; dry load with Celite) afforded 177 mg (32%) of 2-(3,6-bis(3-fluoroazetidin-1-yl)xanthylium-9-yl)-3,4,5,6-tetrafluorobenzoate as a dark red-purple solid. $^1H$ NMR ($CD_3OD$, 400 MHz) δ 7.37 (dd, J=9.1, 0.5 Hz, 2H), 6.72 (dd, J=9.2, 2.2 Hz, 2H), 6.58 (d, J=2.2 Hz, 2H), 5.56 (dtt, $^2J_{HF}$=57.0 Hz, J=6.0, 3.0 Hz, 2H), 4.66-4.53 (m, 4H), 4.44-4.30 (m, 4H); $^{19}F$ NMR ($CD_3OD$, 376 MHz) δ −139.12 (ddd, J=21.0, 12.7, 3.9 Hz, 1F), −140.70 (ddd, J=22.1, 12.8, 4.0 Hz, 1F), −153.21 (ddd, J=22.9, 19.1, 4.2 Hz, 1F), −157.02--157.18 (m, 1F), −180.54 (dtt, $J_{FH}$=57.1, 23.7, 20.4 Hz, 2F); Analytical HPLC: $t_R$=11.1 min, >99% purity (10-95% MeCN/H$_2$O, linear gradient, with constant 0.1% v/v TFA additive; 20 min run; 1 mL/min flow; ESI; positive ion mode; detection at 575 nm); HRMS (ESI) calcd for $C_{26}H_{17}F_6N_2O_3$ [M+H]$^+$ 519.1138, found 519.1138.

Step 4: The product from Step 3 (250 mg, 0.482 mmol) and 2-(methoxymethoxy)malononitrile (60.8 mg, 0.482 mmol, 1 eq) were combined in DMF (10 mL), and DIEA (168 μL, 0.964 mmol, 2 eq) was added. After stirring the reaction at room temperature for 3 h, it was concentrated in vacuo. The crude material was purified by silica gel chromatography (0-15% MeOH/CH$_2$Cl$_2$, linear gradient, with constant 1% v/v AcOH additive) followed by reverse phase HPLC (10-75% MeCN/H$_2$O, linear gradient, with constant 0.1% v/v TFA additive). The pooled HPLC product fractions were partially concentrated to remove MeCN, diluted with saturated NaHCO$_3$, and extracted with CH$_2$Cl$_2$ (2×). The organic extracts were dried over anhydrous MgSO$_4$, filtered, and evaporated to yield 153 mg (51%) of the title compound 2-(3,6-bis(3-fluoroazetidin-1-yl)xanthylium-9-yl)-4-(dicyano(methoxymethoxy)methyl)-3,5,6-trifluorobenzoate as a dark red-purple solid. $^1$H NMR (CDCl$_3$, 400 MHz) δ 6.75 (d, J=8.6 Hz, 2H), 6.26 (d, J=2.3 Hz, 2H), 6.22 (dd, J=8.6, 2.3 Hz, 2H), 5.45 (dtt, $^2J_{HF}$=56.7 Hz, J=6.1, 3.5 Hz, 2H), 5.14 (s, 2H), 4.31-4.19 (m, 4H), 4.12-4.00 (m, 4H), 3.52 (s, 3H); $^{19}$F NMR (CDCl$_3$, 376 MHz) δ 116.80 (d, J=22.5 Hz, 1F), 126.23 (d, J=20.3 Hz, 1F), 139.30 (dd, J=22.5, 20.5 Hz, 1F), 180.63 (dtt, J$_{FH}$=56.6, 23.8, 18.6 Hz, 2F); Analytical HPLC: $t_R$=11.9 min, 97.2% purity (10-95% MeCN/H$_2$O, linear gradient, with constant 0.1% v/v TFA additive; 20 min run; 1 mL/min flow; ESI; positive ion mode; detection at 575 nm); HRMS (ESI) calcd for $C_{31}H_{22}F_5N_4O_5$ [M+H]$^+$ 625.1505, found 625.1514.

Example 5: 2-(3,6-Bis(3-fluoroazetidin-1-yl)xanthylium-9-yl)-4-((2-(2-(((6-chlorohexyl)oxy)ethoxy)ethyl)carbamoyl)-3,5,6-trifluorobenzoate

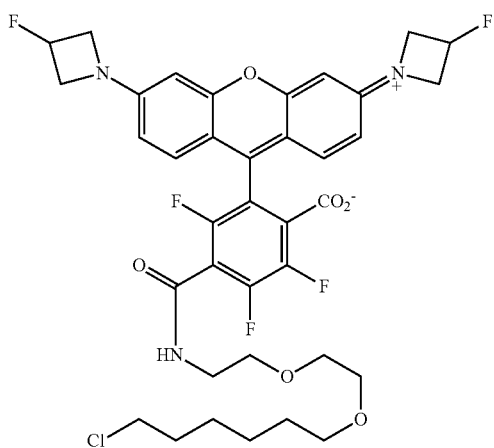

2-(3,6-Bis(3-fluoroazetidin-1-yl)xanthylium-9-yl)-4-(dicyano(methoxymethoxy)methyl)-3,5,6-trifluorobenzoate (Example 4; 80 mg, 0.128 mmol) was taken up in CH$_2$Cl$_2$ (5 mL); triethylsilane (500 μL) was added, followed by trifluoroacetic acid (1 mL). The reaction was stirred at room temperature for 6 h. Toluene (5 mL) was added, and the reaction mixture was concentrated to dryness. The residue was combined with a premixed solution of 2-(2-(((6-chlorohexyl)oxy)ethoxy)ethan-1-amine (TFA salt; 87 mg, 0.256 mmol, 2 eq) and DIEA (223 μL, 1.28 mmol, 10 eq) in DMF (4 mL), and the reaction was stirred at room temperature for 18 h. The solvent was removed by rotary evaporation, and the crude material was purified by reverse phase HPLC (10-75% MeCN/H$_2$O, linear gradient, with constant 0.1% v/v TFA additive). The pooled HPLC product fractions were partially concentrated to remove MeCN, diluted with saturated NaHCO$_3$, and extracted with 10% MeOH/CH$_2$Cl$_2$ (3×). The organic extracts were dried over anhydrous MgSO$_4$, filtered, and evaporated to yield 54.3 mg (57%) of the title compound as a dark red-purple solid. $^1$H NMR (CD$_3$OD, 400 MHz) δ 7.43 (d, J=9.1 Hz, 2H), 6.76 (dd, J=9.2, 2.2 Hz, 2H), 6.62 (d, J=2.2 Hz, 2H), 5.59 (dtt, $^2J_{HF}$=57.0 Hz, J=6.0, 3.0 Hz, 2H), 4.70-4.56 (m, 4H), 4.47-4.34 (m, 4H), 3.69-3.57 (m, 8H), 3.54 (t, J=6.6 Hz, 2H), 3.45 (t, J=6.5 Hz, 2H), 1.78-1.69 (m, 2H), 1.58-1.49 (m, 2H), 1.47-1.30 (m, 4H); $^{19}$F NMR (CD$_3$OD, 376 MHz) δ −117.57 (d, J=15.7 Hz, 1F), −133.24 (d, J=23.1 Hz, 1F), −143.33 (dd, J=23.4, 15.7 Hz, 1F), −180.48 (dtt, J$_{FH}$=56.8, 23.3, 20.3 Hz, 2F); Analytical HPLC: $t_R$=12.4 min, >99% purity (10-95% MeCN/H$_2$O, linear gradient, with constant 0.1% v/v TFA additive; 20 min run; 1 mL/min flow; ESI; positive ion mode; detection at 550 nm); HRMS (ESI) calcd for $C_{37}H_{38}ClF_5N_3O_6$ [M+H]$^+$ 750.2364, found 750.2378.

Example 6: 2-(3,6-Bis(3-fluoroazetidin-1-yl)xanthylium-9-yl)-3,5,6-trifluoro-4-(methoxycarbonyl)benzoate

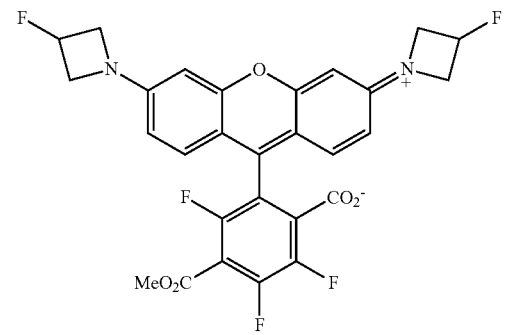

2-(3,6-Bis(3-fluoroazetidin-1-yl)xanthylium-9-yl)-4-(dicyano(methoxymethoxy)methyl)-3,5,6-trifluorobenzoate (Example 4; 40 mg, 64.0 μmol) was taken up in CH$_2$Cl$_2$ (2.5 mL); triethylsilane (250 μL) was added, followed by trifluoroacetic acid (500 μL). The reaction was stirred at room temperature for 6 h. Toluene (3 mL) was added, and the reaction mixture was concentrated to dryness. The residue was combined with a premixed solution of MeOH (64.9 μL, 1.60 mmol, 25 eq) and Et$_3$N (89.3 μL, 0.640 mmol, 10 eq) in CH$_2$Cl$_2$ (3 mL), and the reaction was stirred at room temperature for 18 h. The solvent was removed by rotary evaporation, and the crude material was purified by reverse phase HPLC (20-60% MeCN/H$_2$O, linear gradient, with constant 0.1% v/v TFA additive) to yield 30.7 mg (71%, TFA salt) of the title compound as a dark red-purple solid. $^1$H NMR (CD$_3$OD, 400 MHz) δ 7.37 (d, J=9.1 Hz, 2H), 6.77 (dd, J=9.2, 2.2 Hz, 2H), 6.67 (d, J=2.2 Hz, 2H), 5.57 (dtt, $^2J_{HF}$=56.9 Hz, J=5.9, 2.9 Hz, 2H), 4.70-4.57 (m, 4H), 4.49-4.35 (m, 4H), 3.98 (s, 3H); $^{19}$F NMR (CD$_3$OD, 376 MHz) δ −114.05 (d, J=15.4 Hz, 1F), −129.03 (d, J=21.5 Hz, 1F), −139.23 (dd, J=21.5, 15.4 Hz, 1F), −180.58 (dtt, J$_{FH}$=56.7, 23.2, 20.1 Hz, 2F); Analytical HPLC: $t_R$=11.0 min, >99% purity (10-95% MeCN/H₂O, linear gradient, with constant 0.1% v/v TFA additive; 20 min run; 1 mL/min flow; ESI; positive ion mode; detection at 550 nm); HRMS (ESI) calcd for $C_{28}H_{20}F_5N_2O_5$ [M+H]⁺ 559.1287, found 559.1296.

Example 7: 2-(3,6-Di(azetidin-1-yl)thioxanthylium-9-yl)-4-(dicyano(methoxymethoxy)methyl)-3,5,6-trifluorobenzoate

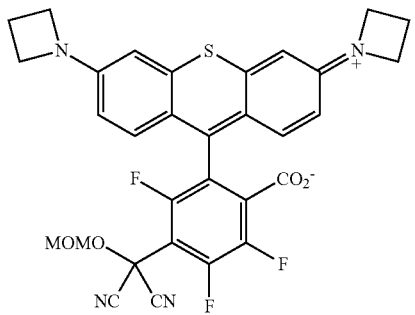

Step 1: An oven-dried round-bottom flask was charged with CuI (604 mg, 3.17 mmol, 0.1 eq) and K₂CO₃ (8.77 g, 63.5 mmol, 2 eq). The flask was sealed and evacuated/backfilled with nitrogen (3×). Isopropanol (125 mL) was added, followed by ethylene glycol (3.54 mL, 63.5 mmol, 2 eq), 3-bromothiophenol (3.28 mL, 31.7 mmol), and 3-bromoiodobenzene (4.45 mL, 34.9 mmol, 1.1 eq). The reaction mixture was stirred at 80° C. for 18 h. It was then diluted with saturated NH₄Cl (200 mL) and EtOAc (200 mL), vigorously stirred for 30 min, and filtered through Celite. The filtrate was separated, and the aqueous layer was extracted again with EtOAc. The combined organics were washed with brine, dried over anhydrous MgSO₄, filtered, and evaporated. Flash chromatography (100% hexanes, linear gradient) afforded 8.93 g (82%) of bis(3-bromophenyl)sulfane as a colorless oil. ¹H NMR (CDCl₃, 400 MHz) δ 7.48 (t, J=1.8 Hz, 2H), 7.40 (ddd, J=7.8, 1.9, 1.2 Hz, 2H), 7.28-7.23 (m, 2H), 7.18 (t, J=7.8 Hz, 2H); ¹³C NMR (CDCl₃, 101 MHz) δ 137.3 (C), 133.8 (CH), 130.79 (CH), 130.75 (CH), 129.8 (CH), 123.3 (C); HRMS (EI) calcd for $C_{12}H_8Br_2S$ [M]⁺. 341.8708, found 341.8732.

Step 2: An oven-dried round-bottom flask was charged with CuI (985 mg, 5.17 mmol, 0.2 eq), L-proline (1.19 g, 10.4 mmol, 0.4 eq), and K₂CO₃ (14.30 g, 103.5 mmol, 4 eq). The flask was sealed and evacuated/backfilled with nitrogen (3×). A solution of the product from Step 1 (8.90 g, 25.9 mmol) in DMSO (100 mL) was added, and the reaction was flushed again with nitrogen (3×). Following the addition of azetidine (10.46 mL, 155.2 mmol, 6 eq), the reaction was stirred at 100° C. for 18 h. It was then cooled to room temperature, diluted with saturated NH₄Cl, and extracted with EtOAc (2×). The combined organic extracts were washed with water and brine, dried over anhydrous MgSO₄, filtered, and concentrated in vacuo. Purification by flash chromatography on silica gel (0-30% EtOAc/hexanes, linear gradient) afforded bis(3-(azetidin-1-yl)phenyl)sulfane (6.08 g, 79%) as a white solid. ¹H NMR (CDCl₃, 400 MHz) δ 7.11 (t, J=7.9 Hz, 2H), 6.68 (ddd, J=7.7, 1.7, 1.0 Hz, 2H), 6.45 (t, J=2.0 Hz, 2H), 6.30 (ddd, J=8.1, 2.3, 0.9 Hz, 2H), 3.83 (t, J=7.2 Hz, 8H), 2.33 (p, J=7.3 Hz, 4H); ¹³C NMR (CDCl₃, 101 MHz) δ 152.8 (C), 136.3 (C), 129.5 (CH), 119.9 (CH), 113.6 (CH), 110.1 (CH), 52.5 (CH₂), 17.1 (CH₂); HRMS (ESI) calcd for $C18H_{21}N_2S$ [M+H]⁺ 297.1420, found 297.1428.

Step 3: The product from Step 2 (6.00 g, 20.2 mmol) was taken up in DMF (100 mL). N-Bromosuccinimide (7.20 g, 40.5 mmol, 2 eq) was added portion-wise over 5 min, and the reaction was then stirred at room temperature for 2 h. The reaction mixture was concentrated in vacuo; the resulting residue was diluted with water and extracted with EtOAc (2×). The combined organic extracts were washed with water and brine, dried over anhydrous MgSO₄, filtered, and concentrated in vacuo. The crude product was triturated with Et₂O, sonicated, and filtered. The filter cake was washed with Et₂O and dried to provide the title compound as a white solid. The filtrate was concentrated, chromatographed on silica gel (0-50% Et₂O/hexanes, linear gradient), and triturated as before to yield additional dibromide product. The two crops of white powder were combined, affording 6.51 g (71%) of bis(5-(azetidin-1-yl)-2-bromophenyl)sulfane. ¹H NMR (CDCl₃, 400 MHz) δ 7.40-7.34 (m, 2H), 6.23-6.18 (m, 4H), 3.76 (t, J=7.3 Hz, 8H), 2.31 (p, J=7.2 Hz, 4H); ¹³C NMR (CDCl₃, 101 MHz) δ 151.9 (C), 135.6 (C), 133.3 (CH), 115.0 (CH), 112.3 (C), 112.1 (CH), 52.4 (CH₂), 16.9 (CH₂); HRMS (ESI) calcd for $C_{18}H_{19}Br_2N_2S$ [M+H]⁺ 452.9630, found 452.9632.

Step 4: A solution of the product from Step 3 (2.00 g, 4.40 mmol) in THF (100 mL) was cooled to −78° C. under nitrogen. tert-Butyllithium (1.7 M in pentane, 11.40 mL, 19.4 mmol, 4.4 eq) was added, and the reaction was stirred at −78° C. for 30 min. It was then warmed to 20° C., and a solution of tetrafluorophthalic anhydride (2.13 g, 9.69 mmol, 2.2 eq) in THF (25 mL) was added dropwise over 30 min via addition funnel. The reaction was allowed to warm to room temperature overnight (18 h). Following the addition of AcOH (1 mL), the mixture was diluted with MeOH, deposited onto Celite, and concentrated to dryness. Silica gel chromatography (0-10% MeOH/CH₂Cl₂, linear gradient, with constant 1% v/v AcOH additive; dry load with Celite) afforded 484 mg (20%) of the acetate salt of 2-(3,6-di (azetidin-1-yl)thioxanthylium-9-yl)-3,4,5,6-tetrafluorobenzoate as a dark purple solid. ¹H NMR (CD₃OD, 400 MHz) δ 7.40 (d, J=9.3 Hz, 2H), 6.83 (d, J=2.3 Hz, 2H), 6.68 (dd, J=9.4, 2.3 Hz, 2H), 4.35-4.22 (m, 8H), 2.54 (p, J=7.6 Hz, 4H); ¹⁹F NMR (CD₃OD, 376 MHz) δ −139.39--139.59 (m, 1F), 140.40--140.62 (m, 1F), 153.89--154.12 (m, 1F), 157.07--157.39 (m, 1F); Analytical HPLC: $t_R$=12.3 min, >99% purity (10-95% MeCN/H₂O, linear gradient, with constant 0.1% v/v TFA additive; 20 min run; 1 mL/min flow; ESI; positive ion mode; detection at 600 nm); HRMS (ESI) calcd for $C_{24}H_{19}F_4N_2O_2S$ [M+H]⁺ 499.1098, found 499.1102.

Step 5: The product from Step 4 (acetate salt; 250 mg, 0.448 mmol) and 2-(methoxymethoxy)malononitrile (56 mg, 0.448 mmol, 1 eq) were combined in DMF (10 mL), and DIEA (234 μL, 1.34 mmol, 3 eq) was added. After stirring the reaction at room temperature for 3 h, it was concentrated in vacuo. The residue was redissolved in MeOH/CH₂Cl₂, deposited onto Celite, and evaporated to dryness. Flash chromatography on silica gel (0-15% MeOH/CH₂Cl₂, linear gradient, with constant 1% v/v AcOH additive; dry load with Celite) afforded the title compound 2-(3,6-di(azetidin-1-yl) thioxanthylium-9-yl)-4-(dicyano(methoxymethoxy) methyl)-3,5,6-trifluorobenzoate as a dark purple solid (164 mg, 55%, acetate salt). ¹H NMR (CD₃OD, 400 MHz) δ 7.38 (d, J=9.4 Hz, 2H), 6.87 (d, J=2.2 Hz, 2H), 6.71 (dd, J=9.4, 2.3 Hz, 2H), 5.21 (s, 2H), 4.31 (t, J=7.7 Hz, 8H), 3.53 (s, 3H), 2.55 (p, J=7.7 Hz, 4H); ¹⁹F NMR (CD₃OD, 376 MHz)

δ −114.32 (d, J=15.0 Hz, 1F), −130.76 (d, J=21.5 Hz, 1F), −143.57 (dd, J=21.8, 15.2 Hz, 1F); Analytical HPLC: $t_R$=12.2 min, >99% purity (10-95% MeCN/H$_2$O, linear gradient, with constant 0.1% v/v TFA additive; 20 min run; 1 mL/min flow; ESI; positive ion mode; detection at 600 nm); HRMS (ESI) calcd for C$_{31}$H$_{24}$F$_3$N$_4$O$_4$S [M+H]$^+$ 605.1465, found 605.1464.

Example 8: 4-((2-(2-((6-Chlorohexyl)oxy)ethoxy)ethyl)carbamoyl)-2-(3,6-di(azetidin-1-yl)thioxanthylium-9-yl)-3,5,6-trifluorobenzoate

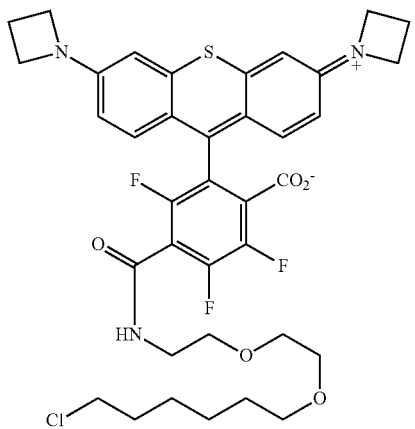

2-(3,6-Di(azetidin-1-yl)thioxanthylium-9-yl)-4-(dicyano(methoxymethoxy)methyl)-3,5,6-trifluorobenzoate (Example 7, acetate salt; 50 mg, 75.2 μmol) was taken up in CH$_2$Cl$_2$ (4 mL); triethylsilane (400 μL) was added, followed by trifluoroacetic acid (800 μL). The reaction was stirred at room temperature for 6 h. Toluene (5 mL) was added, and the reaction mixture was concentrated to dryness. The residue was combined with a premixed solution of 2-(2-((6-chlorohexyl)oxy)ethoxy)ethan-1-amine (TFA salt; 50.8 mg, 0.150 mmol, 2 eq) and DIEA (131 μL, 0.752 mmol, 10 eq) in CH$_2$Cl$_2$ (3 mL), and the reaction was stirred at room temperature for 18 h. The solvent was removed by rotary evaporation, and the crude material was purified by reverse phase HPLC (30-60% MeCN/H$_2$O, linear gradient, with constant 0.1% v/v TFA additive) to afford the title compound as a dark purple solid (28.9 mg, 46%, TFA salt). $^1$H NMR (CD$_3$OD, 400 MHz) δ 9.10 (t, J=5.4 Hz, 1H), 7.39 (d, J=9.3 Hz, 2H), 6.89 (d, J=2.3 Hz, 2H), 6.70 (dd, J=9.4, 2.3 Hz, 2H), 4.32 (t, J=7.7 Hz, 8H), 3.67-3.54 (m, 8H), 3.52 (t, J=6.6 Hz, 2H), 3.42 (t, J=6.5 Hz, 2H), 2.56 (p, J=7.6 Hz, 4H), 1.76-1.67 (m, 2H), 1.54-1.45 (m, 2H), 1.44-1.27 (m, 4H); $^{19}$F NMR (CD$_3$OD, 376 MHz) δ −117.12 (d, J=15.4 Hz, 1F), −133.08 (d, J=22.2 Hz, 1F), −139.93 (dd, J=21.7, 15.8 Hz, 1F); Analytical HPLC: $t_R$=12.5 min, >99% purity (10-95% MeCN/H$_2$O, linear gradient, with constant 0.1% v/v TFA additive; 20 min run; 1 mL/min flow; ESI; positive ion mode; detection at 600 nm); HRMS (ESI) calcd for C$_{37}$H$_{40}$ClF$_3$N$_3$O$_5$S [M+H]$^+$ 730.2324, found 730.2333.

Example 9: 2-(3,6-Di(azetidin-1-yl)thioxanthylium-9-yl)-3,5,6-trifluoro-4-(methoxycarbonyl)benzoate

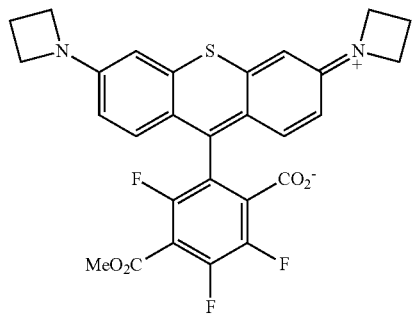

2-(3,6-Di(azetidin-1-yl)thioxanthylium-9-yl)-4-(dicyano(methoxymethoxy)methyl)-3,5,6-trifluorobenzoate (Example 7, acetate salt; 50 mg, 75.2 μmol) was taken up in CH$_2$Cl$_2$ (4 mL); triethylsilane (400 μL) was added, followed by trifluoroacetic acid (800 μL). The reaction was stirred at room temperature for 6 h. Toluene (5 mL) was added, and the reaction mixture was concentrated to dryness. The residue was combined with a premixed solution of MeOH (76.1 μL, 1.88 mmol, 25 eq) and Et$_3$N (105 μL, 0.752 mmol, 10 eq) in CH$_2$Cl$_2$ (3 mL), and the reaction was stirred at room temperature for 18 h. The solvent was removed by rotary evaporation, and the crude material was purified by reverse phase HPLC (30-50% MeCN/H$_2$O, linear gradient, with constant 0.1% v/v TFA additive) to afford the title compound as a dark purple solid (32.1 mg, 65%, TFA salt). $^1$H NMR (CD$_3$OD, 400 MHz) δ 7.38 (d, J=9.4 Hz, 2H), 6.88 (d, J=2.3 Hz, 2H), 6.71 (dd, J=9.4, 2.3 Hz, 2H), 4.31 (t, J=7.7 Hz, 8H), 3.98 (s, 3H), 2.55 (p, J=7.6 Hz, 4H); $^{19}$F NMR (CD$_3$OD, 376 MHz) δ −114.79 (d, J=15.4 Hz, 1F), −130.14 (d, J=21.7 Hz, 1F), −139.89 (dd, J=21.3, 15.6 Hz, 1F); Analytical HPLC: $t_R$=11.4 min, >99% purity (10-95% MeCN/H$_2$O, linear gradient, with constant 0.1% v/v TFA additive; 20 min run; 1 mL/min flow; ESI; positive ion mode; detection at 600 nm); HRMS (ESI) calcd for C$_{28}$H$_{22}$F$_3$N$_2$O$_4$S [M+H]$^+$ 539.1247, found 539.1254.

Example 10: 2-(3,7-Bis(dimethylamino)-5,5-dimethyldibenzo[b,e]silin-10-ylium-10(5H)-yl)-4-(dicyano(methoxymethoxy)methyl)-3,5,6-trifluorobenzoate

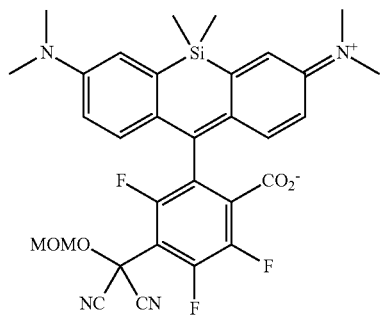

2-(3,7-Bis(dimethylamino)-5,5-dimethyldibenzo[b,e]silin-10-ylium-10(5H)-yl)-3,4,5,6-tetrafluorobenzoate (Grimm, J. B. et al. *ACS Cent. Sci.* 2017, 3, 975-985; 1.50 g, 3.00 mmol) and 2-(methoxymethoxy)malononitrile (378 mg, 3.00 mmol, 1 eq) were combined in DMF (30 mL), and DIEA (1.04 mL, 5.99 mmol, 2 eq) was added. After stirring the reaction at room temperature for 1 h, it was evaporated to dryness. Flash chromatography on silica gel (10-100% EtOAc/hexanes, linear gradient) afforded the title compound as a blue-green solid (1.17 g, 64%). $^1$H NMR (CDCl$_3$, 400 MHz) δ 6.94 (d, J=2.9 Hz, 2H), 6.74 (d, J=8.8 Hz, 2H), 6.62 (dd, J=8.9, 2.9 Hz, 2H), 5.16 (s, 2H), 3.53 (s, 3H), 3.00 (s, 12H), 0.59 (s, 3H), 0.56 (s, 3H); $^{19}$F NMR (CDCl$_3$, 376 MHz) δ −113.66 (d, J=22.7 Hz, 1F), −127.80 (d, J=20.4 Hz, 1F), −139.94 (dd, J=22.6, 20.3 Hz, 1F); Analytical HPLC: $t_R$=12.5 min, >99% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{31}$H$_{30}$F$_3$N$_4$O$_4$Si [M+H]$^+$ 607.1983, found 607.1990.

Example 11: 2-(3,7-Bis(dimethylamino)-5,5-dimethyldibenzo[b,e]silin-10-ylium-10(5H)-yl)-4-((2-(2-((6-chlorohexyl)oxy)ethoxy)ethyl)carbamoyl)-3,5,6-trifluorobenzoate

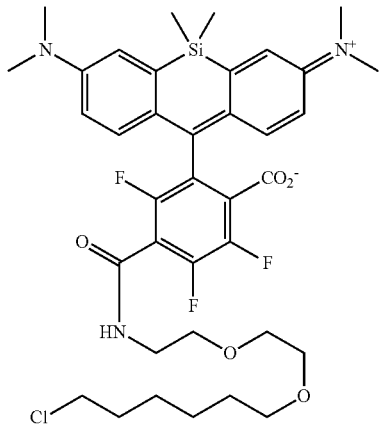

2-(3,7-Bis(dimethylamino)-5,5-dimethyldibenzo[b,e]silin-10-ylium-10(5H)-yl)-4-(dicyano(methoxymethoxy)methyl)-3,5,6-trifluorobenzoate (Example 10; 70 mg, 0.115 mmol) was taken up in CH$_2$Cl$_2$ (4 mL); triethylsilane (400 µL) was added, followed by trifluoroacetic acid (800 µL). The reaction was stirred at room temperature for 18 h. Toluene (5 mL) was added, and the reaction mixture was concentrated to dryness. The residue was combined with a premixed solution of 2-(2-((6-chlorohexyl)oxy)ethoxy) ethan-1-amine (TFA salt; 77.9 mg, 0.231 mmol, 2 eq) and DIEA (201 µL, 1.15 mmol, 10 eq) in CH$_2$Cl$_2$ (3 mL), and the reaction was stirred at room temperature for 2 h. The solvent was removed by rotary evaporation, and the crude material was purified by reverse phase HPLC (30-60% MeCN/H$_2$O, linear gradient, with constant 0.1% v/v TFA additive). The pooled HPLC product fractions were partially concentrated to remove MeCN, diluted with saturated NaHCO$_3$, and extracted with CH$_2$Cl$_2$ (2×). The organic extracts were dried over anhydrous MgSO$_4$, filtered, and evaporated to yield 49.5 mg (59%) of the title compound as a blue-green solid. $^1$H NMR (CDCl$_3$, 400 MHz) δ 6.93 (d, J=2.9 Hz, 2H), 6.81 (d, J=8.9 Hz, 2H), 6.69 (s, 1H), 6.61 (dd, J=8.9, 2.9 Hz, 2H), 3.66-3.58 (m, 6H), 3.54-3.47 (m, 4H), 3.37 (t, J=6.7 Hz, 2H), 2.99 (s, 12H), 1.77-1.68 (m, 2H), 1.53-1.44 (m, 2H), 1.43-1.24 (m, 4H), 0.565 (s, 3H), 0.555 (s, 3H); $^{19}$F NMR (CDCl$_3$, 376 MHz) δ −118.73 (d, J=22.7 Hz, 1F), −133.63 (d, J=21.3 Hz, 1F), −142.40 (t, J=22.1 Hz, 1F); Analytical HPLC: $t_R$=13.2 min, >99% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{37}$H$_{46}$ClF$_3$N$_3$O$_5$Si [M+H]$^+$ 732.2842, found 732.2848.

Example 12: 2-(3,7-Bis(dimethylamino)-5,5-dimethyldibenzo[b,e]silin-10-ylium-10(5H)-yl)-3,5,6-trifluoro-4-(methoxycarbonyl)benzoate 2-(3,7-Bis(dimethylamino)-5,5-dimethyldibenzo[b,e]silin-10-ylium-10(5H)-yl)-4-(dicyano(methoxymethoxy)methyl)-3,5,6-trifluorobenzoate (Example 10; 600 mg, 0.989 mmol) was taken up in CH$_2$Cl$_2$ (30 mL); triethylsilane (3 mL) was added, followed by trifluoroacetic acid (6 mL). The reaction was stirred at room temperature for 18 h. Toluene (15 mL) was added, and the reaction mixture was concentrated to dryness. The residue was combined with a premixed solution of MeOH (1.00 mL, 24.7 mmol, 25 eq) and Et$_3$N (1.38 mL, 9.89 mmol, 10 eq) in CH$_2$Cl$_2$ (20 mL), and the reaction was stirred at room temperature for 30 min. The solvent was removed by rotary evaporation, and the crude material was purified by silica gel chromatography (10-100% EtOAc/hexanes, linear gradient) to yield 392 mg (73%) of the title compound as a yellow-green solid. $^1$H NMR (CDCl$_3$, 400 MHz) δ 6.94 (d, J=2.9 Hz, 2H), 6.78 (d, J=9.0 Hz, 2H), 6.61 (dd, J=8.9, 2.9 Hz, 2H), 3.94 (s, 3H), 2.99 (s, 12H), 0.58 (s, 3H), 0.56 (s, 3H); $^{19}$F NMR (CDCl$_3$, 376 MHz) δ −116.26 (d, J=22.8 Hz, 1F), −131.82 (d, J=20.9 Hz, 1F), −142.43 (dd, J=22.7, 21.0 Hz, 1F); Analytical HPLC: $t_R$=10.3 min, >99% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{28}$H$_{28}$F$_3$N$_2$O$_4$Si [M+H]$^+$ 541.1765, found 541.1769.

Example 13: 2-(3,7-Di(azetidin-1-yl)-5,5-dimethyl-dibenzo[b,e]silin-10-ylium-10(5H)-yl)-4-(dicyano(methoxymethoxy)methyl)-3,5,6-trifluorobenzoate

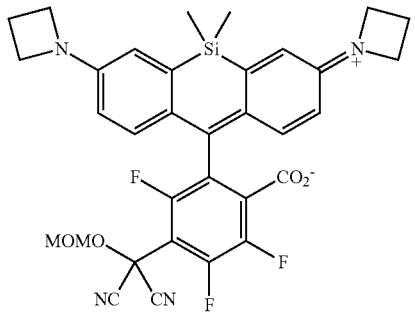

2-(3,7-Di(azetidin-1-yl)-5,5-dimethyldibenzo[b,e]silin-10-ylium-10(5H)-yl)-3,4,5,6-tetrafluorobenzoate (Grimm, J. B. et al. *ACS Cent. Sci.* 2017, 3, 975-985; 72 mg, 0.137 mmol) and DIEA (47.8 µL, 0.275 mmol, 2 eq) were combined in DMF (3 mL), and a solution of 2-(methoxymethoxy)malononitrile (17.3 mg, 0.137 mmol, 1 eq) in DMF (1 mL) was added dropwise. After stirring the reaction at room temperature for 4 h, it was concentrated to dryness. Flash chromatography on silica gel (10-100% EtOAc/hexanes, linear gradient) afforded 44.4 mg (51%) of the title compound as a green foam. $^1$H NMR (CDCl$_3$, 400 MHz) δ 6.70 (d, J=8.7 Hz, 2H), 6.64 (d, J=2.6 Hz, 2H), 6.32 (dd, J=8.7, 2.6 Hz, 2H), 5.16 (s, 2H), 3.93 (t, J=7.2 Hz, 8H), 3.53 (s, 3H), 2.39 (p, J=7.3 Hz, 4H), 0.55 (s, 3H), 0.53 (s, 3H); $^{19}$F NMR (CDCl$_3$, 376 MHz) δ −113.41 (d, J=22.6 Hz, 1F), −127.72 (d, J=20.3 Hz, 1F), −139.78 (dd, J=22.7, 20.2 Hz, 1F); Analytical HPLC: t$_R$=13.0 min, >99% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{33}$H$_{30}$F$_3$N$_4$O$_4$Si [M+H]$^+$ 631.1983, found 631.1989.

Example 14: 4-((2-(2-((6-Chlorohexyl)oxy)ethoxy)ethyl)carbamoyl)-2-(3,7-di(azetidin-1-yl)-5,5-dimethyldibenzo[b,e]silin-10-ylium-10(5H)-yl)-3,5,6-trifluorobenzoate

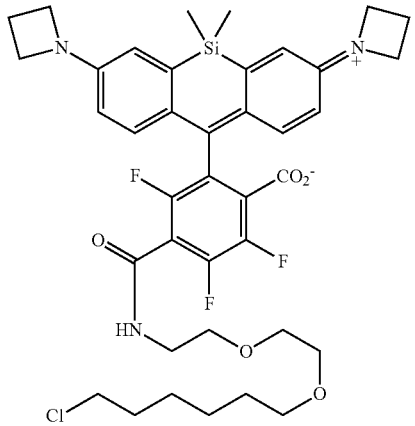

2-(3,7-Di(azetidin-1-yl)-5,5-dimethyldibenzo[b,e]silin-10-ylium-10(5H)-yl)-4-(dicyano(methoxymethoxy)methyl)-3,5,6-trifluorobenzoate (Example 13; 151 mg, 0.239 mmol) was taken up in CH$_2$Cl$_2$ (10 mL); triethylsilane (1 mL) was added, followed by trifluoroacetic acid (2 mL). The reaction was stirred at room temperature for 6 h. Toluene (10 mL) was added, and the reaction mixture was concentrated to dryness. The residue was combined with a premixed solution of 2-(2-((6-chlorohexyl)oxy)ethoxy)ethan-1-amine (TFA salt; 162 mg, 0.479 mmol, 2 eq) and DIEA (417 µL, 2.39 mmol, 10 eq) in CH$_2$Cl$_2$ (10 mL), and the reaction was stirred at room temperature for 18 h. The solvent was removed by rotary evaporation, and the crude material was purified by reverse phase HPLC (10-95% MeCN/H$_2$O, linear gradient, with constant 0.1% v/v TFA additive). The pooled HPLC product fractions were partially concentrated to remove MeCN, diluted with saturated NaHCO$_3$, and extracted with CH$_2$Cl$_2$ (2×). The organic extracts were dried over anhydrous MgSO$_4$, filtered, and evaporated to yield 114 mg (63%) of the title compound as a blue solid. $^1$H NMR (CDCl$_3$, 400 MHz) δ 6.78 (d, J=8.6 Hz, 2H), 6.74 (b s, 1H), 6.63 (d, J=2.7 Hz, 2H), 6.32 (dd, J=8.7, 2.6 Hz, 2H), 3.92 (t, J=7.3 Hz, 8H), 3.66-3.59 (m, 6H), 3.55-3.48 (m, 4H), 3.37 (t, J=6.7 Hz, 2H), 2.38 (p, J=7.3 Hz, 4H), 1.78-1.69 (m, 2H), 1.53-1.45 (m, 2H), 1.43-1.25 (m, 4H), 0.53 (s, 6H); $^{19}$F NMR (CDCl$_3$, 376 MHz) δ −118.50 (d, J=22.5 Hz, 1F), −133.47 (d, J=21.6 Hz, 1F), −142.24 (t, J=22.1 Hz, 1F); Analytical HPLC: t$_R$=13.6 min, >99% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{39}$H$_{46}$ClF$_3$N$_3$O$_5$Si [M+H]$^+$ 756.2842, found 756.2856.

Example 15: 4-((4-(((2-Amino-9H-purin-6-yl)oxy)methyl)benzyl)carbamoyl)-2-(3,7-di(azetidin-1-yl)-5,5-dimethyldibenzo[b,e]silin-10-ylium-10(5H)-yl)-3,5,6-trifluorobenzoate

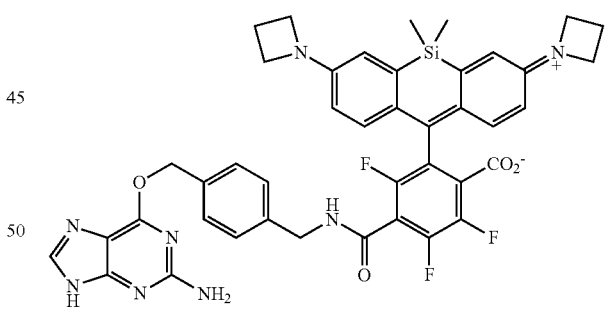

2-(3,7-Di(azetidin-1-yl)-5,5-dimethyldibenzo[b,e]silin-10-ylium-10(5H)-yl)-4-(dicyano(methoxymethoxy)methyl)-3,5,6-trifluorobenzoate (Example 13; 50 mg, 79.3 µmol) was taken up in CH$_2$Cl$_2$ (4 mL); triethylsilane (0.4 mL) was added, followed by trifluoroacetic acid (0.8 mL). The reaction was stirred at room temperature for 6 h. Toluene (5 mL) was added, and the reaction mixture was concentrated to dryness. The residue was combined with a premixed suspension of 6-((4-(aminomethyl)benzyl)oxy)-9H-purin-2-amine (42.9 mg, 0.159 mmol, 2 eq) and DIEA (138 µL, 0.793 mmol, 10 eq) in DMF (5 mL), and the reaction was stirred at room temperature for 18 h. The solvent was removed by rotary evaporation, and the crude material was purified by reverse phase HPLC (10-75% MeCN/H$_2$O, linear gradient, with constant 0.1% v/v TFA additive). The pooled HPLC product fractions were partially concentrated to remove MeCN, neutralized with saturated NaHCO$_3$, and extracted with CH$_2$Cl$_2$ (2×). The organic extracts were dried over anhydrous MgSO$_4$, filtered, and evaporated to yield 35.8 mg (56%) of the title compound as a blue solid. $^1$H NMR (CD$_3$OD, 400 MHz) δ 7.82 (s, 1H), 7.50 (d, J=8.1 Hz, 2H), 7.35 (d, J=8.1 Hz, 2H), 6.92 (dd, J=8.9, 0.8 Hz, 2H), 6.76 (d, J=2.6 Hz, 2H), 6.36 (dd, J=8.9, 2.6 Hz, 2H), 5.53 (s, 2H), 4.57 (s, 2H), 4.03 (t, J=7.4 Hz, 8H), 2.42 (p, J=7.3 Hz, 4H), 0.52 (s, 3H), 0.49 (s, 3H); $^{19}$F NMR (CD$_3$OD, 376 MHz) δ −118.98 (d, J=20.2 Hz, 1F), −135.29 (d, J=21.4 Hz, 1F), −143.71 (t, J=21.0 Hz, 1F); Analytical HPLC: $t_R$=10.2 min, >99% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{42}$H$_{38}$F$_3$N$_8$O$_4$Si [M+H]$^+$ 803.2732, found 803.2738.

Example 16: 4-((4-(((2-Amino-6-chloropyrimidin-4-yl)oxy)methyl)benzyl)carbamoyl)-2-(3,7-di(azetidin-1-yl)-5,5-dimethyldibenzo[b,e]silin-10-ylium-10(5H)-yl)-3,5,6-trifluorobenzoate

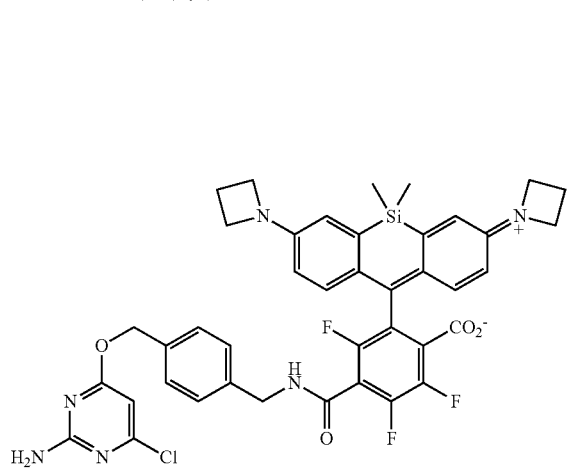

2-(3,7-Di(azetidin-1-yl)-5,5-dimethyldibenzo[b,e]silin-10-ylium-10(5H)-yl)-4-(dicyano(methoxymethoxy)methyl)-3,5,6-trifluorobenzoate (Example 13; 50 mg, 79.3 μmol) was taken up in CH$_2$Cl$_2$ (4 mL); triethylsilane (0.4 mL) was added, followed by trifluoroacetic acid (0.8 mL). The reaction was stirred at room temperature for 6 h. Toluene (5 mL) was added, and the reaction mixture was concentrated to dryness. The residue was combined with a premixed solution of 4-((4-(aminomethyl)benzyl)oxy)-6-chloropyrimidin-2-amine (42.0 mg, 0.159 mmol, 2 eq) and DIEA (138 μL, 0.793 mmol, 10 eq) in DMF (5 mL), and the reaction was stirred at room temperature for 18 h. The solvent was removed by rotary evaporation, and the crude material was purified by reverse phase HPLC (10-75% MeCN/H$_2$O, linear gradient, with constant 0.1% v/v TFA additive). The pooled HPLC product fractions were partially concentrated to remove MeCN, neutralized with saturated NaHCO$_3$, and extracted with CH$_2$Cl$_2$ (2×). The organic extracts were dried over anhydrous MgSO$_4$, filtered, and evaporated to yield 36.9 mg (58%) of the title compound as a blue solid. $^1$H NMR (CD$_3$OD, 400 MHz) δ 7.39 (d, J=8.2 Hz, 2H), 7.34 (d, J=8.2 Hz, 2H), 6.92 (dd, J=8.9, 0.7 Hz, 2H), 6.77 (d, J=2.6 Hz, 2H), 6.37 (dd, J=8.9, 2.6 Hz, 2H), 6.09 (s, 1H), 5.33 (s, 2H), 4.56 (s, 2H), 4.04 (t, J=7.4 Hz, 8H), 2.43 (p, J=7.3 Hz, 4H), 0.52 (s, 3H), 0.50 (s, 3H); $^{19}$F NMR (CD$_3$OD, 376 MHz) δ −119.06 (d, J=20.3 Hz, 1F), −135.33 (d, J=21.6 Hz, 1F), −143.70 (t, J=20.8 Hz, 1F); Analytical HPLC: $t_R$=13.1 min, >99% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{41}$H$_{37}$ClF$_3$N$_6$O$_4$Si [M+H]$^+$ 797.2281, found 797.2297.

Example 17: 2-(3,7-di(azetidin-1-yl)-5,5-dimethyl-dibenzo[b,e]silin-10-ylium-10(5H)-yl)-3,5,6-trifluoro-4-(methoxycarbonyl)benzoate

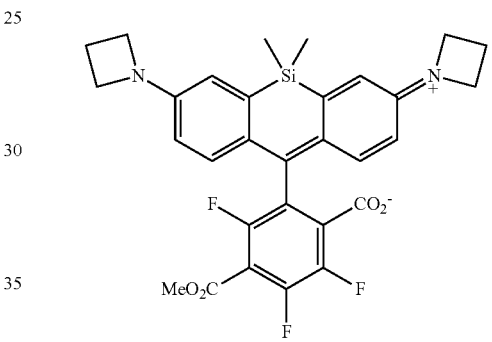

2-(3,7-Di(azetidin-1-yl)-5,5-dimethyldibenzo[b,e]silin-10-ylium-10(5H)-yl)-4-(dicyano(methoxymethoxy)methyl)-3,5,6-trifluorobenzoate (Example 13; 140 mg, 0.222 mmol) was taken up in CH$_2$Cl$_2$ (10 mL); triethylsilane (1 mL) was added, followed by trifluoroacetic acid (2 mL). The reaction was stirred at room temperature for 18 h. Toluene (10 mL) was added, and the reaction mixture was concentrated to dryness. The residue was combined with a premixed solution of MeOH (224 μL, 5.55 mmol, 25 eq) and Et$_3$N (309 μL, 2.22 mmol, 10 eq) in CH$_2$Cl$_2$ (6 mL), and the reaction was stirred at room temperature for 30 min. The solvent was removed by rotary evaporation, and the crude material was purified by silica gel chromatography (10-100% EtOAc/hexanes, linear gradient) to yield 97 mg (77%) of the title compound as a blue-green solid. $^1$H NMR (CDCl$_3$, 400 MHz) δ 6.74 (d, J=8.6 Hz, 2H), 6.64 (d, J=2.7 Hz, 2H), 6.31 (dd, J=8.7, 2.6 Hz, 2H), 3.95 (s, 3H), 3.92 (t, J=7.2 Hz, 8H), 2.38 (p, J=7.3 Hz, 4H), 0.545 (s, 3H), 0.538 (s, 3H); $^{19}$F NMR (CDCl$_3$, 376 MHz) δ −116.04 (d, J=22.6 Hz, 1F), −131.67 (d, J=20.9 Hz, 1F), −142.29 (dd, J=22.9, 20.9 Hz, 1F); Analytical HPLC: $t_R$=12.6 min, >99% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{30}$H$_{28}$F$_3$N$_2$O$_4$Si [M+H]$^+$ 565.1765, found 565.1774.

Example 18: 2-(3,7-Bis(azetidin-1-yl-d₆)-5,5-dimethyldibenzo[b,e]silin-10-ylium-10(5H)-yl)-4-(dicyano(methoxymethoxy)methyl)-3,5,6-trifluorobenzoate

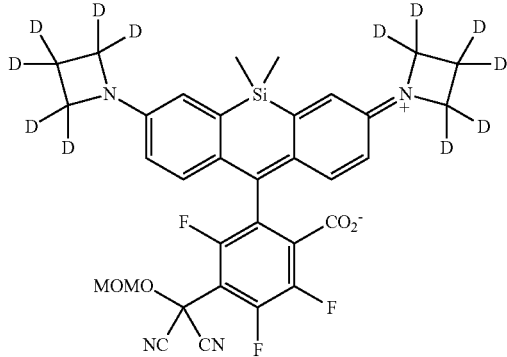

Step 1: A vial was charged with bis(3-bromophenyl)dimethylsilane (1.00 g, 2.70 mmol), Pd₂dba₃ (247 mg, 0.270 mmol, 0.1 eq), XPhos (386 mg, 0.810 mmol, 0.3 eq), and Cs₂CO₃ (2.46 g, 7.56 mmol, 2.8 eq). The vial was sealed and evacuated/backfilled with nitrogen (3×). Dioxane (10 mL) was added, and the reaction was flushed again with nitrogen (3×). Following the addition of azetidine-2,2,3,3,4,4-d₆ (409 mg, 6.48 mmol, 2.4 eq), the reaction was stirred at 100° C. for 4 h. It was then cooled to room temperature, filtered through Celite with CH₂Cl₂, and concentrated to dryness. The resulting residue was purified by flash chromatography (0-10% EtOAc/toluene, linear gradient) to provide 838 mg (93%) of bis(3-(azetidin-1-yl-d₆)phenyl)dimethylsilane as a pale yellow, gummy oil. $^1$H NMR (CDCl₃, 400 MHz) δ 7.22-7.16 (m, 2H), 6.89 (dt, J=7.2, 1.1 Hz, 2H), 6.62-6.58 (m, 2H), 6.46 (ddd, J=8.1, 2.5, 1.1 Hz, 2H), 0.50 (s, 6H); $^{13}$C NMR (CDCl₃, 101 MHz) δ 151.8 (C), 138.9 (C), 128.3 (CH), 123.4 (CH), 116.9 (CH), 112.3 (CH), -2.1 (CH₃); HRMS (ESI) calcd for C₂₀H₁₅D₁₂N₂Si [M+H]⁺ 335.2691, found 335.2695.

Step 2: The product from Step 1 (720 mg, 2.15 mmol) was taken up in DMF (11 mL). N-Bromosuccinimide (766 mg, 4.30 mmol, 2 eq) was added portion-wise over ~5 min, and the reaction was then stirred at room temperature for 2 h. The resulting white suspension was concentrated to remove DMF, diluted with water, and extracted with CH₂Cl₂ (2×). The combined organic extracts were washed with water and brine, dried over anhydrous MgSO₄, filtered, and concentrated in vacuo. The crude product (an off-white solid) was triturated with Et₂O (~25 mL), sonicated for 2 min, and filtered. The filter cake was washed with Et₂O and hexanes and dried to provide bis(5-(azetidin-1-yl-d₆)-2-bromophenyl)dimethylsilane as a white solid (879 mg, 83%). $^1$H NMR (CDCl₃, 400 MHz) δ 7.30 (d, J=8.5 Hz, 2H), 6.51 (d, J=2.9 Hz, 2H), 6.31 (dd, J=8.5, 2.9 Hz, 2H), 0.71 (s, 6H); $^{13}$C NMR (CDCl₃, 101 MHz) δ 150.7 (C), 138.9 (C), 132.9 (CH), 120.4 (CH), 117.5 (C), 114.2 (CH), -0.9 (CH₃); HRMS (ESI) calcd for C₂₀H₁₃D₁₂Br₂N₂Si [M+H]⁺ 491.0901, found 491.0914.

Step 3: A solution of the product from Step 2 (1.00 g, 2.03 mmol) in THF (60 mL) was cooled to -78° C. under nitrogen. tert-Butyllithium (1.7 M in pentane, 5.26 mL, 8.94 mmol, 4.4 eq) was added, and the reaction was stirred at -78° C. for 30 min. It was then warmed to -10° C. before adding a solution of MgBr₂·OEt₂ (1.15 g, 4.47 mmol, 2.2 eq) in THF (20 mL). After an additional 30 min at -10° C., a solution of tetrafluorophthalic anhydride (983 mg, 4.47 mmol, 2.2 eq) in THF (20 mL) was added dropwise over 30 min via addition funnel. The reaction was then allowed to warm to room temperature overnight (18 h). It was subsequently diluted with saturated NH₄Cl and water and extracted with EtOAc (2×). The combined organic extracts were washed with saturated NaHCO₃ and brine, dried over anhydrous MgSO₄, filtered, and concentrated in vacuo. Silica gel chromatography (0-50% EtOAc/hexanes, linear gradient) afforded 542 mg (50%) of 2-(3,7-bis(azetidin-1-yl-d₆)-5,5-dimethyldibenzo[b,e]silin-10-ylium-10(5H)-yl)-3,4,5,6-tetrafluorobenzoate as a light blue-green solid. $^1$H NMR (CDCl₃, 400 MHz) δ 6.74 (dd, J=8.7, 1.2 Hz, 2H), 6.64 (d, J=2.6 Hz, 2H), 6.31 (dd, J=8.6, 2.7 Hz, 2H), 0.55 (s, 3H), 0.53 (s, 3H); $^{19}$F NMR (CDCl₃, 376 MHz) δ -138.96--139.11 (m, 1F), -139.22 (td, J=19.6, 7.7 Hz, 1F), -143.97--144.16 (m, 1F), -151.89--152.04 (m, 1F); Analytical HPLC: $t_R$=13.4 min, 98.5% purity (10-95% MeCN/H₂O, linear gradient, with constant 0.1% v/v TFA additive; 20 min run; 1 mL/min flow; ESI; positive ion mode; detection at 675 nm); HRMS (ESI) calcd for C₂₈H₁₃D₁₂F₄N₂O₂Si [M+H]⁺ 537.2369, found 537.2378.

Step 4: The product from Step 3 (400 mg, 0.745 mmol) and 2-(methoxymethoxy)malononitrile (94.0 mg, 0.745 mmol, 1 eq) were combined in DMF (6 mL), and DIEA (260 µL, 1.49 mmol, 2 eq) was added. After stirring the reaction at room temperature for 1 h, it was concentrated in vacuo and purified by silica gel chromatography (10-100% EtOAc/hexanes, linear gradient) to yield 248 mg (52%) of the title compound 2-(3,7-bis(azetidin-1-yl-d₆)-5,5-dimethyldibenzo[b,e]silin-10-ylium-10(5H)-yl)-4-(dicyano(methoxymethoxy)methyl)-3,5,6-trifluorobenzoate as a blue-green solid. $^1$H NMR (CDCl₃, 400 MHz) δ 6.70 (dd, J=8.6, 1.3 Hz, 2H), 6.64 (d, J=2.6 Hz, 2H), 6.32 (dd, J=8.7, 2.7 Hz, 2H), 5.16 (s, 2H), 3.52 (s, 3H), 0.55 (s, 3H), 0.53 (s, 3H); $^{19}$F NMR (CDCl₃, 376 MHz) δ -113.41 (d, J=22.6 Hz, 1F), -127.73 (dd, J=20.4, 2.0 Hz, 1F), -139.78 (dd, J=22.7, 20.2 Hz, 1F); Analytical HPLC: $t_R$=12.9 min, >99% purity (10-95% MeCN/H₂O, linear gradient, with constant 0.1% v/v TFA additive; 20 min run; 1 mL/min flow; ESI; positive ion mode; detection at 675 nm); HRMS (ESI) calcd for C₃₃H₁₈D₁₂F₃N₄O₄Si [M+H]⁺ 643.2736, found 643.2749.

Example 19: 2-(3,7-Bis(azetidin-1-yl-d$_6$)-5,5-dimethyldibenzo[b,e]silin-10-ylium-10(5H)-yl)-4-((2-(2-((6-chlorohexyl)oxy)ethoxy)ethyl)carbamoyl)-3,5,6-trifluorobenzoate

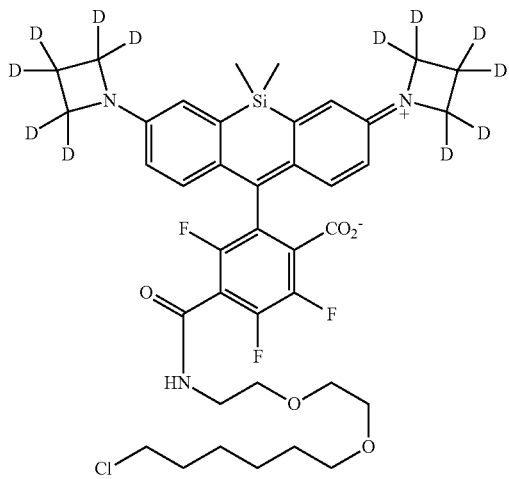

2-(3,7-Bis(azetidin-1-yl-d$_6$)-5,5-dimethyldibenzo[b,e]silin-10-ylium-10(5H)-yl)-4-(dicyano(methoxymethoxy)methyl)-3,5,6-trifluorobenzoate (Example 18; 75 mg, 0.117 mmol) was taken up in CH$_2$Cl$_2$ (4 mL); triethylsilane (0.4 mL) was added, followed by trifluoroacetic acid (0.8 mL). The reaction was stirred at room temperature for 6 h. Toluene (5 mL) was added, and the reaction mixture was concentrated to dryness. The residue was combined with a premixed solution of 2-(2-((6-chlorohexyl)oxy)ethoxy)ethan-1-amine (TFA salt; 78.8 mg, 0.233 mmol, 2 eq) and DIEA (203 μL, 1.17 mmol, 10 eq) in CH$_2$Cl$_2$ (4 mL), and the reaction was stirred at room temperature for 18 h. The solvent was removed by rotary evaporation, and the crude material was purified by reverse phase HPLC (30-60% MeCN/H$_2$O, linear gradient, with constant 0.1% v/v TFA additive). The pooled HPLC product fractions were partially concentrated to remove MeCN, diluted with saturated NaHCO$_3$, and extracted with CH$_2$Cl$_2$ (2×). The organic extracts were dried over anhydrous MgSO$_4$, filtered, and evaporated to yield 51.5 mg (57%) of the title compound as a blue-green solid. $^1$H NMR (CD$_3$OD, 400 MHz) δ 6.93 (dd, J=8.9, 1.2 Hz, 2H), 6.77 (d, J=2.6 Hz, 2H), 6.38 (dd, J=8.9, 2.6 Hz, 2H), 3.65-3.53 (m, 8H), 3.50 (t, J=6.6 Hz, 2H), 3.42 (t, J=6.5 Hz, 2H), 1.74-1.66 (m, 2H), 1.55-1.46 (m, 2H), 1.43-1.28 (m, 4H), 0.54 (s, 3H), 0.50 (s, 3H); $^{19}$F NMR (CD$_3$OD, 376 MHz) δ −118.85 (d, J=20.4 Hz, 1F), −135.23 (dd, J=21.6, 2.1 Hz, 1F), −143.85 (t, J=21.0 Hz, 1F); Analytical HPLC: t$_R$=13.5 min, >99% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{39}$H$_{34}$D$_{12}$ClF$_3$N$_3$O$_5$Si [M+H]$^+$ 768.3595, found 768.3613.

Example 20: 4-((4-(((2-Amino-9H-purin-6-yl)oxy)methyl)benzyl)carbamoyl)-2-(3,7-bis(azetidin-1-yl-d$_6$)-5,5-dimethyldibenzo[b,e]silin-10-ylium-10(5H)-yl)-3,5,6-trifluorobenzoate

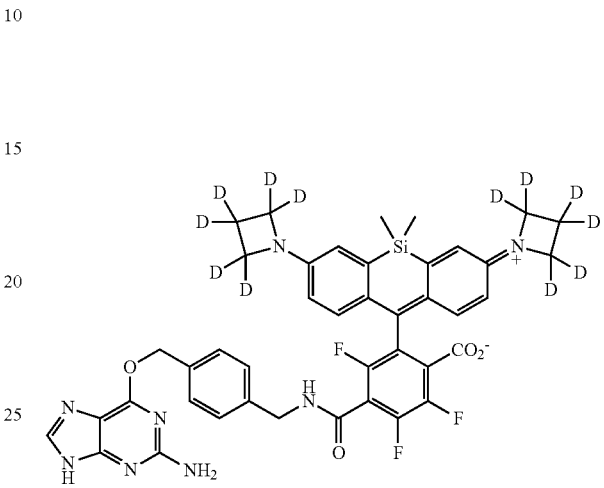

2-(3,7-Bis(azetidin-1-yl-d$_6$)-5,5-dimethyldibenzo[b,e]silin-10-ylium-10(5H)-yl)-4-(dicyano(methoxymethoxy)methyl)-3,5,6-trifluorobenzoate (Example 18; 75 mg, 0.117 mmol) was taken up in CH$_2$Cl$_2$ (4 mL); triethylsilane (0.4 mL) was added, followed by trifluoroacetic acid (0.8 mL). The reaction was stirred at room temperature for 6 h. Toluene (5 mL) was added, and the reaction mixture was concentrated to dryness. The residue was combined with a premixed suspension of 6-((4-(aminomethyl)benzyl)oxy)-9H-purin-2-amine (63.1 mg, 0.233 mmol, 2 eq) and DIEA (203 μL, 1.17 mmol, 10 eq) in DMF (4 mL), and the reaction was stirred at room temperature for 18 h. The solvent was removed by rotary evaporation, and the crude material was purified by reverse phase HPLC (20-50% MeCN/H$_2$O, linear gradient, with constant 0.1% v/v TFA additive). The pooled HPLC product fractions were partially concentrated to remove MeCN, neutralized with saturated NaHCO$_3$, and extracted with CH$_2$Cl$_2$ (2×). The organic extracts were dried over anhydrous MgSO$_4$, filtered, and evaporated to yield 46.3 mg (49%) of the title compound as a blue solid. $^1$H NMR (CD$_3$OD, 400 MHz) δ 7.82 (s, 1H), 7.50 (d, J=8.2 Hz, 2H), 7.36 (d, J=8.2 Hz, 2H), 6.93 (dd, J=8.9, 1.1 Hz, 2H), 6.76 (d, J=2.6 Hz, 2H), 6.36 (dd, J=8.9, 2.6 Hz, 2H), 5.53 (s, 2H), 4.57 (s, 2H), 0.52 (s, 3H), 0.49 (s, 3H); $^{19}$F NMR (CD$_3$OD, 376 MHz) δ −119.01 (d, J=20.1 Hz, 1F), −135.33 (dd, J=21.5, 1.5 Hz, 1F), −143.74 (t, J=20.8 Hz, 1F); Analytical HPLC: t$_R$=10.3 min, >99% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{42}$H$_{26}$D$_{12}$F$_3$N$_8$O$_4$Si [M+H]$^+$ 815.3485, found 815.3492.

Example 21: 4-(Dicyano(methoxymethoxy)methyl)-2-(5,5-dimethyl-3,7-di(pyrrolidin-1-yl)dibenzo[b,e]silin-10-ylium-10(5H)-yl)-3,5,6-trifluorobenzoate

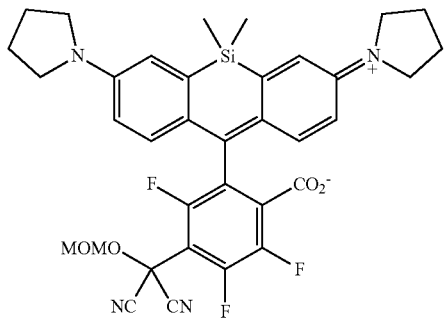

Step 1: A vial was charged with bis(3-bromophenyl)dimethylsilane (1.00 g, 2.70 mmol), Pd$_2$dba$_3$ (247 mg, 0.270 mmol, 0.1 eq), XPhos (386 mg, 0.810 mmol, 0.3 eq), and Cs$_2$CO$_3$ (2.46 g, 7.56 mmol, 2.8 eq). The vial was sealed and evacuated/backfilled with nitrogen (3×). Dioxane (10 mL) was added, and the reaction was flushed again with nitrogen (3×). Following the addition of pyrrolidine (541 μL, 6.48 mmol, 2.4 eq), the reaction was stirred at 100° C. for 18 h. It was then cooled to room temperature, filtered through Celite with CH$_2$Cl$_2$, and concentrated to dryness. The resulting residue was purified by flash chromatography (0-10% Et$_2$O/hexanes, linear gradient, with constant 0.1% v/v Et$_3$N additive) to provide 659 mg (70%) of dimethylbis(3-(pyrrolidin-1-yl)phenyl)silane as a white solid. $^1$H NMR (CDCl$_3$, 400 MHz) δ 7.21 (dd, J=8.2, 7.2 Hz, 2H), 6.84 (dt, J=7.2, 1.1 Hz, 2H), 6.75 (dd, J=2.7, 1.0 Hz, 2H), 6.57 (ddd, J=8.3, 2.6, 1.0 Hz, 2H), 3.32-3.20 (m, 8H), 2.03-1.90 (m, 8H), 0.52 (s, 6H); $^{13}$C NMR (CDCl$_3$, 101 MHz) δ 147.4 (C), 139.2 (C), 128.6 (CH), 121.6 (CH), 117.3 (CH), 112.5 (CH), 47.7 (CH$_2$), 25.6 (CH$_2$), −2.0 (CH$_3$); HRMS (ESI) calcd for C$_{22}$H$_{31}$N$_2$Si [M+H]$^+$ 351.2251, found 351.2251.

Step 2: The product from Step 1 (1.15 g, 3.28 mmol) was taken up in DMF (40 mL). N-Bromosuccinimide (1.17 g, 6.56 mmol, 2 eq) was added portion-wise over 2-3 min, and the reaction was then stirred at room temperature for 4 h. The reaction mixture was concentrated to remove DMF, diluted with water, and extracted with CH$_2$Cl$_2$ (2×). The combined organic extracts were washed with brine, dried over anhydrous MgSO$_4$, filtered, and concentrated in vacuo. The crude was dissolved in a minimum amount of CH$_2$Cl$_2$, diluted with hexanes, and gently concentrated until a pink solid precipitated. The resulting suspension was filtered; the filter cake was washed with Et$_2$O and dried. The solid was further purified by silica gel chromatography (20-100% CH$_2$Cl$_2$/hexanes, linear gradient) to yield 695 mg (42%) of bis(2-bromo-5-(pyrrolidin-1-yl)phenyl)dimethylsilane as a white solid. $^1$H NMR (CDCl$_3$, 400 MHz) δ 7.32 (d, J=8.6 Hz, 2H), 6.67 (d, J=3.1 Hz, 2H), 6.42 (dd, J=8.7, 3.1 Hz, 2H), 3.25-3.16 (m, 8H), 2.03-1.92 (m, 8H), 0.74 (s, 6H); $^{13}$C NMR (CDCl$_3$, 101 MHz) δ 146.3 (C), 139.0 (C), 133.1 (CH), 120.8 (CH), 115.5 (C), 114.3 (CH), 47.7 (CH$_2$), 25.6 (CH$_2$), −0.8 (CH$_3$); HRMS (ESI) calcd for C$_{22}$H$_{29}$Br$_2$N$_2$Si [M+H]$^+$ 507.0461, found 507.0464.

Step 3: A solution of the product from Step 2 (600 mg, 1.18 mmol) in THF (40 mL) was cooled to −78° C. under nitrogen. tert-Butyllithium (1.7 M in pentane, 3.05 mL, 5.19 mmol, 4.4 eq) was added, and the reaction was stirred at −78° C. for 30 min. It was then warmed to −10° C. before adding a solution of MgBr$_2$·OEt$_2$ (670 mg, 2.59 mmol, 2.2 eq) in THF (10 mL). After an additional 30 min at −10° C., a solution of tetrafluorophthalic anhydride (571 mg, 2.59 mmol, 2.2 eq) in THF (10 mL) was added dropwise over 30 min via addition funnel. The reaction was then allowed to warm to room temperature overnight (18 h). It was subsequently diluted with saturated NH$_4$Cl and water and extracted with EtOAc (2×). The combined organic extracts were washed with saturated NaHCO$_3$ and brine, dried over anhydrous MgSO$_4$, filtered, and concentrated in vacuo. Silica gel chromatography (0-75% EtOAc/hexanes, linear gradient) afforded 284 mg (44%) of 2-(5,5-dimethyl-3,7-di(pyrrolidin-1-yl)dibenzo[b,e]silin-10-ylium-10(5H)-yl)-3,4,5,6-tetrafluorobenzoate as a blue solid. $^1$H NMR (CDCl$_3$, 400 MHz) δ 6.78 (d, J=2.8 Hz, 2H), 6.77 (d, J=9.0 Hz, 2H), 6.45 (dd, J=8.8, 2.8 Hz, 2H), 3.37-3.26 (m, 8H), 2.06-1.95 (m, 8H), 0.58 (s, 3H), 0.55 (s, 3H); $^{19}$F NMR (CDCl$_3$, 376 MHz) δ −139.35--139.62 (m, 2F), −144.18--144.36 (m, 1F), −152.27--152.43 (m, 1F); Analytical HPLC: t$_R$=13.5 min, 98.1% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{30}$H$_{29}$F$_4$N$_2$O$_2$Si [M+H]$^+$ 553.1929, found 553.1937.

Step 4: The product from Step 3 (220 mg, 0.398 mmol) and 2-(methoxymethoxy)malononitrile (50.2 mg, 0.398 mmol, 1 eq) were combined in DMF (5 mL), and DIEA (139 μL, 0.796 mmol, 2 eq) was added. After stirring the reaction at room temperature for 2 h, it was concentrated in vacuo and purified by silica gel chromatography (10-100% EtOAc/hexanes, linear gradient) to yield 115 mg (44%) of the title compound 4-(dicyano(methoxymethoxy)methyl)-2-(5,5-dimethyl-3,7-di(pyrrolidin-1-yl)dibenzo[b,e]silin-10-ylium-10(5H)-yl)-3,5,6-trifluorobenzoate as a blue-green solid. $^1$H NMR (CDCl$_3$, 400 MHz) δ 6.78 (d, J=2.7 Hz, 2H), 6.73 (dd, J=8.8, 1.1 Hz, 2H), 6.47 (dd, J=8.9, 2.7 Hz, 2H), 5.16 (s, 2H), 3.53 (s, 3H), 3.39-3.27 (m, 8H), 2.08-1.95 (m, 8H), 0.57 (s, 3H), 0.55 (s, 3H); $^{19}$F NMR (CDCl$_3$, 376 MHz) δ −113.90 (d, J=22.9 Hz, 1F), −128.11 (d, J=20.3 Hz, 1F), −140.20 (dd, J=22.8, 20.2 Hz, 1F); Analytical HPLC: t$_R$=13.3 min, 98.7% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{35}$H$_{34}$F$_3$N$_4$O$_4$Si [M+H]$^+$ 659.2296, found 659.2302.

Example 22: 4-((2-(2-((6-Chlorohexyl)oxy)ethoxy)ethyl)carbamoyl)-2-(5,5-dimethyl-3,7-di(pyrrolidin-1-yl)dibenzo[b,e]silin-10-ylium-10(5H)-yl)-3,5,6-trifluorobenzoate Example 23: 4-(Dicyano(methoxymethoxy)methyl)-2-(5,5-dimethyl-3,7-bis(pyrrolidin-1-yl-$d_8$)dibenzo[b,e]silin-10-ylium-10(5H)-yl)-3,5,6-trifluorobenzoate

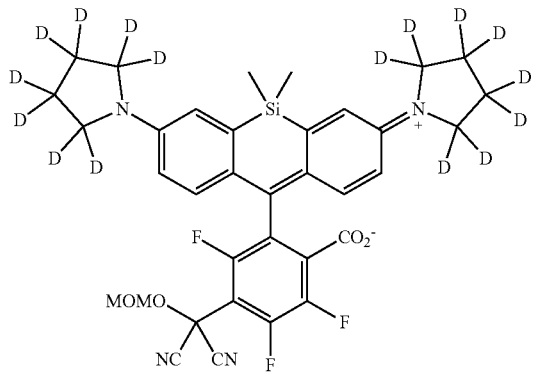

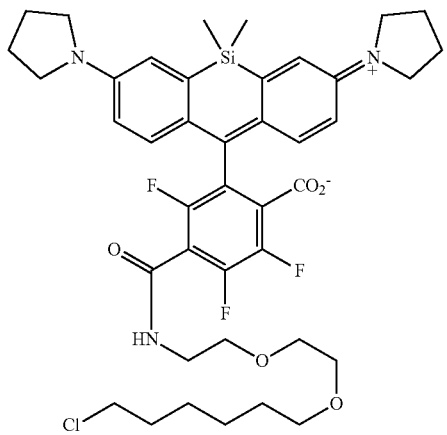

4-(Dicyano(methoxymethoxy)methyl)-2-(5,5-dimethyl-3,7-di(pyrrolidin-1-yl)dibenzo[b,e]silin-10-ylium-10(5H)-yl)-3,5,6-trifluorobenzoate (Example 21; 50 mg, 75.9 μmol) was taken up in $CH_2Cl_2$ (3 mL); triethylsilane (300 μL) was added, followed by trifluoroacetic acid (600 μL). The reaction was stirred at room temperature for 6 h. Toluene (4 mL) was added, and the reaction mixture was concentrated to dryness. The residue was combined with a premixed solution of 2-(2-((6-chlorohexyl)oxy)ethoxy)ethan-1-amine (TFA salt; 51.3 mg, 0.152 mmol, 2 eq) and DIEA (132 μL, 0.759 mmol, 10 eq) in $CH_2Cl_2$ (3 mL), and the reaction was stirred at room temperature for 18 h. The solvent was removed by rotary evaporation, and the crude material was purified by reverse phase HPLC (20-70% $MeCN/H_2O$, linear gradient, with constant 0.1% v/v TFA additive) to afford the title compound as a blue solid (41.5 mg, 61%, TFA salt). $^1H$ NMR ($CD_3OD$, 400 MHz) δ 9.14 (t, J=5.4 Hz, 1H), 7.18 (d, J=2.6 Hz, 2H), 7.16 (dd, J=9.5, 1.0 Hz, 2H), 6.67 (dd, J=9.5, 2.6 Hz, 2H), 3.74-3.54 (m, 16H), 3.51 (t, J=6.7 Hz, 2H), 3.43 (t, J=6.5 Hz, 2H), 2.18-2.06 (m, 8H), 1.75-1.66 (m, 2H), 1.56-1.47 (m, 2H), 1.45-1.27 (m, 4H), 0.61 (s, 3H), 0.53 (s, 3H); $^{19}F$ NMR ($CD_3OD$, 376 MHz) δ −117.75 (d, J=15.6 Hz, 1F), −134.58 (d, J=22.2 Hz, 1F), −141.14−−141.36 (m, 1F); Analytical HPLC: $t_R$=13.6 min, >99% purity (10-95% $MeCN/H_2O$, linear gradient, with constant 0.1% v/v TFA additive; 20 min run; 1 mL/min flow; ESI; positive ion mode; detection at 675 nm); HRMS (ESI) calcd for $C_{41}H_{50}ClF_3N_3O_5Si$ [M+H]$^+$ 784.3155, found 784.3159.

Step 1: A vial was charged with bis(3-bromophenyl)dimethylsilane (1.00 g, 2.70 mmol), $Pd_2dba_3$ (247 mg, 0.270 mmol, 0.1 eq), XPhos (386 mg, 0.810 mmol, 0.3 eq), and $Cs_2CO_3$ (2.46 g, 7.56 mmol, 2.8 eq). The vial was sealed and evacuated/backfilled with nitrogen (3×). Dioxane (10 mL) was added, and the reaction was flushed again with nitrogen (3×). Following the addition of pyrrolidine-2,2,3,3,4,4,5,5-$d_8$ (543 μL, 6.48 mmol, 2.4 eq), the reaction was stirred at 100° C. for 18 h. It was then cooled to room temperature, filtered through Celite with $CH_2Cl_2$, and concentrated to dryness. The resulting residue was purified by flash chromatography (0-10% $Et_2O$/hexanes, linear gradient, with constant 0.1% v/v $Et_3N$ additive) to provide 773 mg (78%) of dimethylbis(3-(pyrrolidin-1-yl-$d_8$)phenyl)silane as a white solid. $^1H$ NMR ($CDCl_3$, 400 MHz) δ 7.21 (dd, J=8.2, 7.1 Hz, 2H), 6.84 (dt, J=7.1, 1.1 Hz, 2H), 6.75 (dd, J=2.6, 1.0 Hz, 2H), 6.57 (ddd, J=8.2, 2.7, 1.1 Hz, 2H), 0.52 (s, 6H); $^{13}C$ NMR ($CDCl_3$, 101 MHz) δ 147.5 (C), 139.2 (C), 128.6 (CH), 121.5 (CH), 117.3 (CH), 112.5 (CH), −2.0 ($CH_3$); HRMS (ESI) calcd for $C_{22}H_{15}D_{16}N_2Si$ [M+H]$^+$ 367.3255, found 367.3259.

Step 2: The product from Step 1 (1.95 g, 5.32 mmol) was taken up in DMF (60 mL). N-Bromosuccinimide (1.89 g, 10.64 mmol, 2 eq) was added portion-wise over 2-3 min, and the reaction was then stirred at room temperature for 1 h. The reaction mixture was concentrated to remove DMF, diluted with water, and extracted with $CH_2Cl_2$ (2×). The combined organic extracts were washed with brine, dried over anhydrous $MgSO_4$, filtered, and concentrated in vacuo. The crude was dissolved in a minimum amount of $CH_2Cl_2$, diluted with an equivalent volume of hexanes, and gently concentrated until a white solid precipitated. The resulting suspension was filtered; the filter cake was washed with $Et_2O$ and dried to yield 2.32 g (83%) of bis(2-bromo-5-(pyrrolidin-1-yl-$d_8$)phenyl)dimethylsilane as a white solid. $^1H$ NMR ($CDCl_3$, 400 MHz) δ 7.32 (d, J=8.7 Hz, 2H), 6.66 (d, J=3.1 Hz, 2H), 6.42 (dd, J=8.7, 3.1 Hz, 2H), 0.74 (s, 6H);

$^{13}$C NMR (CDCl$_3$, 101 MHz) δ 146.5 (C), 139.0 (C), 133.1 (CH), 120.7 (CH), 115.4 (C), 114.3 (CH), −0.8 (CH$_3$); HRMS (ESI) calcd for C$_{22}$H$_{13}$D$_{16}$Br$_2$N$_2$Si [M+H]$^+$ 523.1466, found 523.1466.

Step 3: A solution of the product from Step 2 (600 mg, 1.14 mmol) in THF (40 mL) was cooled to −78° C. under nitrogen. tert-Butyllithium (1.7 M in pentane, 2.96 mL, 5.03 mmol, 4.4 eq) was added, and the reaction was stirred at −78° C. for 30 min. It was then warmed to −10° C. before adding a solution of MgBr$_2$·OEt$_2$ (650 mg, 2.52 mmol, 2.2 eq) in THF (10 mL). After an additional 30 min at −10° C., a solution of tetrafluorophthalic anhydride (554 mg, 2.52 mmol, 2.2 eq) in THF (10 mL) was added dropwise over 30 min via addition funnel. The reaction was then allowed to warm to room temperature overnight (18 h). It was subsequently diluted with saturated NH$_4$Cl and water and extracted with EtOAc (2×). The combined organic extracts were washed with saturated NaHCO$_3$ and brine, dried over anhydrous MgSO$_4$, filtered, and concentrated in vacuo. Silica gel chromatography (0-75% EtOAc/hexanes, linear gradient) afforded 326 mg (50%) of 2-(5,5-dimethyl-3,7-bis(pyrrolidin-1-yl-d$_8$)dibenzo[b,e]silin-10-ylium-10(5H)-yl)-3,4,5,6-tetrafluorobenzoate as a blue solid. $^1$H NMR (CDCl$_3$, 400 MHz) δ 6.78 (d, J=2.9 Hz, 2H), 6.77 (d, J=8.6 Hz, 2H), 6.45 (dd, J=8.8, 2.7 Hz, 2H), 0.58 (s, 3H), 0.55 (s, 3H); $^{19}$F NMR (CDCl$_3$, 376 MHz) δ −139.43--139.69 (m, 2F), −144.25--144.45 (m, 1F), −152.39--152.57 (m, 1F); Analytical HPLC: t$_R$=13.4 min, 98.8% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{30}$H$_{13}$D$_{16}$F$_4$N$_2$O$_2$Si [M+H]$^+$ 569.2933, found 569.2943.

Step 4: The product from Step 3 (300 mg, 0.527 mmol) and 2-(methoxymethoxy)malononitrile (66.5 mg, 0.527 mmol, 1 eq) were combined in DMF (7 mL), and DIEA (184 μL, 1.05 mmol, 2 eq) was added. After stirring the reaction at room temperature for 2 h, it was concentrated in vacuo and purified by silica gel chromatography (10-100% EtOAc/hexanes, linear gradient) to yield 166 mg (47%) of the title compound 4-(dicyano(methoxymethoxy)methyl)-2-(5,5-dimethyl-3,7-bis(pyrrolidin-1-yl-d$_8$)dibenzo[b,e]silin-10-ylium-10(5H)-yl)-3,5,6-trifluorobenzoate as a blue-green solid. $^1$H NMR (CDCl$_3$, 400 MHz) δ 6.77 (d, J=2.7 Hz, 2H), 6.73 (dd, J=8.8, 1.1 Hz, 2H), 6.46 (dd, J=8.8, 2.8 Hz, 2H), 5.16 (s, 2H), 3.53 (s, 3H), 0.57 (s, 3H), 0.55 (s, 3H); $^{19}$F NMR (CDCl$_3$, 376 MHz) δ −113.90 (d, J=22.5 Hz, 1F), −128.13 (d, J=20.2 Hz, 1F), −140.21 (dd, J=22.7, 20.2 Hz, 1F); Analytical HPLC: t$_R$=13.2 min, 97.5% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{35}$H$_{18}$D$_{16}$F$_3$N$_4$O$_4$Si [M+H]$^+$ 675.3300, found 675.3302.

Example 24: 4-((2-(2-((6-Chlorohexyl)oxy)ethoxy)ethyl)carbamoyl)-2-(5,5-dimethyl-3,7-bis(pyrrolidin-1-yl-d$_8$)dibenzo[b,e]silin-10-ylium-10(5H)-yl)-3,5,6-trifluorobenzoate

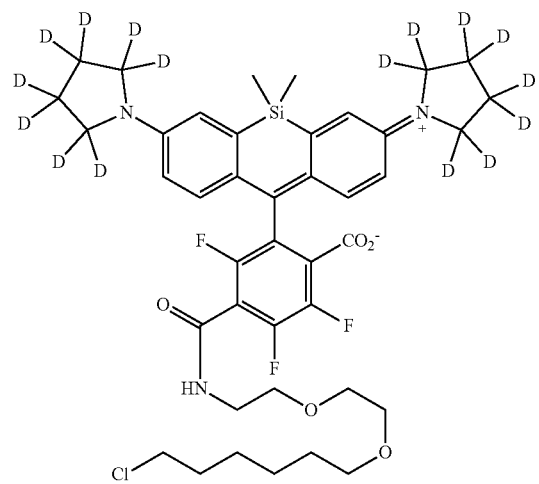

4-(Dicyano(methoxymethoxy)methyl)-2-(5,5-dimethyl-3,7-bis(pyrrolidin-1-yl-ds)dibenzo[b,e]silin-10-ylium-10(5H)-yl)-3,5,6-trifluorobenzoate (Example 23; 50 mg, 74.1 μmol) was taken up in CH$_2$Cl$_2$ (3 mL); triethylsilane (300 μL) was added, followed by trifluoroacetic acid (600 μL). The reaction was stirred at room temperature for 6 h. Toluene (4 mL) was added, and the reaction mixture was concentrated to dryness. The residue was combined with a premixed solution of 2-(2-((6-chlorohexyl)oxy)ethoxy)ethan-1-amine (TFA salt; 50.0 mg, 0.148 mmol, 2 eq) and DIEA (129 μL, 0.741 mmol, 10 eq) in CH$_2$Cl$_2$ (3 mL), and the reaction was stirred at room temperature for 18 h. The solvent was removed by rotary evaporation, and the crude material was purified by reverse phase HPLC (20-70% MeCN/H$_2$O, linear gradient, with constant 0.1% v/v TFA additive) to afford the title compound as a blue solid (40.4 mg, 60%, TFA salt). $^1$H NMR (CD$_3$OD, 400 MHz) δ 9.12 (t, J=5.4 Hz, 1H), 7.16 (dd, J=9.4, 1.0 Hz, 2H), 7.14 (d, J=2.7 Hz, 2H), 6.64 (dd, J=9.4, 2.7 Hz, 2H), 3.67-3.54 (m, 8H), 3.50 (t, J=6.6 Hz, 2H), 3.43 (t, J=6.5 Hz, 2H), 1.75-1.66 (m, 2H), 1.55-1.47 (m, 2H), 1.44-1.27 (m, 4H), 0.58 (s, 3H), 0.54 (s, 3H); $^{19}$F NMR (CD$_3$OD, 376 MHz) δ −118.19 (d, J=16.4 Hz, 1F), −135.10 (d, J=22.6 Hz, 1F), −142.57--142.90 (m, 1F); Analytical HPLC: t$_R$=13.5 min, >99% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{41}$H$_{34}$D$_{16}$ClF$_3$N$_3$O$_5$Si [M+H]$^+$ 800.4159, found 800.4167.

Example 25: 4-(Dicyano(methoxymethoxy)methyl)-2-(5,5-dimethyl-3,7-di(piperidin-1-yl)dibenzo[b,e]silin-10-ylium-10(5H)-yl)-3,5,6-trifluorobenzoate

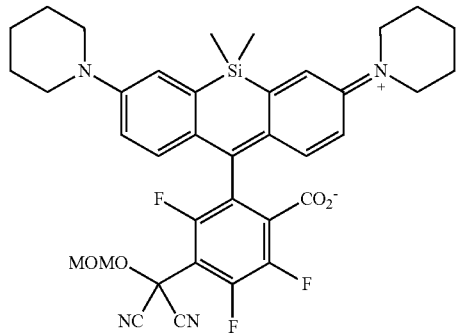

Step 1: A flask was charged with bis(3-bromophenyl)dimethylsilane (1.20 g, 3.24 mmol), $Pd_2dba_3$ (297 mg, 0.324 mmol, 0.1 eq), XPhos (464 mg, 0.973 mmol, 0.3 eq), and $Cs_2CO_3$ (2.96 g, 9.08 mmol, 2.8 eq). The flask was sealed and evacuated/backfilled with nitrogen (3×). Dioxane (12 mL) was added, and the reaction was flushed again with nitrogen (3×). Following the addition of piperidine (769 µL, 7.78 mmol, 2.4 eq), the reaction was stirred at 100° C. for 18 h. It was then cooled to room temperature, filtered through Celite with $CH_2Cl_2$, and concentrated to dryness. The resulting residue was purified by flash chromatography (0-10% $Et_2O$/hexanes, linear gradient) to provide 889 mg (72%) of dimethylbis(3-(piperidin-1-yl)phenyl)silane as a pale yellow gum. $^1H$ NMR ($CDCl_3$, 400 MHz) δ 7.23 (dd, J=8.2, 7.1 Hz, 2H), 7.13 (dd, J=2.6, 1.1 Hz, 2H), 6.99 (dt, J=7.1, 1.0 Hz, 2H), 6.94 (ddd, J=8.2, 2.7, 1.0 Hz, 2H), 3.16-3.07 (m, 8H), 1.75-1.65 (m, 8H), 1.59-1.53 (m, 4H), 0.51 (s, 6H); $^{13}C$ NMR ($CDCl_3$, 101 MHz) δ 151.8 (C), 139.0 (C), 128.6 (CH), 125.5 (CH), 122.8 (CH), 117.5 (CH), 51.1 ($CH_2$), 26.1 ($CH_2$), 24.4 ($CH_2$), -2.0 ($CH_3$); HRMS (ESI) calcd for $C_{24}H_{35}N_2Si$ $[M+H]^+$ 379.2564, found 379.2563.

Step 2: The product from Step 1 (835 mg, 2.21 mmol) was taken up in DMF (10 mL). N-Bromosuccinimide (785 mg, 4.41 mmol, 2 eq) was added portion-wise over ~5 min, and the reaction was then stirred at room temperature for 2 h. The reaction mixture was subsequently diluted with water and extracted with EtOAc (2×). The combined organic extracts were washed with water and brine, dried over anhydrous $MgSO_4$, filtered, and concentrated in vacuo. Silica gel chromatography (0-20% $Et_2O$/hexanes, linear gradient) provided 1.08 g of an off-white solid. Because the product coeluted with a minor impurity, the material obtained from the column was triturated with $Et_2O$/hexanes and filtered. The filter cake was washed with hexanes and dried to give clean bis(2-bromo-5-(piperidin-1-yl)phenyl)dimethylsilane as a white solid (603 mg). The filtrate was concentrated in vacuo and repurified by flash chromatography (0-100% $CH_2Cl_2$/hexanes, linear gradient) to yield an additional 343 mg of bis(2-bromo-5-(piperidin-1-yl)phenyl)dimethylsilane as a white solid (total isolated yield: 946 mg, 80%). $^1H$ NMR ($CDCl_3$, 400 MHz) δ 7.35 (d, J=8.7 Hz, 2H), 7.04 (d, J=3.1 Hz, 2H), 6.79 (dd, J=8.7, 3.1 Hz, 2H), 3.11-3.03 (m, 8H), 1.73-1.63 (m, 8H), 1.57-1.53 (m, 4H), 0.73 (s, 6H); $^{13}C$ NMR ($CDCl_3$, 101 MHz) δ 150.7 (C), 139.0 (C), 133.2 (CH), 126.0 (CH), 119.6 (C), 119.4 (CH), 50.8 ($CH_2$), 25.9 ($CH_2$), 24.3 ($CH_2$), -0.9 ($CH_3$); HRMS (ESI) calcd for $C_{24}H_{33}Br_2N_2Si$ $[M+H]^+$ 535.0774, found 535.0782.

Step 3: A solution of the product from Step 2 (800 mg, 1.49 mmol) in THF (40 mL) was cooled to -78° C. under nitrogen. tert-Butyllithium (1.7 M in pentane, 3.86 mL, 6.56 mmol, 4.4 eq) was added, and the reaction was stirred at -78° C. for 30 min. It was then warmed to -10° C. before adding a solution of $MgBr_2 \cdot OEt_2$ (847 mg, 3.28 mmol, 2.2 eq) in THF (20 mL). After an additional 30 min at -10° C., a solution of tetrafluorophthalic anhydride (722 mg, 3.28 mmol, 2.2 eq) in THF (15 mL) was added dropwise over 30 min via addition funnel. The reaction was then allowed to warm to room temperature overnight (18 h). It was subsequently diluted with saturated $NH_4Cl$ and water and extracted with EtOAc (2×). The combined organic extracts were washed with saturated $NaHCO_3$ and brine, dried over anhydrous $MgSO_4$, filtered, and concentrated in vacuo. Silica gel chromatography (0-25% EtOAc/hexanes, linear gradient) afforded 273 mg (32%) of 2-(5,5-dimethyl-3,7-di(piperidin-1-yl)dibenzo[b,e]silin-10-ylium-10(5H)-yl)-3,4,5,6-tetrafluorobenzoate as a pale blue-green solid. $^1H$ NMR ($CDCl_3$, 400 MHz) δ 7.19-7.15 (m, 2H), 6.82-6.77 (m, 4H), 3.25-3.18 (m, 8H), 1.74-1.65 (m, 8H), 1.64-1.58 (m, 4H), 0.58 (s, 3H), 0.55 (s, 3H); $^{19}F$ NMR ($CDCl_3$, 376 MHz) δ -138.94--139.13 (m, 2F), -143.68--143.91 (m, 1F), -151.62--151.85 (m, 1F); Analytical HPLC: $t_R$=11.6 min, 99.0% purity (10-95% $MeCN/H_2O$, linear gradient, with constant 0.1% v/v TFA additive; 20 min run; 1 mL/min flow; ESI; positive ion mode; detection at 280 nm); HRMS (ESI) calcd for $C_{32}H_{33}F_4N_2O_2Si$ $[M+H]^+$ 581.2242, found 581.2248.

Step 4: The product from Step 3 (200 mg, 0.344 mmol) and 2-(methoxymethoxy)malononitrile (43.4 mg, 0.344 mmol, 1 eq) were combined in DMF (3 mL), and DIEA (120 µL, 0.689 mmol, 2 eq) was added. After stirring the reaction at room temperature for 2 h, it was concentrated in vacuo and purified by silica gel chromatography (0-40% EtOAc/hexanes, linear gradient) to yield 138 mg (58%) of the title compound 4-(dicyano(methoxymethoxy)methyl)-2-(5,5-dimethyl-3,7-di(piperidin-1-yl)dibenzo[b,e]silin-10-ylium-10(5H)-yl)-3,5,6-trifluorobenzoate as a green solid. NMR ($CDCl_3$, 400 MHz) δ 7.17 (d, J=2.7 Hz, 2H), 6.82 (dd, J=8.9, 2.8 Hz, 2H), 6.75 (dd, J=8.9, 1.1 Hz, 2H), 5.17 (s, 2H), 3.53 (s, 3H), 3.27-3.19 (m, 8H), 1.75-1.66 (m, 8H), 1.65-1.58 (m, 4H), 0.58 (s, 3H), 0.54 (s, 3H); $^{19}F$ NMR ($CDCl_3$, 376 MHz) δ -113.58 (d, J=22.5 Hz, 1F), -127.49 (d, J=20.3 Hz, 1F), -139.60 (dd, J=22.6, 20.2 Hz, 1F); Analytical HPLC: $t_R$=9.5 min, >99% purity (30-95% $MeCN/H_2O$, linear gradient, with constant 0.1% v/v TFA additive; 20 min run; 1 mL/min flow; ESI; positive ion mode; detection at 675 nm); HRMS (ESI) calcd for $C_{37}H_{38}F_3N_4O_4Si$ $[M+H]^+$ 687.2609, found 687.2621.

Example 26: 4-((2-(2-((6-Chlorohexyl)oxy)ethoxy)ethyl)carbamoyl)-2-(5,5-dimethyl-3,7-di(piperidin-1-yl)dibenzo[b,e]silin-10-ylium-10(5H)-yl)-3,5,6-trifluorobenzoate

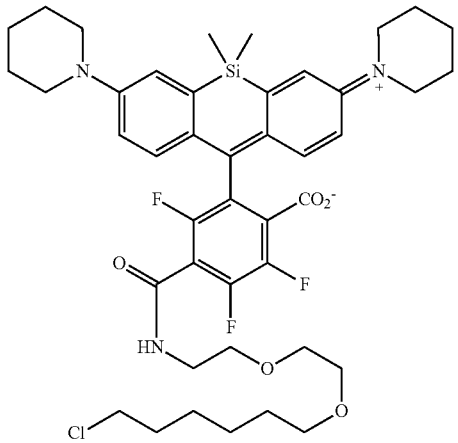

4-(Dicyano(methoxymethoxy)methyl)-2-(5,5-dimethyl-3,7-di(piperidin-1-yl)dibenzo[b,e]silin-10-ylium-10(5H)-yl)-3,5,6-trifluorobenzoate (Example 25; 75 mg, 0.109 mmol) was taken up in $CH_2Cl_2$ (4 mL); triethylsilane (400 µL) was added, followed by trifluoroacetic acid (800 µL). The reaction was stirred at room temperature for 6 h. Toluene (5 mL) was added, and the reaction mixture was concentrated to dryness. The residue was combined with a premixed solution of 2-(2-((6-chlorohexyl)oxy)ethoxy)ethan-1-amine (TFA salt; 73.8 mg, 0.218 mmol, 2 eq) and DIEA (190 µL, 1.09 mmol, 10 eq) in $CH_2Cl_2$ (4 mL), and the reaction was stirred at room temperature for 18 h. The solvent was removed by rotary evaporation, and the crude material was purified by reverse phase HPLC (30-60% $MeCN/H_2O$, linear gradient, with constant 0.1% v/v TFA additive) to afford the title compound as a blue-green solid (61.0 mg, 60%, TFA salt). $^1H$ NMR ($CD_3OD$, 400 MHz) δ 9.16 (t, J=5.4 Hz, 1H), 7.52 (d, J=2.6 Hz, 2H), 7.11 (dd, J=9.0, 2.6 Hz, 2H), 7.06 (d, J=9.0 Hz, 2H), 3.65-3.54 (m, 8H), 3.52-3.44 (m, 10H), 3.43 (t, J=6.5 Hz, 2H), 1.88-1.76 (m, 8H), 1.76-1.65 (m, 6H), 1.55-1.47 (m, 2H), 1.44-1.27 (m, 4H), 0.64 (s, 3H), 0.57 (s, 3H); $^{19}F$ NMR ($CD_3OD$, 376 MHz) δ –118.60 (d, J=20.5 Hz, 1F), –133.98 (d, J=21.1 Hz, 1F), –142.23 (t, J=21.0 Hz, 1F); Analytical HPLC: $t_R$=9.7 min, >99% purity (30-95% $MeCN/H_2O$, linear gradient, with constant 0.1% v/v TFA additive; 20 min run; 1 mL/min flow; ESI; positive ion mode; detection at 254 nm); HRMS (ESI) calcd for $C_{43}H_{54}ClF_3N_3O_5Si$ $[M+H]^+$ 812.3468, found 812.3482.

Example 27: 4-(Dicyano(methoxymethoxy)methyl)-2-(5,5-dimethyl-3,7-dimorpholinodibenzo[b,e]silin-10-ylium-10(5H)-yl)-3,5,6-trifluorobenzoate

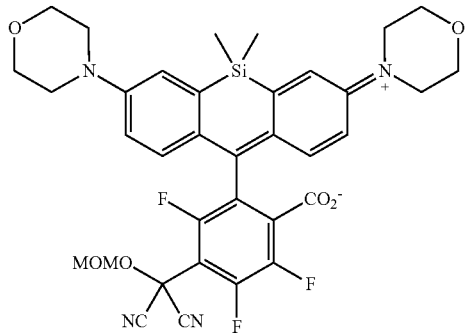

Step 1: A flask was charged with bis(3-bromophenyl)dimethylsilane (1.20 g, 3.24 mmol), $Pd_2dba_3$ (297 mg, 0.324 mmol, 0.1 eq), XPhos (464 mg, 0.973 mmol, 0.3 eq), and $Cs_2CO_3$ (2.96 g, 9.08 mmol, 2.8 eq). The flask was sealed and evacuated/backfilled with nitrogen (3×). Dioxane (12 mL) was added, and the reaction was flushed again with nitrogen (3×). Following the addition of morpholine (681 µL, 7.78 mmol, 2.4 eq), the reaction was stirred at 100° C. for 18 h. It was then cooled to room temperature, filtered through Celite with $CH_2Cl_2$, and concentrated to dryness. The resulting residue was purified by flash chromatography (0-50% EtOAc/hexanes, linear gradient) to provide 909 mg (73%) of dimethylbis(3-morpholinophenyl)silane as a yellow gum. $^1H$ NMR ($CDCl_3$, 400 MHz) δ 7.28 (dd, J=8.3, 7.2 Hz, 2H), 7.09-7.07 (m, 2H), 7.05 (dt, J=7.2, 1.0 Hz, 2H), 6.92 (ddd, J=8.3, 2.7, 1.0 Hz, 2H), 3.89-3.80 (m, 8zH), 3.17-3.10 (m, 8H), 0.53 (s, 6H); $^{13}C$ NMR ($CDCl_3$, 101 MHz) δ 150.8 (C), 139.3 (C), 128.8 (CH), 126.2 (CH), 121.6 (CH), 116.7 (CH), 67.1 ($CH_2$), 49.6 ($CH_2$), –2.1 ($CH_3$); HRMS (ESI) calcd for $C_{22}H_{31}N_2O_2Si$ $[M+H]^+$ 383.2149, found 383.2152.

Step 2: The product from Step 1 (810 mg, 2.12 mmol) was taken up in DMF (10 mL). N-Bromosuccinimide (754 mg, 4.23 mmol, 2 eq) was added portion-wise over ~5 min, and the reaction was then stirred at room temperature for 2 h. The reaction mixture was subsequently diluted with water and extracted with EtOAc (2×). The combined organic extracts were washed with water and brine, dried over anhydrous $MgSO_4$, filtered, and concentrated in vacuo. Silica gel chromatography (0-40% $Et_2O$/toluene, linear gradient) afforded 1.05 g (92%) of bis(2-bromo-5-morpholinophenyl)dimethylsilane as a white solid. $^1H$ NMR ($CDCl_3$, 400 MHz) δ 7.40 (d, J=8.7 Hz, 2H), 7.02 (d, J=3.1 Hz, 2H), 6.78 (dd, J=8.7, 3.1 Hz, 2H), 3.87-3.80 (m, 8H), 3.12-3.05 (m, 8H), 0.74 (s, 6H); $^{13}C$ NMR ($CDCl_3$, 101 MHz) δ 149.8 (C), 139.2 (C), 133.4 (CH), 125.1 (CH), 120.4 (C), 118.6 (CH), 66.9 ($CH_2$), 49.4 ($CH_2$), –1.0 ($CH_3$); HRMS (ESI) calcd for $C_{22}H_{29}Br_2N_2O_2Si$ $[M+H]^+$ 539.0360, found 539.0367.

Step 3: A solution of the product from Step 2 (600 mg, 1.11 mmol) in THF (30 mL) was cooled to –78° C. under nitrogen. tert-Butyllithium (1.7 M in pentane, 2.87 mL, 4.89 mmol, 4.4 eq) was added, and the reaction was stirred at –78° C. for 30 min. It was warmed to –10° C. before adding a solution of $MgBr_2·OEt_2$ (631 mg, 2.44 mmol, 2.2 eq) in THF (15 mL). After an additional 30 min at –10° C., a solution of tetrafluorophthalic anhydride (538 mg, 2.44 mmol, 2.2 eq) in THF (10 mL) was added dropwise over 30 min via addition funnel. The reaction was then allowed to warm to room temperature overnight (18 h). It was subsequently diluted with saturated $NH_4Cl$ and water and extracted with EtOAc (2×). The combined organic extracts were washed with saturated $NaHCO_3$ and brine, dried over anhydrous $MgSO_4$, filtered, and concentrated in vacuo. Silica gel chromatography (5-75% EtOAc/hexanes, linear gradient) afforded 255 mg (39%) of 2-(5,5-dimethyl-3,7-dimorpholinodibenzo[b,e]silin-10-ylium-10(5H)-yl)-3,4,5,6-tetrafluorobenzoate as a pale blue-green solid. $^1H$ NMR ($CDCl_3$, 400 MHz) δ 7.16 (d, J=2.7 Hz, 2H), 6.85 (dd, J=8.8, 1.0 Hz, 2H), 6.80 (dd, J=8.9, 2.7 Hz, 2H), 3.90-3.82 (m, 8H), 3.26-3.16 (m, 8H), 0.59 (s, 3H), 0.56 (s, 3H); $^{19}F$ NMR ($CDCl_3$, 376 MHz) δ –138.56 (td, J=20.0, 8.7 Hz, 1F), –139.14 (td, J=20.1, 19.7, 4.0 Hz, 1F), –143.37 (ddd, J=21.1, 18.3, 8.7 Hz, 1F), –151.23 (ddd, J=21.7, 18.3, 3.9 Hz, 1F); Analytical HPLC: $t_R$=15.4 min, 98.5% purity (10-95% $MeCN/H_2O$, linear gradient, with constant 0.1% v/v TFA additive; 20 min run; 1 mL/min flow; ESI; positive ion mode; detection at 280 nm); HRMS (ESI) calcd for $C_{30}H_{29}F_4N_2O_4Si$ [M+H]$^+$ 585.1827, found 585.1827.

Step 4: The product from Step 3 (200 mg, 0.342 mmol) and 2-(methoxymethoxy)malononitrile (43.1 mg, 0.342 mmol, 1 eq) were combined in DMF (3 mL), and DIEA (119 µL, 0.684 mmol, 2 eq) was added. After stirring the reaction at room temperature for 2 h, it was concentrated in vacuo and purified by silica gel chromatography (0-60% EtOAc/toluene, linear gradient) to yield 130 mg (55%) of the title compound 4-(dicyano(methoxymethoxy)methyl)-2-(5,5-dimethyl-3,7-dimorpholinodibenzo[b,e]silin-10-ylium-10(5H)-yl)-3,5,6-trifluorobenzoate as a pale blue-green solid. $^1$H NMR (CDCl$_3$, 400 MHz) δ 7.18-7.14 (m, 2H), 6.85-6.78 (m, 4H), 5.17 (s, 2H), 3.91-3.83 (m, 8H), 3.53 (s, 3H), 3.27-3.19 (m, 8H), 0.59 (s, 3H), 0.56 (s, 3H); $^{19}$F NMR (CDCl$_3$, 376 MHz) δ −113.79 (d, J=22.6 Hz, 1F), −126.94 (d, J=20.4 Hz, 1F), −139.11 (dd, J=22.7, 20.3 Hz, 1F); Analytical HPLC: $t_R$=13.1 min, >99% purity (30-95% MeCN/H$_2$O, linear gradient, with constant 0.1% v/v TFA additive; 20 min run; 1 mL/min flow; ESI; positive ion mode; detection at 675 nm); HRMS (ESI) calcd for $C_{35}H_{34}F_3N_4O_6Si$ [M+H]$^+$ 691.2194, found 691.2201.

Example 28: 4-((2-(2-((6-Chlorohexyl)oxy)ethoxy)ethyl)carbamoyl)-2-(5,5-dimethyl-3,7-dimorpholinodibenzo[b,e]silin-10-ylium-10(5H)-yl)-3,5,6-trifluorobenzoate

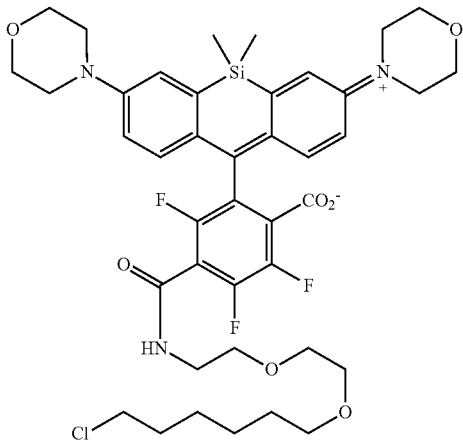

4-(Dicyano(methoxymethoxy)methyl)-2-(5,5-dimethyl-3,7-dimorpholinodibenzo[b,e]silin-10-ylium-10(5H)-yl)-3,5,6-trifluorobenzoate (Example 27; 75 mg, 0.109 mmol) was taken up in CH$_2$Cl$_2$ (4 mL); triethylsilane (400 µL) was added, followed by trifluoroacetic acid (800 µL). The reaction was stirred at room temperature for 6 h. Toluene (5 mL) was added, and the reaction mixture was concentrated to dryness. The residue was combined with a premixed solution of 2-(2-((6-chlorohexyl)oxy)ethoxy)ethan-1-amine (TFA salt; 73.3 mg, 0.217 mmol, 2 eq) and DIEA (189 µL, 1.09 mmol, 10 eq) in CH$_2$Cl$_2$ (4 mL), and the reaction was stirred at room temperature for 18 h. The solvent was removed by rotary evaporation, and the crude material was purified by reverse phase HPLC (20-80% MeCN/H$_2$O, linear gradient, with constant 0.1% v/v TFA additive) to afford the title compound as a blue-green solid (65.8 mg, 65%, TFA salt). $^1$H NMR (CD$_3$OD, 400 MHz) δ 9.15 (t, J=5.4 Hz, 1H), 7.34-7.28 (m, 2H), 6.98-6.90 (m, 4H), 3.89-3.79 (m, 8H), 3.65-3.52 (m, 8H), 3.49 (t, J=6.6 Hz, 2H), 3.41 (t, J=6.5 Hz, 2H), 3.30-3.21 (m, 8H), 1.73-1.64 (m, 2H), 1.53-1.45 (m, 2H), 1.42-1.25 (m, 4H), 0.60 (s, 3H), 0.54 (s, 3H); $^{19}$F NMR (CD$_3$OD, 376 MHz) δ −119.02 (d, J=21.5 Hz, 1F), −134.54 (d, J=20.7 Hz, 1F), −142.80--143.26 (m, 1F); Analytical HPLC: $t_R$=13.6 min, >99% purity (30-95% MeCN/H$_2$O, linear gradient, with constant 0.1% v/v TFA additive; 20 min run; 1 mL/min flow; ESI; positive ion mode; detection at 254 nm); HRMS (ESI) calcd for $C_{41}H_{50}ClF_3N_3O_7Si$ [M+H]$^+$ 816.3053, found 816.3058.

Example 29: Methyl 3,7-di(azetidin-1-yl)-2'-diazo-4',5',7'-trifluoro-5,5-dimethyl-3'-oxo-2',3'-dihydro-5H-spiro[dibenzo[b,e]siline-10,1'-indene]-6'-carboxylate

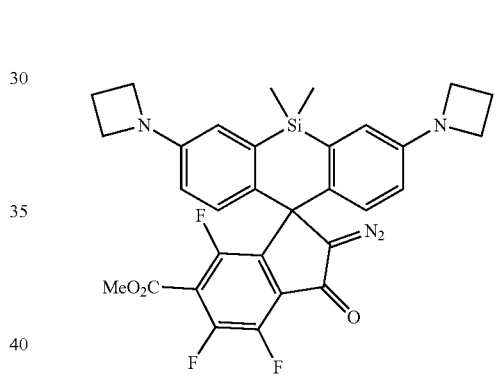

To a solution of 2-(3,7-di(azetidin-1-yl)-5,5-dimethyldibenzo[b,e]silin-10-ylium-10(5H)-yl)-3,5,6-trifluoro-4-(methoxycarbonyl)benzoate (Example 17; 190 mg, 0.336 mmol) in CH$_2$Cl$_2$ (5 mL) was added oxalyl chloride (34.2 µL, 0.404 mmol, 1.2 eq). After stirring the reaction at room temperature for 30 min, triethylamine (70.4 µL, 0.505 mmol, 1.5 eq) and (trimethylsilyl)diazomethane (2.0 M in Et$_2$O, 1.01 mL, 2.02 mmol, 6 eq) were added in succession. The reaction was stirred at room temperature for 90 min, concentrated in vacuo, and purified by flash chromatography on silica gel (0-10% EtOAc/toluene, linear gradient) to afford 76.1 mg (38%) of the title compound as an orange-brown solid. $^1$H NMR (CDCl$_3$, 400 MHz) δ 6.86 (d, J=8.8 Hz, 2H), 6.53 (d, J=2.6 Hz, 2H), 6.38 (dd, J=8.8, 2.7 Hz, 2H), 3.92 (t, J=7.3 Hz, 8H), 3.83 (s, 3H), 2.38 (p, J=7.2 Hz, 4H), 0.48 (s, 3H), 0.43 (s, 3H); $^{19}$F NMR (CDCl$_3$, 376 MHz) δ −119.07 (d, J=21.2 Hz, 1F), −133.91 (d, J=20.8 Hz, 1F), −145.15 (t, J=21.1 Hz, 1F); Analytical HPLC: $t_R$=13.9 min, 96.3% purity (30-95% MeCN/H$_2$O, linear gradient, with constant 0.1% v/v TFA additive; 20 min run; 1 mL/min flow; ESI; positive ion mode; detection at 254 nm); HRMS (ESI) calcd for $C_{31}H_{28}F_3N_4O_3Si$ [M+H]$^+$ 589.1877, found 589.1882.

Example 30: 3,7-Di(azetidin-1-yl)-N-(2-(2-(4(6-chlorohexyl)oxy)ethoxy)ethyl)-2'-diazo-4',5',7'-trifluoro-5,5-dimethyl-3'-oxo-2',3'-dihydro-5H-spiro[dibenzo[b,e]siline-10,1'-indene]-6'-carboxamide

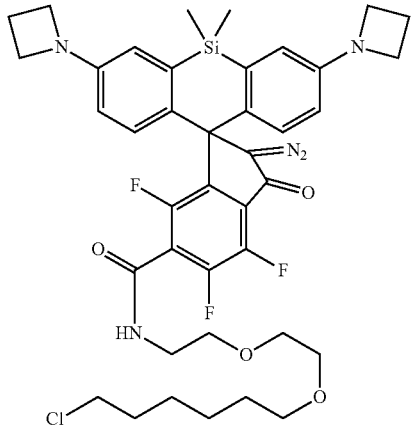

To a solution of methyl 3,7-di(azetidin-1-yl)-2'-diazo-4',5',7'-trifluoro-5,5-dimethyl-3'-oxo-2',3'-dihydro-5H-spiro[dibenzo[b,e]siline-10,1'-indene]-6'-carboxylate (Example 29; 70 mg, 0.119 mmol) in 1:1 MeOH/THF (8 mL) under nitrogen was added 1 M NaOH (595 µL, 0.595 mmol, 5 eq). The reaction was stirred at room temperature for 18 h. It was subsequently acidified with 1 M HCl (625 µL), diluted with water, and extracted with EtOAc (2×). The organic extracts were washed with brine, dried over anhydrous MgSO$_4$, filtered, and concentrated in vacuo to provide an orange-brown residue. This residue was taken up in DMF (5 mL); HBTU (135 mg, 0.357 mmol, 3 eq) and DIEA (124 µL, 0.714 mmol, 6 eq) were added, and the reaction was stirred at room temperature for 20 min. A solution of 2-(2-((6-chlorohexyl)oxy)ethoxy)ethan-1-amine (TFA salt; 161 mg, 0.476 mmol, 4 eq) in DMF (1 mL) was then added. After stirring the reaction at room temperature for an additional 2 h, it was diluted with water and extracted with EtOAc (2×). The combined organic extracts were washed with water and brine, dried over anhydrous MgSO$_4$, filtered, and evaporated. Purification by silica gel chromatography (0-50% EtOAc/toluene, linear gradient) afforded the title compound as a yellow solid (36.1 mg, 39%). $^1$H NMR (CDCl$_3$, 400 MHz) δ 6.88 (d, J=8.7 Hz, 2H), 6.53 (d, J=2.7 Hz, 2H), 6.43 (t, J=5.3 Hz, 1H), 6.38 (dd, J=8.7, 2.7 Hz, 2H), 3.92 (t, J=7.3 Hz, 8H), 3.60-3.46 (m, 10H), 3.34 (t, J=6.6 Hz, 2H), 2.38 (p, J=7.2 Hz, 4H), 1.80-1.70 (m, 2H), 1.53-1.38 (m, 4H), 1.35-1.26 (m, 2H), 0.47 (s, 3H), 0.43 (s, 3H); $^{19}$F NMR (CDCl$_3$, 376 MHz) δ -121.34 (d, J=21.3 Hz, 1F), -135.74 (d, J=21.3 Hz, 1F), -144.93 (t, J=21.4 Hz, 1F); Analytical HPLC: $t_R$=14.9 min, 94.0% purity (30-95% MeCN/H$_2$O, linear gradient, with constant 0.1% v/v TFA additive; 20 min run; 1 mL/min flow; ESI; positive ion mode; detection at 254 nm); HRMS (ESI) calcd for C$_{40}$H$_{46}$ClF$_3$N$_5$O$_4$Si [M+H]$^+$ 780.2954, found 780.2967.

Example 31: 4-((2-(2-((6-Chlorohexyl)oxy)ethoxy)ethyl)carbamoyl)-2-(3,7-di(azetidin-1-yl)-5-hydroxy-5-oxido-10H-acridophosphin-10-ylium-10-yl)-3,5,6-trifluorobenzoate

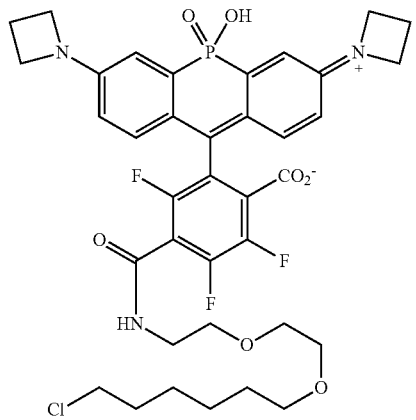

Step 1: To a solution of 3-bromoiodobenzene (11.32 g, 40.0 mmol, 3 eq) in THF (100 mL) at -40° C. was added i-PrMgCl (2.0 M in THF, 20.00 mL, 40.0 mmol, 3 eq). The reaction was then gradually warmed to -25° C. while stirring for 2 h. After cooling the solution to -78° C., N,N-dimethylphosphoramic dichloride (1.59 mL, 13.3 mmol) was added dropwise. The reaction was allowed to warm to room temperature overnight (18 h). After adding 6 N HCl (10 mL), the resulting mixture was vigorously stirred at room temperature for 4 h. It was then diluted with water and extracted with EtOAc (2×). The organics were washed with brine, dried over anhydrous MgSO$_4$, filtered, and concentrated in vacuo. The crude product was dissolved in CH$_2$Cl$_2$ (~100 mL), and hexanes (~100 mL) were slowly added. This solution was gently concentrated with rotary evaporation (~250 Torr) until a pale yellow solid precipitated. The solid was isolated by filtration, washed with 2:1 hexanes/CH$_2$Cl$_2$ and Et$_2$O, and dried to afford 4.13 g (82%) of bis(3-bromophenyl)phosphinic acid as a yellow powder. $^1$H NMR (DMSO-d$_6$, 400 MHz) δ 7.86 (dt, J=12.1, 1.7 Hz, 2H), 7.78-7.69 (m, 4H), 7.46 (td, J=7.8, 3.8 Hz, 2H); $^{13}$C NMR (DMSO-d$_6$, 101 MHz) δ 137.4 (d, $J_{CP}$=133.3 Hz, C), 134.6 (d, $J_{CP}$=2.5 Hz, CH), 133.2 (d, $J_{CP}$=10.7 Hz, CH), 131.1 (d, $J_{CP}$=13.4 Hz, CH), 130.1 (d, $J_{CP}$=9.8 Hz, CH), 122.1 (d, $J_{CP}$=16.4 Hz, C); HRMS (ESI) calcd for C$_{12}$H$_{10}$Br$_2$O$_2$P [M+H]$^+$ 374.8780, found 374.8791.

Step 2: A suspension of the product from Step 1 (3.00 g, 7.98 mmol) in dioxane (25 mL) was heated to 80° C., and N,N-dimethylformamide di-tert-butyl acetal (9.57 mL, 39.9 mmol, 5 eq) was added dropwise over 5 min. The reaction was stirred at 80° C. for 1 h. After cooling the mixture to room temperature, it was diluted with saturated NaHCO$_3$ and extracted with EtOAc (2×). The combined organic extracts were washed with water and brine, dried over anhydrous MgSO$_4$, filtered, and evaporated. Flash chromatography (0-50% EtOAc/hexanes, linear gradient) provided tert-butyl bis(3-bromophenyl)phosphinate as a white solid (1.78 g, 52%). $^1$H NMR (CDCl$_3$, 400 MHz) δ 7.92 (dt, J=12.4, 1.6 Hz, 2H), 7.69 (ddt, J=12.0, 7.6, 1.2 Hz, 2H), 7.62 (ddt, J=8.0, 1.9, 0.9 Hz, 2H), 7.31 (td, J=7.8, 4.0 Hz, 2H), 1.53 (s, 9H); $^{13}$C NMR (CDCl$_3$, 101 MHz) δ 136.8 (d, $J_{CP}$=137.5 Hz, C), 135.0 (d, $J_{CP}$=2.6 Hz, CH), 134.1 (d, $J_{CP}$=10.7 Hz, CH), 130.3 (d, $J_{CP}$=14.2 Hz, CH), 129.9 (d, $J_{CP}$=9.9 Hz, CH), 123.1 (d, $J_{CP}$=16.9 Hz, C), 85.3 (d, $J_{CP}$=8.1 Hz, C), 31.1 (d, $J_{CP}$=4.0 Hz, $CH_3$); HRMS (ESI) calcd for $C_{16}H_{17}Br_2O_{02}PNa$ [M+Na]$^+$ 452.9225, found 452.9243.

Step 3: A vial was charged with the product from Step 2 (1.25 g, 2.89 mmol), RuPhos-G3-palladacycle (484 mg, 0.579 mmol, 0.2 eq), RuPhos (270 mg, 0.579 mmol, 0.2 eq), and $Cs_2CO_3$ (2.83 mg, 8.68 mmol, 3 eq). The vial was sealed and evacuated/backfilled with nitrogen (3×). Dioxane (11 mL) was added, and the reaction was flushed again with nitrogen (3×). Following the addition of azetidine (585 μL, 8.68 mmol, 3 eq), the reaction was stirred at 100° C. for 18 h. It was then cooled to room temperature, filtered through Celite with $CH_2Cl_2$, and concentrated to dryness. Purification by silica gel chromatography (0-40% acetone/$CH_2Cl_2$, linear gradient) afforded tert-butyl bis(3-(azetidin-1-yl)phenyl)phosphinate (1.08 g, 97%) as a pale yellow gum. $^1$H NMR ($CDCl_3$, 400 MHz) δ 7.20 (td, J=7.7, 4.2 Hz, 2H), 7.07 (ddt, J=12.0, 7.5, 1.2 Hz, 2H), 6.89 (ddd, J=13.7, 2.5, 1.3 Hz, 2H), 6.49 (ddt, J=8.1, 2.4, 1.1 Hz, 2H), 3.87 (t, J=7.2 Hz, 8H), 2.34 (p, J=7.2 Hz, 4H), 1.50 (s, 9H); $^{13}$C NMR ($CDCl_3$, 101 MHz) δ 151.8 (d, $J_{CP}$=15.0 Hz, C), 135.3 (d, $J_{CP}$=136.9 Hz, C), 128.8 (d, $J_{CP}$=14.9 Hz, CH), 120.1 (d, $J_{CP}$=9.9 Hz, CH), 114.1 (d, $J_{CP}$=2.9 Hz, CH), 113.9 (d, $J_{CP}$=11.6 Hz, CH), 83.1 (d, $J_{CP}$=8.3 Hz, C), 52.5 ($CH_2$), 31.0 (d, $J_{CP}$=4.0 Hz, $CH_3$), 17.0 ($CH_2$); HRMS (ESI) calcd for $C_{22}H_{29}N_2O_2PNa$ [M+Na]$^+$ 407.1859, found 407.1864.

Step 4: The product from Step 3 (1.00 g, 2.60 mmol) was taken up in DMF (13 mL) and cooled to 0° C. N-Bromosuccinimide (926 mg, 5.20 mmol, 2 eq) was added portionwise over 10 min. The reaction was stirred at 0° C. for 1 h, then warmed to room temperature and stirred 1 h. It was subsequently diluted with water and extracted with EtOAc (2×). The combined organic extracts were washed with water and brine, dried over anhydrous $MgSO_4$, filtered, and concentrated in vacuo. Purification by silica gel chromatography (0-40% MeCN/$CH_2Cl_2$, linear gradient) provided tert-butyl bis(5-(azetidin-1-yl)-2-bromophenyl)phosphinate as an off-white solid (825 mg, 58%). $^1$H NMR ($CDCl_3$, 400 MHz) δ 7.33-7.27 (m, 4H), 6.41-6.34 (m, 2H), 3.89 (t, J=7.2 Hz, 8H), 2.38 (p, J=7.2 Hz, 4H), 1.53 (s, 9H); $^{13}$C NMR ($CDCl_3$, 101 MHz) δ 150.7 (d, $J_{CP}$=13.1 Hz, C), 134.3 (d, $J_{CP}$=11.3 Hz, CH), 133.7 (d, $J_{CP}$=144.4 Hz, C), 119.9 (d, $J_{CP}$=8.5 Hz, CH), 115.9 (d, $J_{CP}$=2.7 Hz, CH), 111.3 (d, $J_{CP}$=6.7 Hz, C), 84.8 (d, $J_{CP}$=8.3 Hz, C), 52.6 ($CH_2$), 30.8 (d, $J_{CP}$=4.0 Hz, $CH_3$), 17.0 ($CH_2$); HRMS (ESI) calcd for $C_{22}H_{27}Br_2N_2O_2PNa$ [M+Na]$^+$ 563.0069, found 563.0080.

Step 5: A solution of the product from Step 4 (200 mg, 0.369 mmol) in THF (8 mL) was cooled to −20° C. under nitrogen. Lithium dibutyl(isopropyl)magnesate (0.7 M in $Et_2O$/hexanes, 632 μL, 0.443 mmol, 1.2 eq) was added, and the reaction was stirred at −20° C. for 20 min. A solution of tetrafluorophthalic anhydride (292 mg, 1.33 mmol, 3.6 eq) in THF (4 mL) was added dropwise over 10 min, and the reaction was allowed to warm to room temperature over ~8 h. It was subsequently quenched with saturated $NH_4Cl$, diluted with water, and extracted with EtOAc (2×). The combined organic extracts were washed with saturated $NaHCO_3$ and brine, dried over anhydrous $MgSO_4$, filtered, and evaporated. Flash chromatography on silica gel (0-50% MeCN/$CH_2Cl_2$, linear gradient) afforded 38 mg (18%) of 2-(3,7-di(azetidin-1-yl)-5-(tert-butoxy)-5-oxido-10H-acridophosphin-10-ylium-10-yl)-3,4,5,6-tetrafluorobenzoate as an off-white solid. $^1$H NMR ($CDCl_3$, 400 MHz) δ 7.02 (dd, J=14.5, 2.6 Hz, 2H), 6.88 (dd, J=8.8, 6.9 Hz, 2H), 6.48 (dd, J=8.8, 2.6 Hz, 2H), 4.03-3.91 (m, 8H), 2.41 (p, J=7.3 Hz, 4H), 1.59 (s, 9H); $^{19}$F NMR ($CDCl_3$, 376 MHz) δ −138.63 (td, J=19.9, 8.8 Hz, 1F), −139.62--139.78 (m, 1F), −142.54--142.73 (m, 1F), −151.67--151.86 (m, 1F); Analytical HPLC: $t_R$=15.3 min, 97.1% purity (10-95% MeCN/$H_2O$, linear gradient, with constant 0.1% v/v TFA additive; 20 min run; 1 mL/min flow; ESI; positive ion mode; detection at 700 nm); HRMS (ESI) calcd for $C_{30}H_{27}F_4N_2O_4PNa$ [M+Na]$^+$ 609.1537, found 609.1546.

Step 6: The product from Step 5 (110 mg, 0.188 mmol) and 2-(methoxymethoxy)malononitrile (23.7 mg, 0.188 mmol, 1 eq) were combined in DMF (4 mL), and DIEA (65.3 μL, 0.375 mmol, 2 eq) was added. After stirring the reaction at room temperature for 2 h, it was evaporated to dryness. Flash chromatography on silica gel (0-40% acetone/$CH_2Cl_2$, linear gradient) afforded the masked acyl cyanide tert-butyl phosphinate adduct as a yellow solid (31 mg, 24%). Analytical HPLC: $t_R$=14.0 min, 96.1% purity (10-95% MeCN/$H_2O$, linear gradient, with constant 0.1% v/v TFA additive; 20 min run; 1 mL/min flow; ESI; positive ion mode; detection at 725 nm); MS (ESI) calcd for $C_{35}H_{33}F_3N_4O_6P$ [M+H]$^+$ 693.2, found 692.8.

Step 7: The product from Step 6 (30 mg, 43.3 μmol) was taken up in $CH_2Cl_2$ (3 mL); triethylsilane (300 μL) was added, followed by trifluoroacetic acid (600 μL). The reaction was stirred at room temperature for 6 h. Toluene (3 mL) was added, and the reaction mixture was concentrated to dryness. The residue was combined with a premixed solution of 2-(2-(((6-chlorohexyl)oxy)ethoxy)ethan-1-amine (TFA salt; 29.3 mg, 86.6 μmol, 2 eq) and DIEA (75.4 μL, 0.433 mmol, 10 eq) in $CH_2Cl_2$ (3 mL), and the reaction was stirred at room temperature for 18 h. The solvent was removed by rotary evaporation, and the crude material was purified by reverse phase HPLC (10-75% MeCN/$H_2O$, linear gradient, with constant 0.1% v/v TFA additive). The pooled HPLC product fractions were partially concentrated to remove MeCN and extracted with $CH_2Cl_2$ (2×). The organic extracts were dried over anhydrous $MgSO_4$, filtered, and evaporated to yield 14.0 mg (42%) of the title compound 4-((2-(2-(((6-chlorohexyl)oxy)ethoxy)ethyl)carbamoyl)-2-(3,7-di(azetidin-1-yl)-5-hydroxy-5-oxido-10H-acridophosphin-10-ylium-10-yl)-3,5,6-trifluorobenzoate as a dark blue-green solid. $^1$H NMR ($CD_3OD$, 400 MHz) δ 7.08 (dd, J=14.5, 2.5 Hz, 2H), 6.98 (dd, J=9.1, 6.0 Hz, 2H), 6.47 (dd, J=9.1, 2.5 Hz, 2H), 4.25 (t, J=7.6 Hz, 8H), 3.67-3.55 (m, 8H), 3.53 (d, J=6.6 Hz, 2H), 3.44 (t, J=6.5 Hz, 2H), 2.52 (p, J=7.6 Hz, 4H), 1.79-1.68 (m, 2H), 1.59-1.49 (m, 2H), 1.47-1.31 (m, 4H); $^{19}$F NMR ($CD_3OD$, 376 MHz) δ −117.71--118.09 (m, 1F), −133.70--133.93 (m, 1F), −141.50--141.84 (m, 1F); Analytical HPLC: $t_R$=12.3 min, >99% purity (10-95% MeCN/$H_2O$, linear gradient, with constant 0.1% v/v TFA additive; 20 min run; 1 mL/min flow; ESI; positive ion mode; detection at 700 nm); HRMS (ESI) calcd for $C_{37}H_{41}ClF_3N_3O_7P$ [M+H]$^+$ 762.2317, found 762.2334.

Example 32: 2-(3,7-Di(azetidin-1-yl)-5-oxido-5-phenyl-10H-acridophosphin-10-ylium-10-yl)-4-(dicyano(methoxymethoxy)methyl)-3,5,6-trifluorobenzoate

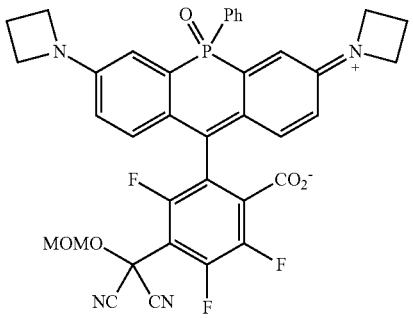

Step 1: To a solution of 3-bromoiodobenzene (21.22 g, 75.0 mmol, 3 eq) in THF (200 mL) at −40° C. was added i-PrMgCl (2.0 M in THF, 37.50 mL, 75.0 mmol, 3 eq). The reaction was then gradually warmed to −20° C. over 2 h while stirring. Dichlorophenylphosphine (3.39 mL, 25.0 mmol) was added; the reaction was then warmed to room temperature and stirred for 2 h. It was subsequently quenched with saturated NH$_4$Cl and diluted with water (~100 mL). After adding H$_2$O$_2$ (30%, 100 mL), the mixture was vigorously stirred at room temperature for 30 min and then extracted with EtOAc (2×). The combined organic extracts were washed with brine, dried over anhydrous MgSO$_4$, filtered, and evaporated. Flash chromatography on silica gel (10-100% EtOAc/toluene, linear gradient) afforded 10.81 g (99%) of bis(3-bromophenyl)(phenyl)phosphine oxide as a colorless gum. $^1$H NMR (CDCl$_3$, 400 MHz) δ 7.82 (dt, J=12.1, 1.6 Hz, 2H), 7.73-7.47 (m, 9H), 7.36 (td, J=7.8, 3.4 Hz, 2H); $^{13}$C NMR (CDCl$_3$, 101 MHz) δ 135.5 (d, $J_{CP}$=2.6 Hz, CH), 134.78 (d, $J_{CP}$=101.6 Hz, C), 134.76 (d, $J_{CP}$=10.6 Hz, CH), 132.7 (d, $J_{CP}$=2.8 Hz, CH), 132.1 (d, $J_{CP}$=10.1 Hz, CH), 131.2 (d, $J_{CP}$=106.0 Hz, C), 130.6 (d, $J_{CP}$=9.6 Hz, CH), 130.4 (d, $J_{CP}$=13.0 Hz, CH), 129.0 (d, $J_{CP}$=12.4 Hz, CH), 123.5 (d, $J_{CP}$=15.4 Hz, C); HRMS (ESI) calcd for C$_{18}$H$_{14}$Br$_2$OP [M+H]$^+$ 434.9144, found 434.9150.

Step 2: A vial was charged with Pd$_2$dba$_3$ (210 mg, 0.229 mmol, 0.1 eq), XPhos (328 mg, 0.668 mmol, 0.3 eq), and Cs$_2$CO$_3$ (2.09 g, 6.42 mmol, 2.8 eq). The vial was sealed and evacuated/backfilled with nitrogen (3×). A solution of the product from Step 1 (1.00 g, 2.29 mmol) in dioxane (10 mL) was added, and the reaction was flushed again with nitrogen (3×). Following the addition of azetidine (371 μL, 5.50 mmol, 2.4 eq), the reaction was stirred at 100° C. for 18 h. It was then cooled to room temperature, filtered through Celite with CH$_2$Cl$_2$, and concentrated to dryness. The crude product was purified by flash chromatography (0-75% acetone/CH$_2$Cl$_2$, linear gradient) to yield 475 mg (53%) of bis(3-(azetidin-1-yl)phenyl)(phenyl)phosphine oxide as a pale yellow solid. $^1$H NMR (CDCl$_3$, 400 MHz) δ 7.70-7.62 (m, 2H), 7.53-7.46 (m, 1H), 7.45-7.38 (m, 2H), 7.21 (td, J=7.8, 3.7 Hz, 2H), 6.92-6.84 (m, 2H), 6.83-6.75 (m, 2H), 6.58-6.51 (m, 2H), 3.86 (t, J=7.2 Hz, 8H), 2.34 (p, J=7.3 Hz, 4H); $^{13}$C NMR (CDCl$_3$, 101 MHz) δ 152.0 (d, $J_{CP}$=13.3 Hz, C), 133.4 (d, $J_{CP}$=103.2 Hz, C), 133.1 (d, $J_{CP}$=103.0 Hz, C), 132.2 (d, $J_{CP}$=9.9 Hz, CH), 131.7 (d, $J_{CP}$=2.7 Hz, CH), 128.8 (d, $J_{CP}$=14.2 Hz, CH), 128.3 (d, $J_{CP}$=12.0 Hz, CH), 120.8 (d, $J_{CP}$=10.7 Hz, CH), 114.53 (d, $J_{CP}$=8.8 Hz, CH), 114.47 (d, $J_{CP}$=0.8 Hz, CH), 52.4 (CH$_2$), 17.0 (CH$_2$); HRMS (ESI) calcd for C$_{24}$H$_{26}$N$_2$OP [M+H]$^+$ 389.1777, found 389.1779.

Step 3: The product from Step 2 (3.00 g, 7.72 mmol) was taken up in DMF (250 mL). N-Bromosuccinimide (2.75 g, 15.5 mmol, 2 eq) was added portion-wise over 5 min, and the reaction was then stirred at room temperature for 18 h. The reaction mixture was concentrated in vacuo; the resulting residue was diluted with water and extracted with CH$_2$Cl$_2$ (2×). The combined organic extracts were washed with brine, dried over anhydrous MgSO$_4$, filtered, and evaporated to dryness. Silica gel chromatography (0-75% EtOAc/CH$_2$Cl$_2$, linear gradient) yielded 3.13 g (74%) of bis(5-(azetidin-1-yl)-2-bromophenyl)(phenyl)phosphine oxide as a white solid. $^1$H NMR (CDCl$_3$, 400 MHz) δ 7.86-7.79 (m, 2H), 7.56-7.50 (m, 1H), 7.48-7.43 (m, 2H), 7.41 (dd, J=8.5, 4.7 Hz, 2H), 6.73 (dd, J=14.7, 2.9 Hz, 2H), 6.40 (ddd, J=8.6, 2.9, 0.7 Hz, 2H), 3.83-3.72 (m, 8H), 2.32 (p, J=7.3 Hz, 4H); $^{13}$C NMR (CDCl$_3$, 101 MHz) δ 150.8 (d, $J_{CP}$=12.8 Hz, C), 134.8 (d, $J_{CP}$=9.1 Hz, CH), 132.9 (d, $J_{CP}$=9.9 Hz, CH), 132.4 (d, $J_{CP}$=108.2 Hz, C), 131.9 (d, $J_{CP}$=2.9 Hz, CH), 131.5 (d, $J_{CP}$=109.7 Hz, C), 128.3 (d, $J_{CP}$=12.6 Hz, CH), 119.1 (d, $J_{CP}$=11.2 Hz, CH), 115.8 (d, $J_{CP}$=2.7 Hz, CH), 112.1 (d, $J_{CP}$=4.6 Hz, C), 52.3 (CH$_2$), 16.8 (CH$_2$); HRMS (ESI) calcd for C$_{24}$H$_{24}$Br$_2$N$_2$OP [M+H]$^+$ 544.9988, found 545.0004.

Step 4: A solution of the product from Step 3 (500 mg, 0.915 mmol) in THF (100 mL) was cooled to −20° C. under nitrogen. Lithium dibutyl(isopropyl)magnesate (0.7 M in Et$_2$O/hexanes, 1.57 mL, 1.10 mmol, 1.2 eq) was added, and the reaction was stirred at −20° C. for 20 min. A solution of tetrafluorophthalic anhydride (725 mg, 3.30 mmol, 3.6 eq) in THF (5 mL) was added dropwise over 5 min, and the reaction was gradually warmed to 0° C. over 4 h. It was subsequently quenched with saturated NH$_4$Cl, diluted with water, and extracted with EtOAc (2×). The combined organic extracts were washed with saturated NaHCO$_3$ and brine, dried over anhydrous MgSO$_4$, filtered, and evaporated. The crude material was purified by silica gel chromatography (0-75% acetone/CH$_2$Cl$_2$, linear gradient) followed by reverse phase HPLC (10-95% MeCN/H$_2$O, linear gradient, with constant 0.1% v/v TFA additive). The pooled HPLC product fractions were partially concentrated to remove MeCN, diluted with saturated NaHCO$_3$, and extracted with CH$_2$Cl$_2$ (2×). The organic extracts were dried over anhydrous MgSO$_4$, filtered, and evaporated to yield 63 mg (12%) of 2-(3,7-di(azetidin-1-yl)-5-oxido-5-phenyl-10H-acridophosphin-10-ylium-10-yl)-3,4,5,6-tetrafluorobenzoate as an off-white solid. $^1$H NMR (CDCl$_3$, 400 MHz) δ 7.75-7.67 (m, 2H), 7.53-7.46 (m, 1H), 7.46-7.39 (m, 2H), 6.78 (dd, J=13.8, 2.6 Hz, 2H), 6.77 (d, J=8.8, 5.9 Hz, 2H), 6.45 (dd, J=8.8, 2.5 Hz, 2H), 3.98-3.82 (m, 8H), 2.36 (p, J=7.3 Hz, 4H); $^{19}$F NMR (CDCl$_3$, 376 MHz) δ 138.39 (td, J=19.8, 9.0 Hz, 1F), −141.27 (td, J=20.3, 3.9 Hz, 1F), −142.40 (ddd, J=20.5, 18.4, 9.1 Hz, 1F), −150.60--150.76 (m, 1F); Analytical HPLC: $t_R$=12.2 min, >99% purity (10-95% MeCN/H$_2$O, linear gradient, with constant 0.1% v/v TFA additive; 20 min run; 1 mL/min flow; ESI; positive ion mode; detection at 725 nm); HRMS (ESI) calcd for C$_{32}$H$_{24}$F$_4$N$_2$O$_3$P [M+H]$^+$ 591.1455, found 591.1464.

Step 5: The product from Step 4 (145 mg, 0.246 mmol) and 2-(methoxymethoxy)malononitrile (31.0 mg, 0.246 mmol, 1 eq) were combined in DMF (8 mL), and DIEA (85.5 μL, 0.491 mmol, 2 eq) was added. After stirring the reaction at room temperature for 2 h, it was evaporated to dryness. Flash chromatography on silica gel (0-75% acetone/CH$_2$Cl$_2$, linear gradient) afforded the title compound 2-(3,7-di(azetidin-1-yl)-5-oxido-5-phenyl-10H-acridophosphin-10-ylium-10-yl)-4-(dicyano(methoxymethoxy)methyl)-3,5,6-trifluorobenzoate as a pale yellow solid (75.4 mg, 44%). $^1$H NMR (CDCl$_3$, 400 MHz) δ 7.74-7.65 (m, 2H), 7.51-7.37 (m, 3H), 6.83 (dd, J=13.7, 2.6 Hz, 2H), 6.76 (dd, J=8.8, 5.9 Hz, 2H), 6.47 (dd, J=8.8, 2.6 Hz, 2H), 5.10 (s, 2H), 4.01-3.83 (m, 8H), 3.48 (s, 3H), 2.37 (p, J=7.3 Hz, 4H); $^{19}$F NMR (CDCl$_3$, 376 MHz) δ −116.06 (d, J=22.6 Hz, 1F), −126.27 (d, J=20.2 Hz, 1F), −138.85 (dd, J=22.5, 20.3 Hz, 1F); Analytical HPLC: $t_R$=13.8 min, >99% purity (10-95% MeCN/H$_2$O, linear gradient, with constant 0.1% v/v TFA additive; 20 min run; 1 mL/min flow; ESI; positive ion mode; detection at 725 nm); HRMS (ESI) calcd for C$_{37}$H$_{29}$F$_3$N$_4$O$_5$P [M+H]$^+$ 697.1822, found 697.1825.

Example 33: 4-((2-(2-((6-Chlorohexyl)oxy)ethoxy)ethyl)carbamoyl)-2-(3,7-di(azetidin-1-yl)-5-oxido-5-phenyl-10H-acridophosphin-10-ylium-10-yl)-3,5,6-trifluorobenzoate

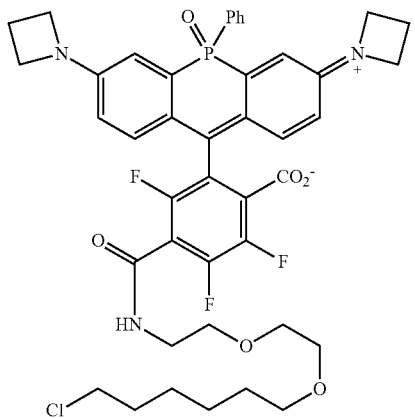

2-(3,7-Di(azetidin-1-yl)-5-oxido-5-phenyl-10H-acridophosphin-10-ylium-10-yl)-4-(dicyano(methoxymethoxy)methyl)-3,5,6-trifluorobenzoate (Example 32; 35 mg, 50.2 μmol) was taken up in CH$_2$Cl$_2$ (3 mL); triethylsilane (300 μL) was added, followed by trifluoroacetic acid (600 μL). The reaction was stirred at room temperature for 6 h. Toluene (5 mL) was added, and the reaction mixture was concentrated to dryness. The residue was combined with a premixed solution of 2-(2-((6-chlorohexyl)oxy)ethoxy)ethan-1-amine (TFA salt; 33.9 mg, 0.100 mmol, 2 eq) and DIEA (87.5 μL, 0.502 mmol, 10 eq) in CH$_2$Cl$_2$ (3 mL), and the reaction was stirred at room temperature for 18 h. The solvent was removed by rotary evaporation, and the crude material was purified by reverse phase HPLC (10-95% MeCN/H$_2$O, linear gradient, with constant 0.1% v/v TFA additive). The pooled HPLC product fractions were partially concentrated to remove MeCN, diluted with saturated NaHCO$_3$, and extracted with CH$_2$Cl$_2$ (2×). The organic extracts were dried over anhydrous MgSO$_4$, filtered, and evaporated to yield 24.3 mg (59%) of the title compound as a blue-green solid. $^1$H NMR (CDCl$_3$, 400 MHz) δ 7.76-7.65 (m, 2H), 7.50-7.37 (m, 3H), 6.76 (dd, J=8.8, 6.0 Hz, 2H), 6.74 (dd, J=13.9, 2.6 Hz, 2H), 6.66 (s, 1H), 6.44 (dd, J=8.8, 2.5 Hz, 2H), 3.96-3.81 (m, 8H), 3.64-3.56 (m, 6H), 3.53-3.47 (m, 4H), 3.36 (t, J=6.7 Hz, 2H), 2.35 (p, J=7.3 Hz, 4H), 1.78-1.69 (m, 2H), 1.54-1.37 (m, 4H), 1.35-1.27 (m, 2H); $^{19}$F NMR (CDCl$_3$, 376 MHz) δ −120.45 (d, J=22.7 Hz, 1F), −132.28 (d, J=21.4 Hz, 1F), −141.55 (t, J=22.2 Hz, 1F); Analytical HPLC: $t_R$=14.8 min, >99% purity (10-95% MeCN/H$_2$O, linear gradient, with constant 0.1% v/v TFA additive; 20 min run; 1 mL/min flow; ESI; positive ion mode; detection at 725 nm); HRMS (ESI) calcd for C$_{43}$H$_{45}$ClF$_3$N$_3$O$_6$P [M+H]$^+$ 822.2681, found 822.2688.

Example 34: 2-(3,7-Di(azetidin-1-yl)-5-oxido-5-phenyl-10H-acridophosphin-10-ylium-10-yl)-3,5,6-trifluoro-4-(methoxycarbonyl)benzoate

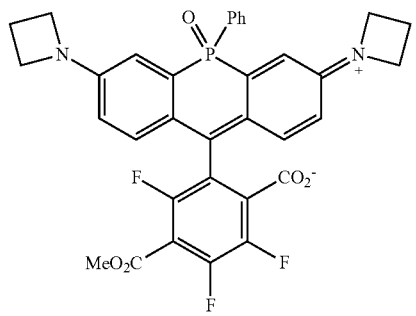

2-(3,7-Di(azetidin-1-yl)-5-oxido-5-phenyl-10H-acridophosphin-10-ylium-10-yl)-4-(dicyano(methoxymethoxy)methyl)-3,5,6-trifluorobenzoate (Example 32; 30 mg, 43.1 μmol) was taken up in CH$_2$Cl$_2$ (3 mL); triethylsilane (300 μL) was added, followed by trifluoroacetic acid (600 μL). The reaction was stirred at room temperature for 6 h. Toluene (4 mL) was added, and the reaction mixture was concentrated to dryness. The residue was combined with a premixed solution of MeOH (43.6 μL, 1.08 mmol, 25 eq) and Et$_3$N (60.0 μL, 0.431 mmol, 10 eq) in CH$_2$Cl$_2$ (3 mL), and the reaction was stirred at room temperature for 18 h. The solvent was removed by rotary evaporation, and the crude material was purified by reverse phase HPLC (40-50% MeCN/H$_2$O, linear gradient, with constant 0.1% v/v TFA additive). The pooled HPLC product fractions were partially concentrated to remove MeCN, diluted with saturated NaHCO$_3$, and extracted with CH$_2$Cl$_2$ (2×). The organic extracts were dried over anhydrous MgSO$_4$, filtered, and evaporated to yield 18.6 mg (68%) of the title compound as an off-white solid. $^1$H NMR (CDCl$_3$, 400 MHz) δ 7.76-7.67 (m, 2H), 7.51-7.38 (m, 3H), 6.76 (dd, J=8.8, 6.0 Hz, 2H), 6.75 (dd, J=13.8, 2.6 Hz, 2H), 6.45 (dd, J=8.8, 2.5 Hz, 2H), 3.96-3.81 (m, 8H), 3.91 (s, 3 Hz), 2.35 (p, J=7.3 Hz, 4H); $^{19}$F NMR (CDCl$_3$, 376 MHz) δ −118.57 (d, J=22.6 Hz, 1F), −130.21 (d, J=20.9 Hz, 1F), 141.33−−141.52 (m, 1F); Analytical HPLC: $t_R$=13.5 min, >99% purity (10-95% MeCN/H$_2$O, linear gradient, with constant 0.1% v/v TFA additive; 20 min run; 1 mL/min flow; ESI; positive ion mode; detection at 725 nm); HRMS (ESI) calcd for C$_{34}$H$_{27}$F$_3$N$_2$O$_5$P [M+H]$^+$ 631.1604, found 631.1608.

Example 35: 2-(3,7-Bis(3-fluoroazetidin-1-yl)-5-oxido-5-phenyl-10H-acridophosphin-10-ylium-10-yl)-4-(dicyano(methoxymethoxy)methyl)-3,5,6-trifluorobenzoate

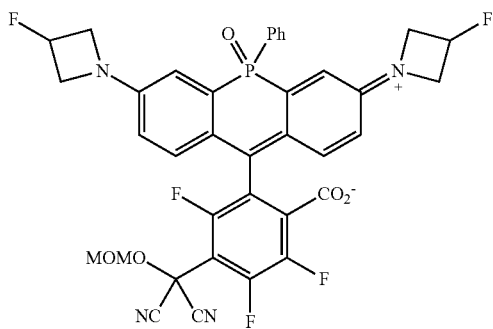

Step 1: An oven-dried round-bottom flask was charged with 3-fluoroazetidine hydrochloride (2.70 g, 24.2 mmol, 2.4 eq), Pd$_2$dba$_3$ (924 mg, 1.01 mmol, 0.1 eq), XPhos (1.44 g, 3.03 mmol, 0.3 eq), and Cs$_2$CO$_3$ (15.78 g, 48.4 mmol, 4.8 eq). The flask was sealed and evacuated/backfilled with nitrogen (3×). A solution of bis(3-bromophenyl)(phenyl)phosphine oxide (Example 32, Step 1; 4.40 g, 10.1 mmol) in dioxane (50 mL) was added, and after flushing the reaction again with nitrogen (3×), it was stirred at 100° C. for 18 h. It was then cooled to room temperature, filtered through Celite with CH$_2$Cl$_2$, and concentrated to dryness. The crude product was purified by flash chromatography (0-60% acetone/CH$_2$Cl$_2$, linear gradient) to yield 2.41 g (56%) of bis(3-(3-fluoroazetidin-1-yl)phenyl)(phenyl)phosphine oxide as a pale yellow solid. $^1$H NMR (CDCl$_3$, 400 MHz) δ 7.69-7.61 (m, 2H), 7.56-7.49 (m, 1H), 7.48-7.40 (m, 2H), 7.25 (td, J=8.0, 3.7 Hz, 2H), 6.93 (ddd, J=13.2, 2.2, 1.4 Hz, 2H), 6.88-6.79 (m, 2H), 6.63-6.56 (m, 2H), 5.39 (dtt, $^2J_{HF}$=57.0 Hz, J=5.9, 3.7 Hz, 2H), 4.24-4.11 (m, 4H), 4.03-3.88 (m, 4H); $^{19}$F NMR (CDCl$_3$, 376 MHz) δ −180.52 (dtt, J$_{FH}$=56.7, 23.8, 18.4 Hz); $^{13}$C NMR (CDCl$_3$, 101 MHz) δ 150.9 (dd, $^3J_{CP}$=13.4 Hz, J$_{CP}$=1.4 Hz, C), 133.3 (d, J$_{CP}$=103.0 Hz, C), 132.9 (d, J$_{CP}$=103.8 Hz, C), 132.2 (d, J$_{CP}$=9.9 Hz, CH), 131.9 (d, J$_{CP}$=2.9 Hz, CH), 129.0 (d, J$_{CP}$=14.0 Hz, CH), 128.5 (d, J$_{CP}$=12.1 Hz, CH), 121.6 (d, J$_{CP}$=10.7 Hz, CH), 115.2 (d, J$_{CP}$=2.8 Hz, CH), 115.0 (d, J$_{CP}$=10.3 Hz, CH), 82.8 (d, $^1J_{CF}$=204.7 Hz, CFH), 59.6 (d, $^2J_{CF}$=23.9 Hz, CH$_2$); HRMS (ESI) calcd for C$_{24}$H$_{24}$F$_2$N$_2$OP [M+H]$^+$ 425.1589, found 425.1596.

Step 2: The product from Step 1 (2.25 g, 5.30 mmol) was taken up in DMF (100 mL). N-Bromosuccinimide (1.89 g, 10.6 mmol, 2 eq) was added portion-wise over 5 min, and the reaction was then stirred at room temperature for 2 h. The reaction mixture was concentrated in vacuo; the resulting residue was diluted with water and extracted with CH$_2$Cl$_2$ (2×). The combined organic extracts were washed with brine, dried over anhydrous MgSO$_4$, filtered, and evaporated to dryness. Silica gel chromatography (0-60% EtOAc/CH$_2$Cl$_2$, linear gradient) afforded 1.53 g (50%) of bis(2-bromo-5-(3-fluoroazetidin-1-yl)phenyl)(phenyl)phosphine oxide as a white solid. $^1$H NMR (CDCl$_3$, 400 MHz) δ 7.88-7.79 (m, 2H), 7.60-7.52 (m, 1H), 7.50-7.42 (m, 4H), 6.79 (dd, J=14.5, 2.9 Hz, 2H), 6.46 (ddd, J=8.6, 2.9, 0.8 Hz, 2H), 5.36 (dtt, $^2J_{HF}$=56.9 Hz, J=5.9, 3.6 Hz, 2H), 4.15-4.03 (m, 4H), 3.95-3.82 (m, 4H); $^{19}$F NMR (CDCl$_3$, 376 MHz) δ −180.60 (dtt, J$_{FH}$=57.1, 23.8, 18.4 Hz); $^{13}$C NMR (CDCl$_3$, 101 MHz) δ 149.8 (dd, $^3J_{CP}$=12.9 Hz, $^4J_{CF}$=1.4 Hz, C), 135.0 (d, J$_{CP}$=9.0 Hz, CH), 132.9 (d, J$_{CP}$=9.9 Hz, CH), 132.8 (d, J$_{CP}$=108.1 Hz, C), 132.2 (d, J$_{CP}$=2.9 Hz, CH), 131.1 (d, J$_{CP}$=110.2 Hz, C), 128.4 (d, J$_{CP}$=12.6 Hz, CH), 119.6 (d, J$_{CP}$=11.2 Hz, CH), 116.5 (d, J$_{CP}$=2.5 Hz, CH), 113.1 (d, J$_{CP}$=4.7 Hz, C), 82.5 (d, $^1J_{CF}$=205.2 Hz, CFH), 59.5 (d, $^2J_{CF}$=24.0 Hz, CH$_2$); HRMS (ESI) calcd for C$_{24}$H$_{22}$Br$_2$F$_2$N$_2$OP [M+H]$^+$ 580.9799, found 580.9811.

Step 3: A solution of the product from Step 2 (1.35 g, 2.32 mmol) in THF (90 mL) was cooled to −20° C. under nitrogen. Lithium dibutyl(isopropyl)magnesate (0.7 M in Et$_2$O/hexanes, 3.97 mL, 2.78 mmol, 1.2 eq) was added, and the reaction was stirred at −20° C. for 20 min. A solution of tetrafluorophthalic anhydride (1.84 g, 8.35 mmol, 3.6 eq) in THF (10 mL) was added dropwise over 5 min, and the reaction was gradually warmed to 0° C. over 4 h. It was subsequently quenched with saturated NH$_4$Cl, diluted with water, and extracted with EtOAc (2×). The combined organic extracts were washed with saturated NaHCO$_3$ and brine, dried over anhydrous MgSO$_4$, filtered, and evaporated. The crude was purified twice by silica gel chromatography (0-50% acetone/CH$_2$Cl$_2$, linear gradient; then, 25-100% EtOAc/hexanes, linear gradient) to afford 223 mg (15%) of 2-(3,7-bis(3-fluoroazetidin-1-yl)-5-oxido-5-phenyl-10H-acridophosphin-10-ylium-10-yl)-3,4,5,6-tetrafluorobenzoate as an off-white solid. $^1$H NMR (CDCl$_3$, 400 MHz) δ 7.76-7.66 (m, 2H), 7.56-7.49 (m, 1H), 7.49-7.41 (m, 2H), 6.83 (dd, J=13.6, 2.7 Hz, 2H), 6.82 (dd, J=8.9, 5.8 Hz, 2H), 6.51 (dd, J=8.9, 2.6 Hz, 2H), 5.38 (dtt, $^2J_{HF}$=56.7 Hz, J=6.1, 3.3 Hz, 2H), 4.29-4.11 (m, 4H), 4.09-3.89 (m, 4H); $^{19}$F NMR (CDCl$_3$, 376 MHz) δ −137.88 (td, J=19.8, 9.2 Hz, 1F), −141.19 (td, J=20.7, 4.1 Hz, 1F), −141.89 (ddd, J=20.5, 18.5, 9.3 Hz, 1F), −150.00−−150.17 (m, 1F), −180.55 (dtt, J$_{FH}$=56.6, 23.4, 18.8 Hz, 2F); Analytical HPLC: t$_R$=12.3 min, 97.6% purity (30-95% MeCN/H$_2$O, linear gradient, with constant 0.1% v/v TFA additive; 20 min run; 1 mL/min flow; ESI; positive ion mode; detection at 254 nm); HRMS (ESI) calcd for C$_{32}$H$_{22}$F$_6$N$_2$O$_3$P [M+H]$^+$ 627.1267, found 627.1276.

Step 4: The product from Step 3 (190 mg, 0.303 mmol) and 2-(methoxymethoxy)malononitrile (38.3 mg, 0.303 mmol, 1 eq) were combined in DMF (6 mL), and DIEA (106 µL, 0.607 mmol, 2 eq) was added. After stirring the reaction at room temperature for 2 h, it was concentrated in vacuo. The crude material was purified by silica gel chromatography (0-40% acetone/CH$_2$Cl$_2$, linear gradient) followed by reverse phase HPLC (20-80% MeCN/H$_2$O, linear gradient, with constant 0.1% v/v TFA additive). The pooled HPLC product fractions were partially concentrated to remove MeCN, diluted with saturated NaHCO$_3$, and extracted with CH$_2$Cl$_2$ (2×). The organic extracts were dried over anhydrous MgSO$_4$, filtered, and evaporated to yield 88 mg (40%) of the title compound 2-(3,7-bis(3-fluoroazetidin-1-yl)-5-oxido-5-phenyl-10H-acridophosphin-10-ylium-10-yl)-4-(dicyano(methoxymethoxy)methyl)-3,5,6-trifluorobenzoate as a blue-green solid. $^1$H NMR (CDCl$_3$, 400 MHz) δ 7.74-7.65 (m, 2H), 7.54-7.48 (m, 1H), 7.47-7.40 (m, 2H), 6.88 (dd, J=13.6, 2.6 Hz, 2H), 6.81 (dd, J=8.8, 5.8 Hz, 2H), 6.54 (dd, J=8.7, 2.6 Hz, 2H), 5.40 (dtt, $^2J_{HF}$=56.8 Hz, J=6.3, 3.5 Hz, 2H), 5.10 (s, 2H), 4.31-4.14 (m, 4H), 4.13-3.92 (m, 4H), 3.49 (s, 3H); $^{19}$F NMR (CDCl$_3$, 376 MHz) δ −116.15 (d, J=22.3 Hz, 1F), −125.67 (d, J=20.1 Hz, 1F), −138.35 (dd, J=22.6, 20.1 Hz, 1F), −180.54 (dtt, J$_{FH}$=56.5, 23.7, 18.9 Hz, 2F); Analytical HPLC: t$_R$=14.5 min, 97.3% purity (10-95% MeCN/H$_2$O, linear gradient, with constant 0.1% v/v TFA additive; 20 min run; 1 mL/min flow; ESI; positive ion mode; detection at 280 nm); HRMS (ESI) calcd for $C_{37}H_{27}F_5N_4O_5P$ [M+H]$^+$ 733.1634, found 733.1651.

Example 36: 2-(3,7-Bis(3-fluoroazetidin-1-yl)-5-oxido-5-phenyl-10H-acridophosphin-10-ylium-10-yl)-4-((2-(2-((6-chlorohexyl)oxy)ethoxy)ethyl)carbamoyl)-3,5,6-trifluorobenzoate

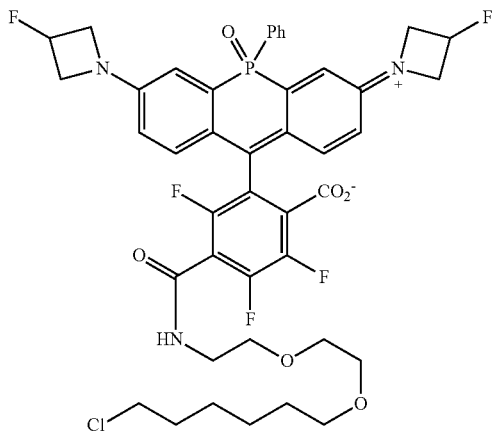

2-(3,7-Bis(3-fluoroazetidin-1-yl)-5-oxido-5-phenyl-10H-acridophosphin-10-ylium-10-yl)-4-(dicyano (methoxymethoxy)methyl)-3,5,6-trifluorobenzoate (Example 35; 50 mg, 68.3 µmol) was taken up in $CH_2Cl_2$ (4 mL); triethylsilane (400 µL) was added, followed by trifluoroacetic acid (800 µL). The reaction was stirred at room temperature for 6 h. Toluene (4 mL) was added, and the reaction mixture was concentrated to dryness. The residue was combined with a premixed solution of 2-(2-((6-chlorohexyl)oxy)ethoxy)ethan-1-amine (TFA salt; 46.1 mg, 0.137 mmol, 2 eq) and DIEA (119 µL, 0.683 mmol, 10 eq) in $CH_2Cl_2$ (3 mL), and the reaction was stirred at room temperature for 18 h. The solvent was removed by rotary evaporation, and the crude material was purified by reverse phase HPLC (30-70% MeCN/H$_2$O, linear gradient, with constant 0.1% v/v TFA additive). The pooled HPLC product fractions were partially concentrated to remove MeCN, diluted with saturated NaHCO$_3$, and extracted with $CH_2Cl_2$ (2×). The organic extracts were dried over anhydrous MgSO$_4$, filtered, and evaporated to yield 32 mg (55%) of the title compound as a pale blue-green solid. $^1$H NMR (CDCl$_3$, 400 MHz) δ 7.76-7.67 (m, 2H), 7.54-7.47 (m, 1H), 7.47-7.40 (m, 2H), 6.82 (dd, J=8.8, 5.7 Hz, 2H), 6.79 (dd, J=13.7, 2.6 Hz, 2H), 6.68 (s, 1H), 6.51 (dd, J=8.8, 2.6 Hz, 2H), 5.38 (dtt, $^2J_{HF}$=56.7 Hz, J=6.0, 3.4 Hz, 2H), 4.28-4.10 (m, 4H), 4.08-3.87 (m, 4H), 3.65-3.55 (m, 6H), 3.54-3.47 (m, 4H), 3.37 (t, J=6.7 Hz, 2H), 1.78-1.70 (m, 2H), 1.55-1.46 (m, 2H), 1.46-1.37 (m, 2H), 1.35-1.26 (m, 2H); $^{19}$F NMR (CDCl$_3$, 376 MHz) δ -120.42 (d, J=22.4 Hz, 1F), -131.74 (d, J=21.8 Hz, 1F), -141.07 (t, J=22.2 Hz, 1F), -180.54 (dtt, $J_{FH}$=56.6, 23.7, 18.8 Hz, 2F); Analytical HPLC: $t_R$=15.1 min, >99% purity (10-95% MeCN/H$_2$O, linear gradient, with constant 0.1% v/v TFA additive; 20 min run; 1 mL/min flow; ESI; positive ion mode; detection at 254 nm); HRMS (ESI) calcd for $C_{43}H_{43}ClF_5N_3O_6P$ [M+H]$^+$ 858.2493, found 858.2518.

Example 37: 4-((4-(((2-Amino-9H-purin-6-yl)oxy)methyl)benzyl)carbamoyl)-2-(3,7-bis(3-fluoroazetidin-1-yl)-5-oxido-5-phenyl-10H-acridophosphin-10-ylium-10-yl)-3,5,6-trifluorobenzoate

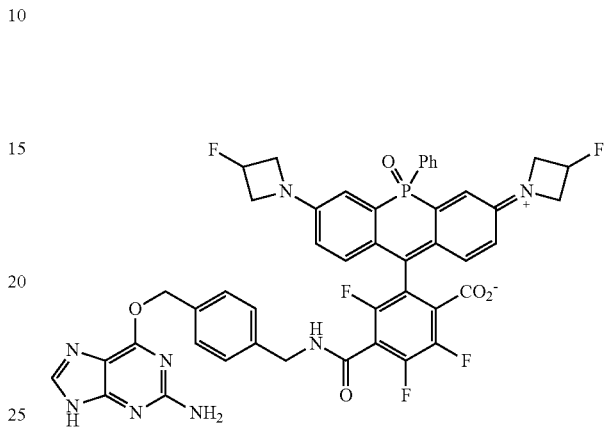

2-(3,7-Bis(3-fluoroazetidin-1-yl)-5-oxido-5-phenyl-10H-acridophosphin-10-ylium-10-yl)-4-(dicyano (methoxymethoxy)methyl)-3,5,6-trifluorobenzoate (Example 35; 50 mg, 68.3 µmol) was taken up in $CH_2Cl_2$ (3 mL); triethylsilane (0.3 mL) was added, followed by trifluoroacetic acid (0.6 mL). The reaction was stirred at room temperature for 6 h. Toluene (4 mL) was added, and the reaction mixture was concentrated to dryness. The residue was combined with a premixed suspension of 6-((4-(aminomethyl)benzyl)oxy)-9H-purin-2-amine (36.9 mg, 0.137 mmol, 2 eq) and DIEA (119 µL, 0.683 mmol, 10 eq) in DMF (4 mL), and the reaction was stirred at room temperature for 18 h. The solvent was removed by rotary evaporation, and the crude material was purified by reverse phase HPLC (10-75% MeCN/H$_2$O, linear gradient, with constant 0.1% v/v TFA additive). The pooled HPLC product fractions were partially concentrated to remove MeCN, neutralized with saturated NaHCO$_3$, and extracted with 10% MeOH/CH$_2$Cl$_2$ (2×). The organic extracts were dried over anhydrous MgSO$_4$, filtered, and evaporated to yield 19.3 mg (31%) of the title compound as a blue-green solid. $^1$H NMR (CD$_3$OD, 400 MHz) δ 7.83 (s, 1H), 7.64 (dd, J=12.9, 7.5 Hz, 2H), 7.57-7.40 (m, 5H), 7.31 (d, J=7.9 Hz, 2H), 7.01 (dd, J=8.5, 6.1 Hz, 2H), 6.73-6.64 (m, 4H), 5.55 (s, 2H), 5.48-5.28 (m, 2H), 4.52 (s, 2H), 4.26-4.08 (m, 4H), 4.02-3.82 (m, 4H); $^{19}$F NMR (CD$_3$OD, 376 MHz) δ -121.34 (d, J=22.0 Hz, 1F), -133.39 (d, J=20.4 Hz, 1F), -142.14 (t, J=21.5 Hz, 1F), -179.95 (dtt, $J_{FH}$=57.1, 23.8, 19.8 Hz, 2F); Analytical HPLC: $t_R$=11.0 min, >99% purity (10-95% MeCN/H$_2$O, linear gradient, with constant 0.1% v/v TFA additive; 20 min run; 1 mL/min flow; ESI; positive ion mode; detection at 254 nm); HRMS (ESI) calcd for $C_{46}H_{35}F_5N_8O_5P$ [M+H]$^+$ 905.2383, found 905.2401.

Example 38: 4-((4-(((2-Amino-6-chloropyrimidin-4-yl)oxy)methyl)benzyl)carbamoyl)-2-(3,7-bis(3-fluoroazetidin-1-yl)-5-oxido-5-phenyl-10H-acridophosphin-10-ylium-10-yl)-3,5,6-trifluorobenzoate

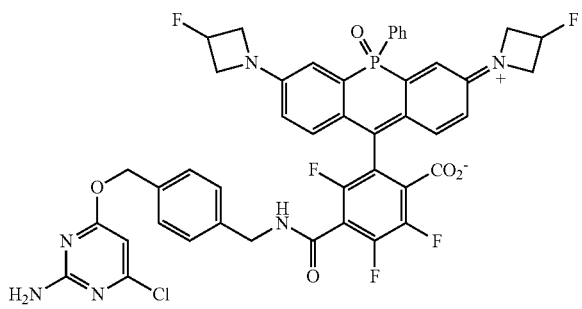

2-(3,7-Bis(3-fluoroazetidin-1-yl)-5-oxido-5-phenyl-10H-acridophosphin-10-ylium-10-yl)-4-(dicyano(methoxymethoxy)methyl)-3,5,6-trifluorobenzoate (Example 35; 60 mg, 81.9 μmol) was taken up in $CH_2Cl_2$ (4 mL); triethylsilane (0.4 mL) was added, followed by trifluoroacetic acid (0.8 mL). The reaction was stirred at room temperature for 6 h. Toluene (4 mL) was added, and the reaction mixture was concentrated to dryness. The residue was combined with a premixed solution of 4-((4-(aminomethyl)benzyl)oxy)-6-chloropyrimidin-2-amine (43.4 mg, 0.164 mmol, 2 eq) and DIEA (143 μL, 0.819 mmol, 10 eq) in DMF (4 mL), and the reaction was stirred at room temperature for 18 h. The solvent was removed by rotary evaporation, and the crude material was purified by reverse phase HPLC (30-70% MeCN/$H_2O$, linear gradient, with constant 0.1% v/v TFA additive). The pooled HPLC product fractions were partially concentrated to remove MeCN, neutralized with saturated $NaHCO_3$, and extracted with 10% MeOH/$CH_2Cl_2$ (2×). The organic extracts were dried over anhydrous $MgSO_4$, filtered, and evaporated to yield 29.8 mg (40%) of the title compound as a blue solid. $^1$H NMR ($CD_3OD$, 400 MHz) δ 7.71-7.62 (m, 2H), 7.61-7.55 (m, 1H), 7.50-7.44 (m, 2H), 7.39 (d, J=8.2 Hz, 2H), 7.30 (d, J=8.2 Hz, 2H), 7.01 (dd, J=8.5, 6.1 Hz, 2H), 6.72-6.65 (m, 4H), 6.08 (s, 1H), 5.48-5.28 (m, 2H), 5.35 (s, 2H), 4.51 (s, 2H), 4.25-4.09 (m, 4H), 4.02-3.84 (m, 4H); $^{19}$F NMR ($CD_3OD$, 376 MHz) δ −121.34 (d, J=21.0 Hz, 1F), −133.40 (d, J=21.1 Hz, 1F), −142.13 (t, J=21.4 Hz, 1F), −179.95 (dtt, $J_{FH}$=57.2, 23.8, 19.9 Hz, 2F); Analytical HPLC: $t_R$=14.4 min, >99% purity (10-95% MeCN/$H_2O$, linear gradient, with constant 0.1% v/v TFA additive; 20 min run; 1 mL/min flow; ESI; positive ion mode; detection at 254 nm); HRMS (ESI) calcd for $C_{45}H_{34}ClF_5N_6O_5P$ $[M+H]^+$ 899.1931, found 899.1943.

Example 39: 2-(3,7-Bis(3-fluoroazetidin-1-yl)-5-oxido-5-phenyl-10H-acridophosphin-10-ylium-10-yl)-3,5,6-trifluoro-4-((2-(2-(2-(4-(4-(6-(4-methylpiperazin-1-yl)-1H,3'H-[2,5'-bibenzo[d]imidazol]-2'-yl)phenoxy)butanamido)ethoxy)ethoxy)ethyl)carbamoyl)benzoate

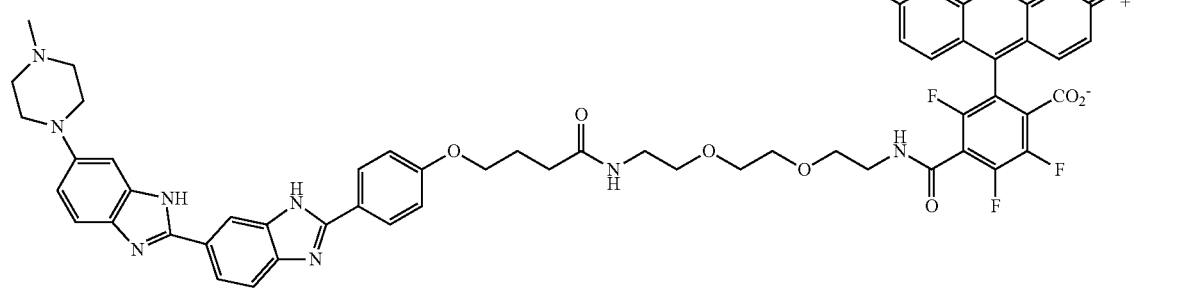

2-(3,7-Bis(3-fluoroazetidin-1-yl)-5-oxido-5-phenyl-10H-acridophosphin-10-ylium-10-yl)-4-(dicyano (methoxymethoxy)methyl)-3,5,6-trifluorobenzoate (Example 35; 50 mg, 68.3 μmol) was taken up in CH₂Cl₂ (3 mL); triethylsilane (0.3 mL) was added, followed by trifluoroacetic acid (0.6 mL). The reaction was stirred at room temperature for 6 h. Toluene (4 mL) was added, and the reaction mixture was concentrated to dryness. The residue was combined with a premixed solution of N-(2-(2-(2-aminoethoxy)ethoxy)ethyl)-4-(4-(6-(4-methylpiperazin-1-yl)-1H,3'H-[2,5'-bibenzo[d]imidazol]-2'-yl)phenoxy)butanamide (Nakamura, A. et al. *Chem. Commun.* 2004, 50, 6149-6152; 4·TFA salt; 112 mg, 0.102 mmol, 1.5 eq) and DIEA (178 μL, 1.02 mmol, 15 eq) in DMF (4 mL), and the reaction was stirred at room temperature for 18 h. The solvent was removed by rotary evaporation, and the crude material was purified by reverse phase HPLC (10-75% MeCN/H₂O, linear gradient, with constant 0.1% v/v TFA additive). The pooled HPLC product fractions were partially concentrated to remove MeCN, neutralized with saturated NaHCO₃, and extracted with 10% MeOH/CH₂Cl₂ (2×). The organic extracts were dried over anhydrous MgSO₄, filtered, and evaporated to yield 20.8 mg (24%) of the title compound as a blue-green solid. ¹H NMR (CD₃OD, 400 MHz) δ 8.27 (s, 1H), 8.04 (d, J=8.8 Hz, 2H), 8.00-7.90 (m, 1H), 7.76-7.63 (m, 3H), 7.63-7.55 (m, 1H), 7.54-7.47 (m, 3H), 7.15 (s, 1H), 7.09-7.04 (m, 3H), 6.99 (dd, J=9.1, 6.1 Hz, 2H), 6.69-6.65 (m, 2H), 6.65-6.59 (m, 2H), 5.36 (dtt, ²J$_{HF}$=57.1 Hz, J=6.0, 3.2 Hz, 2H), 4.22-4.07 (m, 4H), 4.05 (t, J=6.3 Hz, 2H), 3.99-3.81 (m, 4H), 3.60-3.47 (m, 8H), 3.44 (t, J=5.5 Hz, 2H), 3.29-3.20 (m, 6H), 2.77-2.66 (m, 4H), 2.41 (s, 3H), 2.38 (t, J=7.3 Hz, 2H), 2.07 (p, J=6.5 Hz, 2H); ¹⁹F NMR (CD₃OD, 376 MHz) δ -121.33 (d, J=22.7 Hz, 1F), -133.13 (d, J=21.2 Hz, 1F), -142.11 (t, J=21.5 Hz, 1F), -179.90 (dtt, J=57.2, 23.9, 19.8 Hz, 2F); Analytical HPLC: t$_R$=9.8 min, >99% purity (10-95% MeCN/H₂O, linear gradient, with constant 0.1% v/v TFA additive; 20 min run; 1 mL/min flow; ESI; positive ion mode; detection at 254 nm); HRMS (ESI) calcd for C₆₄H₆₅F₅N₁₀O₈P [M+H]⁺ 1275.4639, found 1275.4653.

Example 40: 2-(3,7-Bis(3-fluoroazetidin-1-yl)-5-oxido-5-phenyl-10H-acridophosphin-10-ylium-10-yl)-3,5,6-trifluoro-4-(methoxycarbonyl)benzoate

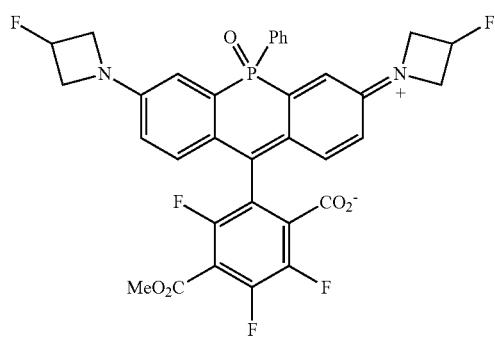

2-(3,7-Bis(3-fluoroazetidin-1-yl)-5-oxido-5-phenyl-10H-acridophosphin-10-ylium-10-yl)-4-(dicyano (methoxymethoxy)methyl)-3,5,6-trifluorobenzoate (Example 35; 25 mg, 34.1 μmol) was taken up in CH₂Cl₂ (2 mL); triethylsilane (200 μL) was added, followed by trifluoroacetic acid (400 μL). The reaction was stirred at room temperature for 6 h. Toluene (3 mL) was added, and the reaction mixture was concentrated to dryness. The residue was combined with a premixed solution of MeOH (34.6 μL, 0.853 mmol, 25 eq) and Et₃N (47.6 μL, 0.341 mmol, 10 eq) in CH₂Cl₂ (3 mL), and the reaction was stirred at room temperature for 18 h. The solvent was removed by rotary evaporation, and the crude material was purified by reverse phase HPLC (20-70% MeCN/H₂O, linear gradient, with constant 0.1% v/v TFA additive). The pooled HPLC product fractions were partially concentrated to remove MeCN, diluted with saturated NaHCO₃, and extracted with CH₂Cl₂ (2×). The organic extracts were dried over anhydrous MgSO₄, filtered, and evaporated to yield 17.7 mg (78%) of the title compound as an off-white solid. ¹H NMR (CDCl₃, 400 MHz) δ 7.72 (dd, J=12.7, 7.4 Hz, 2H), 7.55-7.48 (m, 1H), 7.48-7.41 (m, 2H), 6.81 (dd, J=8.7, 5.9 Hz, 2H), 6.80 (dd, J=13.5, 2.7 Hz, 2H), 6.52 (dd, J=8.8, 2.6 Hz, 2H), 5.38 (dtt, ²J$_{HF}$=56.8 Hz, J=6.1, 3.4 Hz, 2H), 4.29-4.10 (m, 4H), 4.09-3.92 (m, 4H), 3.92 (s, 3H); ¹⁹F NMR (CDCl₃, 376 MHz) δ -118.65 (d, J=22.5 Hz, 1F), -129.59 (d, J=20.7 Hz, 1F), -140.88 (t, J=21.8 Hz, 1F), -180.52 (dtt, J$_{FH}$=57.0, 23.8, 18.8 Hz, 2H); Analytical HPLC: t$_R$=14.1 min, >99% purity (10-95% MeCN/H₂O, linear gradient, with constant 0.1% v/v TFA additive; 20 min run; 1 mL/min flow; ESI; positive ion mode; detection at 280 nm); HRMS (ESI) calcd for C₃₄H₂₅F₅N₂O₅P [M+H]⁺ 667.1416, found 667.1423.

Example 41: 2-(3,7-Bis(3,3-difluoroazetidin-1-yl)-5-oxido-5-phenyl-10H-acridophosphin-10-ylium-10-yl)-4-(dicyano(methoxymethoxy)methyl)-3,5,6-trifluorobenzoate

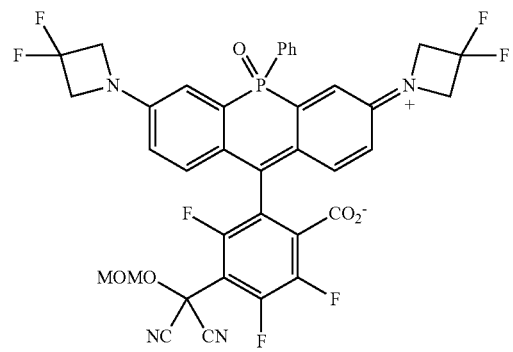

Step 1: An oven-dried round-bottom flask was charged with 3,3-difluoroazetidine hydrochloride (3.14 g, 24.2 mmol, 2.4 eq), Pd₂dba₃ (924 mg, 1.01 mmol, 0.1 eq), XPhos (1.44 g, 3.03 mmol, 0.3 eq), and Cs₂CO₃ (15.78 g, 48.4 mmol, 4.8 eq). The flask was sealed and evacuated/backfilled with nitrogen (3×). A solution of bis(3-bromophenyl)(phenyl)phosphine oxide (Example 32, Step 1; 4.40 g, 10.1 mmol) in dioxane (50 mL) was added, and after flushing the reaction again with nitrogen (3×), it was stirred at 100° C. for 18 h. It was then cooled to room temperature, filtered through Celite with CH₂Cl₂, and concentrated to dryness. The crude product was purified by flash chromatography (0-40% acetone/CH₂Cl₂, linear gradient) to yield 2.91 g (63%) of bis(3-(3,3-difluoroazetidin-1-yl)phenyl)(phenyl) phosphine oxide as a yellow foam. ¹H NMR (CDCl₃, 400 MHz) δ 7.69-7.61 (m, 2H), 7.57-7.51 (m, 1H), 7.49-7.42 (m, 2H), 7.29 (td, J=7.8, 3.7 Hz, 2H), 6.97 (ddd, J=13.1, 2.3, 1.3 Hz, 2H), 6.93-6.85 (m, 2H), 6.66-6.61 (m, 2H), 4.22 (t, $^3J_{HF}$=11.7 Hz, 8H); $^{19}$F NMR (CDCl$_3$, 376 MHz) δ −99.92 (p, $^3J_{FH}$=11.9 Hz); $^{13}$C NMR (CDCl$_3$, 101 MHz) δ 149.7 (dt, $^3J_{CP}$=13.6 Hz, $^3J_{CP}$=2.8 Hz, C), 133.5 (d, $J_{CP}$=103.0 Hz, C), 132.6 (d, $J_{CP}$=104.2 Hz, C), 132.13 (d, $J_{CP}$=9.9 Hz, CH), 132.11 (d, $J_{CP}$=2.7 Hz, CH), 129.2 (d, $J_{CP}$=13.9 Hz, CH), 128.6 (d, $J_{CP}$=12.2 Hz, CH), 122.4 (d, $J_{CP}$=10.7 Hz, CH), 115.8 (t, $^1J_{CF}$=274.6 Hz, CF$_2$), 115.7 (d, $J_{CP}$=2.8 Hz, CH), 115.5 (d, $J_{CP}$=10.2 Hz, CH), 63.4 (t, $^2J_{CF}$=26.0 Hz, CH$_2$); HRMS (ESI) calcd for C$_{24}$H$_{22}$F$_4$N$_2$OP [M+H]$^+$ 461.1400, found 461.1403.

Step 2: The product from Step 1 (3.50 g, 7.60 mmol) was taken up in DMF (50 mL). N-Bromosuccinimide (2.71 g, 15.2 mmol, 2 eq) was added portion-wise over 5 min, and the reaction was then stirred at room temperature for 2 h. The reaction mixture was concentrated in vacuo; the resulting residue was diluted with water and extracted with CH$_2$Cl$_2$ (2×). The combined organic extracts were washed with brine, dried over anhydrous MgSO$_4$, filtered, and evaporated to dryness. Silica gel chromatography (10-100% EtOAc/toluene, linear gradient) afforded an off-white solid that was subsequently triturated with Et$_2$O (~100 mL), sonicated, and filtered. The filter cake was washed with additional Et$_2$O and dried to yield 3.31 g (70%) of bis(2-bromo-5-(3,3-difluoroazetidin-1-yl)phenyl)(phenyl)phosphine oxide as a white solid. $^1$H NMR (CDCl$_3$, 400 MHz) δ 7.89-7.80 (m, 2H), 7.62-7.54 (m, 1H), 7.53-7.45 (m, 4H), 6.84 (dd, J=14.4, 3.0 Hz, 2H), 6.50 (ddd, J=8.6, 3.0, 0.8 Hz, 2H), 4.21-4.06 (m, 8H); $^{19}$F NMR (CDCl$_3$, 376 MHz) δ −99.93 (p, $^3J_{HF}$=11.7 Hz); $^{13}$C NMR (CDCl$_3$, 101 MHz) δ 148.5 (dt, $^3J_{CP}$=12.9 Hz, $^4J_{CF}$=3.0 Hz, C), 135.2 (d, $J_{CP}$=9.1 Hz, CH), 133.1 (d, $J_{CP}$=107.9 Hz, C), 132.8 (d, $J_{CP}$=10.0 Hz, CH), 132.4 (d, $J_{CP}$=2.9 Hz, CH), 130.8 (d, $J_{CP}$=110.4 Hz, C), 128.5 (d, $J_{CP}$=12.7 Hz, CH), 120.0 (d, $J_{CP}$=11.1 Hz, CH), 117.0 (d, $J_{CP}$=2.6 Hz, CH), 115.6 (t, $^1J_{CF}$=274.7 Hz, CF$_2$), 114.1 (d, $J_{CP}$=4.7 Hz, C), 63.4 (t, $^2J_{CF}$=26.3 Hz, CH$_2$); HRMS (ESI) calcd for C$_{24}$H$_{20}$Br$_2$F$_4$N$_2$OP [M+H]$^+$ 616.9611, found 616.9615.

Step 3: A solution of the product from Step 2 (500 mg, 0.809 mmol) in THF (30 mL) was cooled to −20° C. under nitrogen. Lithium dibutyl(isopropyl)magnesate (0.7 M in Et$_2$O/hexanes, 1.39 mL, 0.971 mmol, 1.2 eq) was added, and the reaction was stirred at −20° C. for 20 min. A solution of tetrafluorophthalic anhydride (641 mg, 2.91 mmol, 3.6 eq) in THF (5 mL) was added dropwise over 5 min, and the reaction was gradually warmed to 0° C. over 4 h. It was subsequently quenched with saturated NH$_4$Cl, diluted with water, and extracted with EtOAc (2×). The combined organic extracts were washed with saturated NaHCO$_3$ and brine, dried over anhydrous MgSO$_4$, filtered, and evaporated. Flash chromatography on silica gel (0-100% EtOAc/toluene, linear gradient) afforded 172 mg (32%) of 2-(3,7-bis(3,3-difluoroazetidin-1-yl)-5-oxido-5-phenyl-10H-acridophosphin-10-ylium-10-yl)-3,4,5,6-tetrafluorobenzoate as an off-white solid. $^1$H NMR (CDCl$_3$, 400 MHz) δ 7.76-7.67 (m, 2H), 7.59-7.52 (m, 1H), 7.52-7.44 (m, 2H), 6.90 (dd, J=14.0, 2.6 Hz, 2H), 6.88 (dd, J=9.0, 5.6 Hz, 2H), 6.58 (dd, J=8.8, 2.7 Hz, 2H), 4.34-4.16 (m, 8H); $^{19}$F NMR (CDCl$_3$, 376 MHz) δ −100.01 (p, J=11.6 Hz, 4F), −137.35 (td, J=19.9, 9.7 Hz, 1F), −141.18 (td, J=19.8, 4.1 Hz, 1F), −141.46 (ddd, J=20.8, 18.4, 9.6 Hz, 1F), −149.46-−149.62 (m, 1F); Analytical HPLC: $t_R$=13.0 min, >99% purity (30-95% MeCN/H$_2$O, linear gradient, with constant 0.1% v/v TFA additive; 20 min run; 1 mL/min flow; ESI; positive ion mode; detection at 254 nm); HRMS (ESI) calcd for C$_{32}$H$_{20}$F$_8$N$_2$O$_3$P [M+H]$^+$ 663.1078, found 663.1088.

Step 4: The product from Step 3 (300 mg, 0.453 mmol) and 2-(methoxymethoxy)malononitrile (57.1 mg, 0.453 mmol, 1 eq) were combined in DMF (8 mL), and DIEA (158 μL, 0.906 mmol, 2 eq) was added. After stirring the reaction at room temperature for 1 h, it was concentrated in vacuo. Flash chromatography on silica gel (10-100% EtOAc/hexanes, linear gradient) afforded the title compound 2-(3,7-bis(3,3-difluoroazetidin-1-yl)-5-oxido-5-phenyl-1 OH-acridophosphin-10-ylium-10-yl)-4-(dicyano(methoxymethoxy)methyl)-3,5,6-trifluorobenzoate as a pale yellow solid (163 mg, 47%). $^1$H NMR (CDCl$_3$, 400 MHz) δ 7.74-7.65 (m, 2H), 7.56-7.49 (m, 1H), 7.49-7.41 (m, 2H), 6.92 (dd, J=13.5, 2.6 Hz, 2H), 6.86 (dd, J=8.8, 5.7 Hz, 2H), 6.60 (dd, J=8.8, 2.7 Hz, 2H), 5.11 (s, 2H), 4.37-4.17 (m, 8H), 3.49 (s, 3H); $^{19}$F NMR (CDCl$_3$, 376 MHz) δ −99.99 (p, $^3J_{FH}$=11.6 Hz, 4F), −116.24 (d, J=22.6 Hz, 1F), −125.14 (d, J=20.1 Hz, 1F), −137.91 (dd, J=22.3, 20.5 Hz, 1F); Analytical HPLC: $t_R$=15.0 min, >99% purity (10-95% MeCN/H$_2$O, linear gradient, with constant 0.1% v/v TFA additive; 20 min run; 1 mL/min flow; ESI; positive ion mode; detection at 280 nm); HRMS (ESI) calcd for C$_{37}$H$_{25}$F$_7$N$_4$O$_5$P [M+H]$^+$ 769.1445, found 769.1459.

Example 42: 2-(3,7-Bis(3,3-difluoroazetidin-1-yl)-5-oxido-5-phenyl-10H-acridophosphin-10-ylium-10-yl)-4-((2-(2-((6-chlorohexyl)oxy)ethoxy)ethyl)carbamoyl)-3,5,6-trifluorobenzoate

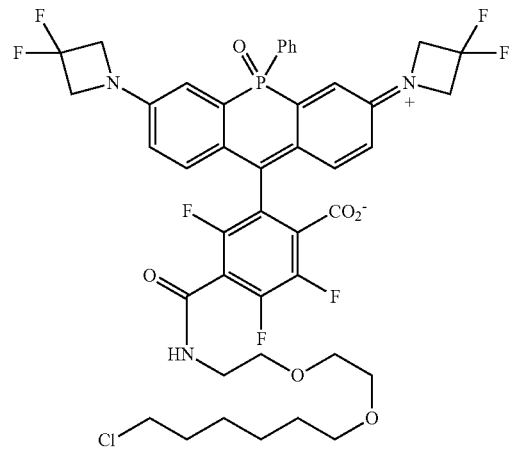

2-(3,7-Bis(3,3-difluoroazetidin-1-yl)-5-oxido-5-phenyl-10H-acridophosphin-10-ylium-10-yl)-4-(dicyano(methoxymethoxy)methyl)-3,5,6-trifluorobenzoate (Example 41; 80 mg, 0.104 mmol) was taken up in CH$_2$Cl$_2$ (5 mL); triethylsilane (500 μL) was added, followed by trifluoroacetic acid (1 mL). The reaction was stirred at room temperature for 6 h. Toluene (5 mL) was added, and the reaction mixture was concentrated to dryness. The residue was combined with a premixed solution of 2-(2-((6-chlorohexyl)oxy)ethoxy)ethan-1-amine (TFA salt; 70.3 mg, 0.208 mmol, 2 eq) and DIEA (181 μL, 1.04 mmol, 10 eq) in CH$_2$Cl$_2$ (4 mL), and the reaction was stirred at room temperature for 18 h. The solvent was removed by rotary evaporation, and the crude material was purified by reverse phase HPLC (40-70% MeCN/H$_2$O, linear gradient, with constant 0.1% v/v TFA additive). The pooled HPLC product fractions were partially concentrated to remove MeCN, diluted with saturated NaHCO$_3$, and extracted with CH$_2$Cl$_2$ (2×). The organic extracts were dried over anhydrous MgSO$_4$, filtered, and evaporated to yield 37 mg (40%) of the title compound as an off-white solid. $^1$H NMR (CDCl$_3$, 400

MHz) δ 7.76-7.67 (m, 2H), 7.56-7.50 (m, 1H), 7.50-7.41 (m, 2H), 6.91-6.79 (m, 4H), 6.67 (s, 1H), 6.57 (dd, J=8.8, 2.6 Hz, 2H), 4.34-4.13 (m, 8H), 3.64-3.56 (m, 6H), 3.54-3.48 (m, 4H), 3.38 (t, J=6.7 Hz, 2H), 1.79-1.69 (m, 2H), 1.56-1.47 (m, 2H), 1.46-1.37 (m, 2H), 1.36-1.26 (m, 2H); $^{19}$F NMR (CDCl$_3$, 376 MHz) δ −99.95 (p, J=11.7 Hz, 4F), −120.39 (d, J=22.6 Hz, 1F), −131.33 (d, J=21.5 Hz, 1F), −140.67 (t, J=22.3 Hz, 1F); Analytical HPLC: $t_R$=15.6 min, >99% purity (10-95% MeCN/H$_2$O, linear gradient, with constant 0.1% v/v TFA additive; 20 min run; 1 mL/min flow; ESI; positive ion mode; detection at 254 nm); HRMS (ESI) calcd for $C_{43}H_{41}ClF_7N_3O_6P$ [M+H]$^+$ 894.2304, found 894.2326.

Example 43: 2-(3,7-Bis(3,3-difluoroazetidin-1-yl)-5-oxido-5-phenyl-10H-acridophosphin-10-ylium-10-yl)-3,5,6-trifluoro-4-(methoxycarbonyl)benzoate

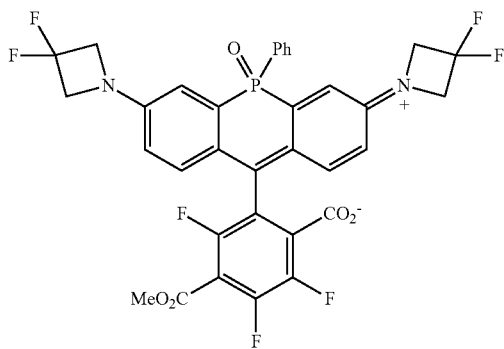

2-(3,7-Bis(3,3-difluoroazetidin-1-yl)-5-oxido-5-phenyl-10H-acridophosphin-10-ylium-10-yl)-4-(dicyano (methoxymethoxy)methyl)-3,5,6-trifluorobenzoate (Example 41; 60 mg, 78.1 μmol) was taken up in CH$_2$Cl$_2$ (4 mL); triethylsilane (400 μL) was added, followed by trifluoroacetic acid (800 μL). The reaction was stirred at room temperature for 6 h. Toluene (4 mL) was added, and the reaction mixture was concentrated to dryness. The residue was combined with a premixed solution of MeOH (79.1 μL, 1.95 mmol, 25 eq) and Et$_3$N (109 μL, 0.781 mmol, 10 eq) in CH$_2$Cl$_2$ (3 mL), and the reaction was stirred at room temperature for 18 h. The solvent was removed by rotary evaporation, and the crude material was purified by reverse phase HPLC (30-65% MeCN/H$_2$O, linear gradient, with constant 0.1% v/v TFA additive). The pooled HPLC product fractions were partially concentrated to remove MeCN, diluted with saturated NaHCO$_3$, and extracted with CH$_2$Cl$_2$ (2×). The organic extracts were dried over anhydrous MgSO$_4$, filtered, and evaporated to yield 36.8 mg (67%) of the title compound as a pale blue-green solid. $^1$H NMR (CDCl$_3$, 400 MHz) δ 7.76-7.67 (m, 2H), 7.57-7.51 (m, 1H), 7.50-7.42 (m, 2H), 6.93-6.81 (m, 4H), 6.57 (dd, J=8.8, 2.6 Hz, 2H), 4.33-4.15 (m, 8H), 3.92 (s, 3H); $^{19}$F NMR (CDCl$_3$, 376 MHz) δ −100.00 (p, J=11.6 Hz, 4F), −118.75 (d, J=22.6 Hz, 1F), −129.10 (d, J=20.6 Hz, 1F), −140.44 (dd, J=22.6, 20.9 Hz, 1F); Analytical HPLC: $t_R$=14.7 min, >99% purity (10-95% MeCN/H$_2$O, linear gradient, with constant 0.1% v/v TFA additive; 20 min run; 1 mL/min flow; ESI; positive ion mode; detection at 254 nm); HRMS (ESI) calcd for $C_{34}H_{23}F_7N_2O_5P$ [M+H]$^+$ 703.1227, found 703.1231.

Example 44: 2-(3,6-Di(azetidin-1-yl)-10,10-dioxido-9H-thioxanthen-9-ylium-9-yl)-4-(dicyano (methoxymethoxy)methyl)-3,5,6-trifluorobenzoate

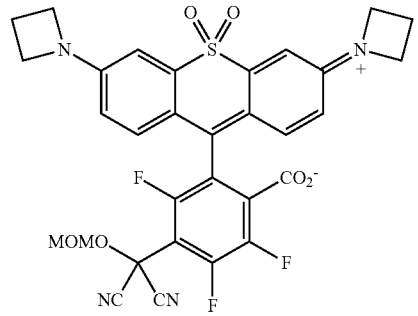

Step 1: To a solution of bis(3-bromophenyl)sulfane (Example 7, Step 1; 6.45 g, 18.7 mmol) in CH$_2$Cl$_2$ (100 mL) was added m-CPBA (9.71 g, 56.2 mmol, 3 eq). After stirring the reaction at room temperature for 4 h, it was diluted with 10% Na$_2$S$_2$O$_3$ and extracted with CH$_2$Cl$_2$ (2×). The combined organic extracts were washed with 10% Na$_2$S$_2$O$_3$, saturated NaHCO$_3$, and brine, dried over anhydrous MgSO$_4$, filtered, and evaporated to provide 3,3'-sulfonylbis(bromobenzene) as a white solid (7.01 g, 99%). Analytical HPLC and NMR indicated that the material was >95% pure and did not require further purification prior to cross-coupling with azetidine. $^1$H NMR (CDCl$_3$, 400 MHz) δ 8.08 (t, J=1.9 Hz, 2H), 7.87 (ddd, J=7.9, 1.8, 1.0 Hz, 2H), 7.72 (ddd, J=8.0, 1.9, 1.0 Hz, 2H), 7.41 (t, J=7.9 Hz, 2H); $^{13}$C NMR (CDCl$_3$, 101 MHz) δ 142.9 (C), 136.8 (CH), 131.1 (CH), 130.8 (CH), 126.5 (CH), 123.6 (C); HRMS (ESI) calcd for $C_{12}H_8Br_2O_2SNa$ [M+Na]$^+$ 396.8504, found 396.8514.

Step 2: An oven-dried round-bottom flask was charged with the product from Step 1 (2.80 g, 7.45 mmol), Pd$_2$dba$_3$ (682 mg, 0.745 mmol, 0.1 eq), XPhos (1.06 g, 2.23 mmol, 0.3 eq), and Cs$_2$CO$_3$ (6.79 g, 20.9 mmol, 2.8 eq). The flask was sealed and evacuated/backfilled with nitrogen (3×). Dioxane (35 mL) was added, and the reaction was flushed again with nitrogen (3×). Following the addition of azetidine (1.51 mL, 22.3 mmol, 3 eq), the reaction was stirred at 100° C. for 4 h. It was then cooled to room temperature, filtered through Celite with CH$_2$Cl$_2$, and concentrated to dryness. The resulting residue was purified by flash chromatography (0-40% EtOAc/hexanes, linear gradient, with constant 40% v/v CH$_2$Cl$_2$ additive) to provide a brown-orange solid. The solid was triturated with Et$_2$O, sonicated, and filtered; the filter cake was washed with additional Et$_2$O and dried to yield 1.97 g (81%) of 1,1'-(sulfonylbis(3,1-phenylene))bis (azetidine) as an off-white solid. $^1$H NMR (CDCl$_3$, 400 MHz) δ 7.26 (t, J=7.9 Hz, 2H), 7.22-7.16 (m, 2H), 6.94 (t, J=2.1 Hz, 2H), 6.52 (ddd, J=8.0, 2.3, 1.0 Hz, 2H), 3.90 (t, J=7.3 Hz, 8H), 2.38 (p, J=7.2 Hz, 4H); $^{13}$C NMR (CDCl$_3$, 101 MHz) δ 152.2 (C), 142.4 (C), 129.7 (CH), 115.9 (CH), 115.3 (CH), 109.4 (CH), 52.4 (CH$_2$), 16.9 (CH$_2$); HRMS (ESI) calcd for $C_{18}H_{20}N_2O_2SNa$ [M+Na]$^+$ 351.1138, found 351.1137.

Step 3: The product from Step 2 (1.82 g, 5.54 mmol) was taken up in DMF (200 mL). N-Bromosuccinimide (1.97 g, 11.1 mmol, 2 eq) was added portion-wise over 10 min, and the reaction was then stirred at room temperature for 72 h. The reaction mixture was concentrated in vacuo; the resulting residue was diluted with saturated NaHCO₃ and extracted with CH₂Cl₂ (2×). The combined organic extracts were washed with brine, dried over anhydrous MgSO₄, filtered, and evaporated. Silica gel chromatography (0-10% EtOAc/toluene, linear gradient) afforded 2.47 g (92%) of 1,1'-(sulfonylbis(4-bromo-3,1-phenylene))bis(azetidine) as a white solid. $^1$H NMR (CDCl₃, 400 MHz) δ 7.51 (d, J=2.9 Hz, 2H), 7.35 (d, J=8.6 Hz, 2H), 6.42 (dd, J=8.6, 2.9 Hz, 2H), 3.95 (t, J=7.3 Hz, 8H), 2.42 (p, J=7.3 Hz, 4H); $^{13}$C NMR (CDCl₃, 101 MHz) δ 150.8 (C), 139.1 (C), 135.3 (CH), 116.8 (CH), 115.9 (CH), 105.8 (C), 52.6 (CH₂), 16.9 (CH₂); HRMS (ESI) calcd for $C_{18}H_{18}Br_2N_2O_2SNa$ [M+Na]⁺ 506.9348, found 506.9362.

Step 4: A solution of the product from Step 3 (800 mg, 1.65 mmol) in THF (125 mL) was cooled to −20° C. under nitrogen. Lithium dibutyl(isopropyl)magnesate (0.7 M in Et₂O/hexanes, 2.82 mL, 1.97 mmol, 1.2 eq) was added, and the reaction was stirred at −20° C. for 20 min. A solution of tetrafluorophthalic anhydride (1.30 g, 5.92 mmol, 3.6 eq) in THF (10 mL) was then added dropwise over 10 min. The reaction was gradually warmed to 0° C. over 4 h while stirring. It was subsequently quenched with saturated NH₄Cl, diluted with water, and extracted with EtOAc (2×). The combined organic extracts were washed with saturated NaHCO₃ and brine, dried over anhydrous MgSO₄, filtered, and evaporated. Flash chromatography on silica gel (0-40% EtOAc/hexanes, linear gradient, with constant 40% v/v CH₂Cl₂ additive) afforded 307 mg (35%) of 2-(3,6-di(azetidin-1-yl)-10,10-dioxido-9H-thioxanthen-9-ylium-9-yl)-3,4,5,6-tetrafluorobenzoate as an off-white solid. $^1$H NMR (CDCl₃, 400 MHz) δ 7.09 (d, J=2.5 Hz, 2H), 6.74 (d, J=8.7 Hz, 2H), 6.40 (dd, J=8.7, 2.5 Hz, 2H), 4.01 (t, J=7.4 Hz, 8H), 2.44 (p, J=7.3 Hz, 4H); $^{19}$F NMR (CDCl₃, 376 MHz) δ −137.58 (td, J=20.0, 9.3 Hz, 1F), −138.15 (td, J=20.0, 4.7 Hz, 1F), −141.77 (ddd, J=20.6, 18.4, 9.2 Hz, 1F), −149.37 (ddd, J=20.4, 18.4, 4.7 Hz, 1F); Analytical HPLC: $t_R$=15.7 min, 98.4% purity (10-95% MeCN/H₂O, linear gradient, with constant 0.1% v/v TFA additive; 20 min run; 1 mL/min flow; ESI; positive ion mode; detection at 280 nm); HRMS (ESI) calcd for $C_{26}H_{19}F_4N_2O_4S$ [M+H]⁺ 531.0996, found 531.1001.

Step 5: To a solution of the product from Step 4 (150 mg, 0.283 mmol) in DMF (5 mL) were added DIEA (99 μL, 0.566 mmol, 2 eq) and 2-(methoxymethoxy)malononitrile (35.7 mg, 0.283 mmol, 1 eq). After stirring the reaction at room temperature for 2 h, it was evaporated to dryness. Flash chromatography on silica gel (0-50% EtOAc/hexanes, linear gradient, with constant 40% v/v CH₂Cl₂ additive) afforded the title compound 2-(3,6-di(azetidin-1-yl)-10,10-dioxido-9H-thioxanthen-9-ylium-9-yl)-4-(dicyano(methoxymethoxy)methyl)-3,5,6-trifluorobenzoate as a yellow-green solid (76.4 mg, 42%). $^1$H NMR (CDCl₃, 400 MHz) δ 7.10 (d, J=2.5 Hz, 2H), 6.67 (d, J=8.7 Hz, 2H), 6.40 (dd, J=8.7, 2.5 Hz, 2H), 5.17 (s, 2H), 4.02 (t, J=7.4 Hz, 8H), 3.54 (s, 3H), 2.45 (p, J=7.4 Hz, 4H); $^{19}$F NMR (CDCl₃, 376 MHz) δ −112.54 (d, J=22.8 Hz, 1F), −124.88 (d, J=20.2 Hz, 1F), −138.16 (dd, J=23.0, 20.3 Hz, 1F); Analytical HPLC: $t_R$=13.0 min, >99% purity (10-95% MeCN/H₂O, linear gradient, with constant 0.1% v/v TFA additive; 20 min run; 1 mL/min flow; ESI; positive ion mode; detection at 725 nm); HRMS (ESI) calcd for $C_{31}H_{24}F_3N_4O_6S$ [M+H]⁺ 637.1363, found 637.1365.

Example 45: 4-((2-(2-((6-Chlorohexyl)oxy)ethoxy)ethyl)carbamoyl)-2-(3,6-di(azetidin-1-yl)-10,10-dioxido-9H-thioxanthen-9-ylium-9-yl)-3,5,6-trifluorobenzoate

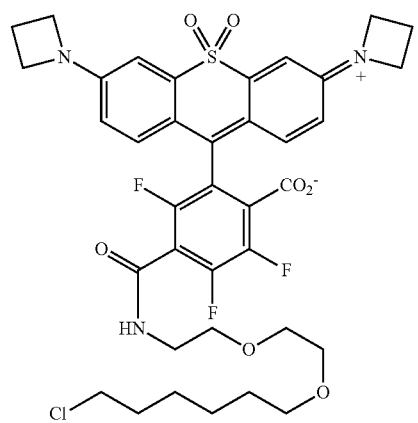

2-(3,6-Di(azetidin-1-yl)-10,10-dioxido-9H-thioxanthen-9-ylium-9-yl)-4-(dicyano(methoxymethoxy)methyl)-3,5,6-trifluorobenzoate (Example 44; 40 mg, 62.8 μmol) was taken up in CH₂Cl₂ (4 mL); triethylsilane (400 μL) was added, followed by trifluoroacetic acid (800 μL). The reaction was stirred at room temperature for 18 h. Toluene (5 mL) was added, and the reaction mixture was concentrated to dryness. The residue was combined with a premixed solution of 2-(2-((6-chlorohexyl)oxy)ethoxy)ethan-1-amine (TFA salt; 42 mg, 0.126 mmol, 2 eq) and DIEA (109 μL, 0.628 mmol, 10 eq) in CH₂Cl₂ (3 mL), and the reaction was stirred at room temperature for 2 h. The solvent was removed by rotary evaporation, and the crude material was purified by reverse phase HPLC (40-70% MeCN/H₂O, linear gradient, with constant 0.1% v/v TFA additive). The pooled HPLC product fractions were partially concentrated to remove MeCN, diluted with saturated NaHCO₃, and extracted with CH₂Cl₂ (2×). The organic extracts were dried over anhydrous MgSO₄, filtered, and evaporated to yield 15.3 mg (32%) of the title compound as an off-white solid. $^1$H NMR (CDCl₃, 400 MHz) δ 7.07 (d, J=2.5 Hz, 2H), 6.77 (d, J=8.8 Hz, 2H), 6.69 (bs, 1H), 6.42 (dd, J=8.7, 2.5 Hz, 2H), 4.00 (t, J=7.3 Hz, 8H), 3.66-3.57 (m, 6H), 3.56-3.48 (m, 4H), 3.38 (t, J=6.6 Hz, 2H), 2.44 (p, J=7.3 Hz, 4H), 1.79-1.69 (m, 2H), 1.55-1.36 (m, 4H), 1.36-1.27 (m, 2H); $^{19}$F NMR (CDCl₃, 376 MHz) δ −117.76 (d, J=22.3 Hz, 1F), −130.89 (d, J=22.2 Hz, 1F), −140.68 (t, J=22.1 Hz, 1F); Analytical HPLC: $t_R$=13.6 min, >99% purity (10-95% MeCN/H₂O, linear gradient, with constant 0.1% v/v TFA additive; 20 min run; 1 mL/min flow; ESI; positive ion mode; detection at 254 nm); HRMS (ESI) calcd for $C_{37}H_{40}ClF_3N_3O_7S$ [M+H]⁺ 762.2222, found 762.2238.

Example 46: 2-(3,6-Di(azetidin-1-yl)-10,10-dioxido-9H-thioxanthen-9-ylium-9-yl)-3,5,6-trifluoro-4-(methoxycarbonyl)benzoate

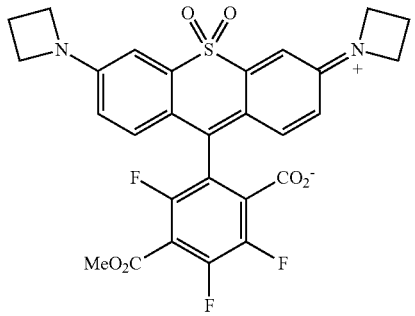

2-(3,6-Di(azetidin-1-yl)-10,10-dioxido-9H-thioxanthen-9-ylium-9-yl)-4-(dicyano(methoxymethoxy)methyl)-3,5,6-trifluorobenzoate (Example 44; 20 mg, 31.4 μmol) was taken up in CH$_2$Cl$_2$ (2 mL); triethylsilane (200 μL) was added, followed by trifluoroacetic acid (400 μL). The reaction was stirred at room temperature for 6 h. Toluene (3 mL) was added, and the reaction mixture was concentrated to dryness. The residue was combined with a premixed solution of MeOH (31.8 μL, 0.785 mmol, 25 eq) and Et$_3$N (43.8 μL, 0.314 mmol, 10 eq) in CH$_2$Cl$_2$ (3 mL), and the reaction was stirred at room temperature for 18 h. The solvent was removed by rotary evaporation, and the crude material was purified by reverse phase HPLC (30-70% MeCN/H$_2$O, linear gradient, with constant 0.1% v/v TFA additive). The pooled product fractions were partially concentrated to remove MeCN, diluted with saturated NaHCO$_3$, and extracted with CH$_2$Cl$_2$ (2×). The organic extracts were dried over anhydrous MgSO$_4$, filtered, and evaporated to yield 11.6 mg (65%) of the title compound as a pale yellow solid. $^1$H NMR (CDCl$_3$, 400 MHz) δ 7.09 (d, J=2.5 Hz, 2H), 6.74 (d, J=8.7 Hz, 2H), 6.41 (dd, J=8.7, 2.6 Hz, 2H), 4.00 (t, J=7.4 Hz, 8H), 3.93 (s, 3H), 2.44 (p, J=7.3 Hz, 4H); $^{19}$F NMR (CDCl$_3$, 376 MHz) δ −115.63 (d, J=22.7 Hz, 1F), −129.24 (d, J=20.7 Hz, 1F), −140.60 (t, J=21.8 Hz, 1F); Analytical HPLC: t$_R$=15.2 min, >99% purity (10-95% MeCN/H$_2$O, linear gradient, with constant 0.1% v/v TFA additive; 20 min run; 1 mL/min flow; ESI; positive ion mode; detection at 254 nm); HRMS (ESI) calcd for C$_{28}$H$_{22}$F$_3$N$_2$O$_6$S [M+H]$^+$ 571.1145, found 571.1156.

Example 47: 4-(Dicyano(methoxymethoxy)methyl)-2,3,5-trifluoro-6-(6-hydroxy-3-oxo-3H-xanthen-9-yl)benzoic Acid

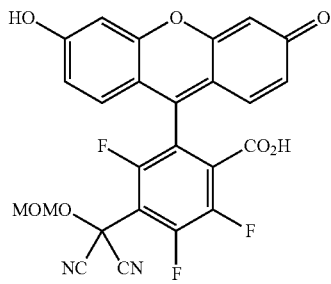

2,3,4,5-Tetrafluoro-6-(6-hydroxy-3-oxo-3H-xanthen-9-yl)benzoic acid (Sun, W.-C. et al. *J. Org. Chem.* 1997, 62, 6469-6475; 100 mg, 0.247 mmol) and 2-(methoxymethoxy)malononitrile (31.2 mg, 0.247 mmol, 1 eq) were combined in DMF (5 mL), and DIEA (129 μL, 0.742 mmol, 3 eq) was added. After stirring the reaction at room temperature for 18 h, it was evaporated to dryness and purified by reverse phase HPLC (30-60% MeCN/H$_2$O, linear gradient, with constant 0.1% v/v TFA additive). The pooled product fractions were partially concentrated to remove MeCN and extracted with CH$_2$Cl$_2$ (3×). The organic extracts were dried over anhydrous MgSO$_4$, filtered, and evaporated to provide the title compound (69 mg, 55%) as a yellow-orange solid. $^1$H NMR (DMSO-d$_6$, 400 MHz) δ 10.26 (s, 2H), 7.05 (d, J=8.7 Hz, 2H), 6.70 (d, J=2.3 Hz, 2H), 6.60 (dd, J=8.7, 2.4 Hz, 2H), 5.11 (s, 2H), 3.34 (s, 3H); $^{19}$F NMR (DMSO-d$_6$, 376 MHz) δ −118.57 (d, J=21.4 Hz, 1F), −129.27 (d, J=21.1 Hz, 1F), −140.99 (t, J=21.3 Hz, 1F); Analytical HPLC: t$_R$=12.9 min, >99% purity (10-95% MeCN/H$_2$O, linear gradient, with constant 0.1% v/v TFA additive; 20 min run; 1 mL/min flow; ESI; positive ion mode; detection at 254 nm); HRMS (ESI) calcd for C$_{25}$H$_{14}$F$_3$N$_2$O$_7$ [M+H]$^+$ 511.0748, found 511.0746.

Example 48: 4-((2-(2-((6-Chlorohexyl)oxy)ethoxy)ethyl)carbamoyl)-2,3,5-trifluoro-6-(6-hydroxy-3-oxo-3H-xanthen-9-yl)benzoic Acid

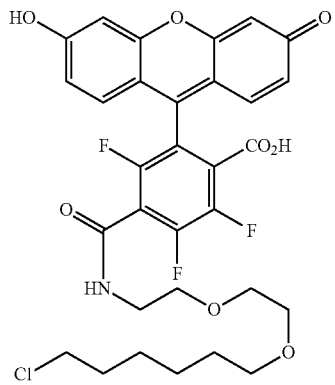 [SMILES: O=C(NCCOCCOCCCCCCCl)c1c(F)c(F)c(C(=O)O)c(-c2c3ccc(=O)cc-3oc3cc(O)ccc23)c1F]

4-(Dicyano(methoxymethoxy)methyl)-2,3,5-trifluoro-6-(6-hydroxy-3-oxo-3H-xanthen-9-yl)benzoic acid (Example 47; 30 mg, 58.8 μmol) was taken up in CH$_2$Cl$_2$ (4 mL); triethylsilane (400 μL) was added, followed by trifluoroacetic acid (800 μL). The reaction was stirred at room temperature for 24 h. Toluene (5 mL) was added, and the reaction mixture was concentrated to dryness. The residue was combined with a premixed solution of 2-(2-((6-chlorohexyl)oxy)ethoxy)ethan-1-amine (TFA salt; 39.7 mg, 0.118 mmol, 2 eq) and DIEA (102 μL, 0.588 mmol, 10 eq) in DMF (4 mL), and the reaction was stirred at room temperature for 18 h. The solvent was removed by rotary evaporation, and the crude material was purified by reverse phase HPLC (20-70% MeCN/H$_2$O, linear gradient, with constant 0.1% v/v TFA additive) to yield 27.1 mg (72%) of the title compound as an orange solid. $^1$H NMR (CD$_3$OD, 400 MHz) δ 9.05 (t, J=5.1 Hz, 1H), 6.89 (d, J=8.7 Hz, 2H), 6.70 (d, J=2.4 Hz, 2H), 6.63 (dd, J=8.7, 2.4 Hz, 2H), 3.61-3.47 (m, 10H), 3.40 (t, J=6.5 Hz, 2H), 1.78-1.69 (m, 2H), 1.55-1.46 (m, 2H), 1.46-1.38 (m, 2H), 1.37-1.28 (m, 2H); $^{19}$F NMR (CD$_3$OD, 376 MHz) δ −122.09--122.44 (m, 1F), −133.85

(d, J=20.3 Hz, 1F), −142.82−−143.23 (m, 1F); Analytical HPLC: $t_R$=13.7 min, >99% purity (10-95% MeCN/H$_2$O, linear gradient, with constant 0.1% v/v TFA additive; 20 min run; 1 mL/min flow; ESI; positive ion mode; detection at 254 nm); HRMS (ESI) calcd for $C_{31}H_{30}ClF_3NO_8$ [M+H]$^+$ 636.1607, found 636.1611.

Example 49: 4-(Dicyano(methoxymethoxy)methyl)-2,3,5-trifluoro-6-(6-hydroxy-10,10-dimethyl-3-oxo-3,10-dihydroanthracen-9-yl)benzoic Acid

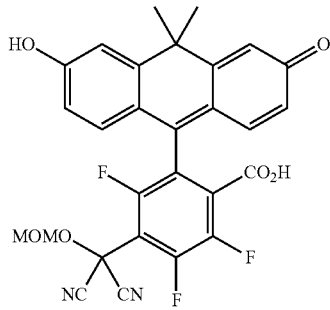

Step 1: To a solution of 1-bromo-2-iodo-4-methoxybenzene (21.83 g, 69.75 mmol, 1.5 eq) in THF (200 mL) at −40° C. was added i-PrMgCl (2.0 M in THF, 34.88 mL, 69.75 mmol, 1.5 eq). The reaction was gradually warmed to −20° C. over 3 h while stirring. A solution of 2-bromo-5-methoxybenzaldehyde (10.00 g, 46.50 mmol) in THF (50 mL) was added; the reaction was then warmed to room temperature and stirred for 18 h. It was subsequently quenched with saturated NH$_4$Cl, diluted with water, and extracted with EtOAc (2×). The combined organic extracts were washed with brine, dried over anhydrous MgSO$_4$, filtered, and evaporated. Flash chromatography on silica gel (0-20% EtOAc/toluene, linear gradient) afforded 16.42 g (88%) of bis(2-bromo-5-methoxyphenyl)methanol as a waxy white solid. $^1$H NMR (CDCl$_3$, 400 MHz) δ 7.46 (d, J=8.7 Hz, 2H), 6.90 (d, J=3.1 Hz, 2H), 6.74 (dd, J=8.7, 3.1 Hz, 2H), 6.29 (d, J=4.0 Hz, 1H), 3.75 (s, 6H), 2.57 (d, J=4.1 Hz, 1H); $^{13}$C NMR (CDCl$_3$, 101 MHz) δ 159.3 (C), 141.9 (C), 133.6 (CH), 114.9 (CH), 114.2 (C), 74.3 (CH), 55.6 (CH$_3$); FIRMS (EI) calcd for $C_{15}H_{14}Br_2O_3$ [M−]$^+$ 399.9304/401.9284/403.9263, found 399.9318/401.9304/403.9285.

Step 2: To a solution of the product from Step 1 (15.00 g, 37.3 mmol) in CH$_2$Cl$_2$ (150 mL) was added MnO$_2$ (60.00 g) in one portion. The black reaction mixture was stirred at room temperature for 96 h. It was then filtered through Celite with CH$_2$Cl$_2$ and concentrated in vacuo. The residue was resubjected to the same reaction conditions with fresh CH$_2$Cl$_2$ (150 mL) and MnO$_2$ (60.00 g) for an additional 48 h. The mixture was again filtered through Celite with CH$_2$Cl$_2$ and evaporated. Flash chromatography on silica gel (0-30% EtOAc/hexanes, linear gradient) yielded 11.81 g (79%) of bis(2-bromo-5-methoxyphenyl)methanone as a pale yellow oil. $^1$H NMR (CDCl$_3$, 400 MHz) δ 7.51 (d, J=8.8 Hz, 2H), 7.01 (d, J=3.1 Hz, 2H), 6.92 (dd, J=8.8, 3.1 Hz, 2H), 3.80 (s, 6H); $^{13}$C NMR (CDCl$_3$, 101 MHz) δ 195.2 (C), 158.9 (C), 140.0 (C), 134.9 (CH), 118.8 (CH), 116.7 (CH), 111.7 (C), 55.8 (CH$_3$); FIRMS (ESI) calcd for $C_{15}H_{13}Br_2O_3$ [M+H]$^+$ 398.9226, found 398.9226.

Step 3: An oven-dried 500 mL 3-neck round-bottom flask equipped with two addition funnels was charged with CH$_2$Cl$_2$ (100 mL) under nitrogen and cooled to −40° C. Solutions of first TiCl$_4$ (1 M in CH$_2$Cl$_2$, 96.98 mL, 96.98 mmol, 8 eq) then Me$_2$Zn (1.2 M in toluene, 80.82 mL, 96.98 mmol, 8 eq) were successively added dropwise via the addition funnels. The reaction was stirred at −40° C. to −30° C. for 20 min. A solution of the product from Step 2 (4.85 g, 12.12 mmol) in CH$_2$Cl$_2$ (20 mL) was added, and the resulting suspension was allowed to warm to room temperature overnight (18 h) while stirring vigorously. The mixture was carefully diluted with water and extracted with CH$_2$Cl$_2$ (2×). The combined organic extracts were washed with brine, dried over anhydrous MgSO$_4$, filtered through Celite, and concentrated in vacuo. Silica gel chromatography (0-20% Et$_2$O/hexanes, linear gradient) afforded 1.41 g (28%) of the desired product 2,2'-(propane-2,2-diyl)bis(1-bromo-4-methoxybenzene), as well as 3.35 g (69%) of the olefin elimination product 2,2'-(ethene-1,1-diyl)bis(1-bromo-4-methoxybenzene). $^1$H NMR (CDCl$_3$, 400 MHz) δ 7.35 (d, J=8.7 Hz, 2H), 7.20 (d, J=3.0 Hz, 2H), 6.63 (dd, J=8.7, 3.0 Hz, 2H), 3.82 (s, 6H), 1.80 (s, 6H); $^{13}$C NMR (CDCl$_3$, 101 MHz) δ 159.0 (C), 147.9 (C), 135.6 (CH), 116.1 (CH), 113.1 (C), 112.4 (CH), 55.6 (CH$_3$), 46.1 (C), 29.2 (CH$_3$); HRMS (EI) calcd for $C_{17}H_{18}Br_2O_{02}$ [M−]$^+$ 411.9668/415.9627, found 411.9674/415.9645.

Step 4: The product from Step 3 (2.60 g, 6.28 mmol) was taken up in CH$_2$Cl$_2$ (36 mL) under nitrogen and cooled to 0° C. Boron tribromide (1 M in CH$_2$Cl$_2$, 18.83 mL, 18.83 mmol, 3 eq) was added dropwise. The reaction was warmed to room temperature and stirred for 2 h. It was then carefully quenched and neutralized through the slow addition of saturated NaHCO$_3$ while stirring vigorously. The biphasic mixture was extracted with CH$_2$Cl$_2$ (2×). The combined organics were dried over anhydrous MgSO$_4$, filtered, and concentrated in vacuo. Flash chromatography on silica gel (0-30% EtOAc/toluene, linear gradient) yielded 2.26 g (93%) of 3,3'-(propane-2,2-diyl)bis(4-bromophenol) as a white solid. $^1$H NMR (CD$_3$CN, 400 MHz) δ 7.25 (d, J=8.5 Hz, 2H), 7.15 (d, J=2.9 Hz, 2H), 7.01 (s, 2H), 6.58 (dd, J=8.6, 2.9 Hz, 2H), 1.74 (s, 6H); $^{13}$C NMR (CD$_3$CN, 101 MHz) δ 157.4 (C), 148.9 (C), 136.4 (CH), 117.4 (CH), 115.8 (CH), 112.2 (C), 46.5 (C), 29.4 (CH$_3$); HRMS (EI) calcd for $C_{15}H_{14}Br_2O_2$ [M−]$^+$ 383.9355/385.9335/387.9314, found 383.9366/385.9343/387.9324.

Step 5: A solution of the product from Step 4 (2.16 g, 5.59 mmol) and DIEA (2.92 mL, 16.78 mmol, 3 eq) in CH$_2$Cl$_2$ (25 mL) was cooled to 0° C. Bromomethyl methyl ether (1.14 mL, 13.99 mmol, 2.5 eq) was added dropwise. The reaction was then warmed to room temperature and stirred for 1 h. It was subsequently diluted with water and extracted with CH$_2$Cl$_2$ (2×). The combined organic extracts were washed with saturated NaHCO$_3$ and brine, dried over anhydrous MgSO$_4$, filtered, and evaporated. Flash chromatography (0-30% EtOAc/hexanes, linear gradient) afforded 2,2'-(propane-2,2-diyl)bis(1-bromo-4-(methoxymethoxy)benzene) as a white solid (1.92 g, 72%). $^1$H NMR (CDCl$_3$, 400 MHz) δ 7.34 (d, J=8.6 Hz, 2H), 7.32 (d, J=2.9 Hz, 2H), 6.79 (dd, J=8.7, 2.9 Hz, 2H), 5.18 (s, 4H), 3.50 (s, 6H), 1.80 (s, 6H); $^{13}$C NMR (CDCl$_3$, 101 MHz) δ 156.8 (C), 147.9 (C), 135.6 (CH), 118.1 (CH), 115.2 (CH), 114.3 (C), 94.9 (CH$_2$), 56.2 (CH$_3$), 46.1 (C), 29.1 (CH$_3$); HRMS (ESI) calcd for $C_{19}H_{23}Br_2O_4$ [M+H]$^+$ 471.9879/473.9859/475.9838, found 471.9885/473.9876/475.9854.

Step 6: A solution of the product from Step 5 (1.00 g, 2.11 mmol) in THF (25 mL) was cooled to −78° C. under nitrogen. tert-Butyllithium (1.7 M in pentane, 5.46 mL, 9.28 mmol, 4.4 eq) was added, and the reaction was stirred at −78° C. for 30 min. It was then warmed to −10° C. before adding a solution of MgBr$_2$·OEt$_2$ (1.20 g, 4.64 mmol, 2.2 eq)

in THF (20 mL). After an additional 30 min at −10° C., a solution of tetrafluorophthalic anhydride (1.02 g, 4.64 mmol, 2.2 eq) in THF (15 mL) was added dropwise over 30 min via addition funnel. The reaction was then allowed to warm to room temperature overnight (18 h). It was subsequently diluted with saturated NH$_4$Cl and water and extracted with EtOAc (2×). The combined organic extracts were washed with saturated NaHCO$_3$ and brine, dried over anhydrous MgSO$_4$, filtered, and concentrated in vacuo. Silica gel chromatography (0-50% EtOAc/hexanes, linear gradient) afforded 595 mg (54%) of 4',5',6',7'-tetrafluoro-3,6-bis(methoxymethoxy)-10,10-dimethyl-3'H,10H-spiro[anthracene-9,1'-isobenzofuran]-3'-one as a white foam. $^1$H NMR (CDCl$_3$, 400 MHz) δ 7.27 (d, J=2.5 Hz, 2H), 6.91 (dd, J=8.8, 2.5 Hz, 2H), 6.79 (d, J=8.7 Hz, 2H), 5.21 (AB quartet, $v_A$=2088.3 Hz, $v_B$=2080.5 Hz, $J_{AB}$=7.0 Hz, 4H), 3.50 (s, 6H), 1.78 (s, 3H), 1.73 (s, 3H); $^{19}$F NMR (CDCl$_3$, 376 MHz) δ −138.72 (td, J=19.9, 9.0 Hz, 1F), −141.73 (td, J=20.0, 4.1 Hz, 1F), −142.59 (ddd, J=20.8, 18.2, 9.1 Hz, 1F), −151.00 (ddd, J=20.5, 18.3, 4.1 Hz, 1F); Analytical HPLC: $t_R$=14.1 min, 97.5% purity (30-95% MeCN/H$_2$O, linear gradient, with constant 0.1% v/v TFA additive; 20 min run; 1 mL/min flow; ESI; positive ion mode; detection at 254 nm); HRMS (ESI) calcd for C$_{27}$H$_{23}$F$_4$O$_6$ [M+H]$^+$ 519.1425, found 519.1436.

Step 7: The product from Step 6 (390 mg, 0.752 mmol) was taken up in CH$_2$Cl$_2$ (7.5 mL), and trifluoroacetic acid (1.5 mL) was added. The reaction was stirred at room temperature for 6 h. Toluene (10 mL) was added, and the reaction mixture was concentrated to dryness. Purification by silica gel chromatography (0-75% EtOAc/hexanes, linear gradient) provided 285 mg (88%) of 2,3,4,5-tetrafluoro-6-(6-hydroxy-10,10-dimethyl-3-oxo-3,10-dihydroanthracen-9-yl)benzoic acid as an off-white solid. $^1$H NMR (DMSO-d$_6$, 400 MHz) δ 9.81 (s, 2H), 7.10 (d, J=2.4 Hz, 2H), 6.84 (d, J=8.6 Hz, 2H), 6.66 (dd, J=8.6, 2.4 Hz, 2H), 1.69 (s, 3H), 1.60 (s, 3H); $^{19}$F NMR (DMSO-d$_6$, 376 MHz) δ −139.94--140.16 (m, 1F), −143.10--143.30 (m, 1F), −143.78 (td, J=21.4, 20.8, 8.4 Hz, 1F), −152.01--152.23 (m, 1F); Analytical HPLC: $t_R$=12.8 min, >99% purity (10-95% MeCN/H$_2$O, linear gradient, with constant 0.1% v/v TFA additive; 20 min run; 1 mL/min flow; ESI; positive ion mode; detection at 254 nm); HRMS (ESI) calcd for C$_{23}$H$_{15}$F$_4$O$_4$ [M+H]$^+$ 431.0901, found 431.0899.

Step 8: The product from Step 7 (125 mg, 0.290 mmol) and 2-(methoxymethoxy)malononitrile (36.6 mg, 0.290 mmol, 1 eq) were combined in DMF (4 mL), and DIEA (152 μL, 0.871 mmol, 3 eq) was added. After stirring the reaction at room temperature for 2 h, it was diluted with 10% citric acid and extracted with EtOAc (2×). The combined organic extracts were washed with water and brine, dried over anhydrous MgSO$_4$, filtered, and concentrated in vacuo. Flash chromatography on silica gel (0-75% EtOAc/toluene, linear gradient) afforded 92 mg (59%) of the title compound 4-(dicyano(methoxymethoxy)methyl)-2,3,5-trifluoro-6-(6-hydroxy-10,10-dimethyl-3-oxo-3,10-dihydroanthracen-9-yl)benzoic acid as an orange solid. $^1$H NMR (DMSO-d$_6$, 400 MHz) δ 9.83 (s, 2H), 7.10 (d, J=2.5 Hz, 2H), 6.87 (d, J=8.6 Hz, 2H), 6.66 (dd, J=8.7, 2.4 Hz, 2H), 5.10 (s, 2H), 3.32 (s, 3H), 1.68 (s, 3H), 1.60 (s, 3H); $^{19}$F NMR (DMSO-d$_6$, 376 MHz) δ −117.77 (d, J=21.4 Hz, 1F), −129.80 (d, J=21.4 Hz, 1F), −141.28 (t, J=21.5 Hz, 1F); Analytical HPLC: $t_R$=13.1 min, 99.0% purity (10-95% MeCN/H$_2$O, linear gradient, with constant 0.1% v/v TFA additive; 20 min run; 1 mL/min flow; ESI; positive ion mode; detection at 254 nm); HRMS (ESI) calcd for C$_{28}$H$_{20}$F$_3$N$_2$O$_6$ [M+H]$^+$ 537.1268, found 537.1268.

Example 50: 4-((2-(2-((6-Chlorohexyl)oxy)ethoxy)ethyl)carbamoyl)-2,3,5-trifluoro-6-(6-hydroxy-10,10-dimethyl-3-oxo-3,10-dihydroanthracen-9-yl)benzoic Acid

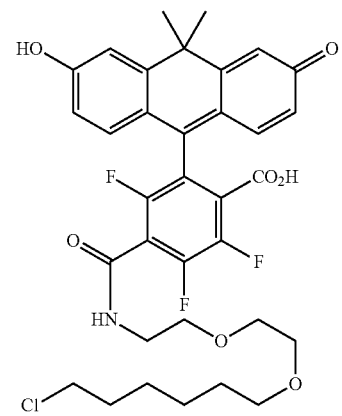 [SMILES: CC1(C)C2=CC(=O)C=CC2=C(c2c(F)c(C(=O)NCCOCCOCCCCCCCl)c(F)c(F)c2C(=O)O)c2ccc(O)cc21]

4-(Dicyano(methoxymethoxy)methyl)-2,3,5-trifluoro-6-(6-hydroxy-10,10-dimethyl-3-oxo-3,10-dihydroanthracen-9-yl)benzoic acid (Example 49; 50 mg, 93.2 μmol) was taken up in CH$_2$Cl$_2$ (3 mL); triethylsilane (300 μL) was added, followed by trifluoroacetic acid (600 μL). The reaction was stirred at room temperature for 18 h. Toluene (4 mL) was added, and the reaction mixture was concentrated to dryness. The residue was combined with a premixed solution of 2-(2-((6-chlorohexyl)oxy)ethoxy)ethan-1-amine (TFA salt; 63.0 mg, 0.186 mmol, 2 eq) and DIEA (162 μL, 0.932 mmol, 10 eq) in DMF (3 mL), and the reaction was stirred at room temperature for 2 h. It was then diluted with 10% citric acid and extracted with EtOAc (2×). The combined organic extracts were dried over anhydrous MgSO$_4$, filtered, and concentrated in vacuo. Purification by reverse phase HPLC (30-70% MeCN/H$_2$O, linear gradient, with constant 0.1% v/v TFA additive) yielded 14.2 mg (23%) of the title compound as a light pink solid. $^1$H NMR (CD$_3$OD, 400 MHz) δ 9.07 (t, J=5.6 Hz, 1H), 7.09 (d, J=2.5 Hz, 2H), 6.77 (d, J=8.6 Hz, 2H), 6.67 (dd, J=8.6, 2.5 Hz, 2H), 3.60-3.46 (m, 10H), 3.40 (t, J=6.5 Hz, 2H), 1.78-1.68 (m, 2H), 1.74 (s, 3H), 1.69 (s, 3H), 1.56-1.46 (m, 2H), 1.46-1.38 (m, 2H), 1.38-1.28 (m, 2H); $^{19}$F NMR (CD$_3$OD, 376 MHz) δ −122.22 (d, J=22.5 Hz, 1F), −134.87 (d, J=20.4 Hz, 1F), −143.66 (t, J=21.6 Hz, 1F); Analytical HPLC: $t_R$=13.9 min, >99% purity (10-95% MeCN/H$_2$O, linear gradient, with constant 0.1% v/v TFA additive; 20 min run; 1 mL/min flow; ESI; positive ion mode; detection at 254 nm); HRMS (ESI) calcd for C$_{34}$H$_{36}$ClF$_3$NO$_7$ [M+H]$^+$ 662.2127, found 662.2129.

Example 51: 4-(Dicyano(methoxymethoxy)methyl)-2,3,5-trifluoro-6-(7-hydroxy-5,5-dimethyl-3-oxo-3,5-dihydrodibenzo[b,e]silin-10-yl)benzoic Acid

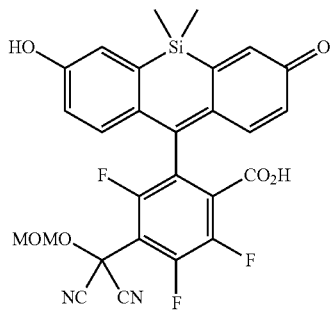

2,3,4,5-Tetrafluoro-6-(7-hydroxy-5,5-dim ethyl-3-oxo-3,5-dihydrodibenzo[b,e]silin-10-yl)benzoic acid (Grimm, J. B. et al. *ACS Cent. Sci.* 2017, 3, 975-985; 45 mg, 0.101 mmol) and 2-(methoxymethoxy)malononitrile (12.7 mg, 0.101 mmol, 1 eq) were combined in DMF (2 mL), and DIEA (52.7 µL, 0.302 mmol, 3 eq) was added. After stirring the reaction at room temperature for 3 h, it was diluted with 10% citric acid and extracted with EtOAc (2×). The combined organic extracts were washed with water and brine, dried over anhydrous MgSO$_4$, filtered, and concentrated in vacuo. Flash chromatography on silica gel (0-60% EtOAc/toluene, linear gradient) afforded 31.6 mg (57%) of the title compound as an off-white solid. $^1$H NMR (CDCl$_3$, 400 MHz) δ 7.14 (d, J=2.6 Hz, 2H), 6.82 (d, J=8.8 Hz, 2H), 6.78 (dd, J=8.7, 2.6 Hz, 2H), 5.17 (s, 2H), 5.01 (s, 2H), 3.52 (s, 3H), 0.57 (s, 3H), 0.54 (s, 3H); $^{19}$F NMR (CDCl$_3$, 376 MHz) δ −113.71 (d, J=22.6 Hz, 1F), −126.48 (d, J=19.9 Hz, 1F), −138.58 (dd, J=22.7, 20.1 Hz, 1F); Analytical HPLC: t$_R$=13.5 min, >99% purity (10-95% MeCN/H$_2$O, linear gradient, with constant 0.1% v/v TFA additive; 20 min run; 1 mL/min flow; ESI; positive ion mode; detection at 254 nm); HRMS (ESI) calcd for C$_{27}$H$_{20}$F$_3$N$_2$O$_6$Si [M+H]$^+$ 553.1037, found 553.1039.

Example 52: 4-((2-(2-((6-Chlorohexyl)oxy)ethoxy)ethyl)carbamoyl)-2,3,5-trifluoro-6-(7-hydroxy-5,5-dimethyl-3-oxo-3,5-dihydrodibenzo[b,e]silin-10-yl)benzoic Acid

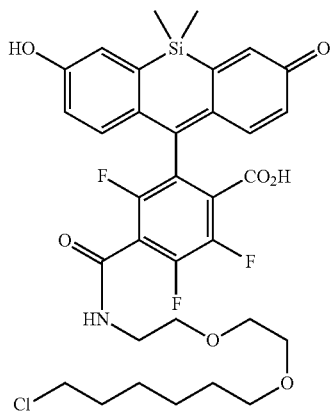 [SMILES: C[Si]1(C)C2=CC(=O)C=CC2=C(c2c(F)c(C(=O)NCCOCCOCCCCCCCl)c(F)c(F)c2C(=O)O)c2ccc(O)cc21]

4-(Dicyano(methoxymethoxy)methyl)-2,3,5-trifluoro-6-(7-hydroxy-5,5-dimethyl-3-oxo-3,5-dihydrodibenzo[b,e]silin-10-yl)benzoic acid (Example 51; 30 mg, 54.3 µmol) was taken up in CH$_2$Cl$_2$ (3 mL); triethylsilane (300 µL) was added, followed by trifluoroacetic acid (600 µL). The reaction was stirred at room temperature for 24 h. Toluene (4 mL) was added, and the reaction mixture was concentrated to dryness. The residue was combined with a premixed solution of 2-(2-(2-((6-chlorohexyl)oxy)ethoxy)ethan-1-amine (TFA salt; 36.7 mg, 0.109 mmol, 2 eq) and DIEA (94.6 µL, 0.543 mmol, 10 eq) in DMF (3 mL), and the reaction was stirred at room temperature for 2 h. The solvent was removed by rotary evaporation, and the crude material was purified by reverse phase HPLC (20-70% MeCN/H$_2$O, linear gradient, with constant 0.1% v/v TFA additive) to yield 20.4 mg (55%) of the title compound as a white solid. $^1$H NMR (CD$_3$OD, 400 MHz) δ 9.15 (t, J=5.3 Hz, 1H), 7.14 (d, J=2.7 Hz, 2H), 6.87 (dd, J=8.7, 1.0 Hz, 2H), 6.74 (dd, J=8.7, 2.8 Hz, 2H), 3.65-3.52 (m, 8H), 3.50 (t, J=6.7 Hz, 2H), 3.42 (t, J=6.6 Hz, 2H), 1.74-1.65 (m, 2H), 1.55-1.46 (m, 2H), 1.44-1.26 (m, 4H), 0.56 (s, 3H), 0.52 (s, 3H); $^{19}$F NMR (CD$_3$OD, 376 MHz) δ −118.77 (d, J=22.2 Hz, 1F), −134.57--134.69 (m, 1F), −143.21 (t, J=21.6 Hz, 1F); Analytical HPLC: t$_R$=14.2 min, >99% purity (10-95% MeCN/H$_2$O, linear gradient, with constant 0.1% v/v TFA additive; 20 min run; 1 mL/min flow; ESI; positive ion mode; detection at 254 nm); HRMS (ESI) calcd for C$_{33}$H$_{36}$ClF$_3$NO$_7$Si [M+H]$^+$ 678.1896, found 678.1907.

Example 53: Di-tert-butyl (6-(dicyano(methoxymethoxy)methyl)-4,5,7-trifluoro-3-oxo-3H-spiro[isobenzofuran-1,9'-xanthene]-3',6'-diyl)dicarbamate

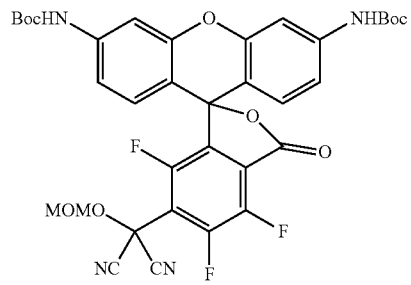

Step 1: 2,3,4,5-Tetrafluoro-6-(6-hydroxy-3-oxo-3H-xanthen-9-yl)benzoic acid (Sun, W.-C. et al. *J. Org. Chem.* 1997, 62, 6469-6475; 1.00 g, 2.47 mmol) was taken up in CH$_2$Cl$_2$ (25 mL) and cooled to 0° C. Pyridine (1.60 mL, 19.79 mmol, 8 eq) and trifluoromethanesulfonic anhydride (1.66 mL, 9.89 mmol, 4 eq) were added, and the reaction was allowed to warm to room temperature overnight (18 h). It was subsequently diluted with water and extracted with CH$_2$Cl$_2$ (2×). The combined organic extracts were washed with saturated CuSO$_4$ and brine, dried over anhydrous MgSO$_4$, filtered, and concentrated in vacuo. Flash chromatography on silica gel (0-40% EtOAc/hexanes, linear gradient) afforded 1.10 g (67%) of 4,5,6,7-tetrafluoro-3-oxo-3H-spiro[isobenzofuran-1,9'-xanthene]-3',6'-diyl bis (trifluoromethanesulfonate) as a white foam. $^1$H NMR (CDCl$_3$, 400 MHz) δ 7.35-7.32 (m, 2H), 7.16-7.10 (m, 4H); $^{19}$F NMR (CDCl$_3$, 376 MHz) δ −73.07 (s, 6F), −136.01 (td, J=19.8, 10.3 Hz, 1F), −139.59 (ddd, J=20.7, 18.0, 10.3 Hz, 1F), −141.78 (td, J=19.9, 5.1 Hz, 1F), −147.64 (ddd, J=20.2, 18.0, 5.1 Hz, 1F); Analytical HPLC: $t_R$=16.2 min, >99% purity (30-95% MeCN/H$_2$O, linear gradient, with constant 0.1% v/v TFA additive; 20 min run; 1 mL/min flow; ESI; positive ion mode; detection at 280 nm); HRMS (ESI) calcd for C$_{22}$H$_7$F$_{10}$O$_9$S$_2$ [M+H]$^+$ 668.9366, found 668.9361.

Step 2: A vial was charged with the product from Step 1 (200 mg, 0.299 mmol), tert-butyl carbamate (84.1 mg, 0.718 mmol, 2.4 eq), Pd$_2$dba$_3$ (27.4 mg, 29.9 μmol, 0.1 eq), XPhos (42.8 mg, 89.8 μmol, 0.3 eq), and Cs$_2$CO$_3$ (273 mg, 0.838 mmol, 2.8 eq). The vial was sealed and evacuated/backfilled with nitrogen (3×). Dioxane (2 mL) was added, and the reaction was flushed again with nitrogen (3×). The reaction was stirred at 80° C. for 4 h. It was then cooled to room temperature, filtered through Celite with CH$_2$Cl$_2$, and evaporated. The residue was purified by silica gel chromatography (0-30% EtOAc/hexanes, linear gradient) to afford di-tert-butyl (4,5,6,7-tetrafluoro-3-oxo-3H-spiro[isobenzofuran-1,9'-xanthene]-3',6'-diyl)dicarbamate (172 mg, 95%) as an off-white solid. $^1$H NMR (CDCl$_3$, 400 MHz) δ 7.49 (d, J=2.2 Hz, 2H), 7.01 (dd, J=8.7, 2.3 Hz, 2H), 6.82 (d, J=8.7 Hz, 2H), 6.61 (s, 2H), 1.53 (s, 18H); $^{19}$F NMR (CDCl$_3$, 376 MHz) δ −138.19 (td, J=19.8, 9.4 Hz, 1F), −141.93 (ddd, J=20.5, 17.6, 9.2 Hz, 1F), −142.12 (td, J=19.8, 4.0 Hz, 1F), −149.98 (ddd, J=20.5, 17.7, 3.9 Hz, 1F); Analytical HPLC: $t_R$=15.6 min, >99% purity (30-95% MeCN/H$_2$O, linear gradient, with constant 0.1% v/v TFA additive; 20 min run; 1 mL/min flow; ESI; positive ion mode; detection at 254 nm); HRMS (ESI) calcd for C$_{30}$H$_{27}$F$_4$N$_2$O$_7$ [M+H]$^+$ 603.1749, found 603.1750.

Step 3: The product from Step 2 (300 mg, 0.498 mmol) and 2-(methoxymethoxy)malononitrile (62.8 mg, 0.498 mmol, 1 eq) were combined in DMF (5 mL), and DIEA (173 μL, 0.996 mmol, 2 eq) was added. After stirring the reaction at room temperature for 2 h, it was concentrated in vacuo and purified by silica gel chromatography (0-50% EtOAc/hexanes, linear gradient) to yield 183 mg (52%) of the title compound di-tert-butyl (6-(dicyano(methoxymethoxy)methyl)-4,5,7-trifluoro-3-oxo-3H-spiro[isobenzofuran-1,9'-xanthene]-3',6'-diyl)dicarbamate as an off-white solid. $^1$H NMR (CDCl$_3$, 400 MHz) δ 7.48 (d, J=2.2 Hz, 2H), 7.06 (dd, J=8.7, 2.2 Hz, 2H), 6.82 (d, J=8.6 Hz, 2H), 6.63 (s, 2H), 5.13 (s, 2H), 3.51 (s, 3H), 1.53 (s, 18H); $^{19}$F NMR (CDCl$_3$, 376 MHz) δ −116.95 (d, J=22.9 Hz, 1F), −125.48 (d, J=19.9 Hz, 1F), −138.65 (dd, J=23.0, 20.2 Hz, 1F); Analytical HPLC: $t_R$=15.2 min, >99% purity (30-95% MeCN/H$_2$O, linear gradient, with constant 0.1% v/v TFA additive; 20 min run; 1 mL/min flow; ESI; positive ion mode; detection at 254 nm); HRMS (ESI) calcd for C$_{35}$H$_{32}$F$_3$N$_4$O$_9$ [M+H]$^+$ 709.2116, found 709.2130.

Example 54: 4-((2-(2-((6-Chlorohexyl)oxy)ethoxy)ethyl)carbamoyl)-2-(3,6-diaminoxanthylium-9-yl)-3,5,6-trifluorobenzoate

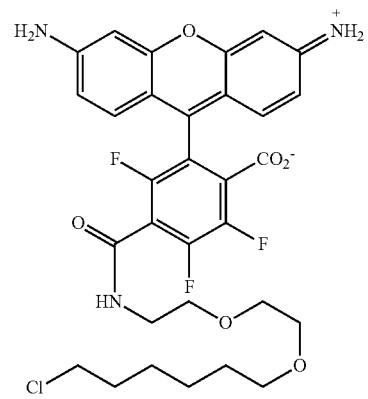

Di-tert-butyl (6-(dicyano(methoxymethoxy)methyl)-4,5,7-trifluoro-3-oxo-3H-spiro[isobenzofuran-1,9'-xanthene]-3',6'-diyl)dicarbamate (Example 53; 90 mg, 0.127 mmol) was taken up in CH$_2$Cl$_2$ (5 mL); triethylsilane (500 μL) was added, followed by trifluoroacetic acid (1 mL). The reaction was stirred at room temperature for 8 h. Toluene (5 mL) was added, and the reaction mixture was concentrated to dryness. The residue was combined with a premixed solution of 2-(2-((6-chlorohexyl)oxy)ethoxy)ethan-1-amine (TFA salt; 85.8 mg, 0.254 mmol, 2 eq) and DIEA (221 μL, 1.27 mmol, 10 eq) in DMF (3 mL), and the reaction was stirred at room temperature for 18 h. The solvent was removed by rotary evaporation, and the crude material was purified by reverse phase HPLC (30-40% MeCN/H$_2$O, linear gradient, with constant 0.1% v/v TFA additive) to afford the title compound as a red-orange solid (20.5 mg, 22%, TFA salt). $^1$H NMR (CD$_3$OD, 400 MHz) δ 9.12 (t, J=5.5 Hz, 1H), 7.29 (dd, J=9.2, 0.9 Hz, 2H), 6.88 (dd, J=9.2, 2.1 Hz, 2H), 6.80 (d, J=2.1 Hz, 2H), 3.68-3.54 (m, 8H), 3.51 (t, J=6.6 Hz, 2H), 3.42 (t, J=6.5 Hz, 2H), 1.76-1.66 (m, 2H), 1.54-1.45 (m, 2H), 1.44-1.27 (m, 4H); $^{19}$F NMR (CD$_3$OD, 376 MHz) δ −116.65 (d, J=15.3 Hz, 1F), −132.55 (d, J=21.7 Hz, 1F), −140.18--140.53 (m, 1F); Analytical HPLC: $t_R$=11.0 min, >99% purity (10-95% MeCN/H$_2$O, linear gradient, with constant 0.1% v/v TFA additive; 20 min run; 1 mL/min flow; ESI; positive ion mode; detection at 525 nm); HRMS (ESI) calcd for C$_{31}$H$_{32}$ClF$_3$N$_3$O$_6$ [M+H]$^+$ 634.1926, found 634.1926.

Example 55: 2-(3,6-Bis(methyl(phenyl)amino)xanthylium-9-yl)-4-(dicyano(methoxymethoxy)methyl)-3,5,6-trifluorobenzoate

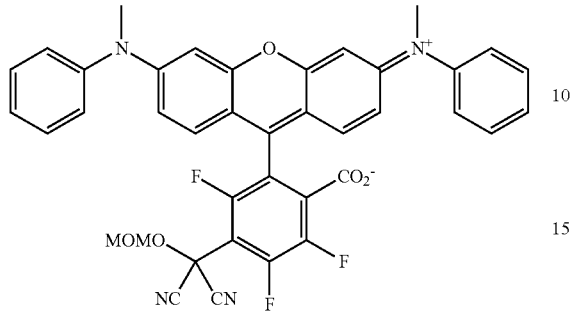

Step 1: A vial was charged with 4,5,6,7-tetrafluoro-3-oxo-3H-spiro[isobenzofuran-1,9'-xanthene]-3',6'-diylbis(trifluoromethanesulfonate) (Example 53, Step 1; 90 mg, 0.135 mmol), $Pd_2dba_3$ (12.3 mg, 13.5 μmol, 0.1 eq), XPhos (19.3 mg, 40.4 μmol, 0.3 eq), and $Cs_2CO_3$ (123 mg, 0.377 mmol, 2.8 eq). The vial was sealed and evacuated/backfilled with nitrogen (3×). Dioxane (1 mL) was added, and the reaction was flushed again with nitrogen (3×). Following the addition of N-methylaniline (32.1 μL, 0.296 mmol, 2.2 eq), the reaction was stirred at 80° C. for 4 h. It was then cooled to room temperature, diluted with $CH_2Cl_2$, deposited onto Celite, and concentrated to dryness. Purification by silica gel chromatography (10-100% EtOAc/hexanes, linear gradient; dry load with Celite) afforded 2-(3,6-bis(methyl(phenyl)amino)xanthylium-9-yl)-3,4,5,6-tetrafluorobenzoate (70.7 mg, 90%) as a pale purple solid. $^1H$ NMR ($CDCl_3$, 400 MHz) δ 7.41-7.35 (m, 4H), 7.22-7.16 (m, 6H), 6.67 (d, J=8.8 Hz, 2H), 6.60 (d, J=2.4 Hz, 2H), 6.52 (dd, J=8.8, 2.5 Hz, 2H), 3.33 (s, 6H); $^{19}F$ NMR ($CDCl_3$, 376 MHz) δ −139.02 (td, J=20.0, 8.7 Hz, 1F), −141.95 (td, J=20.0, 4.0 Hz, 1F), −143.05 (ddd, J=20.4, 18.0, 8.6 Hz, 1F), −150.82−−151.01 (m, 1F); Analytical HPLC: $t_R$=11.0 min, >99% purity (30-95% $MeCN/H_2O$, linear gradient, with constant 0.1% v/v TFA additive; 20 min run; 1 mL/min flow; ESI; positive ion mode; detection at 550 nm); MS (ESI) calcd for $C_{34}H_{23}F_4N_2O_3$ $[M+H]^+$ 583.2, found 583.1.

Step 2: The product from Step 1 (60 mg, 0.103 mmol) and 2-(methoxymethoxy)malononitrile (13.0 mg, 0.103 mmol, 1 eq) were combined in DMF (3 mL), and DIEA (35.9 μL, 0.206 mmol, 2 eq) was added. After stirring the reaction at room temperature for 2 h, it was evaporated to dryness. Flash chromatography on silica gel (25-100% EtOAc/hexanes, linear gradient) afforded the title compound 243,6-bis(methyl(phenyl)amino)xanthylium-9-yl)-4-(dicyano(methoxymethoxy)methyl)-3,5,6-trifluorobenzoate (41.4 mg, 58%) as a purple solid. $^1H$ NMR ($CDCl_3$, 400 MHz) δ 7.45-7.37 (m, 4H), 7.26-7.19 (m, 6H), 6.78 (d, J=8.9 Hz, 2H), 6.61 (d, J=2.4 Hz, 2H), 6.58 (dd, J=8.9, 2.5 Hz, 2H), 5.14 (s, 2H), 3.53 (s, 3H), 3.38 (s, 6H); $^{19}F$ NMR ($CDCl_3$, 376 MHz) δ −116.29 (d, J=21.6 Hz, 1F), −126.47 (d, J=20.8 Hz, 1F), −139.41 (t, J=21.2 Hz, 1F); Analytical HPLC: $t_R$=11.4 min, >99% purity (30-95% $MeCN/H_2O$, linear gradient, with constant 0.1% v/v TFA additive; 20 min run; 1 mL/min flow; ESI; positive ion mode; detection at 550 nm); MS (ESI) calcd for $C_{39}H_{28}F_3N_4O_5$ $[M+H]^+$ 689.2, found 689.1.

Example 56: 2-(3,6-Bis(methyl(phenyl)amino)xanthylium-9-yl)-4-((2-(2-((6-chlorohexyl)oxy)ethoxy)ethyl)carbamoyl)-3,5,6-trifluorobenzoate

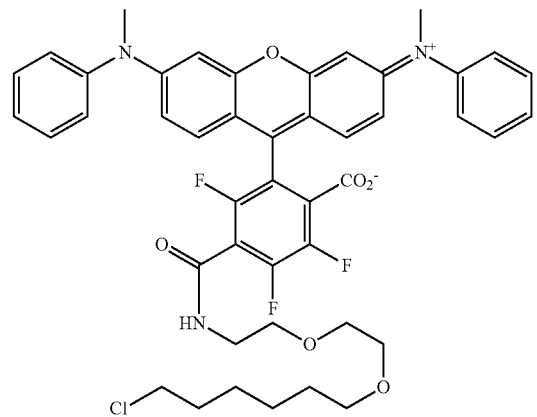

2-(3,6-Bis(methyl(phenyl)amino)xanthylium-9-yl)-4-(dicyano(methoxymethoxy)methyl)-3,5,6-trifluorobenzoate (Example 55; 30 mg, 43.6 μmol) was taken up in $CH_2Cl_2$ (3 mL); triethylsilane (300 μL) was added, followed by trifluoroacetic acid (600 μL). The reaction was stirred at room temperature for 6 h. Toluene (4 mL) was added, and the reaction mixture was concentrated to dryness. The residue was combined with a premixed solution of 2-(2-((6-chlorohexyl)oxy)ethoxy)ethan-1-amine (TFA salt; 29.4 mg, 87.1 μmol, 2 eq) and DIEA (75.9 μL, 0.436 mmol, 10 eq) in $CH_2Cl_2$ (3 mL), and the reaction was stirred at room temperature for 18 h. The solvent was removed by rotary evaporation, and the crude material was purified by reverse phase HPLC (30-95% $MeCN/H_2O$, linear gradient, with constant 0.1% v/v TFA additive) to yield 15.6 mg (39%, TFA salt) of the title compound as a dark purple solid. $^1H$ NMR ($CD_3OD$, 400 MHz) δ 9.08 (t, J=5.2 Hz, 1H), 7.62-7.54 (m, 4H), 7.51-7.45 (m, 2H), 7.41-7.32 (m, 6H), 6.99 (d, J=2.4 Hz, 2H), 6.92 (dd, J=9.4, 2.4 Hz, 2H), 3.66-3.53 (m, 8H), 3.62 (s, 6H), 3.51 (t, J=6.6 Hz, 2H), 3.41 (t, J=6.5 Hz, 2H), 1.75-1.66 (m, 2H), 1.53-1.45 (m, 2H), 1.43-1.27 (m, 4H); $^{19}F$ NMR ($CD_3OD$, 376 MHz) δ −116.81 (d, J=15.4 Hz, 1F), −132.38 (d, J=22.7 Hz, 1F), −140.46−−140.73 (m, 1F); Analytical HPLC: $t_R$=11.5 min, >99% purity (30-95% $MeCN/H_2O$, linear gradient, with constant 0.1% v/v TFA additive; 20 min run; 1 mL/min flow; ESI; positive ion mode; detection at 550 nm); MS (ESI) calcd for $C_{45}H_{44}ClF_3N_3O_6$ $[M+H]^+$ 814.3, found 814.2.

Example 57: Di-tert-butyl (6'-(dicyano (methoxymethoxy)methyl)-4',5',7'-trifluoro-10,10-dimethyl-3'-oxo-3'H,10H-spiro[anthracene-9,1'-isobenzofuran]-3,6-diyl)dicarbamate

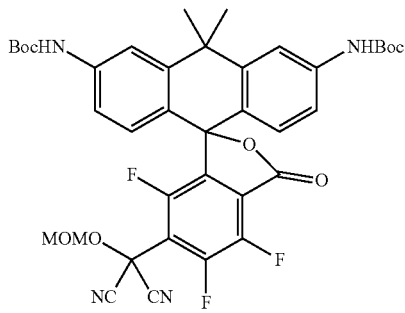

Step 1: To a solution of 2,3,4,5-tetrafluoro-6-(6-hydroxy-10,10-dimethyl-3-oxo-3,10-dihydroanthracen-9-yl)benzoic acid (Example 49, Step 7; 445 mg, 1.03 mmol) in $CH_2Cl_2$ (10 mL) were added pyridine (669 µL, 8.27 mmol, 8 eq) and trifluoromethanesulfonic anhydride (696 µL, 4.14 mmol, 4 eq). The reaction was stirred at room temperature for 1 h. It was subsequently diluted with water and extracted with $CH_2Cl_2$ (2×). The combined organic extracts were washed with saturated $CuSO_4$ and brine, dried over anhydrous $MgSO_4$, filtered, and concentrated in vacuo. Flash chromatography on silica gel (0-30% EtOAc/hexanes, linear gradient) afforded 684 mg (95%) of 4',5',6',7'-tetrafluoro-10, 10-dimethyl-3'-oxo-3'H,10H-spiro[anthracene-9,1'-isobenzofuran]-3,6-diylbis(trifluoromethanesulfonate) as a white solid. $^1$H NMR ($CDCl_3$, 400 MHz) δ 7.56 (d, J=2.6 Hz, 2H), 7.19 (dd, J=8.8, 2.5 Hz, 2H), 7.02 (d, J=8.8 Hz, 2H), 1.84 (s, 3H), 1.79 (s, 3H); $^{19}$F NMR ($CDCl_3$, 376 MHz) δ −73.10 (s, 6F), −136.52 (td, J=19.9, 10.1 Hz, 1F), −140.09 (ddd, J=20.4, 18.1, 10.1 Hz, 1F), −141.51 (td, J=19.9, 4.8 Hz, 1F), −148.41 (ddd, J=20.5, 18.2, 4.8 Hz, 1F); Analytical HPLC: $t_R$=16.4 min, 97.7% purity (30-95% MeCN/$H_2O$, linear gradient, with constant 0.1% v/v TFA additive; 20 min run; 1 mL/min flow; ESI; positive ion mode; detection at 280 nm); HRMS (EI) calcd for $C_{25}H_{12}F_{10}O_8S_2$ [M$^-$]$^+$ 693.9808, found 693.9820.

Step 2: A vial was charged with the product from Step 1 (350 mg, 0.504 mmol), tert-butyl carbamate (142 mg, 1.21 mmol, 2.4 eq), $Pd_2dba_3$ (46.1 mg, 50.4 µmol, 0.1 eq), XPhos (72.1 mg, 0.151 mmol, 0.3 eq), and $Cs_2CO_3$ (460 mg, 1.41 mmol, 2.8 eq). The vial was sealed and evacuated/backfilled with nitrogen (3×). Dioxane (3.5 mL) was added, and the reaction was flushed again with nitrogen (3×). The reaction was stirred at 80° C. for 4 h. It was then cooled to room temperature, filtered through Celite with $CH_2Cl_2$, and evaporated. The residue was purified by silica gel chromatography (0-30% EtOAc/hexanes, linear gradient) to afford di-tert-butyl (4',5',6',7'-tetrafluoro-10,10-dimethyl-3'-oxo-3'H,10H-spiro[anthracene-9,1'-isobenzofuran]-3,6-diyl)dicarbamate (305 mg, 96%) as an off-white solid. $^1$H NMR ($CDCl_3$, 400 MHz) δ 7.79 (d, J=2.2 Hz, 2H), 7.11 (dd, J=8.6, 2.2 Hz, 2H), 6.77 (d, J=8.6 Hz, 2H), 6.59 (s, 2H), 1.81 (s, 3H), 1.74 (s, 3H), 1.53 (s, 18H); $^{19}$F NMR ($CDCl_3$, 376 MHz) δ −138.65 (td, J=20.0, 9.1 Hz), −141.98 (td, J=20.0, 4.0 Hz), −142.47 (td, J=20.3, 19.5, 8.8 Hz), −150.82−−151.01 (m); Analytical HPLC: $t_R$=15.7 min, 98.2% purity (30-95% MeCN/$H_2O$, linear gradient, with constant 0.1% v/v TFA additive; 20 min run; 1 mL/min flow; ESI; positive ion mode; detection at 254 nm); HRMS (ESI) calcd for $C_{33}H_{33}F_4N_2O_6$ [M+H]$^+$ 629.2269, found 629.2280.

Step 3: The product from Step 2 (180 mg, 0.286 mmol) and 2-(methoxymethoxy)malononitrile (36.1 mg, 0.286 mmol, 1 eq) were combined in DMF (3 mL), and DIEA (99.7 µL, 0.573 mmol, 2 eq) was added. After stirring the reaction at room temperature for 2 h, it was concentrated in vacuo and purified by silica gel chromatography (0-50% EtOAc/hexanes, linear gradient) to yield 107 mg (51%) of the title compound di-tert-butyl (6'-(dicyano (methoxymethoxy)methyl)-4',5',7'-trifluoro-10,10-dimethyl-3'-oxo-3'H,10H-spiro[anthracene-9,1'-isobenzofuran]-3,6-diyl)dicarbamate as an off-white solid. $^1$H NMR ($CDCl_3$, 400 MHz) δ 7.78 (d, J=2.2 Hz, 2H), 7.16 (dd, J=8.6, 2.2 Hz, 2H), 6.75 (d, J=8.6 Hz, 2H), 6.61 (s, 2H), 5.12 (s, 2H), 3.50 (s, 3H), 1.81 (s, 3H), 1.75 (s, 3H), 1.53 (s, 18H); $^{19}$F NMR ($CDCl_3$, 376 MHz) δ −116.84 (d, J=22.7 Hz, 1F), −126.32 (d, J=19.7 Hz, 1F), −139.19 (dd, J=22.9, 20.1 Hz, 1F); Analytical HPLC: $t_R$=15.2 min, >99% purity (30-95% MeCN/$H_2O$, linear gradient, with constant 0.1% v/v TFA additive; 20 min run; 1 mL/min flow; ESI; positive ion mode; detection at 254 nm); HRMS (ESI) calcd for $C_{38}H_{38}F_3N_4O_8$ [M+H]$^+$ 735.2636, found 735.2641.

Example 58: 4-((2-(2-((6-Chlorohexyl)oxy)ethoxy) ethyl)carbamoyl)-2-(3,6-diamino-10,10-dimethylan-thracen-9-ylium-9(10H)-yl)-3,5,6-trifluorobenzoate

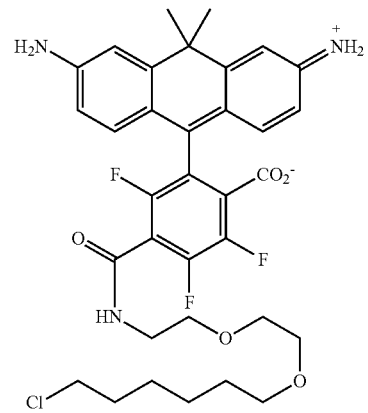

Di-tert-butyl (6'-(dicyano(methoxymethoxy)methyl)-4', 5',7'-trifluoro-10,10-dimethyl-3'-oxo-3'H,10H-spiro[anthracene-9,1'-isobenzofuran]-3,6-diyl)dicarbamate (Example 57; 90 mg, 0.122 mmol) was taken up in $CH_2Cl_2$ (5 mL); triethylsilane (500 µL) was added, followed by trifluoroacetic acid (1 mL). The reaction was stirred at room temperature for 6 h. Toluene (5 mL) was added, and the reaction mixture was concentrated to dryness. The residue was combined with a premixed solution of 2-(2-((6-chlorohexyl) oxy)ethoxy)ethan-1-amine (TFA salt; 82.7 mg, 0.245 mmol, 2 eq) and DIEA (213 µL, 1.22 mmol, 10 eq) in DMF (3 mL), and the reaction was stirred at room temperature for 18 h. The solvent was removed by rotary evaporation, and the crude material was purified by reverse phase HPLC (30-50% MeCN/$H_2O$, linear gradient, with constant 0.1% v/v TFA additive) to provide the title compound as a purple solid (30.5 mg, 32%, TFA salt). $^1$H NMR ($CD_3OD$, 400 MHz) δ 9.14 (t, J=5.4 Hz, 1H), 7.153 (dd, J=9.1, 0.9 Hz, 2H), 7.148 (d, J=2.2 Hz, 2H), 6.67 (dd, J=9.0, 2.2 Hz, 2H), 3.68-3.55 (m, 8H), 3.52 (t, J=6.6 Hz, 2H), 3.44 (t, J=6.5 Hz, 2H), 1.75

(s, 3H), 1.74-1.67 (m, 2H), 1.64 (s, 3H), 1.56-1.47 (m, 2H), 1.45-1.28 (m, 4H); $^{19}$F NMR (CD$_3$OD, 376 MHz) δ −117.19 (d, J=15.3 Hz, 1F), −133.70 (d, J=22.2 Hz, 1F), −140.45 (dd, J=22.1, 15.6 Hz, 1F); Analytical HPLC: $t_R$=11.3 min, >99% purity (10-95% MeCN/H$_2$O, linear gradient, with constant 0.1% v/v TFA additive; 20 min run; 1 mL/min flow; ESI; positive ion mode; detection at 575 nm); HRMS (ESI) calcd for C$_{34}$H$_{38}$ClF$_3$N$_3$O$_5$ [M+H]$^+$ 660.2447, found 660.2459.

Example 59: 4-(Dicyano(methoxymethoxy)methyl)-2-(10,10-dimethyl-3,6-bis(methyl(phenyl)amino)anthracen-9-ylium-9(10H)-yl)-3,5,6-trifluorobenzoate

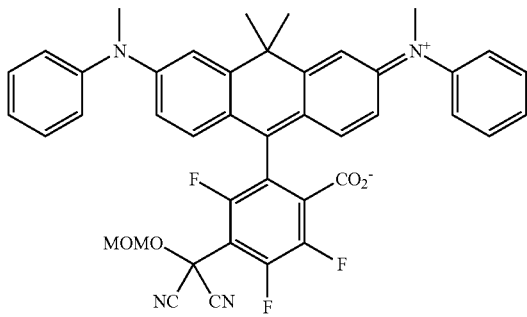

Step 1: A vial was charged with 4',5',6',7'-tetrafluoro-10,10-dimethyl-3'-oxo-3'H,10H-spiro[anthracene-9,1'-isobenzofuran]-3,6-diyl bis(trifluoromethanesulfonate) (Example 57, Step 1; 250 mg, 0.360 mmol), Pd$_2$dba$_3$ (33.0 mg, 36.0 μmol, 0.1 eq), XPhos (51.5 mg, 0.108 mmol, 0.3 eq), and Cs$_2$CO$_3$ (328 mg, 1.01 mmol, 2.8 eq). The vial was sealed and evacuated/backfilled with nitrogen (3×). Dioxane (2 mL) was added, and the reaction was flushed again with nitrogen (3×). Following the addition of N-methylaniline (85.8 μL, 0.792 mmol, 2.2 eq), the reaction was stirred at 80° C. for 8 h. It was then cooled to room temperature, filtered through Celite with CH$_2$Cl$_2$, and concentrated to dryness. Purification by silica gel chromatography (0-25% EtOAc/hexanes, linear gradient) afforded 2-(10,10-dimethyl-3,6-bis(methyl(phenyl)amino)anthracen-9-ylium-9(10H)-yl)-3,4,5,6-tetrafluorobenzoate (167 mg, 76%) as an off-white solid. $^1$H NMR (CDCl$_3$, 400 MHz) δ 7.37-7.31 (m, 4H), 7.17-7.06 (m, 8H), 6.74 (dd, J=8.8, 2.4 Hz, 2H), 6.69 (d, J=8.8 Hz, 2H), 3.36 (s, 6H), 1.65 (s, 3H), 1.63 (s, 3H); $^{19}$F NMR (CDCl$_3$, 376 MHz) δ −139.31 (td, J=20.0, 8.6 Hz, 1F), −141.79 (td, J=20.1, 3.9 Hz, 1F), −143.16 (ddd, J=21.0, 18.6, 8.7 Hz, 1F), −151.67 (ddd, J=21.2, 18.2, 3.7 Hz, 1F); Analytical HPLC: $t_R$=16.4 min, >99% purity (30-95% MeCN/H$_2$O, linear gradient, with constant 0.1% v/v TFA additive; 20 min run; 1 mL/min flow; ESI; positive ion mode; detection at 650 nm); MS (ESI) calcd for C$_{37}$H$_{29}$F$_4$N$_2$O$_2$ [M+H]$^+$ 609.2, found 609.1.

Step 2: 2-(10,10-Dimethyl-3,6-bis(methyl(phenyl)amino)anthracen-9-ylium-9(10H)-yl)-3,4,5,6-tetrafluorobenzoate (150 mg, 0.246 mmol) and 2-(methoxymethoxy)malononitrile (31.1 mg, 0.246 mmol, 1 eq) were combined in DMF (6 mL), and DIEA (85.8 μL, 0.493 mmol, 2 eq) was added. After stirring the reaction at room temperature for 2 h, it was evaporated to dryness. Flash chromatography on silica gel (0-75% EtOAc/hexanes, linear gradient) afforded the title compound 4-(dicyano(methoxymethoxy)methyl)-2-(10,10-dimethyl-3,6-bis(methyl(phenyl)amino)anthracen-9-ylium-9(10H)-yl)-3,5,6-trifluorobenzoate as a yellow-green solid (93.3 mg, 53%). $^1$H NMR (CDCl$_3$, 400 MHz) δ 7.39-7.32 (m, 4H), 7.20-7.15 (m, 4H), 7.14-7.09 (m, 2H), 7.09 (d, J=2.5 Hz, 2H), 6.74 (dd, J=8.8, 2.5 Hz, 2H), 6.64 (d, J=8.8 Hz, 2H), 5.14 (s, 2H), 3.51 (s, 3H), 3.37 (s, 6H), 1.65 (s, 3H), 1.63 (s, 3H); $^{19}$F NMR (CDCl$_3$, 376 MHz) δ −116.51 (d, J=22.7 Hz, 1F), −127.06 (d, J=20.5 Hz, 1F), −140.00 (dd, J=22.9, 20.3 Hz, 1F); Analytical HPLC: $t_R$=14.1 min, >99% purity (30-95% MeCN/H$_2$O, linear gradient, with constant 0.1% v/v TFA additive; 20 min run; 1 mL/min flow; ESI; positive ion mode; detection at 650 nm); MS (ESI) calcd for C$_{42}$H$_{34}$F$_3$N$_4$O$_4$ [M+H]$^+$ 715.3, found 715.2.

Example 60: 4-((2-(2-((6-Chlorohexyl)oxy)ethoxy)ethyl)carbamoyl)-2-(10,10-dimethyl-3,6-bis(methyl(phenyl)amino)anthracen-9-ylium-9(10H)-yl)-3,5,6-trifluorobenzoate

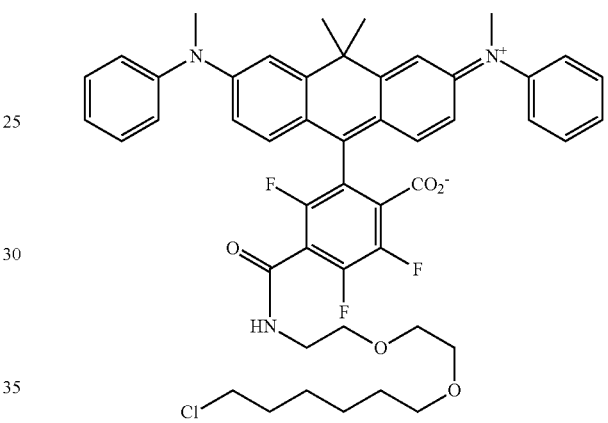

4-(Dicyano(methoxymethoxy)methyl)-2-(10,10-dimethyl-3,6-bis(methyl(phenyl)amino)anthracen-9-ylium-9(10H)-yl)-3,5,6-trifluorobenzoate (Example 59; 50 mg, 70.0 μmol) was taken up in CH$_2$Cl$_2$ (4 mL); triethylsilane (400 μL) was added, followed by trifluoroacetic acid (800 μL). The reaction was stirred at room temperature for 6 h. Toluene (4 mL) was added, and the reaction mixture was concentrated to dryness. The residue was combined with a premixed solution of 2-(2-((6-chlorohexyl)oxy)ethoxy)ethan-1-amine (TFA salt; 47.3 mg, 0.140 mmol, 2 eq) and DIEA (122 μL, 0.700 mmol, 10 eq) in CH$_2$Cl$_2$ (4 mL), and the reaction was stirred at room temperature for 18 h. The solvent was removed by rotary evaporation, and the crude material was purified by silica gel chromatography (5-75% EtOAc/hexanes, linear gradient) to yield 43.0 mg (73%) of the title compound as a pale blue-green solid. $^1$H NMR (CDCl$_3$, 400 MHz) δ 7.37-7.30 (m, 4H), 7.18-7.12 (m, 4H), 7.11-7.05 (m, 4H), 6.75 (dd, J=8.7, 2.4 Hz, 2H), 6.72 (bs, 1H), 6.71 (d, J=8.7 Hz, 2H), 3.65-3.57 (m, 6H), 3.54-3.47 (m, 4H), 3.37 (t, J=6.6 Hz, 2H), 3.36 (s, 6H), 1.78-1.69 (m, 2H), 1.63 (s, 6H), 1.54-1.46 (m, 2H), 1.45-1.37 (m, 2H), 1.34-1.27 (m, 2H); $^{19}$F NMR (CDCl$_3$, 376 MHz) δ −120.93 (d, J=22.7 Hz, 1F), −133.20 (d, J=21.8 Hz, 1F), −142.37 (t, J=22.2 Hz, 1F); Analytical HPLC: $t_R$=15.0 min, >99% purity (30-95% MeCN/H$_2$O, linear gradient, with constant 0.1% v/v TFA additive; 20 min run; 1 mL/min flow; ESI; positive ion mode; detection at 650 nm); MS (ESI) calcd for C$_{48}$H$_{50}$ClF$_3$N$_3$O$_5$ [M+H]$^+$ 840.3, found 840.3.

Example 61: Di-tert-butyl (6'-(dicyano (methoxymethoxy)methyl)-4',5',7'-trifluoro-5,5-dimethyl-3'-oxo-3'H,5H-spiro[dibenzo[b,e]siline-10,1'-isobenzofuran]-3,7-diyl)dicarbamate

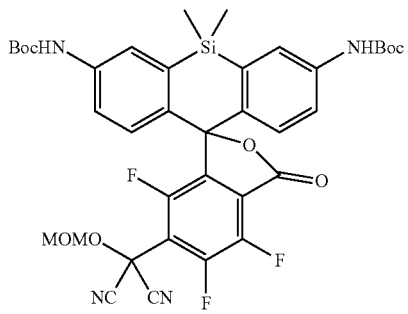

Step 1: To a solution of 2,3,4,5-tetrafluoro-6-(7-hydroxy-5,5-dimethyl-3-oxo-3,5-dihydrodibenzo[b,e]silin-10-yl) benzoic acid (Grimm, J. B. et al. *ACS Cent. Sci.* 2017, 3, 975-985; 170 mg, 0.381 mmol) in $CH_2Cl_2$ (5 mL) were added pyridine (246 μL, 3.05 mmol, 8 eq) and trifluoromethanesulfonic anhydride (256 μL, 1.52 mmol, 4 eq). The reaction was stirred at room temperature for 1 h. It was subsequently diluted with water and extracted with $CH_2Cl_2$ (2×). The combined organic extracts were washed with saturated $CuSO_4$ and brine, dried over anhydrous $MgSO_4$, filtered, and concentrated in vacuo. Flash chromatography on silica gel (0-25% EtOAc/hexanes, linear gradient) afforded 261 mg (96%) of 4',5',6',7'-tetrafluoro-5,5-dimethyl-3'-oxo-3'H,5H-spiro[dibenzo[b,e]siline-10,1'-isobenzofuran]-3,7-diyl bis(trifluoromethanesulfonate) as a white foam. $^1H$ NMR ($CDCl_3$, 400 MHz) δ 7.58 (d, J=2.7 Hz, 2H), 7.27 (dd, J=8.9, 2.7 Hz, 2H), 7.15 (dd, J=8.9, 1.4 Hz, 2H), 0.69 (s, 3H), 0.67 (s, 3H); $^{19}F$ NMR ($CDCl_3$, 376 MHz) δ −73.17 (s, 6F), −135.84 (td, J=19.8, 10.1 Hz, 1F), −137.58–137.80 (m, 1F), −140.68 (ddd, J=21.0, 18.3, 10.1 Hz, 1F), −148.14 (ddd, J=20.5, 18.1, 4.9 Hz, 1F); Analytical HPLC: $t_R$=16.9 min, 97.8% purity (30-95% $MeCN/H_2O$, linear gradient, with constant 0.1% v/v TFA additive; 20 min run; 1 mL/min flow; ESI; positive ion mode; detection at 280 nm); HRMS (ESI) calcd for $C_{24}H_{13}F_{10}O_8S_2Si$ $[M+H]^+$ 710.9656, found 710.9660.

Step 2: A vial was charged with the product from Step 1 (245 mg, 0.345 mmol), tert-butyl carbamate (96.9 mg, 0.828 mmol, 2.4 eq), $Pd_2dba_3$ (31.6 mg, 34.5 μmol, 0.1 eq), XPhos (49.3 mg, 0.103 mmol, 0.3 eq), and $Cs_2CO_3$ (315 mg, 0.965 mmol, 2.8 eq). The vial was sealed and evacuated/backfilled with nitrogen (3×). Dioxane (3 mL) was added, and the reaction was flushed again with nitrogen (3×). The reaction was stirred at 80° C. for 5 h. It was then cooled to room temperature, filtered through Celite with $CH_2Cl_2$, and evaporated. The residue was purified by silica gel chromatography (0-30% EtOAc/hexanes, linear gradient) to afford di-tert-butyl (4',5',6',7'-tetrafluoro-5,5-dimethyl-3'-oxo-3'H, 5H-spiro[dibenzo[b,e]siline-10,1'-isobenzofuran]-3,7-diyl) dicarbamate (212 mg, 95%) as an off-white solid. $^1H$ NMR ($CDCl_3$, 400 MHz) δ 7.70 (d, J=2.5 Hz, 2H), 7.30 (dd, J=8.7, 2.5 Hz, 2H), 6.90 (d, J=8.7 Hz, 2H), 6.56 (s, 2H), 1.52 (s, 18H), 0.60 (s, 3H), 0.56 (s, 3H); $^{19}F$ NMR ($CDCl_3$, 376 MHz) δ −138.04 (td, J=20.0, 8.8 Hz, 1F), −139.27–139.47 (m, 1F), −142.79 (td, J=19.4, 8.8 Hz, 1F), −150.67–150.88 (m, 1F); Analytical HPLC: $t_R$=16.1 min, 98.4% purity (30-95% $MeCN/H_2O$, linear gradient, with constant 0.1% v/v TFA additive; 20 min run; 1 mL/min flow; ESI; positive ion mode; detection at 254 nm); HRMS (ESI) calcd for $C_{32}H_{33}F_4N_2O_6Si$ $[M+H]^+$ 645.2039, found 645.2049.

Step 3: The product from Step 2 (150 mg, 0.233 mmol) and 2-(methoxymethoxy)malononitrile (29.3 mg, 0.233 mmol, 1 eq) were combined in DMF (3 mL), and DIEA (81.1 μL, 0.465 mmol, 2 eq) was added. After stirring the reaction at room temperature for 2 h, it was concentrated in vacuo and purified by silica gel chromatography (0-50% EtOAc/hexanes, linear gradient) to yield 89 mg (51%) of the title compound di-tert-butyl (6'-(dicyano(methoxymethoxy) methyl)-4',5',7'-trifluoro-5,5-dimethyl-3'-oxo-3'H,5H-spiro [dibenzo[b,e]siline-10,1'-isobenzofuran]-3,7-diyl)dicarbamate as an off-white solid. $^1H$ NMR ($CDCl_3$, 400 MHz) δ 7.68 (d, J=2.5 Hz, 2H), 7.36 (dd, J=8.8, 2.5 Hz, 2H), 6.88 (d, J=8.7 Hz, 2H), 6.58 (s, 2H), 5.16 (s, 2H), 3.52 (s, 3H), 1.52 (s, 18H), 0.60 (s, 3H), 0.56 (s, 3H); $^{19}F$ NMR ($CDCl_3$, 376 MHz) δ −114.17 (d, J=22.5 Hz, 1F), −126.44 (d, J=20.0 Hz, 1F), −138.55 (t, J=21.4 Hz, 1F); Analytical HPLC: $t_R$=15.7 min, >99% purity (30-95% $MeCN/H_2O$, linear gradient, with constant 0.1% v/v TFA additive; 20 min run; 1 mL/min flow; ESI; positive ion mode; detection at 254 nm); HRMS (ESI) calcd for $C_{37}H_{38}F_3N_4O_8Si$ $[M+H]^+$ 751.2406, found 751.2413.

Example 62: 4-((2-(2-((6-Chlorohexyl)oxy)ethoxy) ethyl)carbamoyl)-2-(3,7-diamino-5,5-dimethyl-dibenzo[b,e]silin-10-ylium-10(5H)-yl)-3,5,6-trifluorobenzoate

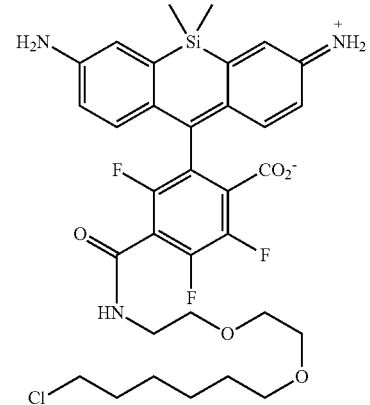

Di-tert-butyl (6'-(dicyano(methoxymethoxy)methyl)-4', 5',7'-trifluoro-5,5-dimethyl-3'-oxo-3'H,5H-spiro[dibenzo[b, e]siline-10,1'-isobenzofuran]-3,7-diyl)dicarbamate (Example 61; 75 mg, 0.100 mmol) was taken up in $CH_2Cl_2$ (4 mL); triethylsilane (400 μL) was added, followed by trifluoroacetic acid (800 μL). The reaction was stirred at room temperature for 6 h. Toluene (4 mL) was added, and the reaction mixture was concentrated to dryness. The residue was combined with a premixed solution of 2-(2-((6-chlorohexyl)oxy)ethoxy)ethan-1-amine (TFA salt; 67.5 mg, 0.200 mmol, 2 eq) and DIEA (174 μL, 1.00 mmol, 10 eq) in DMF (3 mL), and the reaction was stirred at room temperature for 18 h. The solvent was removed by rotary evaporation, and the crude material was purified by reverse phase HPLC (30-50% $MeCN/H_2O$, linear gradient, with constant 0.1% v/v TFA additive) to provide the title compound as a bright blue solid (30.7 mg, 39%, TFA salt). $^1H$ NMR ($CD_3OD$, 400 MHz) δ 9.17 (t, J=5.0 Hz, 1H), 7.21 (d, J=2.5 Hz, 2H), 6.99

(dd, J=8.9, 1.3 Hz, 2H), 6.76 (dd, J=8.9, 2.5 Hz, 2H), 3.67-3.54 (m, 8H), 3.51 (t, J=6.6 Hz, 2H), 3.44 (t, J=6.5 Hz, 2H), 1.75-1.66 (m, 2H), 1.56-1.47 (m, 2H), 1.45-1.28 (m, 4H), 0.57 (s, 3H), 0.51 (s, 3H); $^{19}$F NMR (CD$_3$OD, 376 MHz) δ –118.23 (d, J=19.4 Hz, 1F), –134.29 (d, J=21.2 Hz, 1F), –141.77--142.06 (m, 1F); Analytical HPLC: $t_R$=11.7 min, >99% purity (10-95% MeCN/H$_2$O, linear gradient, with constant 0.1% v/v TFA additive; 20 min run; 1 mL/min flow; ESI; positive ion mode; detection at 625 nm); HRMS (ESI) calcd for C$_{33}$H$_{38}$ClF$_3$N$_3$O$_5$Si [M+H]$^+$ 676.2216, found 676.2222.

Example 63: 4-(Dicyano(methoxymethoxy)methyl)-2-(5,5-dimethyl-3,7-bis(methyl(phenyl)amino)dibenzo[b,e]silin-10-ylium-10(5H)-yl)-3,5,6-trifluorobenzoate

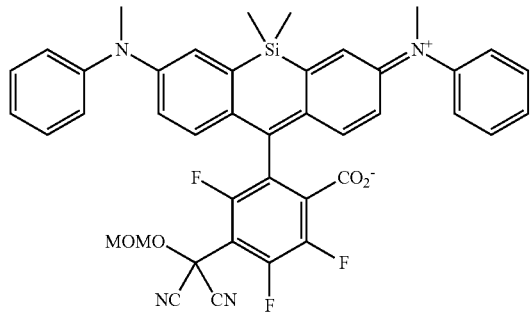

Step 1: A vial was charged with 4',5',6',7'-tetrafluoro-5,5-dimethyl-3'-oxo-3'H,5H-spiro[dibenzo[b,e]siline-10,1'-isobenzofuran]-3,7-diylbis(trifluoromethanesulfonate) (Example 61, Step 1; 175 mg, 0.246 mmol), Pd$_2$dba$_3$ (22.6 mg, 24.6 μmol, 0.1 eq), XPhos (35.2 mg, 73.9 μmol, 0.3 eq), and Cs$_2$CO$_3$ (225 mg, 0.690 mmol, 2.8 eq). The vial was sealed and evacuated/backfilled with nitrogen (3x). Dioxane (2 mL) was added, and the reaction was flushed again with nitrogen (3x). Following the addition of N-methylaniline (58.7 μL, 0.542 mmol, 2.2 eq), the reaction was stirred at 80° C. for 3 h. It was then cooled to room temperature, filtered through Celite with CH$_2$Cl$_2$, and concentrated to dryness. Purification by silica gel chromatography (0-25% EtOAc/hexanes, linear gradient) afforded 2-(5,5-dimethyl-3,7-bis(methyl(phenyl)amino)dibenzo[b,e]silin-10-ylium-10(5H)-yl)-3,4,5,6-tetrafluorobenzoate (144 mg, 94%) as an off-white solid. $^1$H NMR (CDCl$_3$, 400 MHz) δ 7.36-7.30 (m, 4H), 7.20-7.06 (m, 8H), 6.82-6.75 (m, 4H), 3.35 (s, 6H), 0.50 (s, 3H), 0.47 (s, 3H); $^{19}$F NMR (CDCl$_3$, 376 MHz) δ –138.60 (td, J=19.8, 3.0 Hz, 1F), –138.76 (td, J=19.4, 7.8 Hz, 1F), –143.54--143.71 (m, 1F), –151.30--151.47 (m, 1F); Analytical HPLC: $t_R$=16.3 min, >99% purity (50-95% MeCN/H$_2$O, linear gradient, with constant 0.1% v/v TFA additive; 20 min run; 1 mL/min flow; ESI; positive ion mode; detection at 675 nm); MS (ESI) calcd for C$_{36}$H$_{29}$F$_4$N$_2$O$_2$Si [M+H]$^+$ 625.2, found 625.1.

Step 2: The product from Step 1 (125 mg, 0.200 mmol) and 2-(methoxymethoxy)malononitrile (25.2 mg, 0.200 mmol, 1 eq) were combined in DMF (5 mL), and DIEA (69.7 μL, 0.400 mmol, 2 eq) was added. After stirring the reaction at room temperature for 2 h, it was evaporated to dryness. Flash chromatography on silica gel (0-40% EtOAc/hexanes, linear gradient) afforded the title compound 4-(dicyano(methoxymethoxy)methyl)-2-(5,5-dimethyl-3,7-bis(methyl(phenyl)amino)dibenzo[b,e]silin-10-ylium-10(5H)-yl)-3,5,6-trifluorobenzoate as an off-white solid (79.9 mg, 55%). $^1$H NMR (CDCl$_3$, 400 MHz) δ 7.38-7.31 (m, 4H), 7.19-7.09 (m, 8H), 6.79 (dd, J=8.9, 2.7 Hz, 2H), 6.71 (dd, J=8.9, 0.7 Hz, 2H), 5.18 (s, 2H), 3.54 (s, 3H), 3.36 (s, 6H), 0.50 (s, 3H), 0.47 (s, 3H); $^{19}$F NMR (CDCl$_3$, 376 MHz) δ –113.25 (d, J=22.4 Hz, 1F), –127.11 (d, J=20.2 Hz, 1F), –139.39 (dd, J=22.7, 20.2 Hz, 1F); Analytical HPLC: $t_R$=15.0 min, >99% purity (50-95% MeCN/H$_2$O, linear gradient, with constant 0.1% v/v TFA additive; 20 min run; 1 mL/min flow; ESI; positive ion mode; detection at 675 nm); MS (ESI) calcd for C$_{41}$H$_{34}$F$_3$N$_4$O$_4$Si [M+H]$^+$ 731.2, found 731.1.

Example 64: 4-((2-(2-((6-Chlorohexyl)oxy)ethoxy)ethyl)carbamoyl)-2-(5,5-dimethyl-3,7-bis(methyl(phenyl)amino)dibenzo[b,e]silin-10-ylium-10(5H)-yl)-3,5,6-trifluorobenzoate

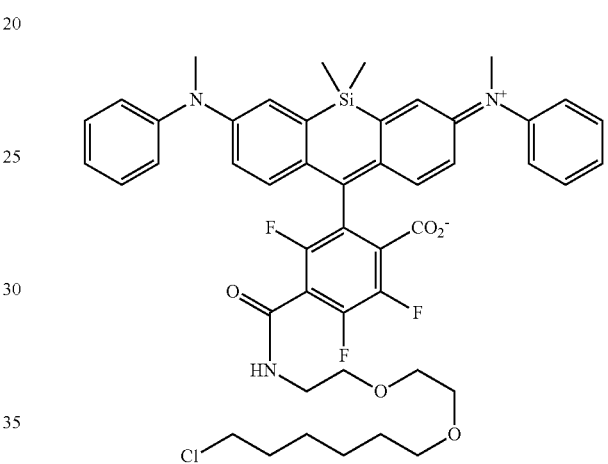

4-(Dicyano(methoxymethoxy)methyl)-2-(5,5-dimethyl-3,7-bis(methyl(phenyl)amino)dibenzo[b,e]silin-10-ylium-10(5H)-yl)-3,5,6-trifluorobenzoate (Example 63; 40 mg, 54.7 μmol) was taken up in CH$_2$Cl$_2$ (3 mL); triethylsilane (300 μL) was added, followed by trifluoroacetic acid (600 μL). The reaction was stirred at room temperature for 6 h. Toluene (3 mL) was added, and the reaction mixture was concentrated to dryness. The residue was combined with a premixed solution of 2-(2-((6-chlorohexyl)oxy)ethoxy)ethan-1-amine (TFA salt; 37.0 mg, 0.109 mmol, 2 eq) and DIEA (95.3 μL, 0.547 mmol, 10 eq) in CH$_2$Cl$_2$ (3 mL), and the reaction was stirred at room temperature for 18 h. The solvent was removed by rotary evaporation, and the crude material was purified by silica gel chromatography (5-75% EtOAc/hexanes, linear gradient) to yield 24.4 mg (52%) of the title compound as an off-white solid. $^1$H NMR (CDCl$_3$, 400 MHz) δ 7.36-7.29 (m, 4H), 7.19-7.11 (m, 6H), 7.11-7.05 (m, 2H), 6.86 (s, 1H), 6.84-6.77 (m, 4H), 3.67-3.58 (m, 6H), 3.55-3.51 (m, 2H), 3.49 (t, J=6.7 Hz, 2H), 3.37 (t, J=6.7 Hz, 2H), 3.35 (s, 6H), 1.76-1.68 (m, 2H), 1.52-1.44 (m, 2H), 1.43-1.35 (m, 2H), 1.32-1.25 (m, 2H), 0.49 (s, 3H), 0.45 (s, 3H); $^{19}$F NMR (CDCl$_3$, 376 MHz) δ –118.19 (d, J=22.7 Hz, 1F), –133.12 (d, J=21.4 Hz, 1F), –141.91 (t, J=22.1 Hz, 1F); Analytical HPLC: $t_R$=15.9 min, 98.8% purity (50-95% MeCN/H$_2$O, linear gradient, with constant 0.1% v/v TFA additive; 20 min run; 1 mL/min flow; ESI; positive ion mode; detection at 675 nm); MS (ESI) calcd for C$_{47}$H$_{50}$ClF$_3$N$_3$O$_5$Si [M+H]$^+$ 856.3, found 856.3.

Example 65: 2-(3,6-Di(azetidin-1-yl)-10,10-dimethylanthracen-9-ylium-9(10H)-yl)-4-(dicyano(methoxymethoxy)methyl)-3,5,6-trifluorobenzoate

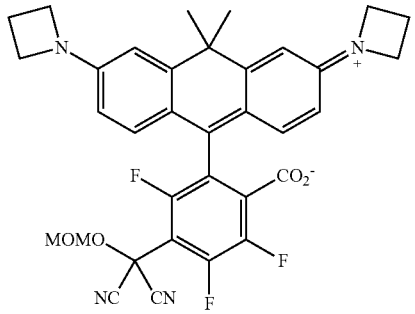

Step 1: 3,6-Dihydroxy-10,10-dimethylanthracen-9(10H)-one (Grimm, J. B. et al. *ACS Chem. Biol.* 2013, 8, 1303-1310; 747 mg, 2.94 mmol) was taken up in $CH_2Cl_2$ (15 mL) and cooled to 0° C. Pyridine (1.90 mL, 23.50 mmol, 8 eq) and trifluoromethanesulfonic anhydride (1.98 mL, 11.75 mmol, 4 eq) were added, and the ice bath was removed. The reaction was stirred at room temperature for 2 h. It was subsequently diluted with water and extracted with $CH_2Cl_2$ (2×). The combined organic extracts were washed with saturated $CuSO_4$ and brine, dried over anhydrous $MgSO_4$, filtered, and concentrated in vacuo. Flash chromatography on silica gel (0-30% EtOAc/hexanes, linear gradient) afforded 1.46 g (96%) of 9,9-dimethyl-10-oxo-9,10-dihydroanthracene-2,7-diylbis(trifluoromethanesulfonate) as a white solid. $^1$H NMR ($CDCl_3$, 400 MHz) δ 8.47 (d, J=8.7 Hz, 2H), 7.58 (d, J=2.4 Hz, 2H), 7.38 (dd, J=8.8, 2.4 Hz, 2H), 1.78 (s, 6H); $^{19}$F NMR ($CDCl_3$, 376 MHz) δ −73.13 (s); $^{13}$C NMR ($CDCl_3$, 101 MHz) δ 180.9 (C), 153.4 (C), 152.7 (C), 130.9 (CH), 129.4 (C), 120.5 (CH), 120.0 (CH), 118.9 (q, $^1J_{CF}$=320.8 Hz, $CF_3$) 38.8 (C), 33.0 ($CH_3$); MS (ESI) calcd for $C_{18}H_{13}F_6O_7S_2$ $[M+H]^+$ 519.0, found 518.9.

Step 2: A vial was charged with the product from Step 1 (1.25 g, 2.41 mmol), $Pd_2dba_3$ (221 mg, 0.241 mmol, 0.1 eq), XPhos (345 mg, 0.723 mmol, 0.3 eq), and $Cs_2CO_3$ (2.20 g, 6.75 mmol, 2.8 eq). The vial was sealed and evacuated/backfilled with nitrogen (3×). Dioxane (12 mL) was added, and the reaction was flushed again with nitrogen (3×). Following the addition of azetidine (390 µL, 5.79 mmol, 2.4 eq), the reaction was stirred at 100° C. for 4 h. It was then cooled to room temperature, filtered through Celite with $CH_2Cl_2$, and concentrated to dryness. Purification by silica gel chromatography (0-40% EtOAc/hexanes, linear gradient, with constant 40% v/v $CH_2Cl_2$ additive) afforded 3,6-di(azetidin-1-yl)-10,10-dimethylanthracen-9(10H)-one (645 mg, 80%) as a yellow solid. $^1$H NMR ($CDCl_3$, 400 MHz) δ 8.26-8.21 (m, 2H), 6.46-6.40 (m, 4H), 4.03 (t, J=7.3 Hz, 8H), 2.43 (p, J=7.2 Hz, 4H), 1.66 (s, 6H); $^{13}$C NMR ($CDCl_3$, 101 MHz) δ 181.4 (C), 154.3 (C), 152.4 (C), 129.3 (CH), 120.7 (C), 109.8 (CH), 106.5 (CH), 51.8 ($CH_2$), 38.1 (C), 33.6 ($CH_3$), 16.7 ($CH_2$); MS (ESI) calcd for $C_{22}H_{25}N_2O$ $[M+H]^+$ 333.2, found 333.3.

Step 3: A solution of 2,3,4,5-tetrafluorobenzoic acid (350 mg, 1.80 mmol, 3 eq) in THF (6 mL) was cooled to −78° C. under nitrogen. N-Butyllithium (2.5 M in hexanes, 1.44 mL, 3.61 mmol, 6 eq) was added, and the reaction was stirred at −78° C. for 3 h. A solution of the product from Step 2 (200 mg, 0.602 mmol) in THF (18 mL) was added; the reaction was gradually warmed to room temperature and stirred for 48 h. It was subsequently diluted with 1 N HCl (20 mL) and vigorously stirred for 15 min. The mixture was then diluted with water and extracted with $CH_2Cl_2$ (2×). The combined organic extracts were dried over anhydrous $MgSO_4$, filtered, and evaporated. The crude material was purified by silica gel chromatography (0-100% acetone/$CH_2Cl_2$, linear gradient) followed by reverse phase HPLC (30-70% MeCN/$H_2O$, linear gradient, with constant 0.1% v/v TFA additive). The pooled HPLC product fractions were partially concentrated to remove MeCN, diluted with saturated $NaHCO_3$, and extracted with $CH_2Cl_2$ (2×). The organic extracts were dried over anhydrous $MgSO_4$, filtered, and evaporated to yield 20.2 mg (7%) of 2-(3,6-di(azetidin-1-yl)-10,10-dimethylanthracen-9-ylium-9(10H)-yl)-3,4,5,6-tetrafluorobenzoate as a light blue solid. $^1$H NMR ($CDCl_3$, 400 MHz) δ 6.66 (d, J=8.6 Hz, 2H), 6.54 (d, J=2.4 Hz, 2H), 6.27 (dd, J=8.6, 2.3 Hz, 2H), 3.93 (t, J=7.4 Hz, 8H), 2.39 (p, J=7.2 Hz, 4H), 1.75 (s, 3H), 1.70 (s, 3H); $^{19}$F NMR ($CDCl_3$, 376 MHz) δ −139.76 (td, J=20.1, 8.6 Hz, 1F), −141.87 (td, J=20.1, 3.9 Hz, 1F), −143.57 (ddd, J=20.4, 18.0, 8.4 Hz, 1F), −152.12 (ddd, J=20.4, 18.6, 3.8 Hz, 1F); Analytical HPLC: $t_R$=12.0 min, >99% purity (10-95% MeCN/$H_2O$, linear gradient, with constant 0.1% v/v TFA additive; 20 min run; 1 mL/min flow; ESI; positive ion mode; detection at 625 nm); MS (ESI) calcd for $C_{29}H_{25}F_4N_2O_2$ $[M+H]^+$ 509.2, found 509.1.

Step 4: The product from Step 3 (45.0 mg, 88.5 µmol) and 2-(methoxymethoxy)malononitrile (11.2 mg, 88.5 µmol, 1 eq) were combined in DMF (2 mL), and DIEA (30.8 µL, 0.177 mmol, 2 eq) was added. After stirring the reaction at room temperature for 3 h, it was concentrated in vacuo and purified by reverse phase HPLC (30-50% MeCN/$H_2O$, linear gradient, with constant 0.1% v/v TFA additive). The pooled HPLC product fractions were partially concentrated to remove MeCN, diluted with saturated $NaHCO_3$, and extracted with $CH_2Cl_2$ (2×). The organic extracts were dried over anhydrous $MgSO_4$, filtered, and evaporated to yield 23.5 mg (43%) of the title compound 2-(3,6-di(azetidin-1-yl)-10,10-dimethylanthracen-9-ylium-9(10H)-yl)-4-(dicyano(methoxymethoxy)methyl)-3,5,6-trifluorobenzoate as a blue solid. $^1$H NMR ($CDCl_3$, 400 MHz) δ 6.63 (d, J=8.6 Hz, 2H), 6.55 (d, J=2.3 Hz, 2H), 6.28 (dd, J=8.6, 2.4 Hz, 2H), 5.11 (s, 2H), 3.95 (t, J=7.3 Hz, 8H), 3.50 (s, 3H), 2.40 (p, J=7.2 Hz, 4H), 1.75 (s, 3H), 1.70 (s, 3H); $^{19}$F NMR ($CDCl_3$, 376 MHz) δ −116.34 (d, J=22.7 Hz, 1F), −127.69 (d, J=20.0 Hz, 1F), −140.39 (dd, J=22.8, 20.1 Hz, 1F); Analytical HPLC: $t_R$=12.5 min, >99% purity (10-95% MeCN/$H_2O$, linear gradient, with constant 0.1% v/v TFA additive; 20 min run; 1 mL/min flow; ESI; positive ion mode; detection at 625 nm); MS (ESI) calcd for $C_{34}H_{30}F_3N_4O_4$ $[M+H]^+$ 615.2, found 615.1.

145

Example 66: 4-((2-(2-((6-Chlorohexyl)oxy)ethoxy)ethyl)carbamoyl)-2-(3,6-di(azetidin-1-yl)-10,10-dimethylanthracen-9-ylium-9(10H)-yl)-3,5,6-trifluorobenzoate

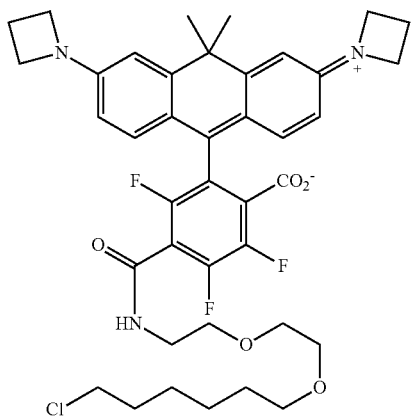

2-(3,6-Di(azetidin-1-yl)-10,10-dimethylanthracen-9-ylium-9(10H)-yl)-4-(dicyano(methoxymethoxy)methyl)-3,5,6-trifluorobenzoate (Example 65; 20.0 mg, 32.5 μmol) was taken up in $CH_2Cl_2$ (2 mL); triethylsilane (200 μL) was added, followed by trifluoroacetic acid (400 The reaction was stirred at room temperature for 6 h. Toluene (3 mL) was added, and the reaction mixture was concentrated to dryness. The residue was combined with a premixed solution of 2-(2-(((6-chlorohexyl)oxy)ethoxy)ethan-1-amine (TFA salt; 22.0 mg, 65.1 μmol, 2 eq) and DIEA (56.7 μL, 0.325 mmol, 10 eq) in $CH_2Cl_2$ (2 mL), and the reaction was stirred at room temperature for 18 h. The solvent was removed by rotary evaporation, and the crude material was purified by reverse phase HPLC (20-80% $MeCN/H_2O$, linear gradient, with constant 0.1% v/v TFA additive) to yield 20.2 mg (73%, TFA salt) of the title compound as a deep blue solid. $^1H$ NMR ($CD_3OD$, 400 MHz) δ 9.09 (t, J=5.4 Hz, 1H), 7.15 (dd, J=9.1, 0.5 Hz, 2H), 6.81 (d, J=2.2 Hz, 2H), 6.45 (dd, J=9.1, 2.2 Hz, 2H), 4.37 (t, J=7.7 Hz, 8H), 3.67-3.55 (m, 8H), 3.52 (t, J=6.7 Hz, 2H), 3.44 (t, J=6.5 Hz, 2H), 2.56 (p, J=7.8 Hz, 4H), 1.77 (s, 3H), 1.75-1.68 (m, 2H), 1.66 (s, 3H), 1.56-1.48 (m, 2H), 1.44-1.30 (m, 4H); $^{19}F$ NMR ($CD_3OD$, 376 MHz) δ −117.35 (d, J=15.2 Hz, 1F), −133.92 (d, J=22.5 Hz, 1F), −140.91 (dd, J=22.1, 15.3 Hz, 1F); Analytical HPLC: $t_R$=12.9 min, >99% purity (10-95% $MeCN/H_2O$, linear gradient, with constant 0.1% v/v TFA additive; 20 min run; 1 mL/min flow; ESI; positive ion mode; detection at 625 nm); MS (ESI) calcd for $C_{40}H_{46}ClF_3N_3O_5$ $[M+H]^+$ 740.3, found 740.2.

146

Example 67: 2-(3,3-Bis(4-(dimethylamino)phenyl)-4,6,7-trifluoro-1-oxo-1,3-dihydroisobenzofuran-5-yl)-2-(methoxymethoxy)malononitrile

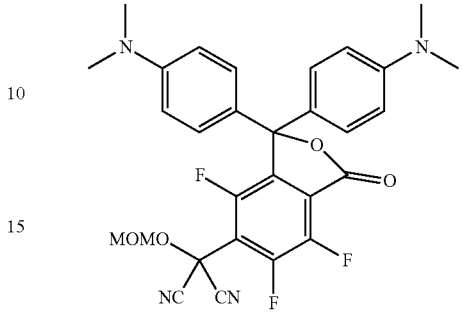

Step 1: Phthalic anhydride (1.82 g, 8.25 mmol), N,N-dimethylaniline (2.00 g, 16.50 mmol, 2 eq), and anhydrous $ZnCl_2$ (2.25 g, 16.50 mmol, 2 eq) were combined in a 20 mL crimp-top vial. The vial was sealed and stirred in a 150° C. oil bath for 3 h. After cooling the mixture to room temperature, the resulting blue glassy solid was dissolved in 1 N HCl (50 mL). The solution was adjusted to pH 5-6 via the addition of 2 M NaOH, which precipitated a green, gummy material. The mixture was extracted with EtOAc (2×); the combined organic extracts were dried over anhydrous $MgSO_4$, filtered, and concentrated in vacuo. The crude was purified by flash chromatography on silica gel (0-50% EtOAc/hexanes, linear gradient) to yield 478 mg (13%) of 3,3-bis(4-(dimethylamino)phenyl)-4,5,6,7-tetrafluoroisobenzofuran-1(3H)-one as a gummy yellow solid. $^1H$ NMR ($CDCl_3$, 400 MHz) δ 7.15 (d, J=9.0 Hz, 4H), 6.64 (d, J=9.0 Hz, 4H), 2.96 (s, 12H); $^{19}F$ NMR ($CDCl_3$, 376 MHz) δ −137.82-−137.98 (m, 1F), −138.99 (td, J=20.0, 8.7 Hz, 1F), −143.58 (ddd, J=21.1, 18.2, 8.7 Hz, 1F), −152.13 (ddd, J=20.8, 18.3, 4.3 Hz, 1F); Analytical HPLC: $t_R$=12.5 min, >99% purity (10-95% $MeCN/H_2O$, linear gradient, with constant 0.1% v/v TFA additive; 20 min run; 1 mL/min flow; ESI; positive ion mode; detection at 280 nm); HRMS (ESI) calcd for $C_{24}H_{21}F_4N_2O_2$ $[M+H]^+$ 445.1534, found 445.1531.

Step 2: The product from Step 1 (300 mg, 0.675 mmol) and 2-(methoxymethoxy)malononitrile (85.1 mg, 0.675 mmol, 1 eq) were combined in DMF (10 mL), and DIEA (235 μL, 1.35 mmol, 2 eq) was added. After stirring the reaction at room temperature for 2 h, it was concentrated in vacuo and purified by flash chromatography on silica gel (0-50% EtOAc/hexanes, linear gradient) to provide the title compound 2-(3,3-bis(4-(dimethylamino)phenyl)-4,6,7-trifluoro-1-oxo-1,3-dihydroisobenzofuran-5-yl)-2-(methoxymethoxy)malononitrile (225 mg, 61%) as a yellow foam. $^1H$ NMR ($CDCl_3$, 400 MHz) δ 7.16-7.09 (m, 4H), 6.65 (d, J=9.0 Hz, 4H), 5.18 (s, 2H), 3.53 (s, 3H), 2.97 (s, 12H); $^{19}F$ NMR ($CDCl_3$, 376 MHz) δ −112.40 (d, J=22.4 Hz, 1F), −127.57 (d, J=20.4 Hz, 1F), −139.50 (dd, J=22.5, 20.3 Hz, 1F); Analytical HPLC: $t_R$=13.4 min, >99% purity (10-95% $MeCN/H_2O$, linear gradient, with constant 0.1% v/v TFA additive; 20 min run; 1 mL/min flow; ESI; positive ion mode; detection at 280 nm); HRMS (ESI) calcd for $C_{29}H_{26}F_3N_4O_4$ $[M+H]^+$ 551.1901, found 551.1910.

Example 68: N-(2-(2-((6-Chlorohexyl)oxy)ethoxy)ethyl)-3,3-bis(4-(dimethylamino)phenyl)-4,6,7-trifluoro-1-oxo-1,3-dihydroisobenzofuran-5-carboxamide

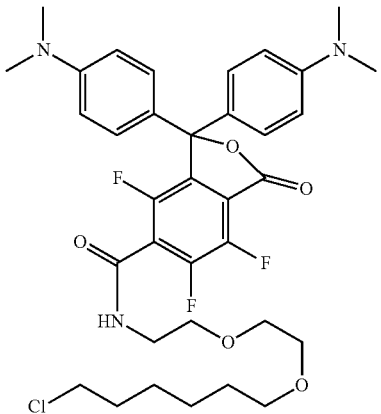

2-(3,3-Bis(4-(dimethylamino)phenyl)-4,6,7-trifluoro-1-oxo-1,3-dihydroisobenzofuran-5-yl)-2-(methoxymethoxy)malononitrile (Example 67; 75 mg, 0.136 mmol) was taken up in CH$_2$Cl$_2$ (5 mL); triethylsilane (500 µL) was added, followed by trifluoroacetic acid (1 mL). The reaction was stirred at room temperature for 18 h. Toluene (5 mL) was added, and the reaction mixture was concentrated to dryness. The residue was combined with a premixed solution of 2-(2-((6-chlorohexyl)oxy)ethoxy)ethan-1-amine (TFA salt; 92.0 mg, 0.272 mmol, 2 eq) and DIEA (237 µL, 1.36 mmol, 10 eq) in CH$_2$Cl$_2$ (4 mL), and the reaction was stirred at room temperature for 6 h. The solvent was removed by rotary evaporation, and the crude material was purified by reverse phase HPLC (20-80% MeCN/H$_2$O, linear gradient, with constant 0.1% v/v TFA additive) to yield 49.5 mg (46%, TFA salt) of the title compound as a blue solid. $^1$H NMR (CD$_3$OD, 400 MHz) δ 9.09 (t, J=5.4 Hz, 1H), 7.21 (d, J=9.0 Hz, 4H), 6.92 (d, J=8.9 Hz, 4H), 3.66-3.54 (m, 8H), 3.52 (t, J=6.7 Hz, 2H), 3.45 (t, J=6.5 Hz, 2H), 3.03 (s, 12H), 1.77-1.68 (m, 2H), 1.58-1.50 (m, 2H), 1.47-1.29 (m, 4H); $^{19}$F NMR (CD$_3$OD, 376 MHz) δ −117.70 (d, J=22.0 Hz, 1F), −134.45 (d, J=21.0 Hz, 1F), −142.89 (t, J=21.5 Hz, 1F); Analytical HPLC: t$_R$=13.5 min, >99% purity (10-95% MeCN/H$_2$O, linear gradient, with constant 0.1% v/v TFA additive; 20 min run; 1 mL/min flow; ESI; positive ion mode; detection at 280 nm); HRMS (ESI) calcd for C$_{35}$H$_{42}$ClF$_3$N$_3$O$_5$ [M+H]$^+$ 676.2760, found 676.2767.

Example 69. 4-(Dicyano(methoxymethoxy)methyl)-2,3,5-trifluoro-6-(1,2,2,4,8,10,10,11-octamethyl-1,2,10,11-tetrahydropyrano[3,2-g:5,6-g']diquinolin-13-ium-6-yl)benzoate

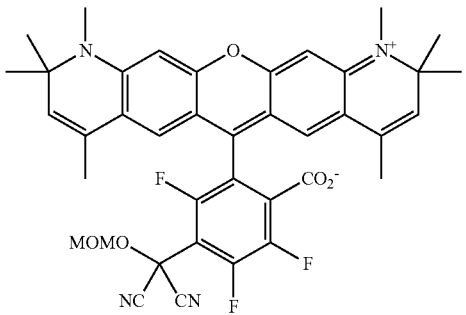

Step 1: To a solution of 3,3'-oxydianiline (1.00 g, 4.99 mmol) in acetone (30 mL) was added Yb(OTf)$_3$ (465 mg, 0.749 mmol, 0.15 eq). After stirring the reaction at room temperature for 72 h, it was concentrated in vacuo, diluted with saturated NaHCO$_3$, and extracted with EtOAc (2×). The combined organic extracts were washed with brine, dried over anhydrous MgSO$_4$, filtered, and concentrated to dryness. Flash chromatography on silica gel (0-25% EtOAc/hexanes, linear gradient) yielded 1.27 g (71%) of 7,7'-oxybis(2,2,4-trimethyl-1,2-dihydroquinoline) as a white solid. $^1$H NMR (CDCl$_3$, 400 MHz) δ 6.98 (d, J=8.3 Hz, 2H), 6.29 (dd, J=8.3, 2.4 Hz, 2H), 6.09 (d, J=2.4 Hz, 2H), 5.23 (q, J=1.3 Hz, 2H), 3.66 (s, 2H), 1.97 (d, J=1.4 Hz, 6H), 1.26 (s, 12H); $^{13}$C NMR (CDCl$_3$, 101 MHz) δ 157.8 (C), 144.7 (C), 128.2 (C), 127.0 (CH), 124.8 (CH), 117.2 (C), 107.7 (CH), 103.3 (CH), 52.1 (C), 31.3 (CH$_3$), 18.8 (CH$_3$); MS (ESI) calcd for C$_{24}$H$_{29}$N$_2$O [M+H]$^+$ 361.2, found 361.4.

Step 2: The product from Step 1 (1.00 g, 2.77 mmol) was taken up in DMF (10 mL); K$_2$CO$_3$ (1.15 g, 8.32 mmol, 3 eq) and iodomethane (414 µL, 6.66 mmol, 2.4 eq) were added, and the reaction was stirred at 50° C. for 18 h. It was subsequently cooled to room temperature, diluted with water, and extracted with EtOAc (2×). The combined organic extracts were washed with brine, dried over anhydrous MgSO$_4$, filtered, and concentrated to dryness. Silica gel chromatography (0-20% EtOAc/hexanes, linear gradient) afforded 7,7'-oxybis(1,2,2,4-tetramethyl-1,2-dihydroquinoline) as a white solid (1.00 g, 93%). $^1$H NMR (CDCl$_3$, 400 MHz) δ 7.00-6.93 (m, 2H), 6.31-6.23 (m, 4H), 5.22 (q, J=1.4 Hz, 2H), 2.74 (s, 6H), 1.97 (d, J=1.4 Hz, 6H), 1.30 (s, 12H); $^{13}$C NMR (CDCl$_3$, 101 MHz) δ 158.2 (C), 146.9 (C), 128.5 (CH), 128.0 (C), 124.2 (CH), 118.9 (C), 105.9 (CH), 102.1 (CH), 56.5 (C), 30.9 (CH$_3$), 27.4 (CH$_3$), 18.8 (CH$_3$); MS (ESI) calcd for C$_{26}$H$_{33}$N$_2$O [M+H]$^+$ 389.3, found 389.4.

Step 3: A solution of 2,3,4,5-tetrafluorobenzoic acid (2.00 g, 10.31 mmol) in THF (30 mL) was cooled to −78° C. under nitrogen. N-Butyllithium (2.5 M in hexanes, 9.89 mL, 24.73 mmol, 2.4 eq) was added, and the reaction was stirred at −78° C. for 3 h. Methyl formate (3.18 mL, 51.53 mmol, 5 eq) was added in one portion; the reaction was then stirred at −78° C. for 30 min, warmed to room temperature, and stirred for 2 h. Following the addition of water (75 mL) and CH$_2$Cl$_2$ (75 mL), the pH was adjusted to 10-11 with 2 M NaOH. The aqueous layer was washed again with CH$_2$Cl$_2$, acidified to pH~2 with 2 M HCl, and extracted with EtOAc (2×). The combined EtOAc layers were dried over anhydrous MgSO$_4$, filtered, and evaporated. Purification by silica gel chromatography (5-100% EtOAc/hexanes, linear gradient, with constant 1% v/v AcOH additive) afforded 4,5,6,7-tetrafluoro-3-hydroxyisobenzofuran-1(3H)-one as a white solid (1.58 g, 69%). $^1$H NMR (DMSO-d$_6$, 400 MHz) δ 8.77 (s, 1H), 6.88 (s, 1H); $^{19}$F NMR (DMSO-d$_6$, 376 MHz) δ −140.20 (td, J=20.6, 8.4 Hz, 1F), −142.72 (t, J=20.1 Hz, 1F), −143.93--144.25 (m, 1F), −150.36 (t, J=20.5 Hz, 1F); Analytical HPLC: t$_R$=9.2 min, 97.6% purity (10-95% MeCN/H$_2$O, linear gradient, with constant 0.1% v/v TFA additive; 20 min run; 1 mL/min flow; ESI; positive ion mode; detection at 230 nm); MS (ESI) calcd for C$_8$H$_3$F$_4$O$_3$ [M+H]$^+$ 223.0, found 223.0.

Step 4: The product from Step 2 (290 mg, 0.746 mmol) and the product from Step 3 (166 mg, 0.746 mmol, 1 eq) were combined in 2,2,2-trifluoroethanol (15 mL) in a round-bottom flask. The reaction mixture was sparged with 02 from a balloon for 10 min, then stirred at 80° C. under the O$_2$ balloon for 18 h. The reaction was cooled to room temperature, concentrated in vacuo, and purified by silica gel chromatography (0-20% MeOH (2 M NH$_3$)/CH$_2$Cl$_2$, linear gradient) to provide 2,3,4,5-tetrafluoro-6-(1,2,2,4,8,10,10,11-octamethyl-1,2,10,11-tetrahydropyrano[3,2-g:5,6-g']diquinolin-13-ium-6-yl)benzoate as a dark blue-purple solid (267 mg, 61%). $^1$H NMR (CD$_3$OD, 400 MHz) δ 6.93 (s, 2H), 6.81 (s, 2H), 5.68 (q, J=1.5 Hz, 2H), 3.19 (s, 6H), 1.93 (d, J=1.4 Hz, 6H), 1.51 (s, 6H), 1.50 (s, 6H); $^{19}$F NMR (CD$_3$OD, 376 MHz) δ −138.84 (ddd, J=21.1, 12.6, 4.0 Hz, 1F), −140.19 (ddd, J=22.4, 12.6, 3.7 Hz, 1F), −152.79 (ddd, J=23.0, 19.2, 4.1 Hz, 1F), −157.56 (ddd, J=21.4, 19.4, 3.8 Hz, 1F); Analytical HPLC: $t_R$=14.2 min, >99% purity (10-95% MeCN/H$_2$O, linear gradient, with constant 0.1% v/v TFA additive; 20 min run; 1 mL/min flow; ESI; positive ion mode; detection at 600 nm); MS (ESI) calcd for C$_{34}$H$_{31}$F$_4$N$_2$O$_3$ [M+H]$^+$ 591.2, found 591.1.

Step 5: 2,3,4,5-Tetrafluoro-6-(1,2,2,4,8,10,10,11-octamethyl-1,2,10,11-tetrahydropyrano[3,2-g:5,6-g']diquinolin-13-ium-6-yl)benzoate (100 mg, 0.169 mmol) and 2-(methoxymethoxy)malononitrile (21.4 mg, 0.169 mmol, 1 eq) were combined in DMF (4 mL), and DIEA (59.0 μL, 0.339 mmol, 2 eq) was added. After stirring the reaction at room temperature for 4 h, it was evaporated to dryness. Flash chromatography on silica gel (0-10% MeOH/CH$_2$Cl$_2$, linear gradient, with constant 1% v/v AcOH additive) afforded the title compound 4-(dicyano(methoxymethoxy)methyl)-2,3,5-trifluoro-6-(1,2,2,4,8,10,10,11-octamethyl-1,2,10,11-tetrahydropyrano[3,2-g:5,6-g']diquinolin-13-ium-6-yl)benzoate as a dark blue solid (93.8 mg, 73%, acetate salt). $^1$H NMR (CD$_3$OD, 400 MHz) δ 6.94 (d, J=1.1 Hz, 2H), 6.81 (s, 2H), 5.68 (q, J=1.4 Hz, 2H), 5.19 (s, 2H), 3.51 (s, 3H), 3.20 (s, 6H), 1.94 (d, J=1.4 Hz, 6H), 1.52 (s, 6H), 1.51 (s, 6H); $^{19}$F NMR (CD$_3$OD, 376 MHz) δ −111.06 (d, J=14.9 Hz, 1F), −127.94 (d, J=21.9 Hz, 1F), −140.94 (dd, J=21.8, 14.9 Hz, 1F); Analytical HPLC: $t_R$=13.9 min, 93.9% purity (10-95% MeCN/H$_2$O, linear gradient, with constant 0.1% v/v TFA additive; 20 min run; 1 mL/min flow; ESI; positive ion mode; detection at 600 nm); MS (ESI) calcd for C$_{39}$H$_{36}$F$_3$N$_4$O$_5$ [M+H]$^+$ 697.3, found 697.2.

Example 70: 4-Carboxy-2,3,5-trifluoro-6-(1,2,2,4,8,10,10,11-octamethyl-1,2,10,11-tetrahydropyrano[3,2-g:5,6-g']diquinolin-13-ium-6-yl)benzoate

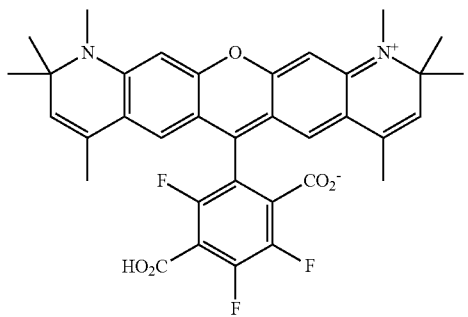

A mixture of 4-(dicyano(methoxymethoxy)methyl)-2,3,5-trifluoro-6-(1,2,2,4,8,10,10,11-octamethyl-1,2,10,11-tetrahydropyrano[3,2-g:5,6-g']diquinolin-13-ium-6-yl)benzoate (Example 69; acetate salt; 10 mg, 13.2 μmol), THF (1 mL), and 1 M H$_2$SO$_4$ (1 mL) was stirred at 60° C. for 72 h. The reaction was concentrated in vacuo, and the crude residue was purified by reverse phase HPLC (35-45% MeCN/H$_2$O, linear gradient, with constant 0.1% v/v TFA additive) to provide the title compound as a dark blue solid (6.4 mg, 66%, TFA salt). $^1$H NMR (DMSO-d$_6$, 400 MHz) δ 6.82 (s, 2H), 6.80 (s, 2H), 5.79 (s, 2H), 3.17 (s, 6H), 1.83 (s, 6H), 1.48 (s, 6H), 1.46 (s, 6H); $^{19}$F NMR (DMSO-d$_6$, 376 MHz) δ −112.95 (d, J=14.3 Hz, 1F), −129.50 (d, J=23.2 Hz, 1F), −138.78 (dd, J=23.5, 14.6 Hz, 1F); Analytical HPLC: $t_R$=11.7 min, >99% purity (10-95% MeCN/H$_2$O, linear gradient, with constant 0.1% v/v TFA additive; 20 min run; 1 mL/min flow; ESI; positive ion mode; detection at 600 nm); MS (ESI) calcd for C$_{35}$H$_{32}$F$_3$N$_2$O$_5$ [M+H]$^+$ 617.2, found 617.1.

Example 71: 4-((2-(2-((6-Chlorohexyl)oxy)ethoxy)ethyl)carbamoyl)-2,3,5-trifluoro-6-(1,2,2,4,8,10,10,11-octamethyl-1,2,10,11-tetrahydropyrano [3,2-g:5,6-g']diquinolin-13-ium-6-yl)benzoate

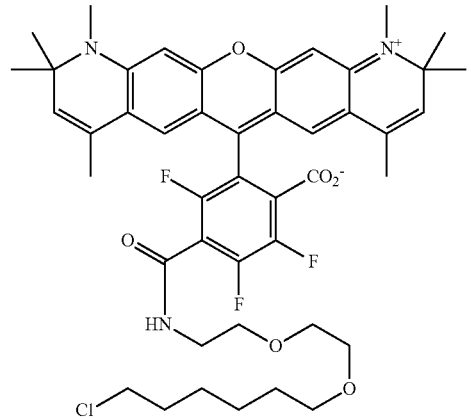

4-Carboxy-2,3,5-trifluoro-6-(1,2,2,4,8,10,10,11-octamethyl-1,2,10,11-tetrahydropyrano[3,2-g:5,6-g']diquinolin-13-ium-6-yl)benzoate (Example 70; TFA salt; 7.8 mg, 10.7 μmol) was combined with BOP (5.2 mg, 11.7 μmol, 1.1 eq) in DMF (1 mL). After adding DIEA (9.3 μL, 53.4 μmol, 5 eq), the reaction was stirred at room temperature for 10 min. A solution of 2-(2-((6-chlorohexyl)oxy)ethoxy)ethan-1-amine (TFA salt; 4.3 mg, 12.8 μmol, 1.2 eq) in DMF (100 μL) was then added. The reaction was stirred for 2 h at room temperature, concentrated in vacuo, and purified by reverse phase HPLC (20-80% MeCN/H$_2$O, linear gradient, with constant 0.1% v/v TFA additive) to yield 1.7 mg (17%, TFA salt) of the title compound as a blue-purple solid. $^1$H NMR (CD$_3$OD, 400 MHz) δ 9.12 (t, J=5.4 Hz, 1H), 6.89 (s, 2H), 6.84 (s, 2H), 5.74-5.70 (m, 2H), 3.67-3.55 (m, 8H), 3.50 (t, J=6.7 Hz, 2H), 3.42 (t, J=6.5 Hz, 2H), 3.21 (s, 6H), 1.92 (d, J=1.4 Hz, 6H), 1.73-1.66 (m, 2H), 1.525 (s, 6H), 1.523 (s, 6H), 1.50-1.45 (m, 2H), 1.41-1.28 (m, 4H); $^{19}$F NMR (CD$_3$OD, 376 MHz) δ −115.98 (d, J=15.4 Hz, 1F), −131.78 (d, J=22.2 Hz, 1F), −139.85-−140.17 (m, 1F); Analytical HPLC: $t_R$=14.1 min, >99% purity (10-95% MeCN/H$_2$O, linear gradient, with constant 0.1% v/v TFA additive; 20 min run; 1 mL/min flow; ESI; positive ion mode; detection at 600 nm); MS (ESI) calcd for C$_{45}$H$_{52}$ClF$_3$N$_3$O$_6$ [M+H]$^+$ 822.3, found 822.3.

Example 72: 4-Carboxy-2,3,5-trifluoro-6-(1,2,2,10, 10,11-hexamethyl-4,8-bis(sulfomethyl)-1,2,10,11-tetrahydropyrano[3,2-g:5,6-g']diquinolin-13-ium-6-yl)benzoate

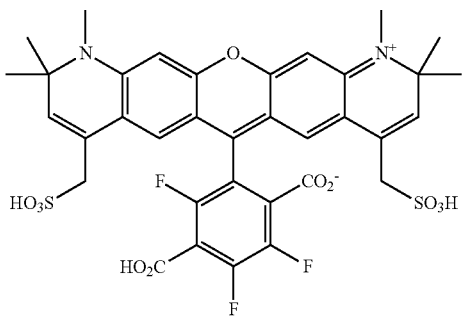

4-Carboxy-2,3,5-trifluoro-6-(1,2,2,4,8,10,10,11-octamethyl-1,2,10,11-tetrahydropyrano[3,2-g:5,6-g']diquinolin-13-ium-6-yl)benzoate (Example 70; TFA salt; 15.0 mg, 20.5 μmol) was taken up in concentrated $H_2SO_4$ (1 mL) and stirred at room temperature for 72 h. The reaction mixture was then added dropwise to dioxane (3 mL) in an ice bath while stirring vigorously. The resulting solution was gradually diluted with a large volume of $Et_2O$ (100 mL) and vigorously stirred for 30 min to precipitate a dark blue solid. The solvents were carefully decanted away, and the residue was purified by reverse phase HPLC (10-75% $MeCN/H_2O$, linear gradient, with constant 0.1% v/v TFA additive) to afford 13.9 mg (76%, TFA salt) of the title compound as a dark blue solid. $^1H$ NMR ($CD_3OD$, 400 MHz) δ 7.42 (s, 2H), 6.82 (s, 2H), 5.93 (s, 2H), 3.87 (d, J=14.3 Hz, 2H), 3.75 (d, J=14.2 Hz, 2H), 3.20 (s, 6H), 1.56 (s, 6H), 1.56 (s, 6H); $^{19}F$ NMR ($CD_3OD$, 376 MHz) δ −111.60 (d, J=14.7 Hz, 1F), −128.91 (d, J=21.7 Hz, 1F), −138.40 (dd, J=21.5, 14.9 Hz, 1F); Analytical HPLC: $t_R$=9.8 min, >99% purity (10-95% $MeCN/H_2O$, linear gradient, with constant 0.1% v/v TFA additive; 20 min run; 1 mL/min flow; ESI; positive ion mode; detection at 600 nm); MS (ESI) calcd for $C_{35}H_{32}F_3N_2O_{11}S_2$ [M+H]$^+$ 777.1, found 777.0.

Example 73: 4-((2-(2-((6-Chlorohexyl)oxy)ethoxy)ethyl)carbamoyl)-2,3,5-trifluoro-6-(1,2,2,10,10,11-hexamethyl-4,8-bis(sulfomethyl)-1,2,10,11-tetrahydropyrano[3,2-g:5,6-g']diquinolin-13-ium-6-yl)benzoate

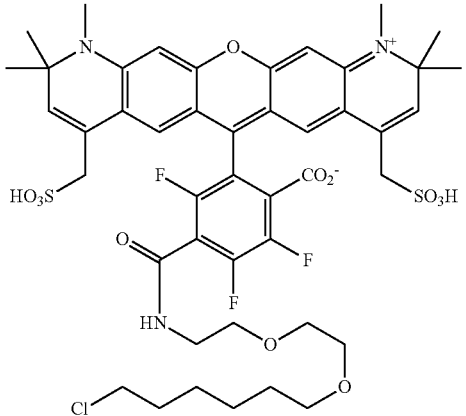

4-Carboxy-2,3,5-trifluoro-6-(1,2,2,10,10,11-hexamethyl-4,8-bis(sulfomethyl)-1,2,10,11-tetrahydropyrano[3,2-g:5,6-g']diquinolin-13-ium-6-yl)benzoate (Example 72; TFA salt; 10 mg, 11.2 μmol) was combined with BOP (5.0 mg, 11.2 μmol, 1 eq) in DMF (1 mL). After adding DIEA (19.6 μL, 0.112 mmol, 10 eq), the reaction was stirred at room temperature for 10 min. A solution of 2-(2-((6-chlorohexyl)oxy)ethoxy)ethan-1-amine (TFA salt; 5.7 mg, 16.8 μmol, 1.5 eq) in DMF (100 μL) was then added. The reaction was stirred for 18 h at room temperature, concentrated in vacuo, and purified by reverse phase HPLC (20-80% $MeCN/H_2O$, linear gradient, with constant 0.1% v/v TFA additive) to yield 4.1 mg (33%, TFA salt) of the title compound as a dark blue solid. $^1H$ NMR ($CD_3OD$, 400 MHz) δ 7.40 (s, 2H), 6.82 (s, 2H), 5.93 (s, 2H), 3.87 (d, J=14.2 Hz, 2H), 3.73 (d, J=14.4 Hz, 2H), 3.70-3.55 (m, 8H), 3.52 (t, J=6.7 Hz, 2H), 3.44 (t, J=6.5 Hz, 2H), 3.20 (s, 6H), 1.77-1.68 (m, 2H), 1.57 (s, 6H), 1.56 (s, 6H), 1.53-1.47 (m, 2H), 1.44-1.31 (m, 4H); $^{19}F$ NMR ($CDCl_3$, 376 MHz) δ −113.35 (d, J=14.8 Hz, 1F), −131.12 (d, J=21.6 Hz, 1F), −138.82 (dd, J=21.9, 14.9 Hz, 1F); Analytical HPLC: $t_R$=12.2 min, >99% purity (10-95% $MeCN/H_2O$, linear gradient, with constant 0.1% v/v TFA additive; 20 min run; 1 mL/min flow; ESI; positive ion mode); detection at 600 nm); MS (ESI) calcd for $C_{45}H_{52}ClF_3N_3O_{12}S_2$ [M+H]$^+$ 982.3, found 982.2.

Example 74: 4-(Dicyano(methoxymethoxy)methyl)-2,3,5-trifluoro-6-(2,2,4,8,10,10-hexamethyl-1,2,3,4,8,9,10,11-octahydropyrano[3,2-g:5,6-g']diquinolin-13-ium-6-yl)benzoate

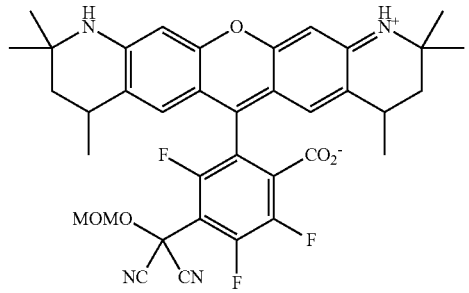

Step 1: 7,7'-Oxybis(2,2,4-trimethyl-1,2-dihydroquinoline) (Example 69, Step 1; 1.50 g, 4.16 mmol) was dissolved in EtOH (100 mL) in a round-bottom flask under nitrogen, and Pd/C (10%, 886 mg, 0.832 mmol, 0.2 eq) was added. The sealed flask was evacuated/backfilled with $H_2$ from a balloon (4×) and then stirred under the $H_2$ balloon at room temperature for 18 h. The reaction mixture was filtered through Celite with EtOH and concentrated in vacuo. Silica gel chromatography (0-20% EtOAc/hexanes, linear gradient) yielded 1.46 g (96%) of 7,7'-oxybis(2,2,4-trimethyl-1,2,3,4-tetrahydroquinoline) (a mixture of diastereomers) as a white solid. $^1H$ NMR ($CDCl_3$, 400 MHz) δ 7.08-7.02 (m, 2H), 6.35-6.28 (m, 2H), 6.09-6.03 (m, 2H), 3.51 (s, 2H), 2.93-2.79 (m, 2H), 1.77-1.65 (m, 2H), 1.47-1.36 (m, 2H), 1.32 (s, 3H), 1.30 (s, 3H), 1.20 (s, 6H), 1.16 (s, 6H); $^{13}C$ NMR ($CDCl_3$, 101 MHz) δ 156.6 (C), 144.9 (C), 127.91/127.86 (CH), 120.17/120.15 (C), 107.76/107.67 (CH), 104.13/104.10 (CH), 49.5 (C), 44.7 ($CH_2$), 31.6 (CH), 28.04/27.96 ($CH_3$), 27.4 ($CH_3$), 20.57/20.54 ($CH_3$); MS (ESI) calcd for $C_{24}H_{33}N_2O$ [M+H]$^+$ 365.3, found 365.4.

Step 2: The product from Step 1 (273 mg, 0.749 mmol) and 4,5,6,7-tetrafluoro-3-hydroxyisobenzofuran-1(3H)-one (Example 69, Step 3; 166 mg, 0.749 mmol, 1 eq) were combined in 2,2,2-trifluoroethanol (15 mL) in a round-bottom flask. The reaction mixture was sparged with $O_2$ from a balloon for 10 min, then stirred at 80° C. under the O2 balloon for 48 h. The reaction was cooled to room temperature, concentrated in vacuo, and purified by silica gel chromatography (0-20% MeOH (2 M NH$_3$)/CH$_2$Cl$_2$, linear gradient) to provide 2,3,4,5-tetrafluoro-6-(2,2,4,8,10,10-hexamethyl-1,2,3,4,8,9,10,11-octahydropyrano[3,2-g:5,6-g']diquinolin-13-ium-6-yl)benzoate (a mixture of diastereomers) as a dark blue-purple solid (101 mg, 24%). $^1$H NMR (CD$_3$OD, 400 MHz) δ 7.15-7.10 (m, 2H), 6.63-6.58 (m, 2H), 2.99-2.86 (m, 2H), 1.93-1.82 (m, 2H), 1.48-1.22 (m, 20H); $^{19}$F NMR (CD$_3$OD, 376 MHz) δ −138.47-139.23 (m, 1F), −139.52--140.42 (m, 1F), −152.78--153.26 (m, 1F), −156.57--158.07 (m, 1F); Analytical HPLC: $t_R$ (three isomers)=13.7 min, 13.9 min, 14.2 min; >99% total purity (10-95% MeCN/H$_2$O, linear gradient, with constant 0.1% v/v TFA additive; 20 min run; 1 mL/min flow; ESI; positive ion mode; detection at 550 nm); MS (ESI) calcd for C$_{32}$H$_{31}$F$_4$N$_2$O$_3$ [M+H]$^+$ 567.2, found 567.2.

Step 3: The product from Step 2 (50 mg, 88.2 μmol) and 2-(methoxymethoxy)malononitrile (11.1 mg, 88.2 μmol, 1 eq) were combined in DMSO (5 mL), and DIEA (30.7 μL, 0.176 mmol, 2 eq) was added. The resulting dark red solution was stirred at room temperature for 4 h. A second portion of 2-(methoxymethoxy)malononitrile (2.8 mg, 22.1 μmol, 0.25 eq) was added, and stirring was continued for an additional 2 h at room temperature. The reaction was then concentrated to dryness and purified by silica gel chromatography (0-20% MeOH/CH$_2$Cl$_2$, linear gradient, with constant 1% v/v AcOH additive) to provide the title compound 4-(dicyano(methoxymethoxy)methyl)-2,3,5-trifluoro-6-(2,2,4,8,10,10-hexamethyl-1,2,3,4,8,9,10,11-octahydropyrano[3,2-g:5,6-g']diquinolin-13-ium-6-yl)benzoate (a mixture of diastereomers) as a dark red-purple solid (30.5 mg, 47%, acetate salt). $^1$H NMR (CD$_3$OD, 400 MHz) δ 7.16-7.09 (m, 2H), 6.64-6.59 (m, 2H), 5.21-5.18 (m, 2H), 3.55-3.50 (m, 3H), 3.00-2.85 (m, 2H), 1.91-1.84 (m, 2H), 1.49-1.23 (m, 20H); $^{19}$F NMR (CD$_3$OD, 376 MHz) δ −111.22--111.37 (m, 1F), −128.02--128.46 (m, 1F), −140.92--141.30 (m, 1F); Analytical HPLC: $t_R$ (three isomers)=13.2 min, 13.4 min, 13.6 min; 95.1% total purity (10-95% MeCN/H$_2$O, linear gradient, with constant 0.1% v/v TFA additive; 20 min run; 1 mL/min flow; ESI; positive ion mode; detection at 550 nm); MS (ESI) calcd for C$_{37}$H$_{36}$F$_3$N$_4$O$_5$ [M+H]$^+$ 673.3, found 673.2.

Example 75: 4-Carboxy-2,3,5-trifluoro-6-(2,2,4,8,10,10-hexamethyl-1,2,3,4,8,9,10,11-octahydropyrano[3,2-g:5,6-g']diquinolin-13-ium-6-yl)benzoate

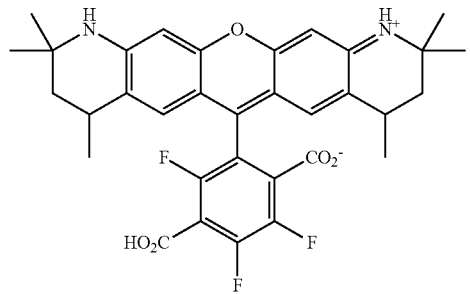

A mixture of 4-(dicyano(methoxymethoxy)methyl)-2,3,5-trifluoro-6-(2,2,4,8,10,10-hexamethyl-1,2,3,4,8,9,10,11-octahydropyrano[3,2-g:5,6-g']diquinolin-13-ium-6-yl)benzoate (Example 74; acetate salt; 25 mg, 34.1 μmol), THF (1.5 mL), and 1 M H$_2$SO$_4$ (1.5 mL) was stirred at 60° C. for 48 h. The reaction was concentrated in vacuo, and the crude residue was purified by reverse phase HPLC (10-75% MeCN/H$_2$O, linear gradient, with constant 0.1% v/v TFA additive) to provide the title compound (a mixture of diastereomers) as a dark red-purple solid (13.4 mg, 56%, TFA salt). $^1$H NMR (CD$_3$OD, 400 MHz) δ 7.13-7.06 (m, 2H), 6.67-6.60 (m, 2H), 3.00-2.87 (m, 2H), 1.94-1.85 (m, 2H), 1.48-1.20 (m, 20H); $^{19}$F NMR (CD$_3$OD, 376 MHz) δ −114.68--115.11 (m, 1F), −130.86--131.50 (m, 1F), −139.60--140.43 (m, 1F); Analytical HPLC: $t_R$=11.2 min (mixture of diastereomers, three close-running peaks), 96.5% purity (10-95% MeCN/H$_2$O, linear gradient, with constant 0.1% v/v TFA additive; 20 min run; 1 mL/min flow; ESI; positive ion mode; detection at 550 nm); MS (ESI) calcd for C$_{33}$H$_{32}$F$_3$N$_2$O$_5$ [M+H]$^+$ 593.2, found 593.2.

Example 76: 4-((2-(2-((6-Chlorohexyl)oxy)ethoxy)ethyl)carbamoyl)-2,3,5-trifluoro-6-(2,2,4,8,10,10-hexamethyl-1,2,3,4,8,9,10,11-octahydropyrano[3,2-g:5,6-g']diquinolin-13-ium-6-yl)benzoate

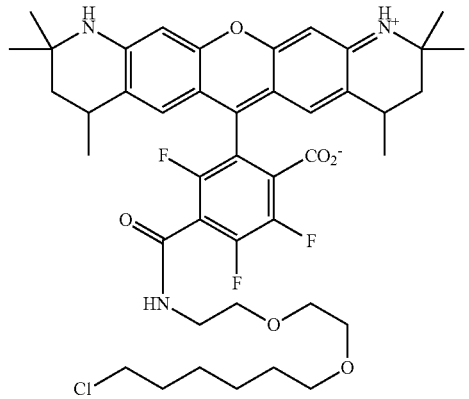

4-Carboxy-2,3,5-trifluoro-6-(2,2,4,8,10,10-hexamethyl-1,2,3,4,8,9,10,11-octahydropyrano[3,2-g:5,6-g']diquinolin-13-ium-6-yl)benzoate (Example 75; TFA salt; 10 mg, 14.2 μmol) was combined with BOP (6.9 mg, 15.6 μmol, 1.1 eq) in DMF (1 mL). After adding DIEA (12.3 μL, 70.8 μmol, 5 eq), the reaction was stirred at room temperature for 10 min. A solution of 2-(2-((6-chlorohexyl)oxy)ethoxy)ethan-1-amine (TFA salt; 5.7 mg, 17.0 μmol, 1.2 eq) in DMF (100 μL) was then added. The reaction was stirred for 18 h at room temperature, concentrated in vacuo, and purified by reverse phase HPLC (20-80% MeCN/H$_2$O, linear gradient, with constant 0.1% v/v TFA additive) to provide the title compound (a mixture of diastereomers) as a blue-purple solid (5.1 mg, 40%, TFA salt). $^1$H NMR (CD$_3$OD, 400 MHz) δ 9.19-9.08 (m, 1H), 7.15-7.05 (m, 2H), 6.67-6.61 (m, 2H), 3.70-3.52 (m, 8H), 3.53-3.47 (m, 2H), 3.45-3.40 (m, 2H), 2.98-2.87 (m, 2H), 1.95-1.86 (m, 2H), 1.75-1.66 (m, 2H), 1.54-1.19 (m, 26H); $^{19}$F NMR (CD$_3$OD, 376 MHz) δ −116.07--116.23 (m, 1F), −132.05--132.22 (m, 1F), −139.69--140.86 (m, 1F); Analytical HPLC: $t_R$ (three isomers)=13.7 min, 13.8 min, 14.0 min; >99% total purity (10-95% MeCN/H$_2$O, linear gradient, with constant 0.1% v/v TFA additive; 20 min run; 1 mL/min flow; ESI; positive ion mode; detection at 550 nm); MS (ESI) calcd for C$_{43}$H$_{52}$ClF$_3$N$_3$O$_6$ [M+H]$^+$ 798.3, found 798.3.

Example 77: 2-(3,6-Di(azetidin-1-yl)xanthylium-9-yl)-4-(1,3-di-tert-butoxy-1,3-dioxopropan-2-yl)-3,5,6-trifluorobenzoate

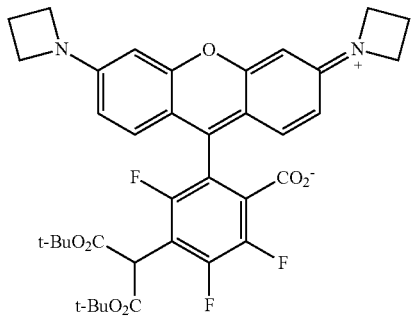

2-(3,6-Di(azetidin-1-yl)xanthylium-9-yl)-3,4,5,6-tetrafluorobenzoate (Grimm, J. B. et al. *ACS Cent. Sci.* 2017, 3, 975-985; 75 mg, 0.155 mmol) and di-tert-butyl malonate (41.8 µL, 0.187 mmol, 1.2 eq) were combined in DMF (2 mL), and $K_2CO_3$ (51.6 mg, 0.373 mmol, 2.4 eq) was added. After stirring the reaction at 50° C. for 18 h, it was directly purified by reverse phase HPLC (30-60% MeCN/$H_2O$, linear gradient, with constant 0.1% v/v TFA additive). The pooled HPLC product fractions were partially concentrated to remove MeCN, diluted with saturated $NaHCO_3$, and extracted with $CH_2Cl_2$ (2×). The organic extracts were dried over anhydrous $MgSO_4$, filtered, and evaporated to yield 57 mg (54%) of the title compound as a dark red-purple solid. $^1$H NMR ($CDCl_3$, 400 MHz) δ 6.82 (d, J=8.6 Hz, 2H), 6.20 (d, J=2.2 Hz, 2H), 6.17 (dd, J=8.6, 2.3 Hz, 2H), 4.75 (s, 1H), 3.96 (t, J=7.4 Hz, 8H), 2.41 (p, J=7.3 Hz, 4H), 1.38 (s, 18H); $^{19}$F NMR ($CDCl_3$, 376 MHz) δ 119.24--119.66 (m, 1F), −131.54 (d, J=21.0 Hz, 1F), −142.90--143.40 (m, 1F); Analytical HPLC: $t_R$=10.9 min, >99% purity (30-95% MeCN/$H_2O$, linear gradient, with constant 0.1% v/v TFA additive; 20 min run; 1 mL/min flow; ESI; positive ion mode; detection at 575 nm); HRMS (ESI) calcd for $C_{37}H_{38}F_3N_2O_7$ [M+H]$^+$ 679.2626, found 679.2623.

Example 78: 4-(Carboxymethyl)-2-(3,6-di(azetidin-1-yl)xanthylium-9-yl)-3,5,6-trifluorobenzoate

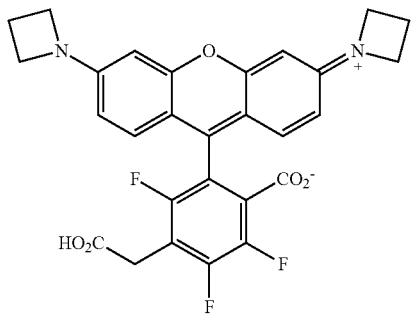

2-(3,6-Di(azetidin-1-yl)xanthylium-9-yl)-4-(1,3-di-tert-butoxy-1,3-dioxopropan-2-yl)-3,5,6-trifluorobenzoate (Example 77; 40 mg, 58.9 µmol) was taken up in $CH_2Cl_2$ (2.5 mL); triethylsilane (250 µL) was added, followed by trifluoroacetic acid (500 µL). The reaction was stirred at room temperature for 6 h. Toluene (3 mL) was added; the reaction mixture was concentrated to dryness and azeotroped with MeOH (3×). The crude material was purified by reverse phase HPLC (10-75% MeCN/$H_2O$, linear gradient, with constant 0.1% v/v TFA additive) to provide the title compound as a dark red-purple solid (26.4 mg, 70%, TFA salt). $^1$H NMR ($CD_3OD$, 400 MHz) δ 7.26 (d, J=9.1 Hz, 2H), 6.67 (dd, J=9.2, 2.2 Hz, 2H), 6.52 (d, J=2.2 Hz, 2H), 4.33 (t, J=7.7 Hz, 8H), 3.89 (s, 2H), 2.57 (p, J=7.6 Hz, 4H); $^{19}$F NMR ($CD_3OD$, 376 MHz) δ −116.91--117.02 (m, 1F), −132.96--133.10 (m, 1F), −140.23--140.42 (m, 1F); Analytical HPLC: $t_R$=11.1 min, >99% purity (10-75% MeCN/$H_2O$, linear gradient, with constant 0.1% v/v TFA additive; 20 min run; 1 mL/min flow; ESI; positive ion mode; detection at 575 nm); HRMS (ESI) calcd for $C_{24}H_{22}F_3N_2O_5$ [M+H]$^+$ 523.1475, found 523.1480.

Example 79: 2-(3,7-Bis(dimethylamino)-5,5-dimethyldibenzo[b,e]silin-10-ylium-10(5H)-yl)-4-(1,3-di-tert-butoxy-1,3-dioxopropan-2-yl)-3,5,6-trifluorobenzoate

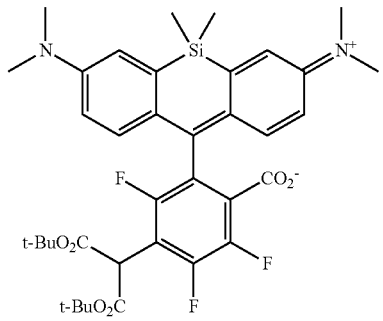

2-(3,7-Bis(dimethylamino)-5,5-dimethyldibenzo[b,e]silin-10-ylium-10(5H)-yl)-3,4,5,6-tetrafluorobenzoate (Grimm, J. B. et al. *ACS Cent. Sci.* 2017, 3, 975-985; 100 mg, 0.200 mmol) and di-tert-butyl malonate (49.2 µL, 0.220 mmol, 1.1 eq) were combined in DMF (2 mL), and $K_2CO_3$ (55.2 mg, 0.400 mmol, 2 eq) was added. After stirring the reaction at room temperature for 18 h, additional di-tert-butyl malonate (49.2 µL, 0.220 mmol, 1.1 eq) and $K_2CO_3$ (55.2 mg, 0.400 mmol, 2 eq) were added. The mixture was stirred at 50° C. for 24 h. It was then cooled to room temperature, diluted with water, and extracted with EtOAc (2×). The combined organic extracts were washed with brine, dried over anhydrous $MgSO_4$, filtered, and evaporated. Purification of the crude by silica gel chromatography (0-50% EtOAc/hexanes, linear gradient) yielded 83 mg (60%) of the title compound as a blue-green solid. $^1$H NMR ($CDCl_3$, 400 MHz) δ 6.96 (d, J=2.9 Hz, 2H), 6.79 (dd, J=8.8, 1.4 Hz, 2H), 6.55 (dd, J=8.9, 2.9 Hz, 2H), 4.83 (s, 1H), 2.97 (s, 12H), 1.41 (s, 18H), 0.583 (s, 3H), 0.581 (s, 3H); $^{19}$F NMR ($CDCl_3$, 376 MHz, $^1$H decoupled) δ −115.39 (d, J=21.5 Hz, 1F), −132.72 (d, J=20.7 Hz, 1F), −143.43 (t, J=21.3 Hz, 1F); Analytical HPLC: $t_R$=12.8 min, >99% purity (30-95% MeCN/$H_2O$, linear gradient, with constant 0.1% v/v TFA additive; 20 min run; 1 mL/min flow; ESI; positive ion mode; detection at 675 nm); HRMS (ESI) calcd for $C_{37}H_{44}F_3N_2O_6Si$ [M+H]$^+$ 697.2915, found 697.2920.

Example 80: 2-(3,7-Bis(dimethylamino)-5,5-dimethyldibenzo[b,e]silin-10-ylium-10(5H)-yl)-4-(carboxymethyl)-3,5,6-trifluorobenzoate

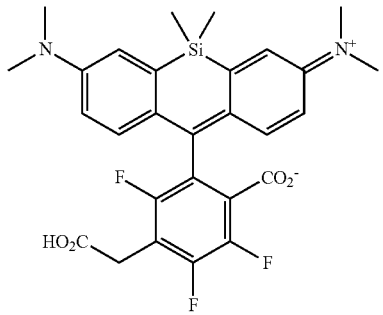

2-(3,7-Bis(dimethylamino)-5,5-dimethyldibenzo[b,e]silin-10-ylium-10(5H)-yl)-4-(1,3-di-tert-butoxy-1,3-dioxopropan-2-yl)-3,5,6-trifluorobenzoate (Example 79; 40 mg, 57.4 μmol) was taken up in $CH_2Cl_2$ (3 mL); triethylsilane (300 μL) was added, followed by trifluoroacetic acid (600 μL). The reaction was stirred at room temperature for 4 h. Toluene (3 mL) was added; the reaction mixture was concentrated to dryness and azeotroped with MeOH (3×). The crude material was purified by reverse phase HPLC (10-75% MeCN/$H_2O$, linear gradient, with constant 0.1% v/v TFA additive) to provide the title compound as a dark blue solid (35.4 mg, 94%, TFA salt). $^1H$ NMR ($CD_3OD$, 400 MHz) δ 7.30 (d, J=2.9 Hz, 2H), 7.11 (dd, J=9.4, 0.8 Hz, 2H), 6.81 (dd, J=9.5, 2.9 Hz, 2H), 3.88 (s, 2H), 3.29 (s, 12H), 0.63 (s, 3H), 0.54 (s, 3H); $^{19}F$ NMR ($CD_3OD$, 376 MHz) δ −117.94−−118.05 (m, 1F), −134.81−−134.93 (m, 1F), −141.78−−142.08 (m, 1F); Analytical HPLC: $t_R$=10.8 min, >99% purity (10-95% MeCN/$H_2O$, linear gradient, with constant 0.1% v/v TFA additive; 20 min run; 1 mL/min flow; ESI; positive ion mode; detection at 675 nm); HRMS (ESI) calcd for $C_{28}H_{28}F_3N_2O_4Si$ [M+H]$^+$ 541.1765, found 541.1771.

Example 81: 2-(3,7-Di(azetidin-1-yl)-5,5-dimethyldibenzo[b,e]silin-10-ylium-10(5H)-yl)-4-(1,3-di-tert-butoxy-1,3-dioxopropan-2-yl)-3,5,6-trifluorobenzoate

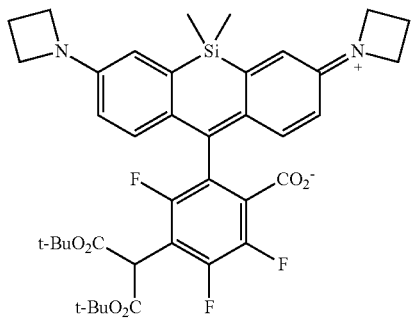

2-(3,7-Di(azetidin-1-yl)-5,5-dimethyldibenzo[b,e]silin-10-ylium-10(5H)-yl)-3,4,5,6-tetrafluorobenzoate (Grimm, J. B. et al. *ACS Cent. Sci.* 2017, 3, 975-985; 150 mg, 0.286 mmol) and di-tert-butyl malonate (76.8 μL, 0.343 mmol, 1.2 eq) were combined in DMF (3 mL), and $K_2CO_3$ (94.8 mg, 0.686 mmol, 2.4 eq) was added. After stirring the reaction at 50° C. for 48 h, it was cooled to room temperature, diluted with water, and extracted with EtOAc (2×). The combined organic extracts were washed with brine, dried over anhydrous $MgSO_4$, filtered, and evaporated. Purification of the crude by silica gel chromatography (0-50% EtOAc/hexanes, linear gradient) yielded 101 mg (49%) of the title compound as a blue-green solid. $^1H$ NMR ($CDCl_3$, 400 MHz) δ 6.75 (dd, J=8.6, 1.7 Hz, 2H), 6.66 (d, J=2.6 Hz, 2H), 6.25 (dd, J=8.6, 2.6 Hz, 2H), 4.84 (s, 1H), 3.90 (t, J=7.2 Hz, 8H), 2.37 (p, J=7.2 Hz, 4H), 1.42 (s, 18H), 0.56 (s, 3H), 0.55 (s, 3H); $^{19}F$ NMR ($CDCl_3$, 376 MHz, 41 decoupled) δ −114.87 (d, J=21.3 Hz, 1F), −132.66 (d, J=20.8 Hz, 1F), −143.30 (t, J=21.2 Hz, 1F); Analytical HPLC: $t_R$=13.4 min, 98.0% purity (30-95% MeCN/$H_2O$, linear gradient, with constant 0.1% v/v TFA additive; 20 min run; 1 mL/min flow; ESI; positive ion mode; detection at 675 nm); HRMS (ESI) calcd for $C_{39}H_{44}F_3N_2O_6Si$ [M+H]$^+$ 721.2915, found 721.2924.

Example 82: 4-(Carboxymethyl)-2-(3,7-di(azetidin-1-yl)-5,5-dimethyldibenzo[b,e]silin-10-ylium-10(5H)-yl)-3,5,6-trifluorobenzoate

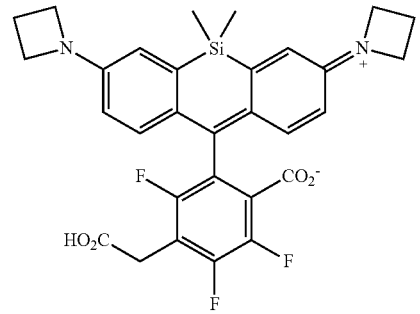

2-(3,7-Di(azetidin-1-yl)-5,5-dimethyldibenzo[b,e]silin-10-ylium-10(5H)-yl)-4-(1,3-di-tert-butoxy-1,3-dioxopropan-2-yl)-3,5,6-trifluorobenzoate (Example 81; 75 mg, 0.104 mmol) was taken up in $CH_2Cl_2$ (6 mL); triethylsilane (600 μL) was added, followed by trifluoroacetic acid (1.2 mL). The reaction was stirred at room temperature for 6 h. Toluene (7 mL) was added; the reaction mixture was concentrated to dryness and azeotroped with MeOH (3×). The crude material was purified by reverse phase HPLC (20-60% MeCN/$H_2O$, linear gradient, with constant 0.1% v/v TFA additive). The pooled HPLC product fractions were combined, partially concentrated to remove MeCN, and extracted with $CH_2Cl_2$ (3×). The organic extracts were dried over anhydrous $MgSO_4$, filtered, and evaporated to yield 29.0 mg (49%) of the title compound as a blue solid. $^1H$ NMR ($CD_3OD$, 400 MHz) δ 6.86 (dd, J=8.8, 1.4 Hz, 2H), 6.78 (d, J=2.6 Hz, 2H), 6.36 (dd, J=8.8, 2.6 Hz, 2H), 4.02 (t, J=7.4 Hz, 8H), 3.85 (s, 2H), 2.42 (p, J=7.4 Hz, 4H), 0.56 (s, 3H), 0.50 (s, 3H); $^{19}F$ NMR ($CD_3OD$, 376 MHz) δ −118.41−−118.55 (m), −135.09−−135.20 (m), −144.45−−144.76 (m); Analytical HPLC: $t_R$=11.4 min, >99% purity (10-95% MeCN/$H_2O$, linear gradient, with constant 0.1% v/v TFA additive; 20 min run; 1 mL/min flow; ESI; positive ion mode; detection at 675 nm); HRMS (ESI) calcd for $C_{30}H_{28}F_3N_2O_4Si$ [M+H]$^+$ 565.1765, found 565.1772.

Example 83: 4-(1-(tert-Butoxy)-3-ethoxy-1,3-dioxopropan-2-yl)-2-(3,6-di(azetidin-1-yl)xanthylium-9-yl)-3,5,6-trifluorobenzoate

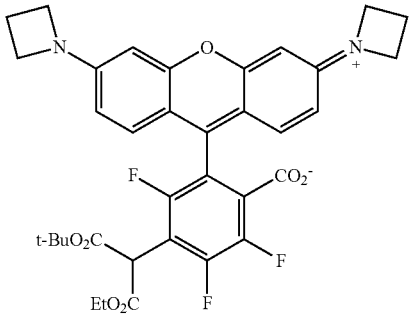

2-(3,6-Di(azetidin-1-yl)xanthylium-9-yl)-3,4,5,6-tetrafluorobenzoate (Grimm, J. B. et al. *ACS Cent. Sci.* 2017, 3, 975-985; 75 mg, 0.155 mmol) and tert-butyl ethyl malonate (35.3 µL, 0.187 mmol, 1.2 eq) were combined in DMF (2 mL), and $K_2CO_3$ (51.6 mg, 0.373 mmol, 2.4 eq) was added. After stirring the reaction at 50° C. for 18 h, it was directly purified by reverse phase HPLC (30-60% MeCN/$H_2O$, linear gradient, with constant 0.1% v/v TFA additive). The pooled HPLC product fractions were partially concentrated to remove MeCN, diluted with saturated $NaHCO_3$, and extracted with $CH_2Cl_2$ (2×). The organic extracts were dried over anhydrous $MgSO_4$, filtered, and evaporated to yield 60 mg (59%) of the title compound as a dark red-purple solid. $^1H$ NMR ($CDCl_3$, 400 MHz) δ 6.90-6.82 (m, 2H), 6.22-6.17 (m, 4H), 4.83 (s, 1H), 4.24-4.12 (m, 2H), 3.98 (t, J=7.3 Hz, 8H), 2.42 (p, J=7.2 Hz, 4H), 1.38 (s, 9H), 1.20 (t, J=7.1 Hz, 3H); $^{19}F$ NMR ($CDCl_3$, 376 MHz) δ −119.43−−119.90 (m, 1F), −131.51 (d, J=21.1 Hz, 1F), −142.52−−143.06 (m, 1F); Analytical HPLC: $t_R$=9.9 min, >99% purity (30-95% MeCN/$H_2O$, linear gradient, with constant 0.1% v/v TFA additive; 20 min run; 1 mL/min flow; ESI; positive ion mode; detection at 575 nm); HRMS (ESI) calcd for $C_{35}H_{34}F_3N_2O_7$ [M+H]$^+$ 651.2313, found 651.2315.

Example 84: 2-(3,6-Di(azetidin-1-yl)xanthylium-9-yl)-4-(2-ethoxy-2-oxoethyl)-3,5,6-trifluorobenzoate

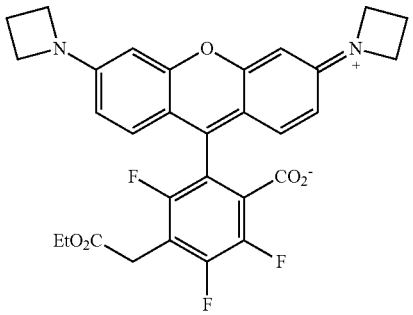

4-(1-(tert-Butoxy)-3-ethoxy-1,3-dioxopropan-2-yl)-2-(3,6-di(azetidin-1-yl)xanthylium-9-yl)-3,5,6-trifluorobenzoate (Example 83; 40 mg, 61.5 µmol) was taken up in $CH_2Cl_2$ (2.5 mL); triethylsilane (250 µL) was added, followed by trifluoroacetic acid (500 µL). The reaction was stirred at room temperature for 6 h. Toluene (3 mL) was added; the reaction mixture was concentrated to dryness and azeotroped with MeOH (3×). The crude material was purified by reverse phase HPLC (10-75% MeCN/$H_2O$, linear gradient, with constant 0.1% v/v TFA additive) to provide the title compound as a dark red-purple solid (33.2 mg, 81%, TFA salt). $^1H$ NMR ($CD_3OD$, 400 MHz) δ 7.25 (d, J=9.1 Hz, 2H), 6.67 (dd, J=9.2, 2.2 Hz, 2H), 6.53 (d, J=2.2 Hz, 2H), 4.33 (t, J=7.6 Hz, 8H), 4.21 (q, J=7.1 Hz, 2H), 3.94 (s, 2H), 2.57 (p, J=7.7 Hz, 4H), 1.27 (t, J=7.1 Hz, 3H); $^{19}F$ NMR ($CD_3OD$, 376 MHz) δ −116.62 (dd, J=14.9, 4.9 Hz, 1F), −132.83 (dd, J=21.1, 4.8 Hz, 1F), −139.86 (dd, J=21.1, 14.8 Hz, 1F); Analytical HPLC: $t_R$=11.6 min, >99% purity (10-95% MeCN/$H_2O$, linear gradient, with constant 0.1% v/v TFA additive; 20 min run; 1 mL/min flow; ESI; positive ion mode; detection at 575 nm); HRMS (ESI) calcd for $C_{30}H_{26}F_3N_2O_5$ [M+H]$^+$ 551.1788, found 551.1800.

Example 85: 2-(3,7-Bis(dimethylamino)-5,5-dimethyldibenzo[b,e]silin-10-ylium-10(5H)-yl)-4-(1-(tert-butoxy)-3-ethoxy-1,3-dioxopropan-2-yl)-3,5,6-trifluorobenzoate

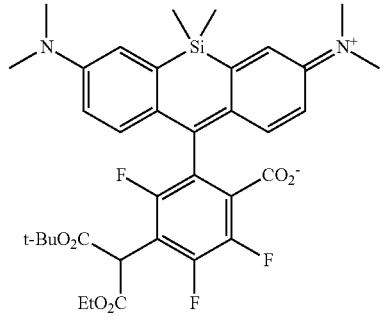

2-(3,7-Bis(dimethylamino)-5,5-dimethyldibenzo[b,e]silin-10-ylium-10(5H)-yl)-3,4,5,6-tetrafluorobenzoate (Grimm, J. B. et al. *ACS Cent. Sci.* 2017, 3, 975-985; 90 mg, 0.180 mmol) and tert-butyl ethyl malonate (40.9 µL, 0.216 mmol, 1.2 eq) were combined in DMF (2 mL), and $K_2CO_3$ (59.6 mg, 0.432 mmol, 2.4 eq) was added. After stirring the reaction at 50° C. for 18 h, it was cooled to room temperature, diluted with water, and extracted with EtOAc (2×). The combined organic extracts were washed with brine, dried over anhydrous $MgSO_4$, filtered, and evaporated. Purification of the crude by silica gel chromatography (0-50% EtOAc/hexanes, linear gradient) yielded 84 mg (70%) of the title compound as a blue-green solid. $^1H$ NMR ($CDCl_3$, 400 MHz) δ 6.96 (d, J=2.9 Hz, 2H), 6.81-6.74 (m, 2H), 6.58-6.52 (m, 2H), 4.93 (s, 1H), 4.28-4.19 (m, 2H), 2.98 (s, 12H), 1.42 (s, 9H), 1.25 (t, J=7.1 Hz, 3H), 0.59 (s, 3H), 0.58 (s, 3H); $^{19}F$ NMR ($CDCl_3$, 376 MHz) δ −115.61 (d, J=21.9 Hz, 1F), −132.63 (d, J=20.6 Hz, 1F), −143.27 (t, J=21.3 Hz, 1F); Analytical HPLC: $t_R$=11.6 min, >99% purity (30-95% MeCN/$H_2O$, linear gradient, with constant 0.1% v/v TFA additive; 20 min run; 1 mL/min flow; ESI; positive ion mode; detection at 675 nm); HRMS (ESI) calcd for $C_{35}H_{40}F_3N_2O_6Si$ [M+H]$^+$ 669.2602, found 669.2610.

Example 86: 2-(3,7-Bis(dimethylamino)-5,5-dimethyldibenzo[b,e]silin-10-ylium-10(5H)-yl)-4-(2-ethoxy-2-oxoethyl)-3,5,6-trifluorobenzoate

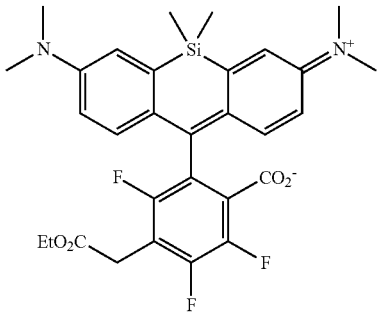

2-(3,7-Bis(dimethylamino)-5,5-dimethyldibenzo[b,e]silin-10-ylium-10(5H)-yl)-4-(1-(tert-butoxy)-3-ethoxy-1,3-dioxopropan-2-yl)-3,5,6-trifluorobenzoate (Example 85; 60 mg, 89.7 µmol) was taken up in CH$_2$Cl$_2$ (3 mL); triethylsilane (300 µL) was added, followed by trifluoroacetic acid (600 µL). The reaction was stirred at room temperature for 4 h. Toluene (3 mL) was added; the reaction mixture was concentrated to dryness and azeotroped with MeOH (3×). The resulting residue was diluted with saturated NaHCO$_3$ and extracted with EtOAc (2×). The combined organic extracts were washed with brine, dried over anhydrous MgSO$_4$, filtered, and concentrated in vacuo. Purification of the crude product by flash chromatography on silica gel (0-75% EtOAc/hexanes, linear gradient) afforded the title compound as a blue-green solid (49 mg, 96%). $^1$H NMR (CDCl$_3$, 400 MHz) δ 6.96 (d, J=2.9 Hz, 2H), 6.78 (dd, J=8.8, 1.5 Hz, 2H), 6.58 (dd, J=8.9, 2.9 Hz, 2H), 4.18 (q, J=7.2 Hz, 2H), 3.79 (s, 2H), 2.98 (s, 12H), 1.23 (t, J=7.1 Hz, 3H), 0.59 (s, 3H), 0.58 (s, 3H); $^{19}$F NMR (CDCl$_3$, 376 MHz) δ −119.21 (d, J=22.2 Hz, 1F), −134.27-−134.43 (m, 1F), −143.84 (t, J=21.4 Hz, 1F); Analytical HPLC: t$_R$=12.7 min, >99% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{30}$H$_{32}$F$_3$N$_2$O$_4$Si [M+H]$^+$ 569.2078, found 569.2085.

Example 87: 4-(1-(tert-Butoxy)-3-ethoxy-1,3-dioxopropan-2-yl)-2-(3,7-di(azetidin-1-yl)-5,5-dimethyldibenzo[b,e]silin-10-ylium-10(5H)-yl)-3,5,6-trifluorobenzoate

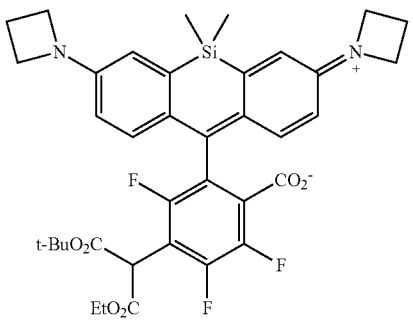

2-(3,7-Di(azetidin-1-yl)-5,5-dimethyldibenzo[b,e]silin-10-ylium-10(5H)-yl)-3,4,5,6-tetrafluorobenzoate (Grimm, J. B. et al. *ACS Cent. Sci.* 2017, 3, 975-985; 150 mg, 0.286 mmol) and tert-butyl ethyl malonate (65.0 µL, 0.343 mmol, 1.2 eq) were combined in DMF (3 mL), and K$_2$CO$_3$ (94.8 mg, 0.686 mmol, 2.4 eq) was added. After stirring the reaction at 50° C. for 18 h, it was cooled to room temperature, diluted with water, and extracted with EtOAc (2×). The combined organic extracts were washed with brine, dried over anhydrous MgSO$_4$, filtered, and evaporated. Purification of the crude by silica gel chromatography (0-50% EtOAc/hexanes, linear gradient) yielded 122 mg (62%) of the title compound as a blue-green solid. $^1$H NMR (CDCl$_3$, 400 MHz) δ 6.77-6.71 (m, 2H), 6.66 (d, J=2.6 Hz, 2H), 6.29-6.23 (m, 2H), 4.93 (s, 1H), 4.28-4.19 (m, 2H), 3.90 (t, J=7.2 Hz, 8H), 2.37 (p, J=7.2 Hz, 4H), 1.43 (s, 9H), 1.25 (t, J=7.1 Hz, 3H), 0.57 (s, 3H), 0.55 (s, 3H); $^{19}$F NMR (CDCl$_3$, 376 MHz) δ 115.07 (d, J=21.7 Hz, 1F), 132.59 (d, J=20.7 Hz, 1F), 143.13 (t, J=21.2 Hz, 1F); Analytical HPLC: t$_R$=12.1 min, >99% purity (30-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{37}$H$_{40}$F$_3$N$_2$O$_6$Si [M+H]$^+$ 693.2602, found 693.2608.

Example 88: 2-(3,7-Di(azetidin-1-yl)-5,5-dimethyldibenzo[b,e]silin-10-ylium-10(5H)-yl)-4-(2-ethoxy-2-oxoethyl)-3,5,6-trifluorobenzoate

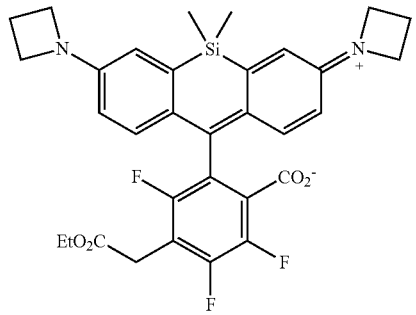

4-(1-(tert-Butoxy)-3-ethoxy-1,3-dioxopropan-2-yl)-2-(3,7-di(azetidin-1-yl)-5,5-dimethyldibenzo[b,e]silin-10-ylium-10(5H)-yl)-3,5,6-trifluorobenzoate (Example 87; 100 mg, 0.144 mmol) was taken up in CH$_2$Cl$_2$ (8 mL); triethylsilane (800 µL) was added, followed by trifluoroacetic acid (1.6 mL). The reaction was stirred at room temperature for 6 h. Toluene (10 mL) was added; the reaction mixture was concentrated to dryness and azeotroped with MeOH (3×). The resulting residue was diluted with saturated NaHCO$_3$ and extracted with EtOAc (2×). The combined organic extracts were washed with brine, dried over anhydrous MgSO$_4$, filtered, and concentrated in vacuo. Purification of the crude product by flash chromatography on silica gel (0-75% EtOAc/hexanes, linear gradient) afforded the title compound as a pale blue solid (41 mg, 48%). $^1$H NMR (CDCl$_3$, 400 MHz) δ 6.74 (dd, J=8.6, 1.6 Hz, 2H), 6.66 (d, J=2.6 Hz, 2H), 6.28 (dd, J=8.6, 2.6 Hz, 2H), 4.18 (q, J=7.1 Hz, 2H), 3.91 (t, J=7.3 Hz, 8H), 3.79 (s, 2H), 2.37 (p, J=7.2 Hz, 4H), 1.24 (t, J=7.1 Hz, 3H), 0.559 (s, 3H), 0.557 (s, 3H); $^{19}$F NMR (CDCl$_3$, 376 MHz) δ −118.80 (d, J=21.7 Hz, 1F), −134.18-−134.29 (m, 1F), −143.70 (t, J=21.4 Hz, 1F); Analytical HPLC: t$_R$=13.3 min, 97.8% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for $C_{32}H_{32}F_3N_2O_4Si$ [M+H]$^+$ 593.2078, found 593.2082.

Example 89: 4-(2-(tert-Butoxy)-1-cyano-2-oxoethyl)-2-(3,6-di(azetidin-1-yl)xanthylium-9-yl)-3,5,6-trifluorobenzoate

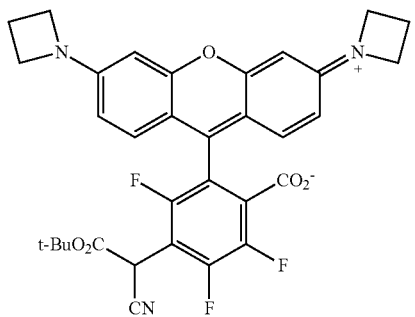

2-(3,6-Di(azetidin-1-yl)xanthylium-9-yl)-3,4,5,6-tetrafluorobenzoate (Grimm, J. B. et al. *ACS Cent. Sci.* 2017, 3, 975-985; 75 mg, 0.155 mmol) and tert-butyl cyanoacetate (26.7 μL, 0.187 mmol, 1.2 eq) were combined in DMF (2 mL), and $K_2CO_3$ (51.6 mg, 0.373 mmol, 2.4 eq) was added. After stirring the reaction at room temperature for 18 h, it was directly purified by reverse phase HPLC (30-60% MeCN/H$_2$O, linear gradient, with constant 0.1% v/v TFA additive). The pooled HPLC product fractions were partially concentrated to remove MeCN, diluted with saturated NaHCO$_3$, and extracted with CH$_2$Cl$_2$ (2×). The organic extracts were dried over anhydrous MgSO$_4$, filtered, and evaporated to yield 59 mg (63%) of the title compound as a dark red-purple solid. $^1$H NMR (CDCl$_3$, 400 MHz) δ 6.96 (d, J=8.7 Hz, 2H), 6.26 (dd, J=8.8, 2.3 Hz, 2H), 6.22 (d, J=2.2 Hz, 2H), 4.97 (s, 1H), 4.04 (t, J=7.4 Hz, 8H), 2.46 (p, J=7.4 Hz, 4H), 1.44 (s, 9H); $^{19}$F NMR (CDCl$_3$, 376 MHz) δ −120.49 (d, J=20.0 Hz, 1F), −131.85 (d, J=21.6 Hz, 1F), −141.12 (t, J=20.8 Hz, 1F); Analytical HPLC: $t_R$=12.2 min, >99% purity (10-95% MeCN/H$_2$O, linear gradient, with constant 0.1% v/v TFA additive; 20 min run; 1 mL/min flow; ESI; positive ion mode; detection at 575 nm); HRMS (ESI) calcd for $C_{33}H_{29}F_3N_3O_5$ [M+H]$^+$ 604.2054, found 604.2050.

Example 90: 4-(Cyanomethyl)-2-(3,6-di(azetidin-1-yl)xanthylium-9-yl)-3,5,6-trifluorobenzoate

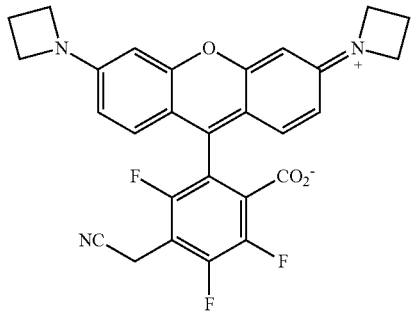

4-(2-(tert-Butoxy)-1-cyano-2-oxoethyl)-2-(3,6-di(azetidin-1-yl)xanthylium-9-yl)-3,5,6-trifluorobenzoate (Example 89; 40 mg, 66.3 μmol) was taken up in CH$_2$Cl$_2$ (2.5 mL); triethylsilane (250 μL) was added, followed by trifluoroacetic acid (500 μL). The reaction was stirred at room temperature for 6 h. Toluene (3 mL) was added; the reaction mixture was concentrated to dryness and azeotroped with MeOH (3×). The crude material was purified by reverse phase HPLC (10-75% MeCN/H$_2$O, linear gradient, with constant 0.1% v/v TFA additive) to provide the title compound as a dark red-purple solid (28.2 mg, 69%, TFA salt). $^1$H NMR (CD$_3$OD, 400 MHz) δ 7.26 (d, J=9.2 Hz, 2H), 6.67 (dd, J=9.2, 2.2 Hz, 2H), 6.53 (d, J=2.2 Hz, 2H), 4.34 (t, J=7.7 Hz, 8H), 4.12 (s, 2H), 2.57 (p, J=7.6 Hz, 4H); $^{19}$F NMR (CD$_3$OD, 376 MHz) δ −116.59 (dd, J=15.0, 2.3 Hz, 1F), −131.83 (dd, J=21.0, 2.8 Hz, 1F), −139.35 (dd, J=20.6, 15.3 Hz, 1F); Analytical HPLC: $t_R$=12.0 min, >99% purity (10-75% MeCN/H$_2$O, linear gradient, with constant 0.1% v/v TFA additive; 20 min run; 1 mL/min flow; ESI; positive ion mode; detection at 575 nm); HRMS (ESI) calcd for $C_{24}1_{21}F_3N_3O_3$ [M+H]$^+$ 504.1530, found 504.1538.

Example 91: 2-(3,7-Bis(dimethylamino)-5,5-dimethyldibenzo[b,e]silin-10-ylium-10(5H)-yl)-4-(2-(tert-butoxy)-1-cyano-2-oxoethyl)-3,5,6-trifluorobenzoate

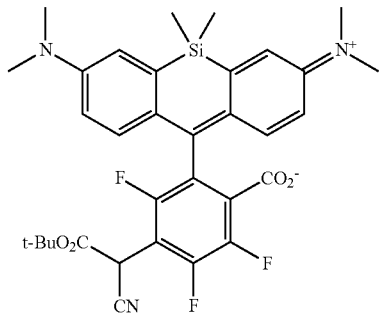

2-(3,7-Bis(dimethylamino)-5,5-dimethyldibenzo[b,e]silin-10-ylium-10(5H)-yl)-3,4,5,6-tetrafluorobenzoate (Grimm, J. B. et al. *ACS Cent. Sci.* 2017, 3, 975-985; 90 mg, 0.180 mmol) and tert-butyl cyanoacetate (30.8 μL, 0.216 mmol, 1.2 eq) were combined in DMF (2 mL), and K$_2$CO$_3$ (59.6 mg, 0.432 mmol, 2.4 eq) was added. After stirring the reaction at room temperature for 18 h, it was diluted with water and extracted with EtOAc (2×). The combined organic extracts were washed with brine, dried over anhydrous MgSO$_4$, filtered, and evaporated. Purification of the crude by silica gel chromatography (10-75% EtOAc/hexanes, linear gradient) yielded 95 mg (85%) of the title compound as a blue-green foam. $^1$H NMR (CDCl$_3$, 400 MHz) δ 6.97-6.93 (m, 2H), 6.77-6.71 (m, 2H), 6.61-6.55 (m, 2H), 5.03 (s, 1H), 2.99 (s, 6H), 2.99 (s, 6H), 1.46 (s, 9H), 0.59 (s, 3H), 0.57 (s, 3H); $^{19}$F NMR (CDCl$_3$, 376 MHz) δ 117.92 (d, J=22.3 Hz, 1F), 132.35 (d, J=20.4 Hz, 1F), 141.60 (dd, J=22.4, 20.4 Hz, 1F); Analytical HPLC: $t_R$=10.4 min, >99% purity (30-95% MeCN/H$_2$O, linear gradient, with constant 0.1% v/v TFA additive; 20 min run; 1 mL/min flow; ESI; positive ion mode; detection at 675 nm); HRMS (ESI) calcd for $C_{33}H_{35}F_3N_3O_4Si$ [M+H]$^+$ 622.2343, found 622.2345.

Example 92: 2-(3,7-Bis(dimethylamino)-5,5-dimethyldibenzo[b,e]silin-10-ylium-10(5H)-yl)-4-(cyanomethyl)-3,5,6-trifluorobenzoate

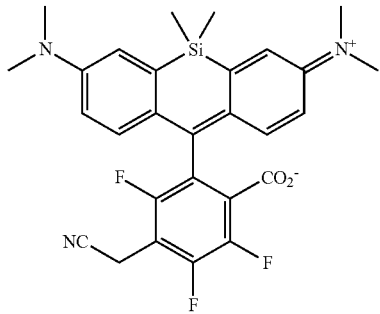

2-(3,7-Bis(dimethylamino)-5,5-dimethyldibenzo[b,e]silin-10-ylium-10(5H)-yl)-4-(2-(tert-butoxy)-1-cyano-2-oxoethyl)-3,5,6-trifluorobenzoate (Example 91; 60 mg, 96.5 μmol) was taken up in $CH_2Cl_2$ (3 mL); triethylsilane (300 μL) was added, followed by trifluoroacetic acid (500 μL). The reaction was stirred at room temperature for 5 h. Toluene (3 mL) was added; the reaction mixture was concentrated to dryness and azeotroped with MeOH (3×). The resulting residue was diluted with saturated $NaHCO_3$ and extracted with EtOAc (2×). The combined organic extracts were washed with brine, dried over anhydrous $MgSO_4$, filtered, and concentrated in vacuo. Purification of the crude product by flash chromatography on silica gel (0-75% EtOAc/toluene, linear gradient) afforded the title compound as a blue-green solid (46 mg, 91%). $^1$H NMR ($CDCl_3$, 400 MHz) δ 6.94 (d, J=2.9 Hz, 2H), 6.76 (dd, J=8.9, 0.8 Hz, 2H), 6.61 (dd, J=8.9, 2.9 Hz, 2H), 3.76 (s, 2H), 2.99 (s, 12H), 0.59 (s, 3H), 0.56 (s, 3H); $^{19}$F NMR ($CDCl_3$, 376 MHz) δ −119.66 (d, J=22.5 Hz, 1F), −133.13 (d, J=20.4 Hz, 1F), −141.88 (dd, J=22.6, 20.6 Hz, 1F); Analytical HPLC: $t_R$=11.6 min, >99% purity (10-95% MeCN/$H_2O$, linear gradient, with constant 0.1% v/v TFA additive; 20 min run; 1 mL/min flow; ESI; positive ion mode; detection at 675 nm); HRMS (ESI) calcd for $C_{28}H_{27}F_3N_3O_2Si$ [M+H]$^+$ 522.1819, found 522.1832.

Example 93: 4-(2-(tert-Butoxy)-1-cyano-2-oxoethyl)-2-(3,7-di(azetidin-1-yl)-5,5-dimethyldibenzo[b,e]silin-10-ylium-10(5H)-yl)-3,5,6-trifluorobenzoate

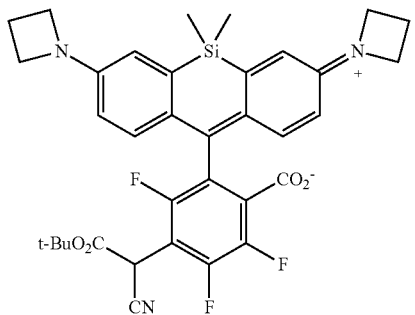

2-(3,7-Di(azetidin-1-yl)-5,5-dimethyldibenzo[b,e]silin-10-ylium-10(5H)-yl)-3,4,5,6-tetrafluorobenzoate (Grimm, J. B. et al. *ACS Cent. Sci.* 2017, 3, 975-985; 150 mg, 0.286 mmol) and tert-butyl cyanoacetate (49.0 μL, 0.343 mmol, 1.2 eq) were combined in DMF (3 mL), and $K_2CO_3$ (94.8 mg, 0.686 mmol, 2.4 eq) was added. After stirring the reaction at room temperature for 48 h, it was diluted with water and extracted with EtOAc (2×). The combined organic extracts were washed with brine, dried over anhydrous $MgSO_4$, filtered, and evaporated. Purification of the crude by silica gel chromatography (10-75% EtOAc/hexanes, linear gradient) yielded 155 mg (84%) of the title compound as a blue-green solid. $^1$H NMR ($CDCl_3$, 400 MHz) δ 6.73-6.67 (m, 2H), 6.67-6.63 (m, 2H), 6.29 (dd, J=8.7, 2.7 Hz, 2H), 5.03 (s, 1H), 3.92 (t, J=7.3 Hz, 8H), 2.44-2.33 (m, 4H), 1.46 (s, 9H), 0.56 (s, 3H), 0.55 (s, 3H); $^{19}$F NMR ($CDCl_3$, 376 MHz) δ −117.51 (d, J=22.4 Hz, 1F), +132.27 (d, J=20.5 Hz, 1F), −141.37−−141.55 (m, 1F); Analytical HPLC: $t_R$=10.9 min, 99.0% purity (30-95% MeCN/$H_2O$, linear gradient, with constant 0.1% v/v TFA additive; 20 min run; 1 mL/min flow; ESI; positive ion mode; detection at 675 nm); HRMS (ESI) calcd for $C_{35}H_{35}F_3N_3O_4Si$ [M+H]$^+$ 646.2343, found 646.2350.

Example 94: 4-(Cyanomethyl)-2-(3,7-di(azetidin-1-yl)-5,5-dimethyldibenzo[b,e]silin-10-ylium-10(5H)-yl)-3,5,6-trifluorobenzoate

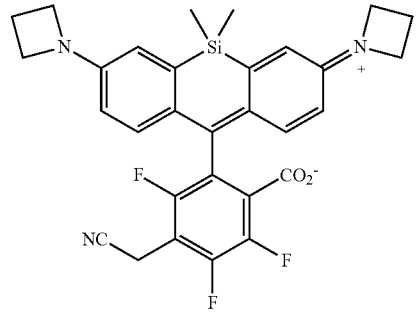

4-(2-(tert-Butoxy)-1-cyano-2-oxoethyl)-2-(3,7-di(azetidin-1-yl)-5,5-dimethyldibenzo[b,e]silin-10-ylium-10(5H)-yl)-3,5,6-trifluorobenzoate (Example 93; 120 mg, 0.186 mmol) was taken up in $CH_2Cl_2$ (9 mL); triethylsilane (900 μL) was added, followed by trifluoroacetic acid (1.8 mL). The reaction was stirred at room temperature for 6 h. Toluene (10 mL) was added; the reaction mixture was concentrated to dryness and azeotroped with MeOH (3×). The resulting residue was diluted with saturated $NaHCO_3$ and extracted with EtOAc (2×). The combined organic extracts were washed with brine, dried over anhydrous $MgSO_4$, filtered, and concentrated in vacuo. Purification of the crude product by flash chromatography on silica gel (0-75% EtOAc/toluene, linear gradient) afforded the title compound as a blue-green solid (58 mg, 57%). NMR ($CDCl_3$, 400 MHz) δ 6.72 (dd, J=8.6, 1.0 Hz, 2H), 6.64 (d, J=2.6 Hz, 2H), 6.31 (dd, J=8.7, 2.6 Hz, 2H), 3.92 (t, J=7.2 Hz, 8H), 3.77 (s, 2H), 2.38 (p, J=7.2 Hz, 4H), 0.55 (s, 3H), 0.54 (s, 3H); $^{19}$F NMR ($CDCl_3$, 376 MHz) δ −119.39 (d, J=22.6 Hz, 1F), −133.01 (d, J=20.4 Hz, 1F), −141.74 (dd, J=22.7, 20.4 Hz, 1F); Analytical HPLC: $t_R$=12.1 min, >99% purity (10-95% MeCN/$H_2O$, linear gradient, with constant 0.1% v/v TFA additive; 20 min run; 1 mL/min flow; ESI;

Example 95: 4-Amino-2-(3,7-di(azetidin-1-yl)-5,5-dimethyldibenzo[b,e]silin-10-ylium-10(5H)-yl)-3,5,6-trifluorobenzoate

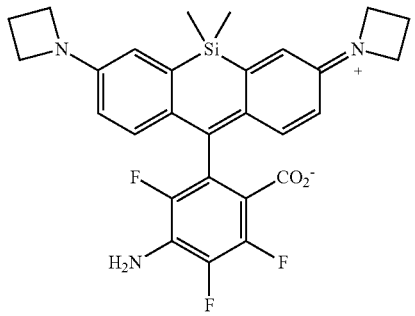

To a solution of 2-(3,7-di(azetidin-1-yl)-5,5-dimethyldibenzo[b,e]silin-10-ylium-10(5H)-yl)-3,4,5,6-tetrafluorobenzoate (Grimm, J. B. et al. *ACS Cent. Sci.* 2017, 3, 975-985; 100 mg, 0.191 mmol) in DMF (2.5 mL) was added NH$_3$ in dioxane (0.5 M, 2.29 mL, 1.14 mmol, 6 eq). After stirring the sealed reaction at room temperature for 72 h, it was concentrated in vacuo and purified by flash chromatography on silica gel (0-75% EtOAc/hexanes, linear gradient) to provide 78 mg (78%) of the title compound as a pale blue solid. $^1$H NMR (CDCl$_3$, 400 MHz) δ 6.84 (dd, J=8.6, 0.8 Hz, 2H), 6.64 (d, J=2.6 Hz, 2H), 6.31 (dd, J=8.6, 2.6 Hz, 2H), 4.36 (s, 2H), 3.91 (t, J=7.2 Hz, 8H), 2.37 (p, J=7.3 Hz, 4H), 0.54 (s, 3H), 0.53 (s, 3H); $^{19}$F NMR (CDCl$_3$, 376 MHz) δ -140.63 (dd, J=18.1, 11.5 Hz, 1F), -143.85 (dd, J=20.3, 18.1 Hz, 1F), -154.70 (dd, J=20.3, 11.6 Hz, 1F); Analytical HPLC: $t_R$=12.3 min, >99% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{28}$H$_{27}$F$_3$N$_3$O$_2$Si [M+H]$^+$ 522.1819, found 522.1828.

Example 96: 2-(3,7-Di(azetidin-1-yl)-5,5-dimethyldibenzo[b,e]silin-10-ylium-10(5H)-yl)-3,5,6-trifluoro-4-morpholinobenzoate

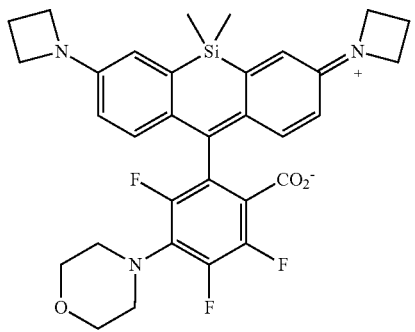

2-(3,7-Di(azetidin-1-yl)-5,5-dimethyldibenzo[b,e]silin-10-ylium-10(5H)-yl)-3,4,5,6-tetrafluorobenzoate (Grimm, J. B. et al. *ACS Cent. Sci.* 2017, 3, 975-985; 100 mg, 0.191 mmol) was dissolved in DMF (2 mL); DIEA (99.6 µL, 0.572 mmol, 3 eq) and morpholine (33.3 µL, 0.381 mmol, 2 eq) were added, and the reaction was stirred at room temperature for 4 h. It was then concentrated to dryness and purified by reverse phase HPLC (10-75% MeCN/H$_2$O, linear gradient, with constant 0.1% v/v TFA additive). The pooled product fractions were partially concentrated to remove MeCN, diluted with saturated NaHCO$_3$, and extracted with CH$_2$Cl$_2$ (2×). The organic extracts were dried over anhydrous MgSO$_4$, filtered, and evaporated to provide the title compound (83 mg, 73%) as a blue-green solid. $^1$H NMR (CDCl$_3$, 400 MHz) δ 6.79 (dd, J=8.7, 0.9 Hz, 2H), 6.63 (d, J=2.6 Hz, 2H), 6.32 (dd, J=8.7, 2.7 Hz, 2H), 3.91 (t, J=7.3 Hz, 8H), 3.78-3.73 (m, 4H), 3.34-3.28 (m, 4H), 2.38 (p, J=7.3 Hz, 4H), 0.54 (s, 3H), 0.53 (s, 3H); $^{19}$F NMR (CDCl$_3$, 376 MHz) δ -128.54 (dd, J=18.6, 7.7 Hz, 1F), -142.49 (t, J=19.1 Hz, 1F), -143.24 (dd, J=19.9, 7.8 Hz, 1F); Analytical HPLC: $t_R$=13.1 min, >99% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{32}$H$_{33}$F$_3$N$_3$O$_3$Si [M+H]$^+$ 592.2238, found 592.2239.

Example 97: 2-(3,7-Di(azetidin-1-yl)-5,5-dimethyldibenzo[b,e]silin-10-ylium-10(5H)-yl)-3,5,6-trifluoro-4-(hydroxyamino)benzoate

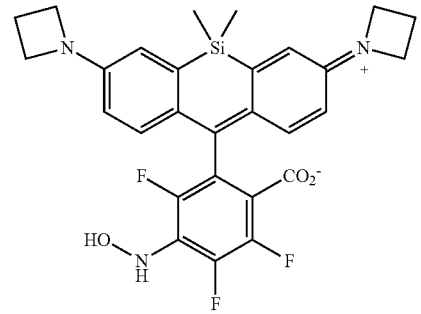

2-(3,7-Di(azetidin-1-yl)-5,5-dimethyldibenzo[b,e]silin-10-ylium-10(5H)-yl)-3,4,5,6-tetrafluorobenzoate (Grimm, J. B. et al. *ACS Cent. Sci.* 2017, 3, 975-985; 100 mg, 0.191 mmol) was dissolved in DMF (2 mL); DIEA (99.6 µL, 0.572 mmol, 3 eq) and hydroxylamine hydrochloride (14.6 mg, 0.210 mmol, 1.1 eq) were added, and the reaction was stirred at room temperature for 4 h. It was then concentrated to dryness and purified by flash chromatography on silica gel (0-50% EtOAc/toluene, linear gradient) to provide 52 mg (51%) of the title compound as a blue solid. $^1$H NMR (CDCl$_3$, 400 MHz) δ 6.98 (s, 1H), 6.79 (dd, J=8.6, 1.0 Hz, 2H), 6.64 (d, J=2.7 Hz, 2H), 6.31 (dd, J=8.6, 2.6 Hz, 2H), 5.87 (s, 1H), 3.91 (t, J=7.2 Hz, 8H), 2.37 (p, J=7.2 Hz, 4H), 0.55 (s, 3H), 0.54 (s, 3H); $^{19}$F NMR (CDCl$_3$, 376 MHz, $^1$H decoupled) δ -132.16 (dd, J=19.5, 6.9 Hz, 1F), -142.58 (t, J=20.1 Hz, 1F), -145.42 (dd, J=20.5, 6.9 Hz, 1F); Analytical HPLC: $t_R$=10.0 min, 96.8% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{28}$H$_{27}$F$_3$N$_3$O$_3$Si [M+H]$^+$ 538.1768, found 538.1779.

Example 98: 4-(1,4,7,10,13-Pentaoxa-16-azacyclooctadecan-16-yl)-2-(3,7-di(azetidin-1-yl)-5,5-dimethyldibenzo[b,e]silin-10-ylium-10(5H)-yl)-3,5,6-trifluorobenzoate

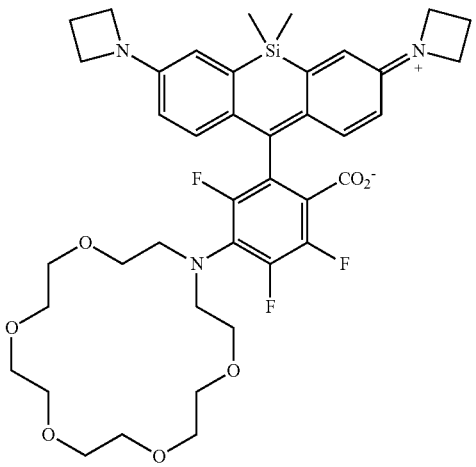

2-(3,7-Di(azetidin-1-yl)-5,5-dimethyldibenzo[b,e]silin-10-ylium-10(5H)-yl)-3,4,5,6-tetrafluorobenzoate (Grimm, J. B. et al. *ACS Cent. Sci.* 2017, 3, 975-985; 100 mg, 0.191 mmol) and 1-aza-18-crown-6 (100 mg, 0.381 mmol, 2 eq) were combined in DMF (2 mL). After adding DIEA (99.6 µL, 0.572 mmol, 3 eq), the reaction was stirred at 50° C. for 72 h. The crude reaction mixture was directly purified by reverse phase HPLC (30-50% MeCN/H$_2$O, linear gradient, with constant 0.1% v/v TFA additive). The pooled product fractions were partially concentrated to remove MeCN, diluted with saturated NaHCO$_3$, and extracted with CH$_2$Cl$_2$ (2×). The organic extracts were dried over anhydrous MgSO$_4$, filtered, and evaporated to provide 54.0 mg (37%) of the title compound as a light blue solid. $^1$H NMR (CDCl$_3$, 400 MHz) δ 6.79 (dd, J=8.6, 0.9 Hz, 2H), 6.64 (d, J=2.6 Hz, 2H), 6.28 (dd, J=8.6, 2.6 Hz, 2H), 3.91 (t, J=7.3 Hz, 8H), 3.70 (t, J=5.5 Hz, 4H), 3.68-3.52 (m, 20H), 2.37 (p, J=7.2 Hz, 4H), 0.54 (s, 3H), 0.54 (s, 3H); $^{19}$F NMR (CDCl$_3$, 376 MHz) δ −126.05 (dd, J=18.0, 8.1 Hz, 1F), −141.75 (dd, J=20.1, 8.1 Hz, 1F), −142.95 (dd, J=19.9, 18.2 Hz, 1F); Analytical HPLC: t$_R$=12.9 min, >99% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{40}$H$_{49}$F$_3$N$_3$O$_7$Si [M+H]$^+$ 768.3286, found 768.3298.

Example 99: 4-((2-(Bis(pyridin-2-ylmethyl)amino)ethyl)(pyridin-2-ylmethyl)amino)-2-(3,7-di(azetidin-1-yl)-5,5-dimethyldibenzo[b,e]silin-10-ylium-10(5H)-yl)-3,5,6-trifluorobenzoate

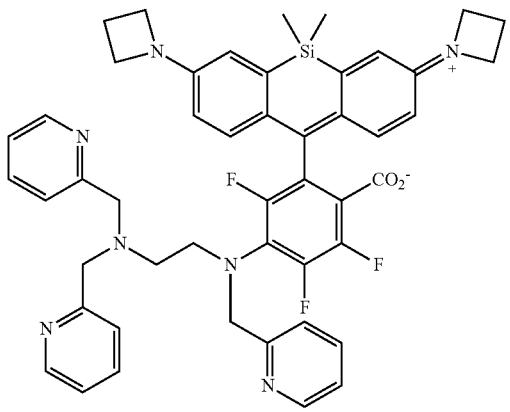

2-(3,7-Di(azetidin-1-yl)-5,5-dimethyldibenzo[b,e]silin-10-ylium-10(5H)-yl)-3,4,5,6-tetrafluorobenzoate (Grimm, J. B. et al. *ACS Cent. Sci.* 2017, 3, 975-985; 75 mg, 0.143 mmol) and N$^1$,N$^1$,N$^2$-tris(pyridin-2-ylmethyl)ethane-1,2-diamine (Que, E. L. et al. *Nat. Chem.* 2015, 7, 130-139; Hureau, C. et al. *Inorg. Chem.* 2008, 47, 9238-9247; 95.3 mg, 0.286 mmol, 2 eq) were combined in DMF (2 mL). After adding DIEA (74.7 µL, 0.429 mmol, 3 eq), the reaction was stirred at 50° C. for 96 h. The reaction mixture was concentrated to dryness and purified by reverse phase HPLC (10-75% MeCN/H$_2$O, linear gradient, with constant 0.1% v/v TFA additive). The pooled product fractions were partially concentrated to remove MeCN, diluted with saturated NaHCO$_3$, and extracted with CH$_2$Cl$_2$ (2×). The organic extracts were dried over anhydrous MgSO$_4$, filtered, and evaporated to provide 55.6 mg (46%) of the title compound as a purple solid. $^1$H NMR (CD$_3$OD, 400 MHz) δ 8.41-8.36 (m, 3H), 7.72-7.64 (m, 3H), 7.45 (dt, J=7.9, 1.1 Hz, 2H), 7.29-7.24 (m, 2H), 7.23 (ddd, J=7.5, 4.9, 1.2 Hz, 2H), 6.70 (d, J=2.6 Hz, 2H), 6.54 (dd, J=8.7, 1.0 Hz, 2H), 6.23 (dd, J=8.7, 2.7 Hz, 2H), 4.49 (s, 2H), 3.89 (t, J=7.3 Hz, 8H), 3.75 (s, 4H), 3.46 (t, J=6.3 Hz, 2H), 2.76 (t, J=6.2 Hz, 2H), 2.38 (p, J=7.2 Hz, 4H), 0.53 (s, 3H), 0.46 (s, 3H); $^{19}$F NMR (CD$_3$OD, 376 MHz) δ −123.75 (dd, J=17.9, 7.1 Hz, 1F), −139.44 (dd, J=19.5, 7.3 Hz, 1F), −143.27 (t, J=18.8 Hz, 1F); Analytical HPLC: t$_R$=9.4 min, 97.7% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{48}$H$_{47}$F$_3$N$_7$O$_2$Si [M+H]$^+$ 838.3507, found 838.3526.

Example 100: 4-Azido-2-(3,6-di(azetidin-1-yl)xanthylium-9-yl)-3,5,6-trifluorobenzoate

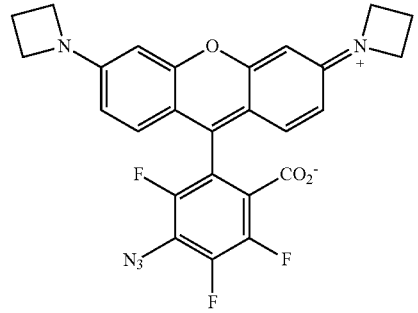

To a solution of 2-(3,6-di(azetidin-1-yl)xanthylium-9-yl)-3,4,5,6-tetrafluorobenzoate (Grimm, J. B. et al. *ACS Cent. Sci.* 2017, 3, 975-985; 20 mg, 41.5 µmol) in DMSO (1 mL) was added NaN$_3$ (3.0 mg, 45.6 µmol, 1.1 eq). After stirring the reaction at room temperature for 2 h, it was directly purified by reverse phase HPLC (30-60% MeCN/H$_2$O, linear gradient, with constant 0.1% v/v TFA additive) to provide 17.0 mg (66%, TFA salt) of the title compound as a dark red-purple solid. $^1$H NMR (CD$_3$OD, 400 MHz) δ 7.29 (d, J=9.2 Hz, 2H), 6.67 (dd, J=9.2, 2.2 Hz, 2H), 6.54 (d, J=2.2 Hz, 2H), 4.34 (t, J=7.6 Hz, 8H), 2.57 (p, J=7.7 Hz, 4H); $^{19}$F NMR (CD$_3$OD, 376 MHz) δ −126.37 (dd, J=12.6, 6.2 Hz, 1F), −137.79 (dd, J=19.6, 12.6 Hz, 1F), −142.08 (dd, J=20.0, 6.3 Hz, 1F); Analytical HPLC: t$_R$=11.7 min, >99% purity (10-95% MeCN/H$_2$O, linear gradient, with constant 0.1% v/v TFA additive; 20 min run; 1 mL/min flow; ESI; positive ion mode; detection at 575 nm); HRMS (ESI) calcd for C$_{26}$H$_{19}$F$_3$N$_5$O$_3$ [M+H]$^+$ 506.1435, found 506.1439.

Example 101: 4-Azido-2-(3,7-bis(dimethylamino)-5,5-dimethyldibenzo[b,e]silin-10-ylium-10(5H)-yl)-3,5,6-trifluorobenzoate

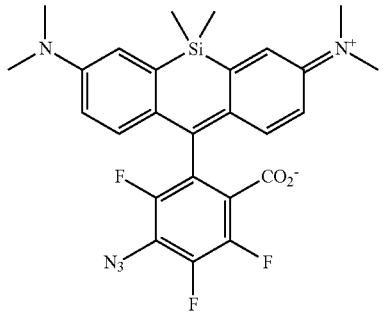

To a solution of 2-(3,7-bis(dimethylamino)-5,5-dimethyldibenzo[b,e]silin-10-ylium-10(5H)-yl)-3,4,5,6-tetrafluorobenzoate (Grimm, J. B. et al. *ACS Cent. Sci.* 2017, 3, 975-985; 100 mg, 0.200 mmol) in DMSO (2 mL) was added NaN$_3$ (14.3 mg, 0.220 mmol, 1.1 eq). After stirring the reaction at room temperature for 1 h, it was diluted with water and extracted with EtOAc (2×). The combined organic extracts were washed with brine, dried over anhydrous MgSO$_4$, filtered, and evaporated. Silica gel chromatography (0-50% EtOAc/hexanes, linear gradient) afforded the title compound as a blue-green solid (94 mg, 90%). $^1$H NMR (CDCl$_3$, 400 MHz) δ 6.93 (d, J=2.9 Hz, 2H), 6.82 (dd, J=8.9, 0.8 Hz, 2H), 6.62 (dd, J=8.9, 2.9 Hz, 2H), 2.99 (s, 12H), 0.58 (s, 3H), 0.55 (s, 3H); $^{19}$F NMR (CDCl$_3$, 376 MHz) δ −129.60 (dd, J=20.3, 4.7 Hz, 1F), −141.41 (t, J=19.8 Hz, 1F), −142.94 (dd, J=19.7, 4.7 Hz, 1F); Analytical HPLC: t$_R$=13.2 min, 98.1% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{26}$H$_{25}$F$_3$N$_5$O$_2$Si [M+H]$^+$ 524.1724, found 524.1731.

Example 102: 4-Azido-2-(3,7-di(azetidin-1-yl)-5,5-dimethyldibenzo[b,e]silin-10-ylium-10(5H)-yl)-3,5,6-trifluorobenzoate

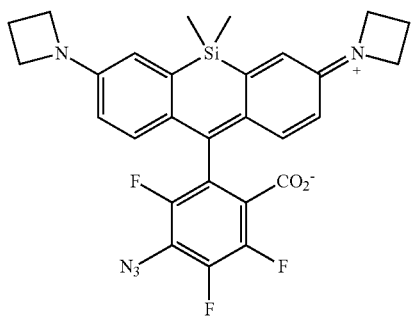

To a solution of 2-(3,7-di(azetidin-1-yl)-5,5-dimethyldibenzo[b,e]silin-10-ylium-10(5H)-yl)-3,4,5,6-tetrafluorobenzoate (Grimm, J. B. et al. *ACS Cent. Sci.* 2017, 3, 975-985; 200 mg, 0.381 mmol) in DMSO (4 mL) was added NaN$_3$ (24.8 mg, 0.381 mmol, 1 eq). After stirring the reaction at room temperature for 2 h, it was diluted with water and extracted with EtOAc (2×). The combined organic extracts were washed with water and brine, dried over anhydrous MgSO$_4$, filtered, and evaporated. Silica gel chromatography (0-50% EtOAc/hexanes, linear gradient) afforded the title compound as a blue-green solid (186 mg, 89%). $^1$H NMR (CDCl$_3$, 400 MHz) δ 6.77 (dd, J=8.7, 0.8 Hz, 2H), 6.63 (d, J=2.6 Hz, 2H), 6.32 (dd, J=8.7, 2.7 Hz, 2H), 3.92 (t, J=7.3 Hz, 8H), 2.38 (p, J=7.2 Hz, 4H), 0.54 (s, 3H), 0.52 (s, 3H); $^{19}$F NMR (CDCl$_3$, 376 MHz) δ 129.29 (dd, J=19.8, 4.7 Hz, 1F), 141.30 (t, J=19.8 Hz, 1F), 142.83 (dd, J=19.6, 4.8 Hz, 1F); Analytical HPLC: t$_R$=13.8 min, >99% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{28}$H$_{25}$F$_3$N$_5$O$_2$Si [M+H]$^+$ 548.1724, found 548.1722.

Example 103: 4-Azido-2-(3,7-di(azepan-1-yl)-5,5-dimethyldibenzo[b,e]silin-10-ylium-10(5H)-yl)-3,5,6-trifluorobenzoate

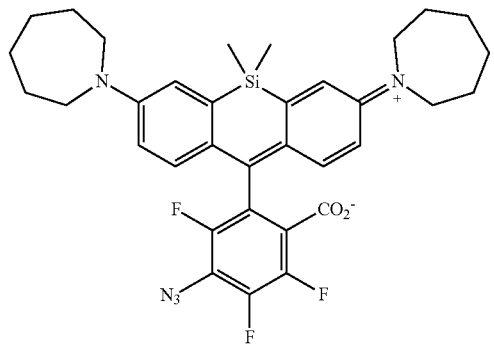

To a solution of 2-(3,7-di(azepan-1-yl)-5,5-dimethyldibenzo[b,e]silin-10-ylium-10(5H)-yl)-3,4,5,6-tetrafluorobenzoate (Grimm, J. B. et al. *ACS Cent. Sci.* 2017, 3, 975-985; 30 mg, 49.3 μmol) in DMSO (1.5 mL) was added NaN$_3$ (3.2 mg, 49.3 μmol, 1 eq). After stirring the reaction at room temperature for 2 h, it was diluted with water and extracted with EtOAc (2×). The combined organic extracts were washed with brine, dried over anhydrous MgSO$_4$, filtered, and evaporated. Silica gel chromatography (0-40% EtOAc/hexanes, linear gradient) afforded the title compound as a green solid (28.3 mg, 91%). $^1$H NMR (CDCl$_3$, 400 MHz) δ 6.90 (d, J=2.9 Hz, 2H), 6.75 (dd, J=8.9, 0.7 Hz, 2H), 6.57 (dd, J=9.0, 2.9 Hz, 2H), 3.50-3.43 (m, 8H), 1.85-1.72 (m, 8H), 1.55-1.50 (m, 8H), 0.56 (s, 3H), 0.54 (s, 3H); $^{19}$F NMR (CDCl$_3$, 376 MHz) δ −129.01 (dd, J=19.7, 4.5 Hz, 1F), −141.65 (t, J=19.8 Hz, 1F), −143.12 (dd, J=19.8, 4.6 Hz, 1F); Analytical HPLC: t$_R$=12.9 min, 97.5% purity (30-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{34}$H$_{37}$F$_3$N$_5$O$_2$Si [M+H]$^+$ 632.2663, found 632.2674.

Example 104: 4-Cyano-2-(3,6-di(azetidin-1-yl)xanthylium-9-yl)-3,5,6-trifluorobenzoate

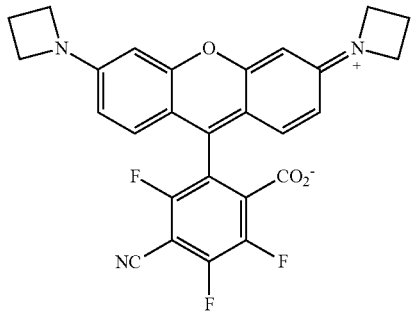

To a solution of 2-(3,6-di(azetidin-1-yl)xanthylium-9-yl)-3,4,5,6-tetrafluorobenzoate (Grimm, J. B. et al. *ACS Cent. Sci.* 2017, 3, 975-985; 75 mg, 0.155 mmol) in DMSO (1.5 mL) was added NaCN (11.4 mg, 0.233 mmol, 1.5 eq). After stirring the reaction at room temperature for 18 h, it was directly purified by reverse phase HPLC (30-50% MeCN/H$_2$O, linear gradient, with constant 0.1% v/v TFA additive) to provide 16.1 mg (17%, TFA salt) of the title compound as a dark red solid. $^1$H NMR (CD$_3$OD, 400 MHz) δ 7.29 (d, J=9.2 Hz, 2H), 6.67 (dd, J=9.2, 2.2 Hz, 2H), 6.52 (d, J=2.2 Hz, 2H), 4.34 (t, J=7.6 Hz, 8H), 2.57 (p, J=7.7 Hz, 4H); $^{19}$F NMR (CD$_3$OD, 376 MHz) δ −109.22 (d, J=14.9 Hz, 1F), −123.89 (d, J=21.3 Hz, 1F), −139.51 (dd, J=21.2, 15.0 Hz, 1F); Analytical HPLC: t$_R$=11.6 min, 99.0% purity (10-95% MeCN/H$_2$O, linear gradient, with constant 0.1% v/v TFA additive; 20 min run; 1 mL/min flow; ESI; positive ion mode; detection at 575 nm); HRMS (ESI) calcd for C$_{27}$H$_{19}$F$_3$N$_3$O$_3$ [M+H]$^+$ 490.1373, found 490.1376.

Example 105: 2-(3,7-Bis(dimethylamino)-5,5-dimethyldibenzo[b,e]silin-10-ylium-10(5H)-yl)-4-cyano-3,5,6-trifluorobenzoate

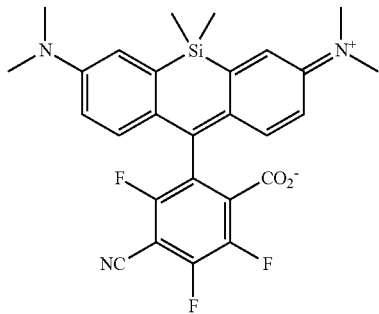

To a solution of 2-(3,7-bis(dimethylamino)-5,5-dimethyldibenzo[b,e]silin-10-ylium-10(5H)-yl)-3,4,5,6-tetrafluorobenzoate (Grimm, J. B. et al. *ACS Cent. Sci.* 2017, 3, 975-985; 100 mg, 0.200 mmol) in DMSO (2 mL) was added NaCN (14.7 mg, 0.300 mmol, 1.5 eq). After stirring the reaction at room temperature for 4 h, it was diluted with water and extracted with EtOAc (2×). The combined organic extracts were washed with brine, dried over anhydrous MgSO$_4$, filtered, and evaporated. Silica gel chromatography (25-100% EtOAc/hexanes, linear gradient) afforded the title compound as a dark green solid (17.0 mg, 17%). $^1$H NMR (CDCl$_3$, 400 MHz) δ 6.94 (d, J=2.8 Hz, 2H), 6.74 (dd, J=8.9, 0.8 Hz, 2H), 6.61 (dd, J=8.9, 2.9 Hz, 2H), 3.00 (s, 12H), 0.59 (s, 3H), 0.55 (s, 3H); $^{19}$F NMR (CDCl$_3$, 376 MHz, $^1$H decoupled) δ −109.43 (d, J=22.8, 2.2 Hz, 1F), −124.68 (dd, J=20.1, 2.2 Hz, 1F), −140.75 (dd, J=22.7, 20.1 Hz, 1F); Analytical HPLC: t$_R$=12.0 min, 98.7% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{27}$H$_{25}$F$_3$N$_3$O$_2$Si [M+H]$^+$ 508.1663, found 508.1667.

Example 106: 4-Cyano-2-(3,7-di(azetidin-1-yl)-5,5-dimethyldibenzo[b,e]silin-10-ylium-10(5H)-yl)-3,5,6-trifluorobenzoate

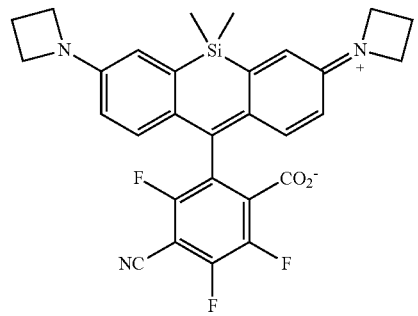

To a solution of 2-(3,7-di(azetidin-1-yl)-5,5-dimethyldibenzo[b,e]silin-10-ylium-10(5H)-yl)-3,4,5,6-tetrafluorobenzoate (Grimm, J. B. et al. *ACS Cent. Sci.* 2017, 3, 975-985; 200 mg, 0.381 mmol) in DMSO (4 mL) was added NaCN (28.0 mg, 0.572 mmol, 1.5 eq). After stirring the reaction at room temperature for 2 h, it was diluted with water and extracted with EtOAc (2×). The combined organic extracts were washed with brine, dried over anhydrous MgSO$_4$, filtered, and evaporated. Silica gel chromatography (25-100% EtOAc/hexanes, linear gradient) afforded the title compound as a dark green solid (40.2 mg, 20%). $^1$H NMR (CDCl$_3$, 400 MHz) δ 6.69 (dd, J=8.7, 0.8 Hz, 2H), 6.63 (d, J=2.7 Hz, 2H), 6.31 (dd, J=8.7, 2.6 Hz, 2H), 3.93 (t, J=7.3 Hz, 8H), 2.39 (p, J=7.2 Hz, 4H), 0.56 (s, 3H), 0.53 (s, 3H); $^{19}$F NMR (CDCl$_3$, 376 MHz, $^1$H decoupled) δ −109.23 (dd, J=22.6, 2.2 Hz, 1F), −124.52 (dd, J=20.0, 2.1 Hz, 1F), −140.61 (dd, J=22.7, 20.1 Hz, 1F); Analytical HPLC: t$_R$=12.5 min, 98.9% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{29}$H$_{25}$F$_3$N$_3$O$_2$Si [M+H]$^+$ 532.1663, found 532.1667.

Example 107: 2-(3-(Azetidin-1-ium-1-ylidene)-7-(azetidin-1-yl)-5,5-dimethyl-3,5-dihydrodibenzo[b,e]silin-10-yl)-3,5,6-trifluoro-4-(5aR,6S,6aS)-6-(hydroxymethyl)-5,5a,6,6a,7,8-hexahydrocyclopropa[5,6]cycloocta[1,2-d][1,2,3]triazol-1(4H)-yl)benzoate-and-2-(3-(azetidin-1-ium-1-ylidene)-7-(azetidin-1-yl)-5,5-dimethyl-3,5-dihydrodibenzo[b,e]silin-10-yl)-3,5,6-trifluoro-4-((5aS,6R,6aR)-6-(hydroxymethyl)-5,5a,6,6a,7,8-hexahydrocyclopropa[5,6]cycloocta[1,2-d][1,2,3]triazol-1(4H)-yl)benzoate

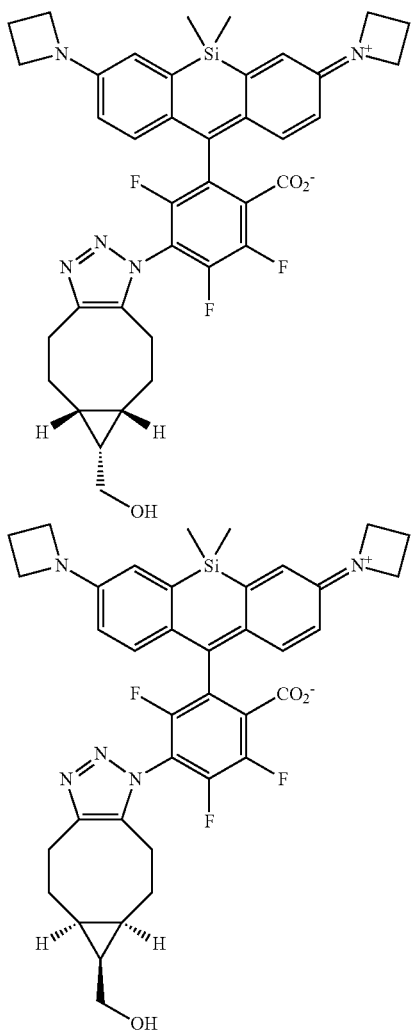

4-Azido-2-(3,7-di(azetidin-1-yl)-5,5-dimethyldibenzo[b,e]silin-10-ylium-10(5H)-yl)-3,5,6-trifluorobenzoate (Example 102; 40 mg, 73.0 μmol) and (1R,8S,9s)-bicyclo[6.1.0]non-4-yn-9-ylmethanol (14.3 mg, 95.0 μmol, 1.3 eq) were combined in DMF (1.5 mL) and stirred at room temperature for 1 h. The reaction was concentrated to dryness and purified by flash chromatography on silica gel (25-100% EtOAc/CH$_2$Cl$_2$, linear gradient) to afford the title mixture as a dark blue-green solid (48.2 mg, 95%). $^1$H NMR (DMSO-d$_6$, 400 MHz, 350 K) δ 6.87 (d, J=8.6 Hz, 2H), 6.71 (d, J=2.6 Hz, 2H), 6.38-6.32 (m, 2H), 4.04-3.99 (m, 1H), 3.89 (t, J=7.3 Hz, 8H), 3.56-3.43 (m, 2H), 3.14-3.07 (m, 1H), 2.93-2.77 (m, 2H), 2.69-2.55 (m, 1H), 2.34 (p, J=7.2 Hz, 4H), 2.19-2.09 (m, 1H), 2.07-1.98 (m, 1H), 1.64-1.49 (m, 2H), 1.07-0.96 (m, 1H), 0.94-0.75 (m, 2H), 0.54 (s, 3H), 0.48 (s, 3H); $^{19}$F NMR (DMSO-d$_6$, 376 MHz, 350 K) δ −124.27 (d, J=20.8 Hz, 1F), −137.21 (d, J=22.1 Hz, 1F), −140.63 (t, J=21.3 Hz, 1F); Analytical HPLC: t$_R$=11.7 min, >99% purity (10-95% MeCN/H$_2$O, linear gradient, with constant 0.1% v/v TFA additive; 20 min run; 1 mL/min flow; ESI; positive ion mode; detection at 675 nm); HRMS (ESI) calcd for C$_{38}$H$_{39}$F$_3$N$_5$O$_3$Si [M+H]$^+$ 698.2769, found 698.2779.

Example 108: 2-(3-(Azetidin-1-ium-1-ylidene)-7-(azetidin-1-yl)-5,5-dimethyl-3,5-dihydrodibenzo[b,e]silin-10-yl)-4-(8-(3-((tert-butoxycarbonyl)amino)propanoyl)-8,9-dihydro-1H-dibenzo[b,f][1,2,3]triazolo[4,5-d]azocin-1-yl)-3,5,6-trifluorobenzoate-and-2-(3-(azetidin-1-ium-1-ylidene)-7-(azetidin-1-yl)-5,5-dimethyl-3,5-dihydrodibenzo[b,e]silin-10-yl)-4-(8-(3-((tert-butoxycarbonyl)amino)propanoyl)-8,9-dihydro-3H-dibenzo[b,f][1,2,3]triazolo[4,5-d]azocin-3-yl)-3,5,6-trifluorobenzoate

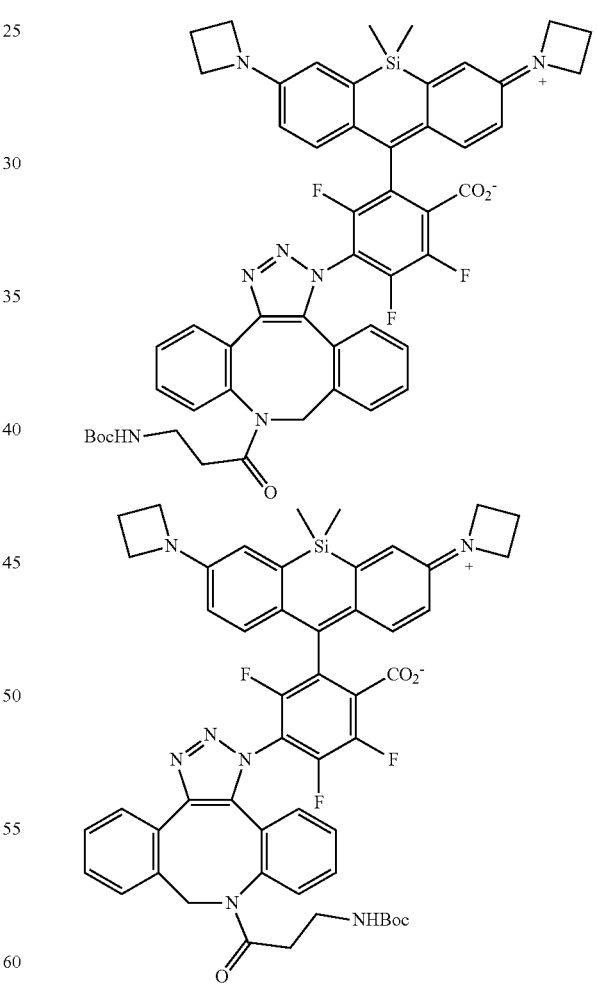

4-Azido-2-(3,7-di(azetidin-1-yl)-5,5-dimethyldibenzo[b,e]silin-10-ylium-10(5H)-yl)-3,5,6-trifluorobenzoate (Example 102; 30 mg, 54.8 μmol) and DBCO—NH—Boc (24.8 mg, 65.7 μmol, 1.2 eq) were combined in DMF (1 mL) and stirred at room temperature for 1 h. The reaction was concentrated to dryness and purified by flash chromatography on silica gel (25-100% EtOAc/hexanes, linear gradient) to provide the title mixture of regioisomers (pale green solid, 50.1 mg, 99%). Although the NMR spectra were not interpretable, HPLC and HRMS analyses were consistent with the expected product mixture. Analytical HPLC: $t_R$ (major isomer)=11.5 min, 60.3% by peak integration; $t_R$ (minor isomer)=11.9 min, 39.7% by peak integration (45-55% MeCN/$H_2O$, linear gradient, with constant 0.1% v/v TFA additive; 20 min run; 1 mL/min flow; ESI; positive ion mode; detection at 675 nm); HRMS (ESI) calcd for $C_{51}H_{49}F_3N_7O_5Si$ [M+H]$^+$ 924.3511, found 924.3531.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Lavis, L. D., *Biochemistry* 56, 5165-5170 (2017).
2. Abdelfattah, A. S., Kawashima, T., Singh, A. et al., *Science* 365, 699-704 (2019).
3. Grimm, J. B., English, B. P., Chen, J. et al., *Nat. Methods* 12, 244-250 (2015).
4. Grimm, J. B., Muthusamy, A. K., Liang, Y. et al., *Nat. Methods* 14, 987-994 (2017).
5. Grimm, J. B., Brown, T. A., Tkachuk, A. N. et al., *ACS Cent. Sci.* 3, 975-985 (2017).
6. Zheng, Q., Ayala, A. X., Chung, I. et al., *ACS Cent. Sci.*, 10.1021/acscentsci.1029b00676 (2019).
7. Panchuk-Voloshina, N., Haugland, R. P., Bishop-Stewart, J. et al., *J. Histochem. Cytochem.* 47, 1179-1188 (1999).
8. Lukinavičius, G., Umezawa, K., Olivier, N. et al., *Nature Chem.* 5, 132-139 (2013).
9. Ioffe, I. S. and Zelenin, K. N., *Zh. Obshch. Khim.* 34, 2811 (1964).
10. Van Duuren, B. L., Goldschmidt, B. M., and Seltzman, H. H., *Journal of the Chemical Society B: Physical Organic,* 814-819 (1967).
11. Liu, J., Sun, Y. Q., Zhang, H. et al., *ACS Appl. Mater. Interfaces* 8, 22953-22962 (2016).
12. Gannon, M. K., 2nd, Holt, J. J., Bennett, S. M. et al., *J. Med. Chem.* 52, 3328-3341 (2009).
13. Zhou, X., Lai, R., Beck, J. R. et al., *Chem. Commun. (Camb)* 52, 12290-12293 (2016).
14. Grzybowski, M., Taki, M., Senda, K. et al., *Angew. Chem. Int. Ed.* 57, 10137-10141 (2018).
15. Los, G. V., Encell, L. P., Mcdougall, M. G. et al., *ACS Chem. Biol.* 3, 373-382 (2008).
16. Liu, J., Diwu, Z., Leung, W.-Y. et al., *Tetrahedron Lett.* 44, 4355-4359 (2003).
17. Gee, K. R., Sun, W.-C., Klaubert, D. H. et al., *Tetrahedron Lett.* 37, 7905-7908 (1996).
18. Patterson, D. M., Nazarova, L. A., and Prescher, J. A., *ACS Chem. Biol.* 9, 592-605 (2014).
19. Nemoto, H., Kubota, Y., and Yamamoto, Y., *J. Org. Chem.* 55, 4515-4516 (1990).
20. Wysocki, L. M., Grimm, J. B., Tkachuk, A. N. et al., *Angew. Chem., Int. Ed.* 50, 11206-11209 (2011).
21. Hinckley, D. A. and Seybold, P. G., *Spectrochim. Acta, Part A* 44, 1053-1059 (1988).
22. Suzuki, K., Kobayashi, A., Kaneko, S. et al., *Phys. Chem. Chem. Phys.* 11, 9850-9860 (2009).

It will be understood that various details of the presently disclosed subject matter can be changed without departing from the scope of the subject matter disclosed herein. Furthermore, the foregoing description is for the purpose of illustration only, and not for the purpose of limitation.

What is claimed is:
1. A compound of the following structure:

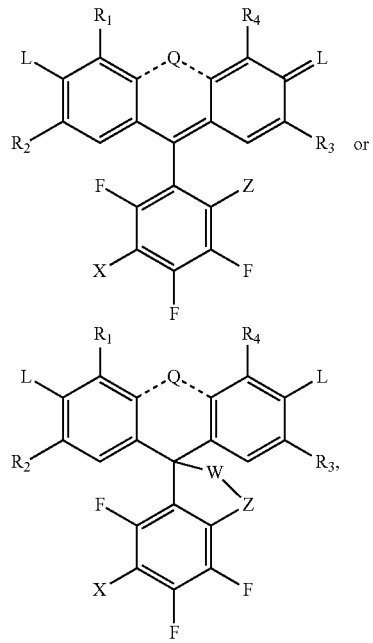

wherein
Q is selected from the group consisting of CH(alkyl), C(alkyl)$_2$, NH, N(alkyl), O, S, SO$_2$, Si(alkyl)$_2$, P(O) (aryl), P(O)(alkyl), PO$_2$H, PO$_2$(alkyl), Se, and replaced with two H atoms;
L is independently selected from the group consisting of O, OH, NH$_2$, NH(alkyl), NH(deuterated alkyl), N(alkyl)$_2$, N(deuterated alkyl)$_2$, NH(aryl), N(aryl)$_2$, N(alkyl)(aryl), N(deuterated alkyl) (aryl), substituted or unsubstituted cyclic amines with a ring size of 3, 4, 5, 6, 7, 8, or 9 atoms, and substituted or unsubstituted deuterated cyclic amines with a ring size of 3, 4, 5, 6, 7, 8, or 9 atoms, so long as when Q is O then L is not O or OH;
R$_1$, R$_2$, R$_3$, and R$_4$ are independently selected from the group consisting of H, D, halogen, CN, OH, O(alkyl), O(aryl), SH, S(alkyl), S(aryl), N$_3$, NH$_2$, NH(alkyl), N(alkyl)$_2$, NH(aryl), N(aryl)$_2$, NO$_2$, CHO, C(O)(alkyl), C(O)(aryl), COOH, COO(alkyl), COO(aryl), C(O)NH (alkyl), C(O)NH(aryl), PO$_3$H$_2$, SO$_3$H, alkyl and substituted alkyl, aryl and substituted aryl, alkenyl and substituted alkenyl, alkynyl or substituted alkynyl, or where each adjacent R substituent and L substituent, taken together with the carbon atoms to which they are bonded, independently form a substituted or unsubstituted ring containing 3, 4, 5, 6, 7, 8, or 9 atoms;
X is selected from the group consisting of alkyl, substituted alkyl, alkenyl, substituted alkenyl, alkynyl, substituted alkynyl, CN, COOH, COO(alkyl), COO(aryl), C(O)NH(alkyl), C(O)N(alkyl)$_2$, C(O)NH(aryl), and C(O)N(aryl)$_2$;
when W is not present in the structure, Z is selected from the group consisting of H, halogen, OH, O(alkyl), O(aryl), COO, COOH, COO(alkyl), COO(aryl), C(O)

NH(alkyl), C(O)N(alkyl)$_2$, C(O)NH(aryl), C(O)N(aryl)$_2$, PO$_3$H$_2$, SO$_3$H, alkyl, substituted alkyl, alkenyl, and substituted alkenyl; and when W is present in the structure, Z is selected from the group consisting of C(O), SO$_2$, PO$_2$H, or CR$_2$ where each R is independently selected from the group consisting of H, alkyl, and substituted alkyl; and W is selected from the group consisting of O, S, C(O), C(N$_2$), NH, N(alkyl), N(aryl), N(SO$_2$R) where R can be alkyl, substituted alkyl, or CN.

2. The compound of claim 1, wherein X is selected from the group consisting of

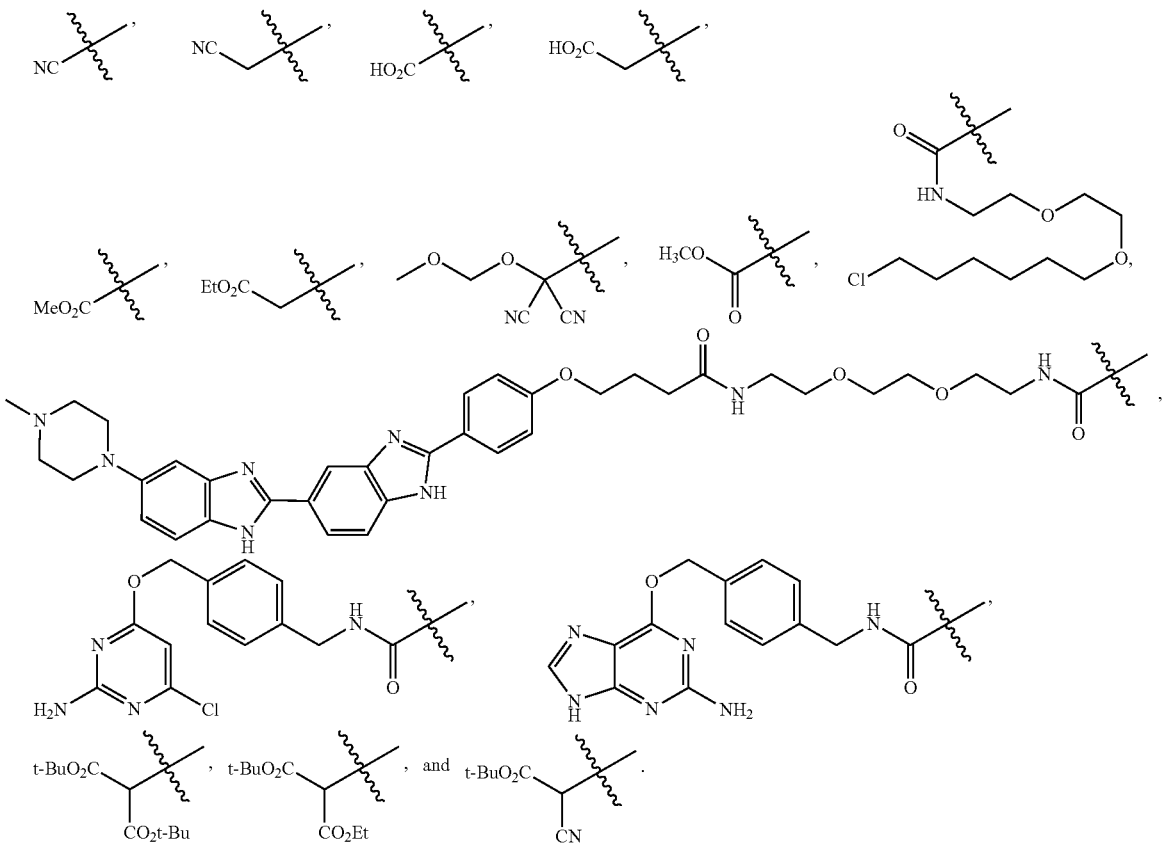

3. The compound of claim 1, wherein Q is selected from the group consisting of C(alkyl)$_2$, O, S, SO$_2$, Si(alkyl)$_2$, P(O)(aryl), P(O)(alkyl), PO$_2$H, and replaced with two H atoms.

4. The compound of claim 1, wherein Q is selected from selected from the group consisting of

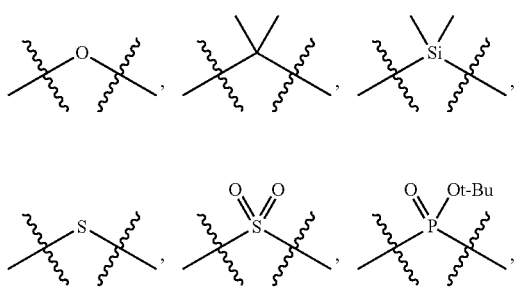

and replaced with two H atoms.

5. The compound of claim 1, wherein one or both L substituents are independently selected from the group consisting of O and OH.

6. The compound of claim 1, wherein one or both L substituents are independently selected from the group consisting of NH$_2$, NCH$_3$(phenyl), NH(tert-butoxycarbonyl), and N(CH$_3$)$_2$.

7. The compound of claim 1, wherein one or both L substituents are independently selected from the group consisting of substituted or unsubstituted cyclic amines with a ring size of 4, 5, 6, 7, or 8 atoms.

8. The compound of claim 7, wherein the substituted or unsubstituted cyclic amine with a ring size of 4, 5, 6, or 7 atoms is selected from the group consisting of

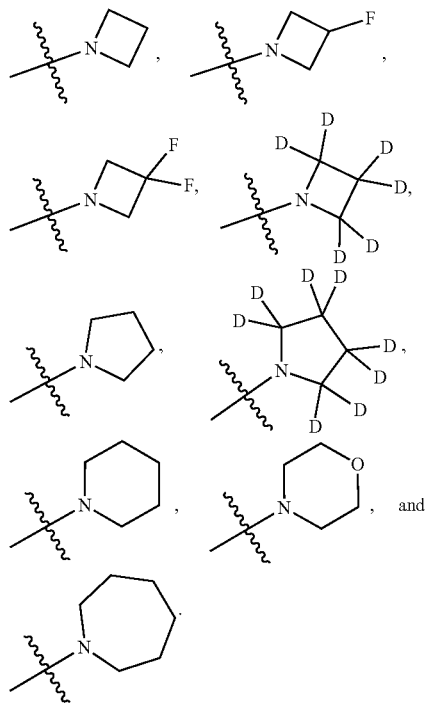

9. The compound of claim 1, wherein the $R_2$ substituents, or the $R_3$ substituents, and L substituents are taken together with the carbon atoms to which they are bonded to form a substituted or unsubstituted ring containing 5, 6, 7, 8, or 9 atoms.

10. The compound of claim 1, having a structure chosen from:

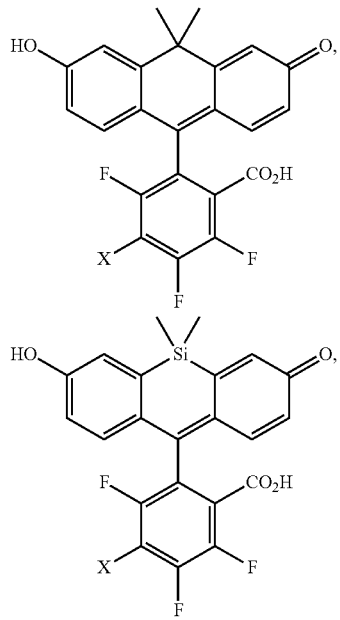

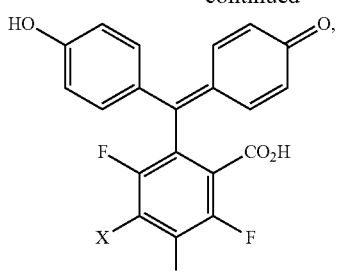

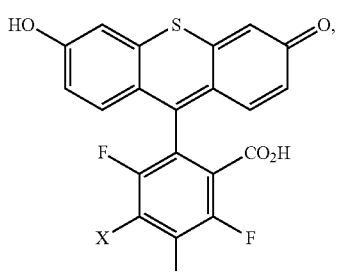

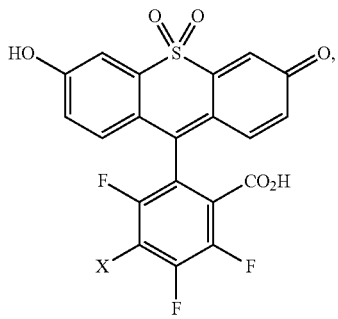

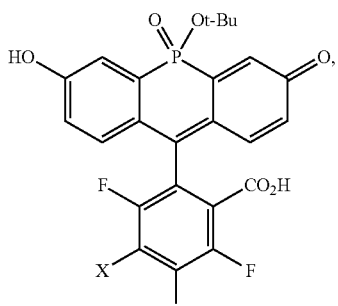

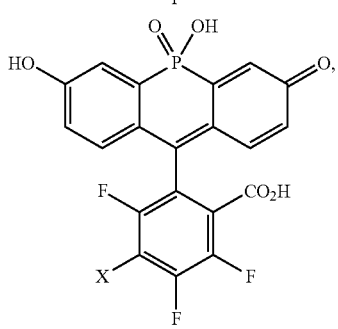

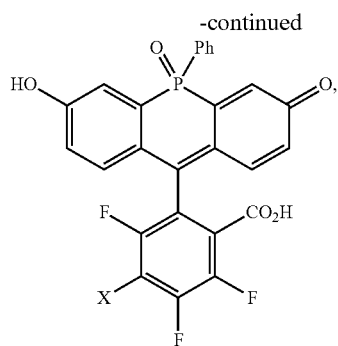
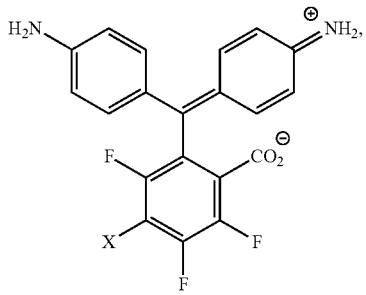
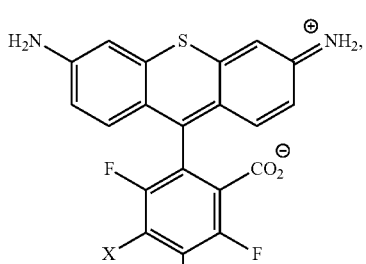
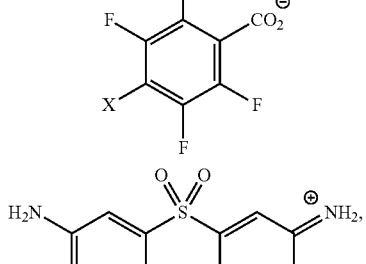
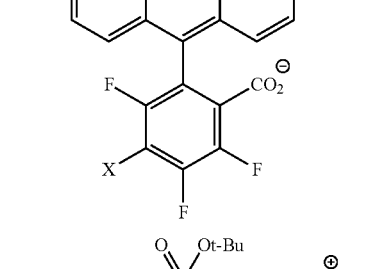
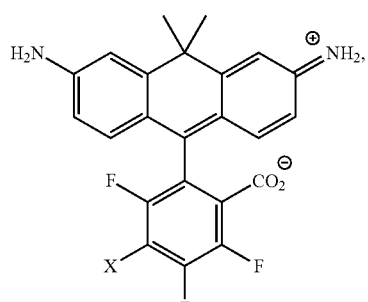
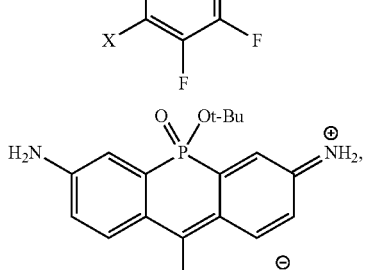
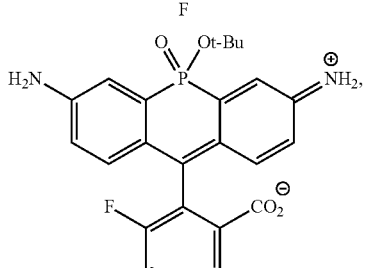
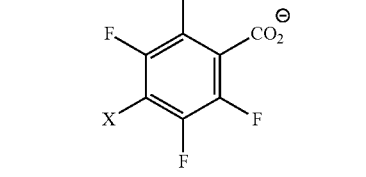
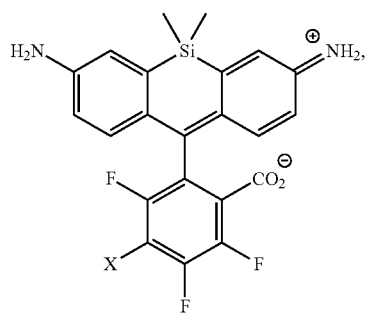
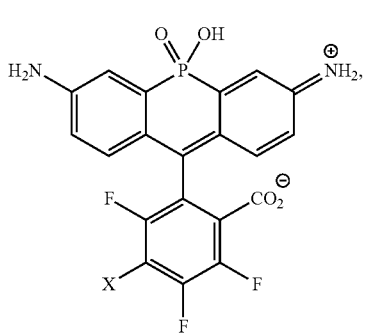

185
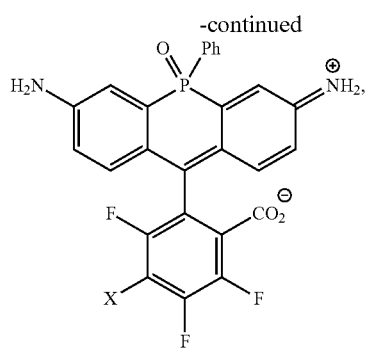
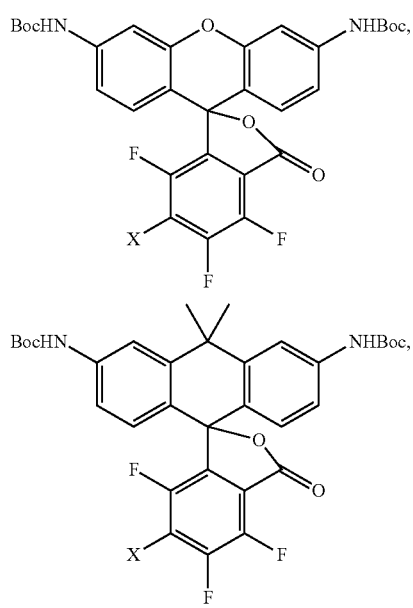
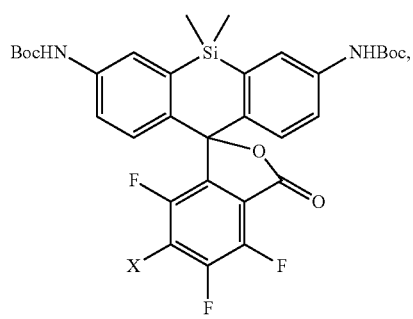
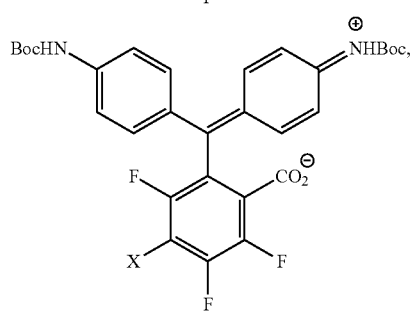
186
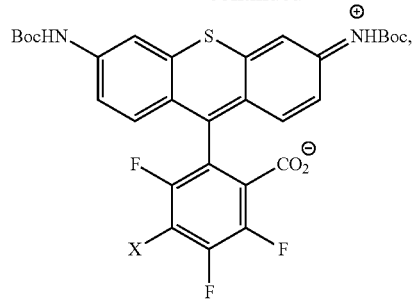
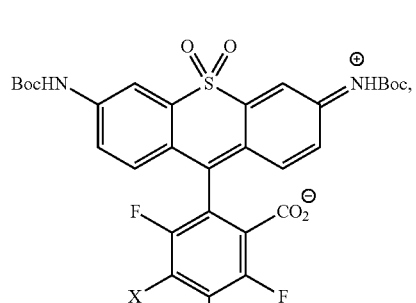
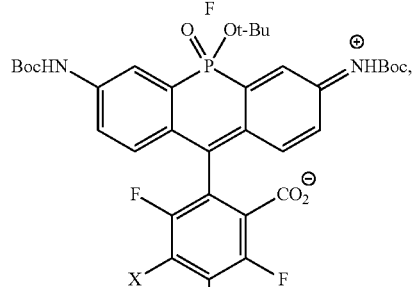
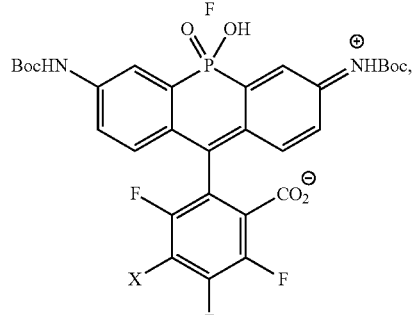
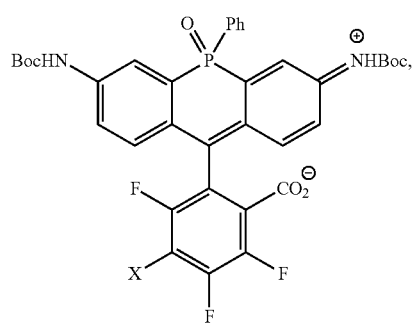

187
-continued
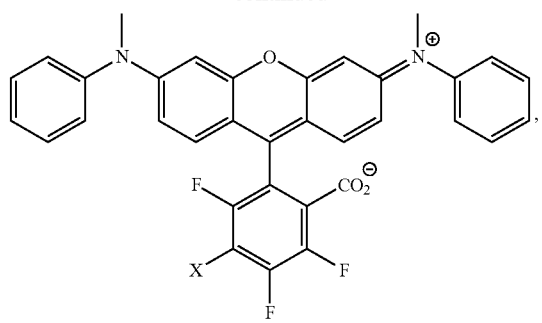
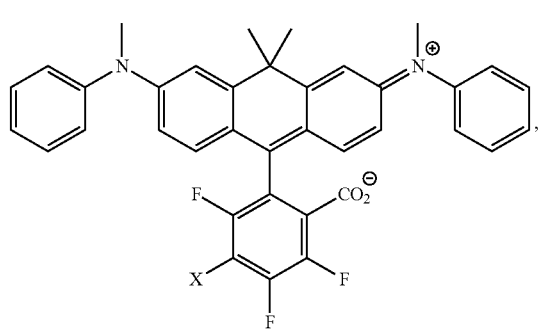
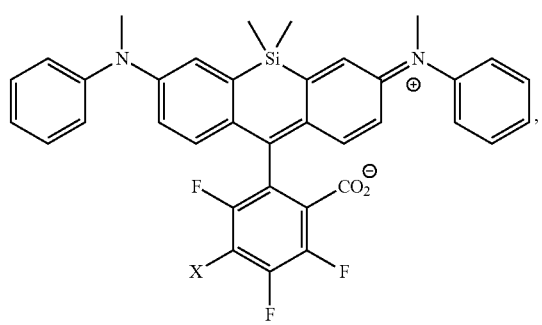
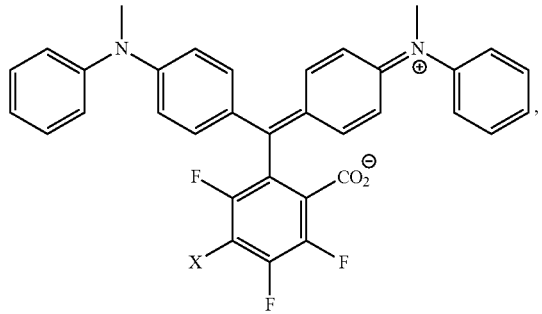
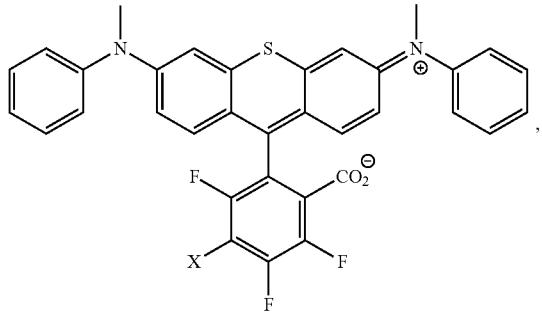
188
-continued
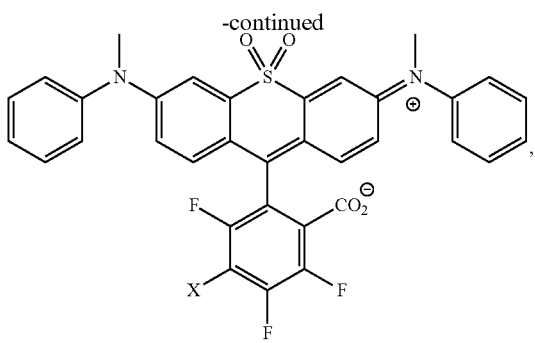
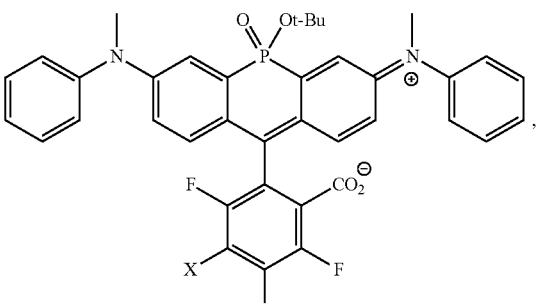
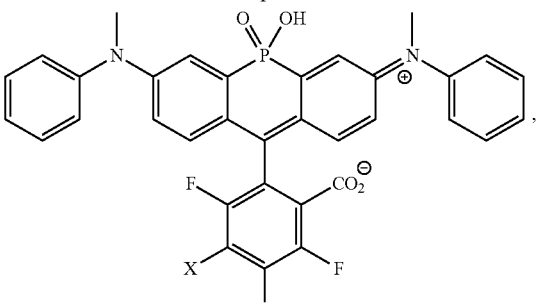
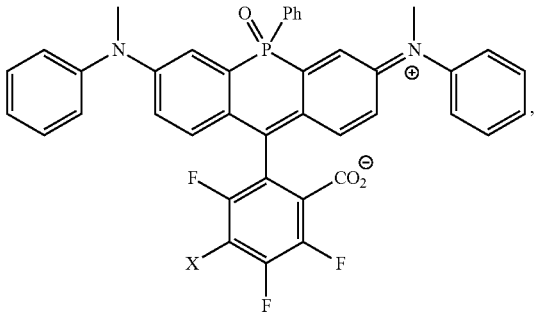
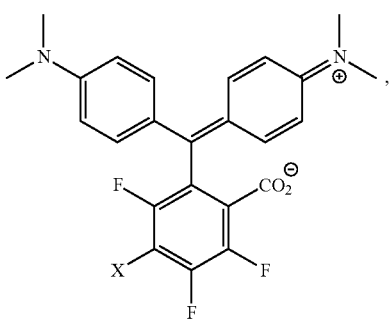

189
-continued
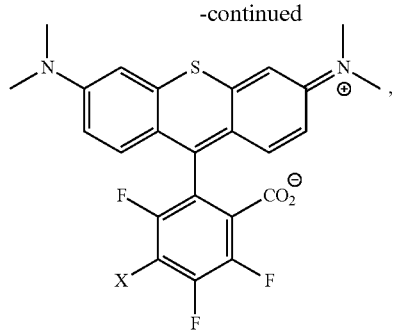
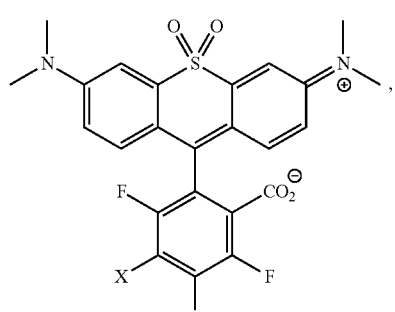
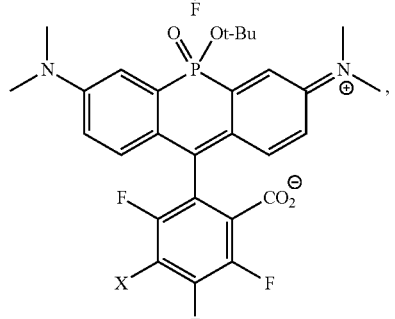
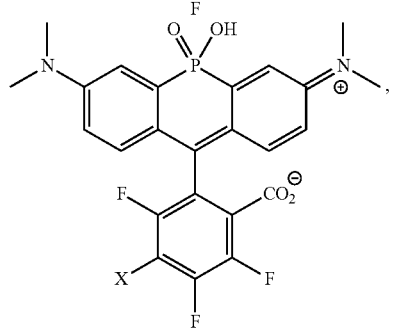
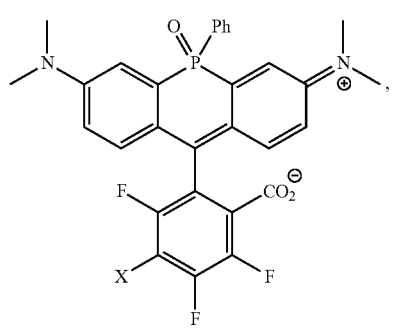
190
-continued
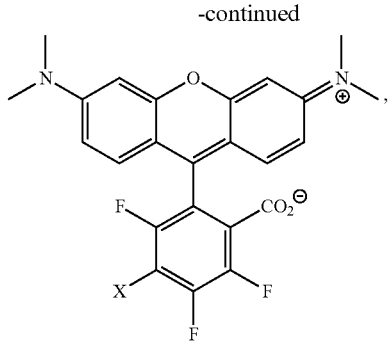
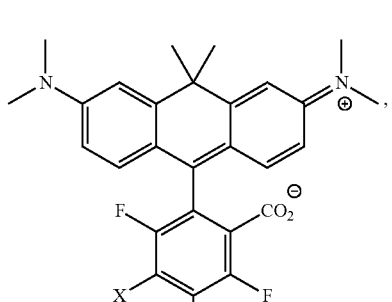
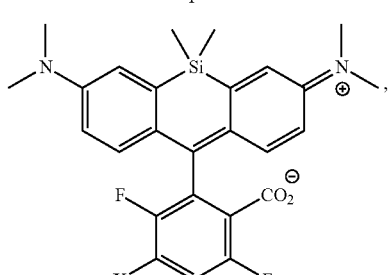
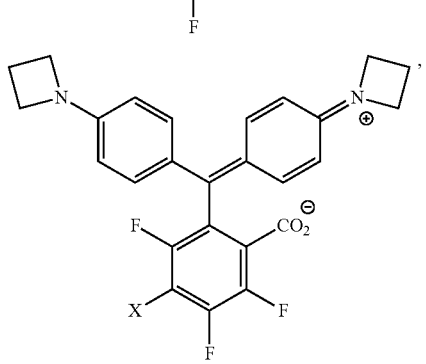
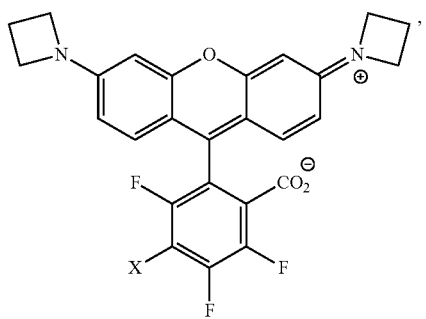

191
-continued
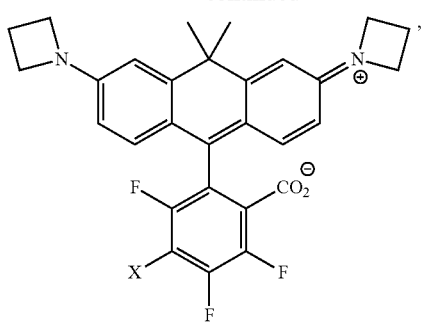
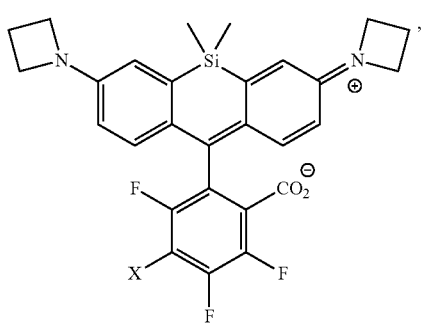
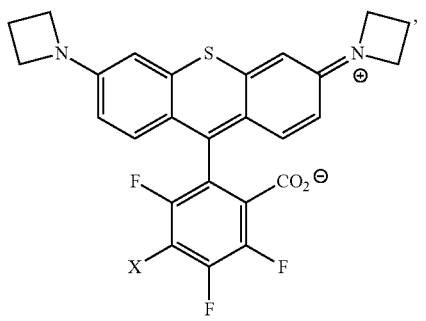
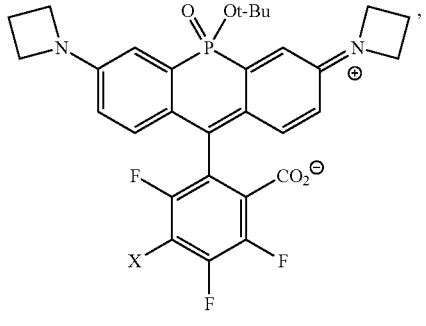
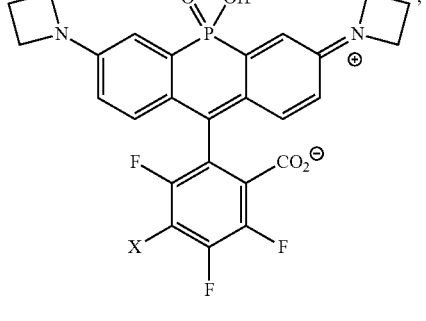
192
-continued
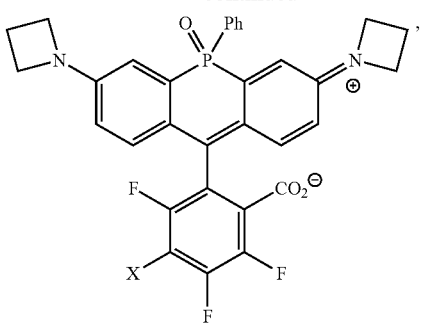
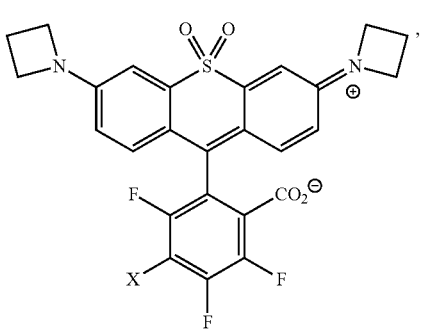
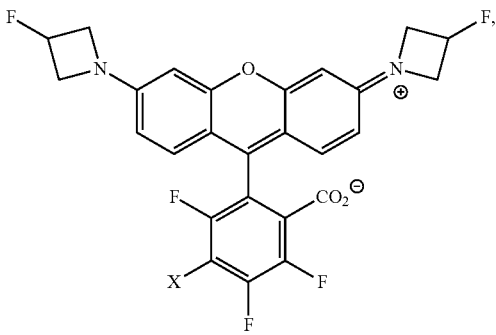
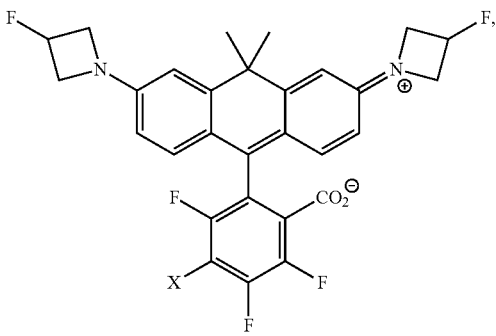
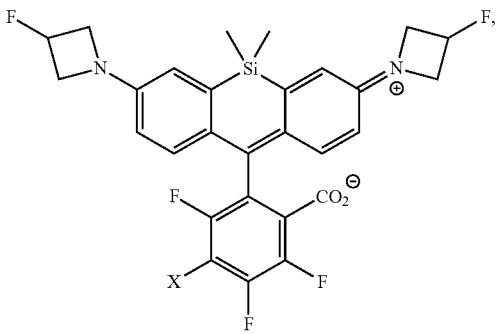

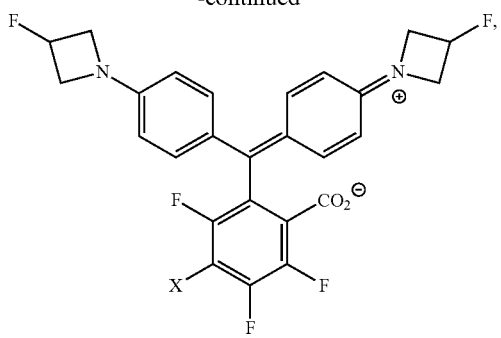
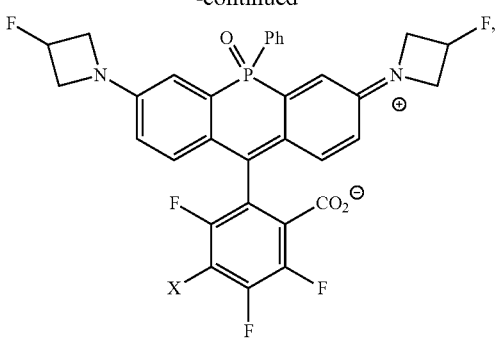

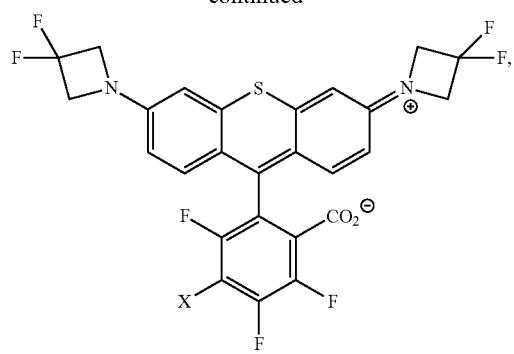
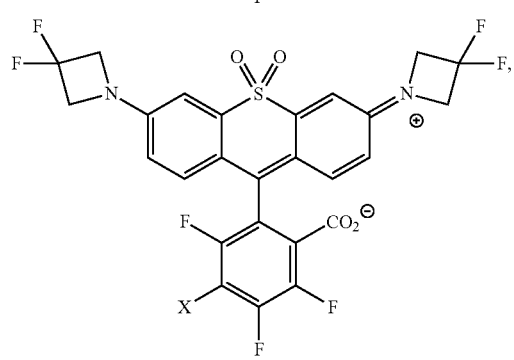
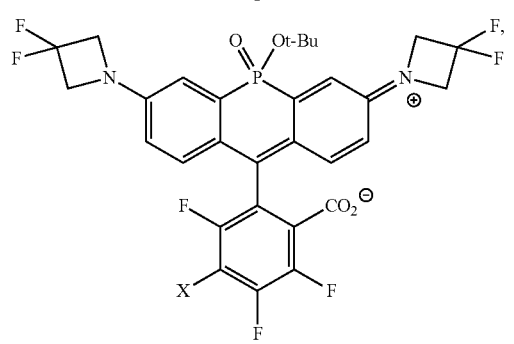
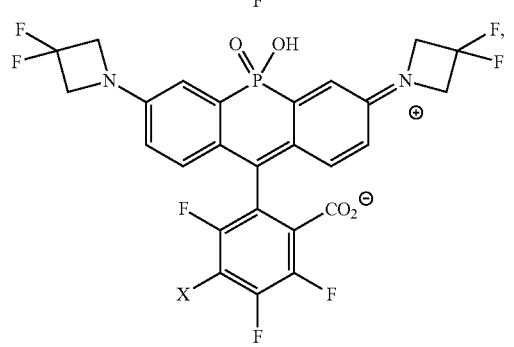
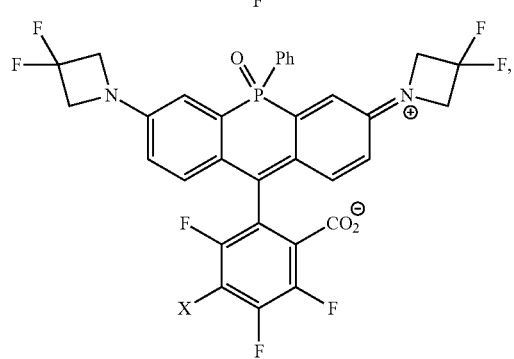
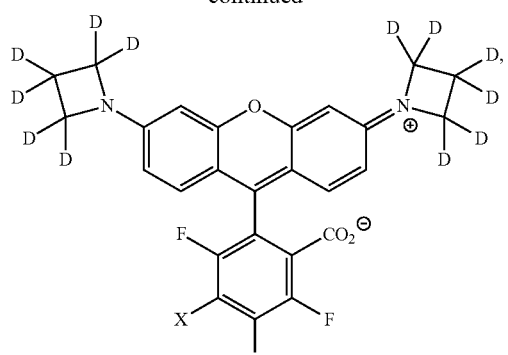
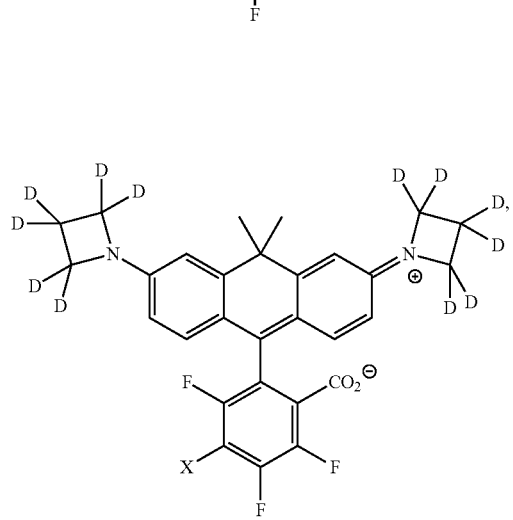
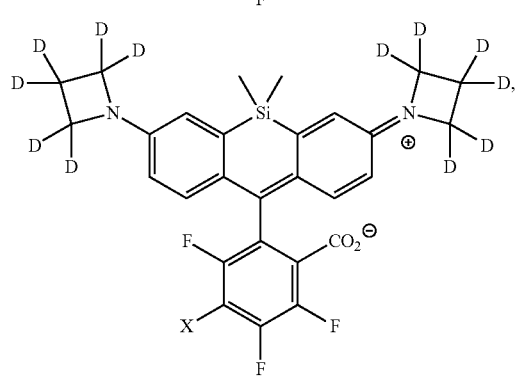
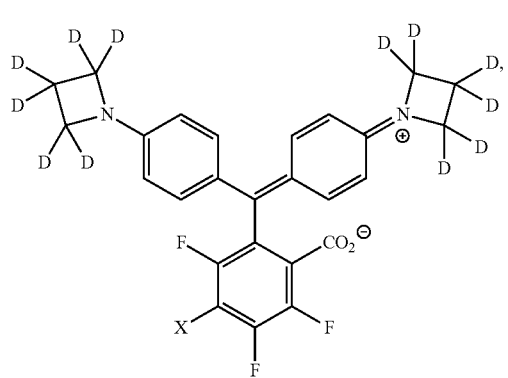

197
-continued
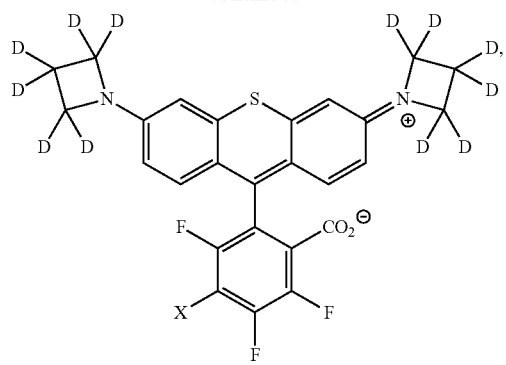
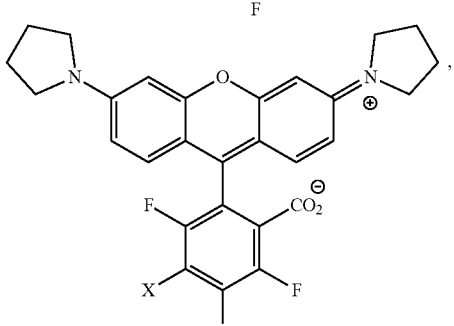
198
-continued
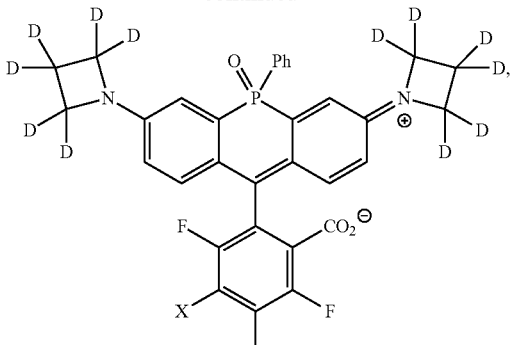
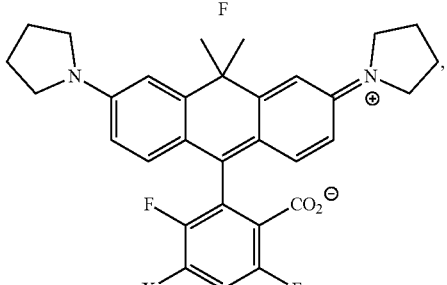
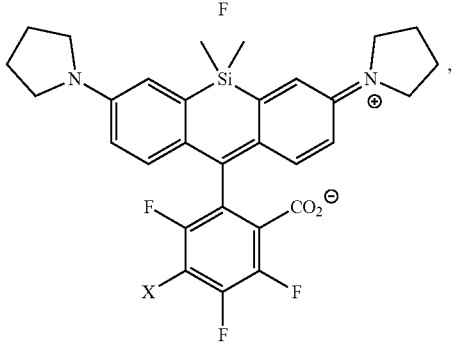
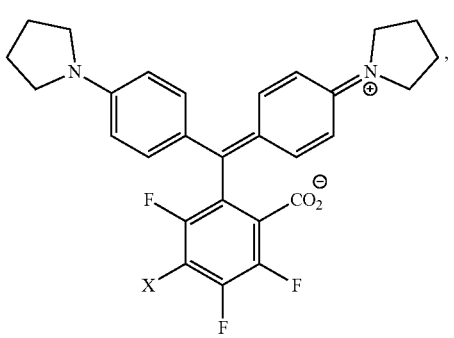

199
-continued
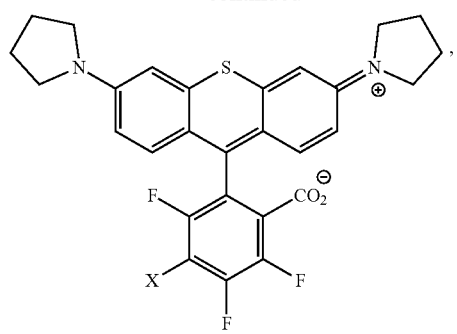
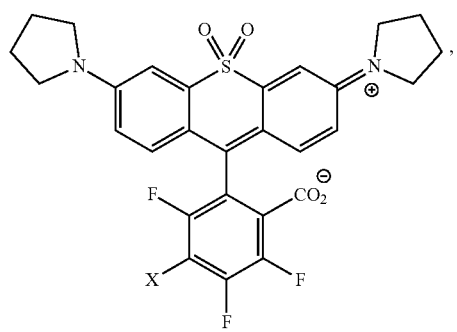
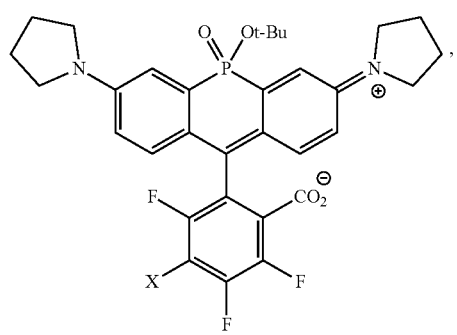
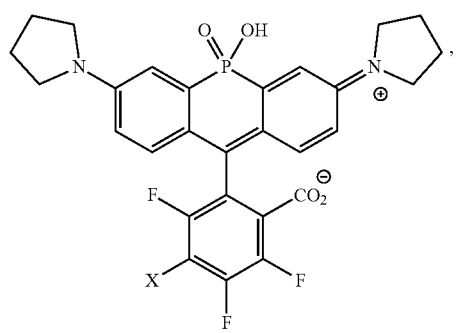
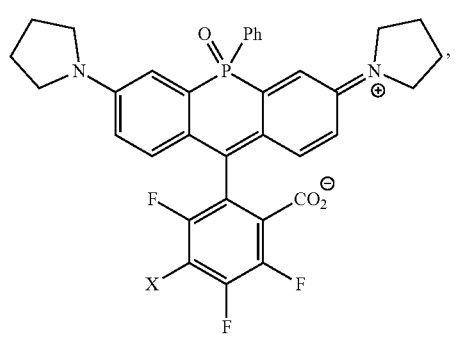
200
-continued
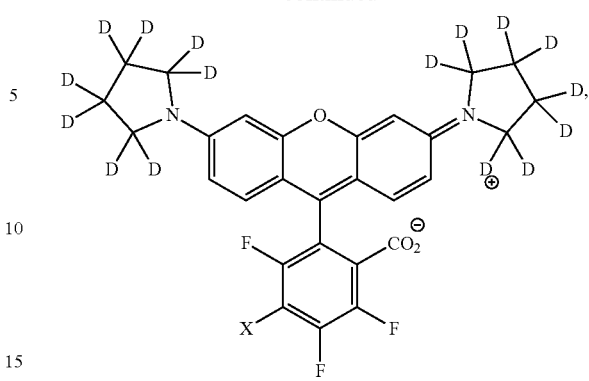
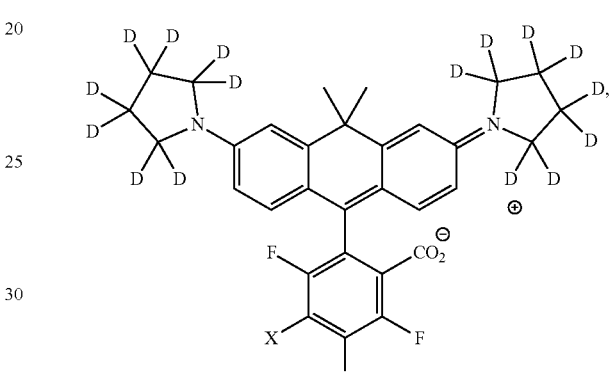
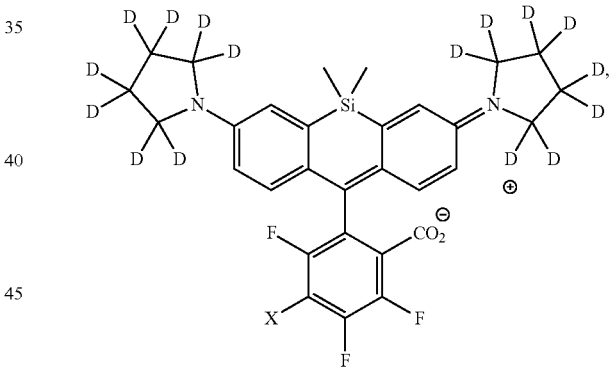
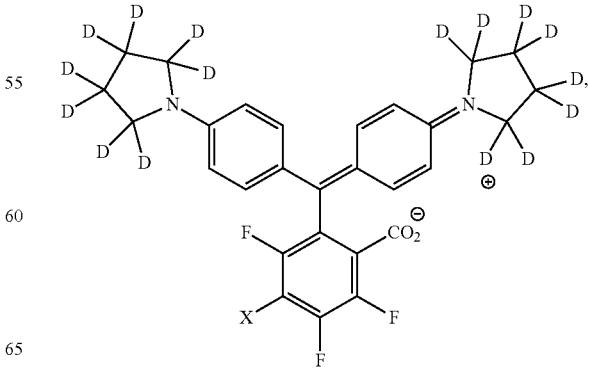

201
-continued
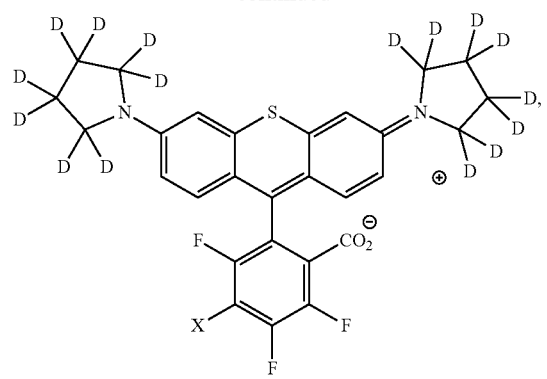
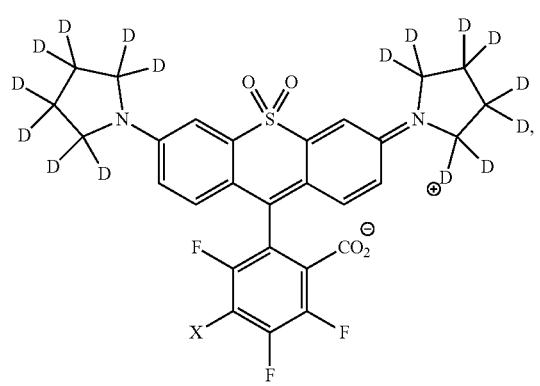
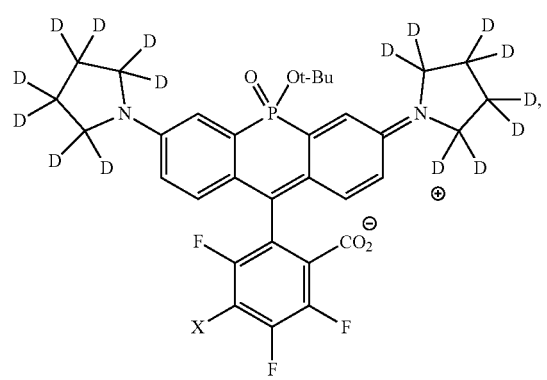
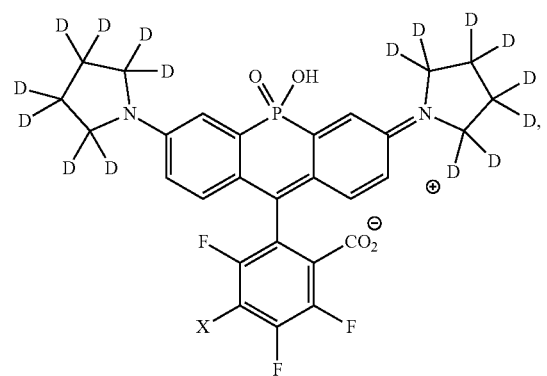
202
-continued
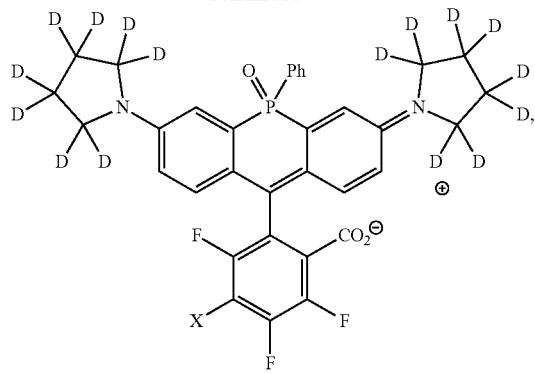
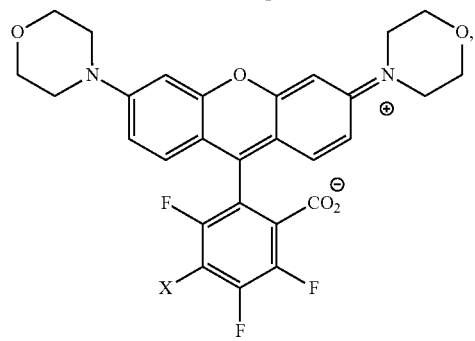
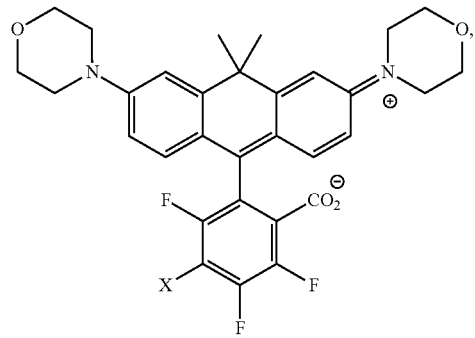
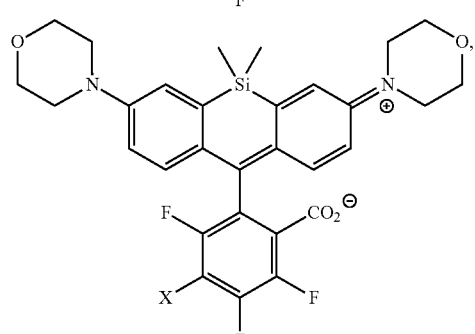

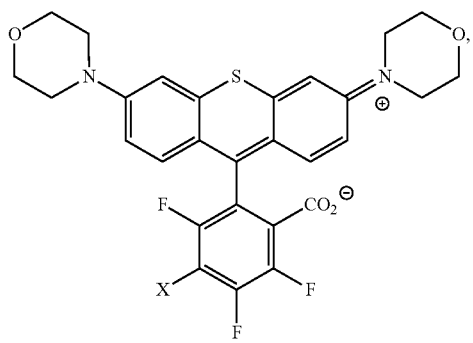
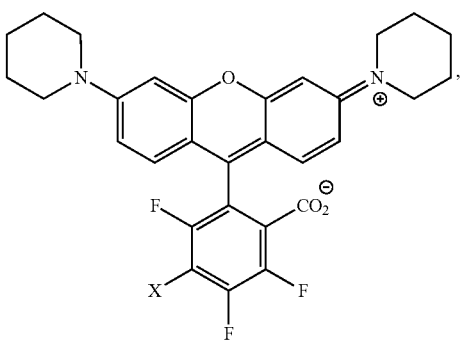

205
-continued
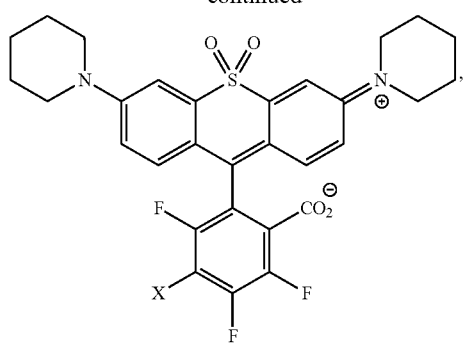
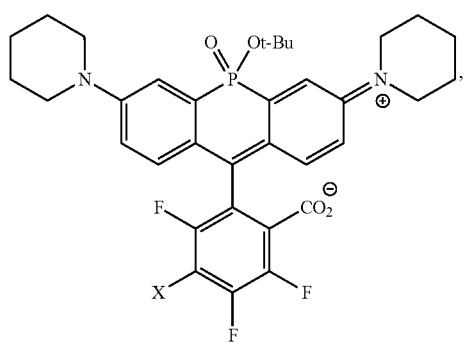
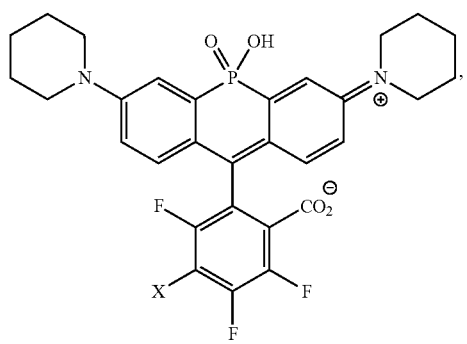
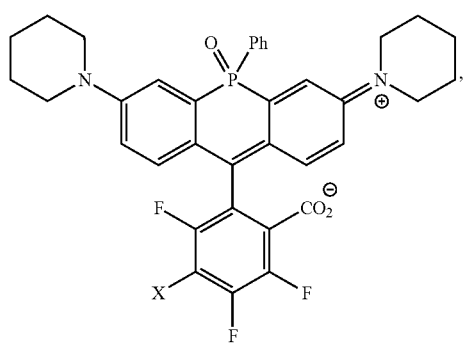
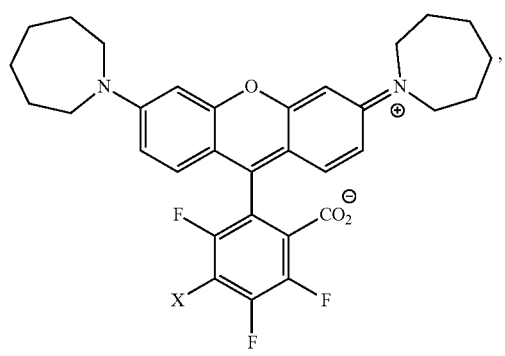
206
-continued
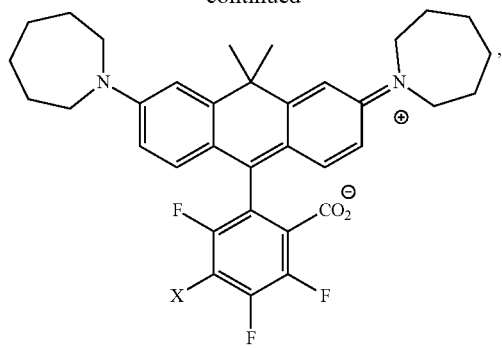
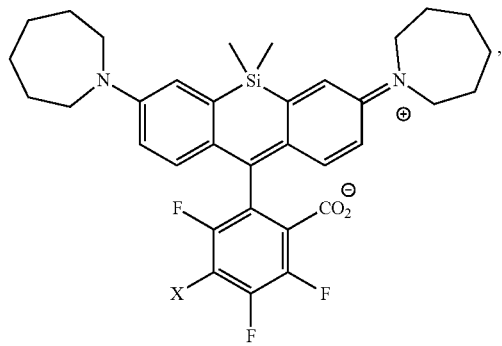
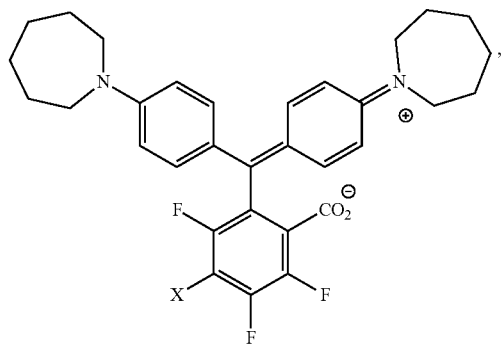
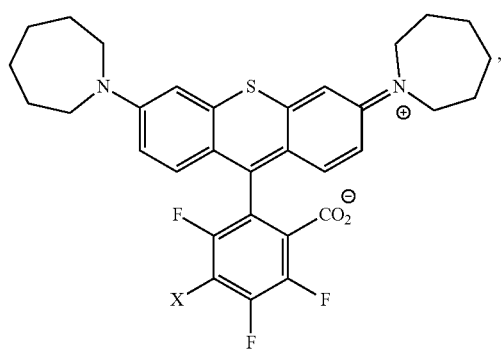
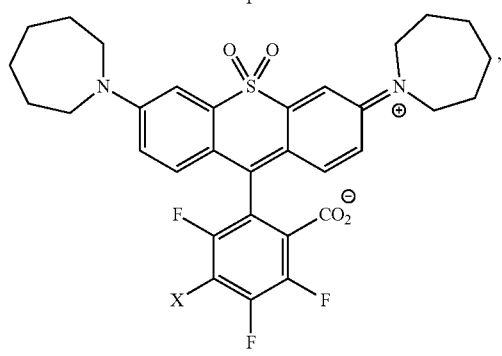

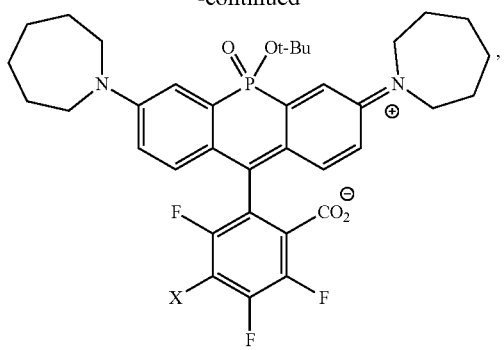
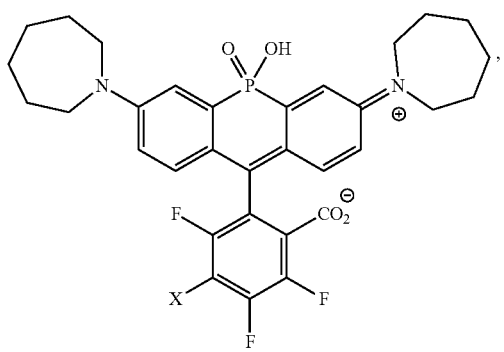
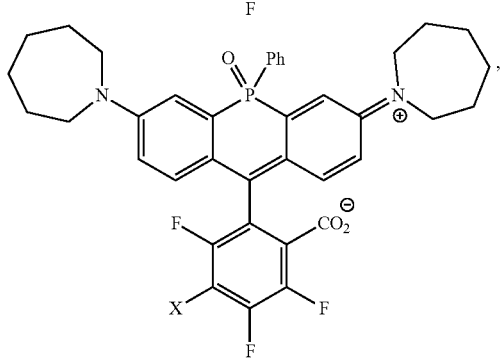
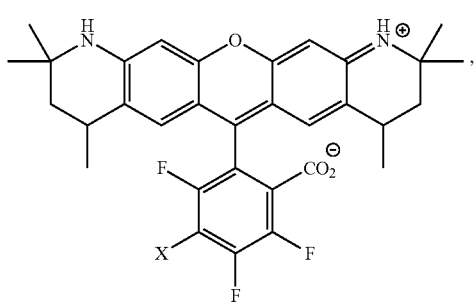
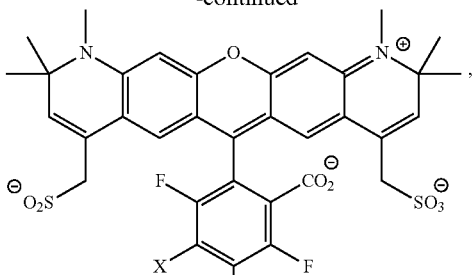
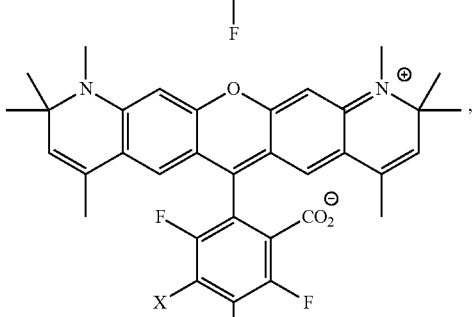
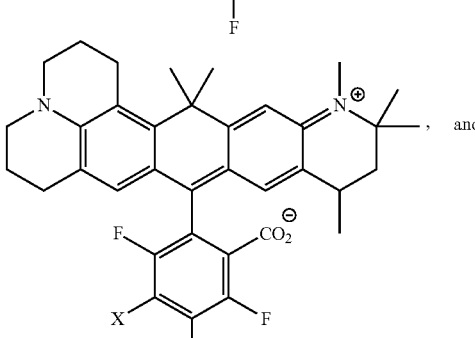
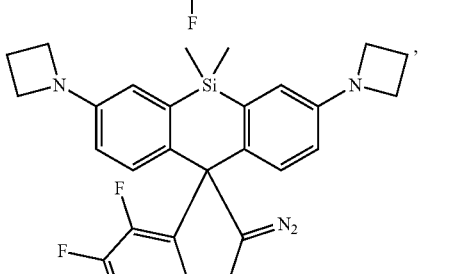
wherein X is selected from the group consisting of alkyl, substituted alkyl, alkenyl, substituted alkenyl, alkynyl, substituted alkynyl, CN, COOH, COO(alkyl), COO(aryl), C(O)NH(alkyl), C(O)N(alkyl)₂, C(O)NH(aryl), and C(O)N(aryl)₂.
11. The compound of claim 10, wherein X is selected from the group consisting of
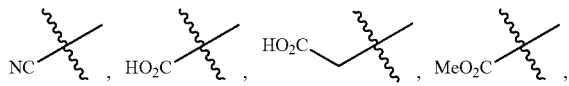

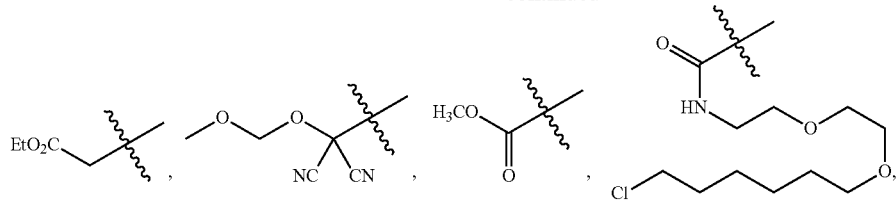

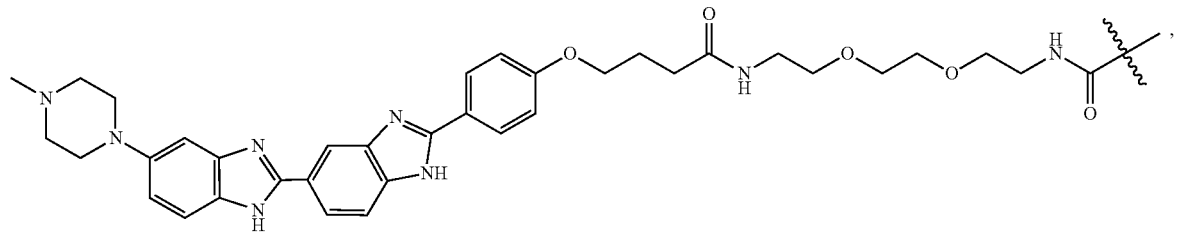

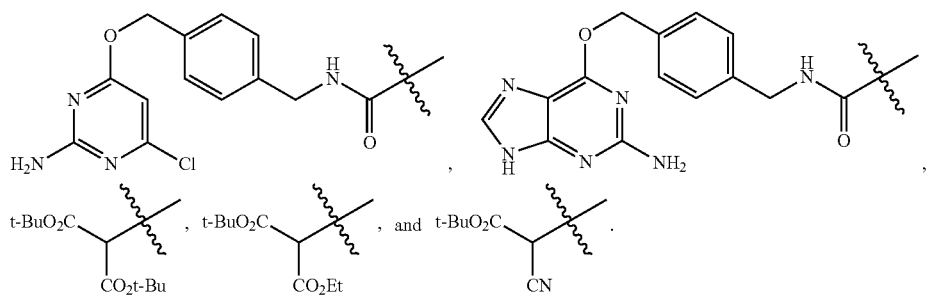

12. A method for detecting a target substance, comprising: contacting a sample with the compound of claim 1; and detecting an emission light from the compound, the emission light indicating the presence of the target substance.

13. The method of claim 12, wherein the target substance is selected from a protein, a carbohydrate, a polysaccharide, a glycoprotein, a hormone, a receptor, an antigen, an antibody, a virus, a substrate, a metabolite, an inhibitor, a drug, a nutrient, a growth factor, a liprotein, and a combination thereof.

14. The method of claim 12, wherein the detecting step is performed with a microscope.

15. The method of claim 12, wherein the contacting step and the detecting step are performed in a live cell.

16. The method of claim 12, wherein: the compound is a mixture of a first compound and a second compound; the first compound being selective for a first target substance and capable of emitting a first emission light; the second compound being selective for a second target substance and capable of emitting a second emission light, and the detecting step includes detecting the first emission light that indicates the presence of the first target substance and the second emission light that indicates the presence of the second target substance.

17. The method of claim 12, wherein one or both L substituents in the compound are independently selected from the group consisting of O and OH.

18. The method of claim 12, wherein one or both L substituents in the compound are independently selected from the group consisting of $NH_2$, $NCH_3$(phenyl), NH(tert-butoxycarbonyl), $N(CH_3)_2$, and substituted or unsubstituted cyclic amines with a ring size of 4, 5, 6, 7, or 8 atoms.

19. The compound of claim 1, where $R_1$ and L, taken together with the carbon atoms to which they are bonded, form a ring containing 3, 4, 5, 6, 7, 8, or 9 atoms, and $R_2$ and L, taken together with the carbon atoms to which they are bonded, form a substituted or unsubstituted ring containing 3, 4, 5, 6, 7, 8, or 9 atoms.

20. The compound of claim 19, where $R_3$ and L, taken together with the carbon atoms to which they are bonded, form a substituted or unsubstituted ring containing 3, 4, 5, 6, 7, 8, or 9 atoms.

21. The compound of claim 20, where $R_4$ and L, taken together with the carbon atoms to which they are bonded, form a substituted or unsubstituted ring containing 3, 4, 5, 6, 7, 8, or 9 atoms.

22. The compound of claim 21, where each L is N and Z is $CO_2H$.

23. The compound of claim 22, where Q is O, $C(CH_3)_2$, or $Si(CH_3)_2$.

24. The compound of claim 20, where Q is $C(CH_3)_2$, L is N in the ring structure containing $R_1$ and $R_2$, and L is N(alkyl) in the ring structure containing $R_3$, and Z is $CO_2H$.

25. The compound of claim 24, L is N(methyl) or N(ethyl) in the ring structure containing $R_3$, and Z is $CO_2H$.

26. The compound of claim 1, having the following structure:

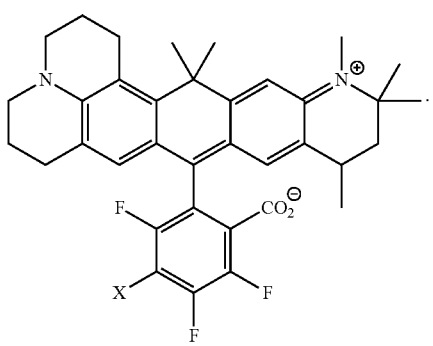

27. The compound of claim 1, where $R_2$ and L, taken together with the carbon atoms to which they are bonded, form a ring containing 3, 4, 5, 6, 7, 8, or 9 atoms, and $R_3$ and L, taken together with the carbon atoms to which they are bonded, form a substituted or unsubstituted ring containing 3, 4, 5, 6, 7, 8, or 9 atoms.

28. The compound of claim 27, where $R_2$ and L, taken together with the carbon atoms to which they are bonded, form a ring containing 5 or 6 atoms, and $R_3$ and L, taken together with the carbon atoms to which they are bonded, form a substituted or unsubstituted ring containing 5 or 6 atoms.

29. The compound of claim 28, where Q is O, $C(CH_3)_2$, or $Si(CH_3)_2$; each L is independently NH or N(alkyl); and Z is $CO_2H$.

30. The compound of claim 29, where $R_1$ and $R_4$ are $SO_3H$.

31. The compound of claim 1, having a structure selected from the group consisting of:

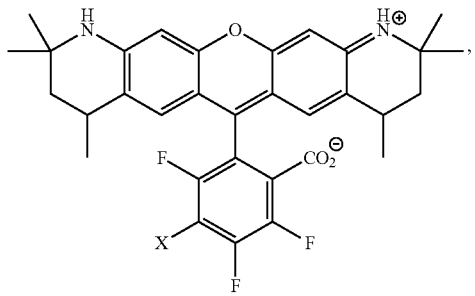

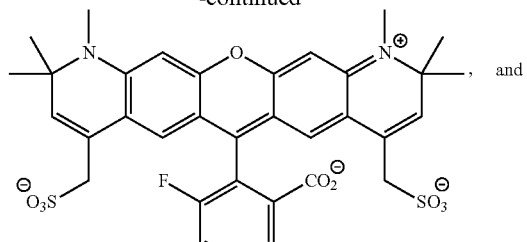

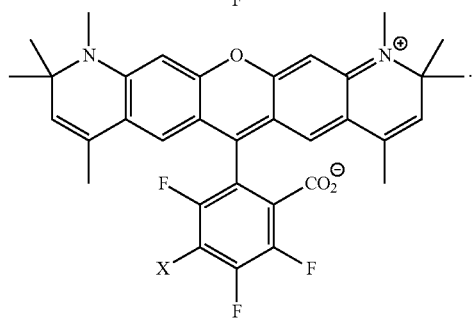

32. The compound of claim 1, wherein one L is OH and other L is O, and Z is $CO_2H$.

33. The compound of claim 1, wherein Q is O, each L is $NH_2$, and Z is $CO_2H$.

34. The compound of claim 33, wherein $R_1$ and $R_4$ are $SO_3H$.

35. A compound of the following structure:

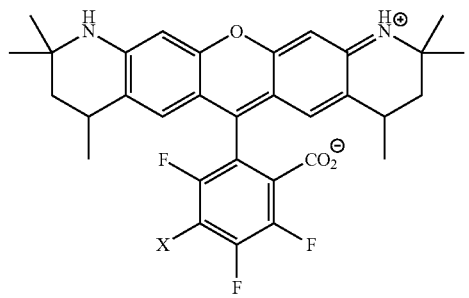

wherein X is selected from the group consisting of alkyl, substituted alkyl, aryl, substituted aryl, alkenyl, substituted alkenyl, alkynyl, substituted alkynyl, CN, COOH, COO(alkyl), COO(aryl), C(O)NH(alkyl), C(O)N(alkyl)$_2$, C(O)NH(aryl), and C(O)N(aryl)$_2$.

* * * * *